US012655189B2

(12) United States Patent
Powell et al.

(10) Patent No.: US 12,655,189 B2
(45) Date of Patent: Jun. 16, 2026

(54) DOTA BINDING CHIMERIC ANTIGEN RECEPTOR FOR CELLULAR THERAPY

(71) Applicant: THE TRUSTEES OF THE UNIVERSITY OF PENNSYLVANIA, Philadelphia, PA (US)

(72) Inventors: Daniel J. Powell, Bala Cynwyd, PA (US); Nicholas Minutolo, Philadelphia, PA (US); Michael Farwell, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1164 days.

(21) Appl. No.: 17/605,945

(22) PCT Filed: Apr. 23, 2020

(86) PCT No.: PCT/US2020/029576
§ 371 (c)(1),
(2) Date: Oct. 22, 2021

(87) PCT Pub. No.: WO2020/219715
PCT Pub. Date: Oct. 29, 2020

(65) Prior Publication Data

US 2022/0403051 A1 Dec. 22, 2022

Related U.S. Application Data

(60) Provisional application No. 62/837,569, filed on Apr. 23, 2019.

(51) Int. Cl.

| | |
|---|---|
| ***C07K 16/44*** | (2006.01) |
| ***A61K 40/11*** | (2025.01) |
| ***A61K 40/31*** | (2025.01) |
| ***A61K 40/42*** | (2025.01) |
| ***A61K 47/68*** | (2017.01) |
| ***A61K 51/04*** | (2006.01) |
| ***A61K 51/10*** | (2006.01) |
| ***A61P 35/00*** | (2006.01) |
| ***C07D 257/02*** | (2006.01) |
| ***C07K 14/705*** | (2006.01) |

(52) U.S. Cl.
CPC .......... *C07K 14/7051* (2013.01); *A61K 40/11* (2025.01); *A61K 40/31* (2025.01); *A61K 40/4202* (2025.01); *A61K 40/4204* (2025.01); *A61K 40/4205* (2025.01); *A61K 40/428* (2025.01); *A61K 47/6803* (2017.08); *A61K 51/0482* (2013.01); *A61K 51/1045* (2013.01); *A61P 35/00* (2018.01); *C07D 257/02* (2013.01); *C07K 16/44* (2013.01); *A61K 2239/28* (2023.05); *A61K 2239/31* (2023.05); *A61K 2239/38* (2023.05); *C07K 2317/24* (2013.01); *C07K 2317/622* (2013.01); *C07K 2319/03* (2013.01)

(58) Field of Classification Search
None
See application file for complete search history.

(56) References Cited

U.S. PATENT DOCUMENTS

| | | | | |
|---|---|---|---|---|
| 7,230,085 | B2 | 6/2007 | Griffiths et al. | |
| 8,648,176 | B2 | 2/2014 | Orcutt et al. | |
| 2015/0238631 | A1 | 8/2015 | Kim et al. | |
| 2018/0282416 | A1 | 10/2018 | Riley et al. | |
| 2023/0108300 | A1* | 4/2023 | Powell ............... | C07K 16/2809 424/185.1 |

FOREIGN PATENT DOCUMENTS

| | | | |
|---|---|---|---|
| CN | 104877028 | A | 9/2015 |
| WO | 2016130539 | A2 | 8/2016 |
| WO | 2017020812 | A2 | 2/2017 |
| WO | 2017112784 | A1 | 6/2017 |
| WO | 2018204873 | A1 | 11/2018 |
| WO | 2019177970 | A1 | 9/2019 |

OTHER PUBLICATIONS

Altai, M., et al., "Pretargeted Imaging and Therapy", J Nucl Med, 2017; 58(10):1553-1559.
Bhatnagar, P., et al., "Imaging of Genetically Engineered T Cells by PET using Gold Nanoparticle Complexed to Copper-64", Integr. Biol., Jan. 2013; 5(1): 231-238.
Corneillie, T.M., et al., "Converting Weak Binders into Infinite Binders", Bioconjugate Chem., 2004; 15(6):1389-1391.
Corneillie, T.M., et al., "Irreversible Engineering of the Multielement-Binding Antibody 2D12.5 and its Complementary Ligands", Bioconjugate Chem., 2004; 15(6):1392-1402.

(Continued)

*Primary Examiner* — Daniel E Kolker
*Assistant Examiner* — Cheom-Gil Cheong
(74) *Attorney, Agent, or Firm* — Saul Ewing LLP; Kathryn Doyle; Domingos J. Silva

(57) ABSTRACT

The present invention includes compositions and methods that utilize a Universal Immune Receptor (UnivIR) CAR system comprising a modified T cell comprising a DOTA CAR and a DOTA-conjugated targeting ligand. In certain embodiments, the invention includes methods for treating, ameliorating, and/or preventing cancer. In certain embodiments, the invention provides a set of complementary molecular imaging tools that is applicable to CAR T cell therapy.

4 Claims, 48 Drawing Sheets

Specification includes a Sequence Listing.

(56) References Cited

OTHER PUBLICATIONS

Heskamp, S., et al.: "89Zr-Immuno-Positron Emission Tomography in Oncology: State-of the-Art 89Zr Radiochemistry", Bioconjugate Chem., vol. 28, 2017; 28:2211-2223, XP055734862, DOI: 10.1021/acs.bioconjchem.7b00325.
Krebs, S., et al., "Antibody with Infinite Affinity for In Vivo Tracking of Genetically Engineered Lymphocytes", J Nucl Med., 2018; 59(12):1894-1900.
Marquez, B.V., et al., "Enhancing Peptide Ligand Binding to Vascular Endothelial Growth Factor by Covalent Bond Formation", Bioconjugate Chem., May 16, 2012; 23(5):1080-1089.
Orcutt, K.D., et al., "Engineering an antibody with picomolar affinity to DOTA chelates of multiple radionuclides for pretargeted radioimmunotherapy and imaging", Nucl Med, 2011; 38, 223-233.
Wei, L.H., et al., "Engineered Antibody Fragments with Infinite Affinity as Reporter Genes for PET Imaging", J Nucl Med., 2008; 49(11):1828-1835.

* cited by examiner

2:1 E:T ratio, 16 hour time point

2.5:1 E:T ratio

DOTA-NHS-ester

P-SCN-Bn-DOTA

| Targeting Ligand | EC50 |
|---|---|
| Herceptin-DOTA | 285.2pM |
| Herceptin-DOTA-Y | 13.2pM |
| Herceptin-Bn-DOTA-Y | 0.79pM |
| Herceptin-Bn-DOTA | 0.09pM |

5 Groups (5 mice per):

- Vehicle
- GFP-DOTA-dz T+ Ab(25ug)
- GFP-DOTA-BBz T + Ab(25ug)
- GFP-DOTA-BBz T + Ab(12.5ug)
- GFP-DOTA-BBz T + Ab(6.25ug)

Targeting Ligand Dosing

- Herceptin-DOTA-Y dosed one days before initial T cell injection, followed by injection every 6 days

Readouts:

- Body weight
- Tumor progression

1

2

3

4

5

6 im-Y-DOTA-$N_3$-TFP

1

7 rev-Y-DOTA-$N_3$-TFP $[^{90}Y]AABD$ irr-$[^{90}Y]DOTA$ $[^{90}Y]DOTA$-Bn-$NH_2$

3

[$^{18}F$]irr-Y-DOTA

7

[$^{18}F$]rev-Y-DOTA

| | DOTA BBz | DOTA IgG4 | DOTA IgG4m | DOTA CH2CH3 |
|---|---|---|---|---|
| EC50 | 1.253 | 0.5263 | 0.4794 | 0.6966 |

Her-Bn-DOTA-Y 1x

Dynabeads-DOTA-Y:

163

164

Tris-DOTA (PEG-n):

Bis-DOTA (PEG-n):

SEQUENCE LISTING

<160> NUMBER OF SEQ ID NOS: 40

<210> SEQ ID NO 1
<211> LENGTH: 732
<212> TYPE: DNA
<213> ORGANISM: Artificial Sequence
<220> FEATURE:
<223> OTHER INFORMATION: Humanized DOTA-binding scFV (hC825)

<400> SEQUENCE: 1
catgttcagt tagtcgagtc cggtggagga ctggtgcaac caggaggttc tctgagattg 60
tcctgtgccg cctctggctt tagtctgaca gattacggag tgcactgggt taggcaggcc 120
cctgggaaag gtttggaatg gttaggagtt atttggtccg gcggagggac agcttacaat 180
accgcactga tttcaagatt cactatctca agggataaca gcaagaacac attgtatctg 240
caaatgaata gcttgagagc cgaggacacc gctgtctatt actgtgctag aaggggtagt 300
tatccctaca actatttcga cgcatggggc tgcggaactc tggtcacagt gtcttccggt 360
ggaggaggga gcggtggagg agggagtggt ggaggagggt ctcaggcagt ggtgacacaa 420
gaacccagtt tgaccgtctc tccaggtggc actgtgacat taacctgtgg gtcaagcact 480
ggtgctgtta cagcaagcaa ctacgcaaat tgggtgcagc agaaacctgg gcagtgtcct 540
cggggcctga ttggcgggca taataacaga cctcctgggg tgccagctcg gttcagcggc 600
agcctgctgg gagggaaggc agctctgacc ctgctgggag cacagcctga ggacgaagca 660
gagtactatt gcgccctgtg gtactctgat cactgggtca tcggtggtgg aaccaagctg 720
actgtcttgg gc 732

<210> SEQ ID NO 2
<211> LENGTH: 244
<212> TYPE: PRT
<213> ORGANISM: Artificial Sequence
<220> FEATURE:
<223> OTHER INFORMATION: Humanized DOTA-binding scFV (hC825)

<400> SEQUENCE: 2

His Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Thr Asp Tyr
20 25 30

Gly Val His Trp Val Arg Gln Ala Pro Gly Lys Gly Leu Glu Trp Leu
35 40 45

Gly Val Ile Trp Ser Gly Gly Gly Thr Ala Tyr Asn Thr Ala Leu Ile
50 55 60

Ser Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Arg Gly Ser Tyr Pro Tyr Asn Tyr Phe Asp Ala Trp Gly Cys Gly
100 105 110

Thr Leu Val Thr Val Ser Ser Gly Gly Gly Gly Ser Gly Gly Gly Gly
115 120 125

Ser Gly Gly Gly Gly Ser Gln Ala Val Val Thr Gln Glu Pro Ser Leu
130 135 140

Thr Val Ser Pro Gly Gly Thr Val Thr Leu Thr Cys Gly Ser Ser Thr
145 150 155 160

Gly Ala Val Thr Ala Ser Asn Tyr Ala Asn Trp Val Gln Gln Lys Pro

```
                165                 170                 175

Gly Gln Cys Pro Arg Gly Leu Ile Gly Gly His Asn Asn Arg Pro Pro
            180                 185                 190

Gly Val Pro Ala Arg Phe Ser Gly Ser Leu Leu Gly Gly Lys Ala Ala
        195                 200                 205

Leu Thr Leu Leu Gly Ala Gln Pro Glu Asp Glu Ala Glu Tyr Tyr Cys
    210                 215                 220

Ala Leu Trp Tyr Ser Asp His Trp Val Ile Gly Gly Gly Thr Lys Leu
225                 230                 235                 240

Thr Val Leu Gly


<210> SEQ ID NO 3
<211> LENGTH: 732
<212> TYPE: DNA
<213> ORGANISM: Artificial Sequence
<220> FEATURE:
<223> OTHER INFORMATION: Humanized DOTA-binding scFV (hC825/G54C)

<400> SEQUENCE: 3

catgttcagt tagtcgagtc cggtggagga ctggtgcaac caggaggttc tctgagattg      60

tcctgtgccg cctctggctt tagtctgaca gattacggag tgcactgggt taggcaggcc     120

cctgggaaag gtttggaatg gttaggagtt atttggtcct gcggagggac agcttacaat     180

accgcactga tttcaagatt cactatctca agggataaca gcaagaacac attgtatctg     240

caaatgaata gcttgagagc cgaggacacc gctgtctatt actgtgctag aaggggtagt     300

tatccctaca actatttcga cgcatggggc tgcggaactc tggtcacagt gtcttccggt     360

ggaggaggga gcggtggagg agggagtggt ggaggagggt ctcaggcagt ggtgacacaa     420

gaacccagtt tgaccgtctc tccaggtggc actgtgacat taacctgtgg gtcaagcact     480

ggtgctgtta cagcaagcaa ctacgcaaat tgggtgcagc agaaacctgg gcagtgtcct     540

cggggcctga ttggcgggca taataacaga cctcctgggg tgccagctcg gttcagcggc     600

agcctgctgg gagggaaggc agctctgacc ctgctgggag cacagcctga ggacgaagca     660

gagtactatt gcgccctgtg gtactctgat cactgggtca tcggtggtgg aaccaagctg     720

actgtcttgg gc                                                         732


<210> SEQ ID NO 4
<211> LENGTH: 244
<212> TYPE: PRT
<213> ORGANISM: Artificial Sequence
<220> FEATURE:
<223> OTHER INFORMATION: Humanized DOTA-binding scFV (hC825/G54C)

<400> SEQUENCE: 4

His Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asp Tyr
            20                  25                  30

Gly Val His Trp Val Arg Gln Ala Pro Gly Lys Gly Leu Glu Trp Leu
        35                  40                  45

Gly Val Ile Trp Ser Cys Gly Gly Thr Ala Tyr Asn Thr Ala Leu Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

-continued

```
Arg Arg Gly Ser Tyr Pro Tyr Asn Tyr Phe Asp Ala Trp Gly Cys Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Ala Val Val Thr Gln Glu Pro Ser Leu
    130                 135                 140

Thr Val Ser Pro Gly Gly Thr Val Thr Leu Thr Cys Gly Ser Ser Thr
145                 150                 155                 160

Gly Ala Val Thr Ala Ser Asn Tyr Ala Asn Trp Val Gln Gln Lys Pro
                165                 170                 175

Gly Gln Cys Pro Arg Gly Leu Ile Gly Gly His Asn Asn Arg Pro Pro
            180                 185                 190

Gly Val Pro Ala Arg Phe Ser Gly Ser Leu Leu Gly Gly Lys Ala Ala
        195                 200                 205

Leu Thr Leu Leu Gly Ala Gln Pro Glu Asp Glu Ala Glu Tyr Tyr Cys
    210                 215                 220

Ala Leu Trp Tyr Ser Asp His Trp Val Ile Gly Gly Gly Thr Lys Leu
225                 230                 235                 240

Thr Val Leu Gly


<210> SEQ ID NO 5
<211> LENGTH: 1491
<212> TYPE: DNA
<213> ORGANISM: Artificial Sequence
<220> FEATURE:
<223> OTHER INFORMATION: DOTA CAR hC825-28z

<400> SEQUENCE: 5

atggccttac cagtgaccgc cttgctcctg ccgctggcct tgctgctcca cgccgccagg     60

ccgggatccc atgttcagtt agtcgagtcc ggtggaggac tggtgcaacc aggaggttct    120

ctgagattgt cctgtgccgc ctctggcttt agtctgacag attacggagt gcactgggtt    180

aggcaggccc ctgggaaagg tttggaatgg ttaggagtta tttggtccgg cggagggaca    240

gcttacaata ccgcactgat ttcaagattc actatctcaa gggataacag caagaacaca    300

ttgtatctgc aaatgaatag cttgagagcc gaggacaccg ctgtctatta ctgtgctaga    360

aggggtagtt atccctacaa ctatttcgac gcatggggct gcggaactct ggtcacagtg    420

tcttccggtg gaggagggag cggtggagga gggagtggtg gaggagggtc tcaggcagtg    480

gtgacacaag aacccagttt gaccgtctct ccaggtggca ctgtgacatt aacctgtggg    540

tcaagcactg gtgctgttac agcaagcaac tacgcaaatt gggtgcagca gaaacctggg    600

cagtgtcctc ggggcctgat tggcgggcat aataacagac ctcctggggt gccagctcgg    660

ttcagcggca gcctgctggg agggaaggca gctctgaccc tgctgggagc acagcctgag    720

gacgaagcag agtactattg cgccctgtgg tactctgatc actgggtcat cggtggtgga    780

accaagctga ctgtcttggg cgctagcacc acgacgccag cgccgcgacc accaacaccg    840

gcgcccacca tcgcgtcgca gcccctgtcc ctgcgcccag aggcgtgccg gccagcggcg    900

gggggcgcag tgcacacgag ggggctggac ttcgcctgtg atttttgggt gctggtggtg    960

gttggtggag tcctggcttg ctatagcttg ctagtaacag tggcctttat tattttctgg   1020

gtgaggagta agaggagcag gctcctgcac agtgactaca tgaacatgac tccccgccgc   1080

cccgggccca cccgcaagca ttaccagccc tatgccccac cacgcgactt cgcagcctat   1140

cgctccatcg atagagtgaa gttcagcagg agcgcagacg cccccgcgta ccagcagggc   1200
```

cagaaccagc tctataacga gctcaatcta ggacgaagag aggagtacga tgttttggac 1260
aagagacgtg gccgggaccc tgagatgggg ggaaagccga gaaggaagaa ccctcaggaa 1320
ggcctgtaca atgaactgca gaaagataag atggcggagg cctacagtga gattgggatg 1380
aaaggcgagc gccggagggg caaggggcac gatggccttt accagggtct cagtacagcc 1440
accaaggaca cctacgacgc ccttcacatg caggccctgc cccctcgcta a 1491

<210> SEQ ID NO 6
<211> LENGTH: 496
<212> TYPE: PRT
<213> ORGANISM: Artificial Sequence
<220> FEATURE:
<223> OTHER INFORMATION: DOTA CAR hC825-28z

<400> SEQUENCE: 6

Met Ala Leu Pro Val Thr Ala Leu Leu Leu Pro Leu Ala Leu Leu Leu
1 5 10 15

His Ala Ala Arg Pro Gly Ser His Val Gln Leu Val Glu Ser Gly Gly
20 25 30

Gly Leu Val Gln Pro Gly Gly Ser Leu Arg Leu Ser Cys Ala Ala Ser
35 40 45

Gly Phe Ser Leu Thr Asp Tyr Gly Val His Trp Val Arg Gln Ala Pro
50 55 60

Gly Lys Gly Leu Glu Trp Leu Gly Val Ile Trp Ser Gly Gly Gly Thr
65 70 75 80

Ala Tyr Asn Thr Ala Leu Ile Ser Arg Phe Thr Ile Ser Arg Asp Asn
85 90 95

Ser Lys Asn Thr Leu Tyr Leu Gln Met Asn Ser Leu Arg Ala Glu Asp
100 105 110

Thr Ala Val Tyr Tyr Cys Ala Arg Arg Gly Ser Tyr Pro Tyr Asn Tyr
115 120 125

Phe Asp Ala Trp Gly Cys Gly Thr Leu Val Thr Val Ser Ser Gly Gly
130 135 140

Gly Gly Ser Gly Gly Gly Gly Ser Gly Gly Gly Gly Ser Gln Ala Val
145 150 155 160

Val Thr Gln Glu Pro Ser Leu Thr Val Ser Pro Gly Gly Thr Val Thr
165 170 175

Leu Thr Cys Gly Ser Ser Thr Gly Ala Val Thr Ala Ser Asn Tyr Ala
180 185 190

Asn Trp Val Gln Gln Lys Pro Gly Gln Cys Pro Arg Gly Leu Ile Gly
195 200 205

Gly His Asn Asn Arg Pro Pro Gly Val Pro Ala Arg Phe Ser Gly Ser
210 215 220

Leu Leu Gly Gly Lys Ala Ala Leu Thr Leu Leu Gly Ala Gln Pro Glu
225 230 235 240

Asp Glu Ala Glu Tyr Tyr Cys Ala Leu Trp Tyr Ser Asp His Trp Val
245 250 255

Ile Gly Gly Gly Thr Lys Leu Thr Val Leu Gly Ala Ser Thr Thr Thr
260 265 270

Pro Ala Pro Arg Pro Pro Thr Pro Ala Pro Thr Ile Ala Ser Gln Pro
275 280 285

Leu Ser Leu Arg Pro Glu Ala Cys Arg Pro Ala Ala Gly Gly Ala Val
290 295 300

His Thr Arg Gly Leu Asp Phe Ala Cys Asp Phe Trp Val Leu Val Val

-continued

```
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
            340                 345                 350

Tyr Met Asn Met Thr Pro Arg Arg Pro Gly Pro Thr Arg Lys His Tyr
        355                 360                 365

Gln Pro Tyr Ala Pro Pro Arg Asp Phe Ala Ala Tyr Arg Ser Ile Asp
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495


<210> SEQ ID NO 7
<211> LENGTH: 1479
<212> TYPE: DNA
<213> ORGANISM: Artificial Sequence
<220> FEATURE:
<223> OTHER INFORMATION: DOTA CAR hC825-BBz

<400> SEQUENCE: 7

atggccttac cagtgaccgc cttgctcctg ccgctggcct tgctgctcca cgccgccagg     60

ccgggatccc atgttcagtt agtcgagtcc ggtggaggac tggtgcaacc aggaggttct    120

ctgagattgt cctgtgccgc ctctggcttt agtctgacag attacggagt gcactgggtt    180

aggcaggccc ctgggaaagg tttggaatgg ttaggagtta tttggtccgg cggagggaca    240

gcttacaata ccgcactgat ttcaagattc actatctcaa gggataacag caagaacaca    300

ttgtatctgc aaatgaatag cttgagagcc gaggacaccg ctgtctatta ctgtgctaga    360

aggggtagtt atccctacaa ctatttcgac gcatggggct gcggaactct ggtcacagtg    420

tcttccggtg gaggagggag cggtggagga gggagtggtg gaggagggtc tcaggcagtg    480

gtgacacaag aacccagttt gaccgtctct ccaggtggca ctgtgacatt aacctgtggg    540

tcaagcactg gtgctgttac agcaagcaac tacgcaaatt gggtgcagca gaaacctggg    600

cagtgtcctc ggggcctgat tggcgggcat aataacagac ctcctggggt gccagctcgg    660

ttcagcggca gcctgctggg agggaaggca gctctgaccc tgctgggagc acagcctgag    720

gacgaagcag agtactattg cgccctgtgg tactctgatc actgggtcat cggtggtgga    780

accaagctga ctgtcttggg cgctagcacc acgacgccag cgccgcgacc accaacaccg    840

gcgcccacca tcgcgtcgca gcccctgtcc ctgcgcccag aggcgtgccg gccagcggcg    900

gggggcgcag tgcacacgag ggggctggac ttcgcctgtg atatctacat ctgggcgccc    960

ttggccggga cttgtggggt ccttctcctg tcactggtta tcaccettta ctgcaaacgg   1020
```

-continued ggcagaaaga aactcctgta tatattcaaa caaccattta tgagaccagt acaaactact 1080
caagaggaag atggctgtag ctgccgattt ccagaagaag aagaaggagg atgtgaactg 1140
agagtgaagt tcagcaggag cgcagacgcc cccgcgtaca agcagggcca gaaccagctc 1200
tataacgagc tcaatctagg acgaagagag gagtacgatg ttttggacaa gagacgtggc 1260
cgggaccctg agatgggggg aaagccgaga aggaagaacc ctcaggaagg cctgtacaat 1320
gaactgcaga aagataagat ggcggaggcc tacagtgaga ttgggatgaa aggcgagcgc 1380
cggaggggca aggggcacga tggcctttac cagggtctca gtacagccac caaggacacc 1440
tacgacgccc ttcacatgca ggccctgccc cctcgctaa 1479

<210> SEQ ID NO 8
<211> LENGTH: 492
<212> TYPE: PRT
<213> ORGANISM: Artificial Sequence
<220> FEATURE:
<223> OTHER INFORMATION: DOTA CAR hC825-BBz

<400> SEQUENCE: 8

Met Ala Leu Pro Val Thr Ala Leu Leu Leu Pro Leu Ala Leu Leu Leu
1 5 10 15

His Ala Ala Arg Pro Gly Ser His Val Gln Leu Val Glu Ser Gly Gly
20 25 30

Gly Leu Val Gln Pro Gly Gly Ser Leu Arg Leu Ser Cys Ala Ala Ser
35 40 45

Gly Phe Ser Leu Thr Asp Tyr Gly Val His Trp Val Arg Gln Ala Pro
50 55 60

Gly Lys Gly Leu Glu Trp Leu Gly Val Ile Trp Ser Gly Gly Gly Thr
65 70 75 80

Ala Tyr Asn Thr Ala Leu Ile Ser Arg Phe Thr Ile Ser Arg Asp Asn
85 90 95

Ser Lys Asn Thr Leu Tyr Leu Gln Met Asn Ser Leu Arg Ala Glu Asp
100 105 110

Thr Ala Val Tyr Tyr Cys Ala Arg Arg Gly Ser Tyr Pro Tyr Asn Tyr
115 120 125

Phe Asp Ala Trp Gly Cys Gly Thr Leu Val Thr Val Ser Ser Gly Gly
130 135 140

Gly Gly Ser Gly Gly Gly Gly Ser Gly Gly Gly Gly Ser Gln Ala Val
145 150 155 160

Val Thr Gln Glu Pro Ser Leu Thr Val Ser Pro Gly Gly Thr Val Thr
165 170 175

Leu Thr Cys Gly Ser Ser Thr Gly Ala Val Thr Ala Ser Asn Tyr Ala
180 185 190

Asn Trp Val Gln Gln Lys Pro Gly Gln Cys Pro Arg Gly Leu Ile Gly
195 200 205

Gly His Asn Asn Arg Pro Pro Gly Val Pro Ala Arg Phe Ser Gly Ser
210 215 220

Leu Leu Gly Gly Lys Ala Ala Leu Thr Leu Leu Gly Ala Gln Pro Glu
225 230 235 240

Asp Glu Ala Glu Tyr Tyr Cys Ala Leu Trp Tyr Ser Asp His Trp Val
245 250 255

Ile Gly Gly Gly Thr Lys Leu Thr Val Leu Gly Ala Ser Thr Thr Thr
260 265 270

Pro Ala Pro Arg Pro Pro Thr Pro Ala Pro Thr Ile Ala Ser Gln Pro
275 280 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 9
<211> LENGTH: 1041
<212> TYPE: DNA
<213> ORGANISM: Artificial Sequence
<220> FEATURE:
<223> OTHER INFORMATION: DOTA CAR hC825-dz

<400> SEQUENCE: 9
atggccttac cagtgaccgc cttgctcctg ccgctggcct tgctgctcca cgccgccagg 60
ccgggatccc atgttcagtt agtcgagtcc ggtggaggac tggtgcaacc aggaggttct 120
ctgagattgt cctgtgccgc ctctggcttt agtctgacag attacggagt gcactgggtt 180
aggcaggccc ctgggaaagg tttggaatgg ttaggagtta tttggtccgg cggagggaca 240
gcttacaata ccgcactgat ttcaagattc actatctcaa gggataacag caagaacaca 300
ttgtatctgc aaatgaatag cttgagagcc gaggacaccg ctgtctatta ctgtgctaga 360
aggggtagtt atccctacaa ctatttcgac gcatggggct gcggaactct ggtcacagtg 420
tcttccggtg gaggagggag cggtggagga gggagtggtg gaggagggtc tcaggcagtg 480
gtgacacaag aacccagttt gaccgtctct ccaggtggca ctgtgacatt aacctgtggg 540
tcaagcactg gtgctgttac agcaagcaac tacgcaaatt gggtgcagca gaaacctggg 600
cagtgtcctc ggggcctgat tggcgggcat aataacagac ctcctggggt gccagctcgg 660
ttcagcggca gcctgctggg agggaaggca gctctgaccc tgctgggagc acagcctgag 720
gacgaagcag agtactattg cgccctgtgg tactctgatc actgggtcat cggtggtgga 780
accaagctga ctgtcttggg cgctagcacc acgacgccag cgccgcgacc accaacaccg 840
gcgcccacca tcgcgtcgca gcccctgtcc ctgcgcccag aggcgtgccg gccagcggcg 900

-continued

```
gggggcgcag tgcacacgag ggggctggac ttcgcctgtg atttttgggt gctggtggtg    960

gttggtggag tcctggcttg ctatagcttg ctagtaacag tggcctttat tattttctgg   1020

gtgaggagta agaggagcta a                                              1041


<210> SEQ ID NO 10
<211> LENGTH: 346
<212> TYPE: PRT
<213> ORGANISM: Artificial Sequence
<220> FEATURE:
<223> OTHER INFORMATION: DOTA CAR hC825-dz

<400> SEQUENCE: 10

Met Ala Leu Pro Val Thr Ala Leu Leu Leu Pro Leu Ala Leu Leu Leu
1               5                   10                  15

His Ala Ala Arg Pro Gly Ser His Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Ser Leu Thr Asp Tyr Gly Val His Trp Val Arg Gln Ala Pro
    50                  55                  60

Gly Lys Gly Leu Glu Trp Leu Gly Val Ile Trp Ser Gly Gly Gly Thr
65                  70                  75                  80

Ala Tyr Asn Thr Ala Leu Ile Ser Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Arg Gly Ser Tyr Pro Tyr Asn Tyr
        115                 120                 125

Phe Asp Ala Trp Gly Cys Gly Thr Leu Val Thr Val Ser Ser Gly Gly
    130                 135                 140

Gly Gly Ser Gly Gly Gly Gly Ser Gly Gly Gly Gly Ser Gln Ala Val
145                 150                 155                 160

Val Thr Gln Glu Pro Ser Leu Thr Val Ser Pro Gly Gly Thr Val Thr
                165                 170                 175

Leu Thr Cys Gly Ser Ser Thr Gly Ala Val Thr Ala Ser Asn Tyr Ala
            180                 185                 190

Asn Trp Val Gln Gln Lys Pro Gly Gln Cys Pro Arg Gly Leu Ile Gly
        195                 200                 205

Gly His Asn Asn Arg Pro Pro Gly Val Pro Ala Arg Phe Ser Gly Ser
    210                 215                 220

Leu Leu Gly Gly Lys Ala Ala Leu Thr Leu Leu Gly Ala Gln Pro Glu
225                 230                 235                 240

Asp Glu Ala Glu Tyr Tyr Cys Ala Leu Trp Tyr Ser Asp His Trp Val
                245                 250                 255

Ile Gly Gly Gly Thr Lys Leu Thr Val Leu Gly Ala Ser Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Phe Trp Val Leu Val Val
305                 310                 315                 320

Val Gly Gly Val Leu Ala Cys Tyr Ser Leu Leu Val Thr Val Ala Phe
                325                 330                 335
```

Ile Ile Phe Trp Val Arg Ser Lys Arg Ser
340 345

<210> SEQ ID NO 11
<211> LENGTH: 1491
<212> TYPE: DNA
<213> ORGANISM: Artificial Sequence
<220> FEATURE:
<223> OTHER INFORMATION: Covalent (G54C) DOTA CAR hC825G54C-28z

<400> SEQUENCE: 11
atggccttac cagtgaccgc cttgctcctg ccgctggcct tgctgctcca cgccgccagg 60
ccgggatccc atgttcagtt agtcgagtcc ggtggaggac tggtgcaacc aggaggttct 120
ctgagattgt cctgtgccgc ctctggcttt agtctgacag attacggagt gcactgggtt 180
aggcaggccc ctgggaaagg tttggaatgg ttaggagtta tttggtcctg cggagggaca 240
gcttacaata ccgcactgat ttcaagattc actatctcaa gggataacag caagaacaca 300
ttgtatctgc aaatgaatag cttgagagcc gaggacaccg ctgtctatta ctgtgctaga 360
aggggtagtt atccctacaa ctatttcgac gcatggggct gcggaactct ggtcacagtg 420
tcttccggtg gaggagggag cggtggagga gggagtggtg gaggagggtc tcaggcagtg 480
gtgacacaag aacccagttt gaccgtctct ccaggtggca ctgtgacatt aacctgtggg 540
tcaagcactg gtgctgttac agcaagcaac tacgcaaatt gggtgcagca gaaacctggg 600
cagtgtcctc ggggcctgat tggcgggcat aataacagac ctcctggggt gccagctcgg 660
ttcagcggca gcctgctggg agggaaggca gctctgaccc tgctgggagc acagcctgag 720
gacgaagcag agtactattg cgccctgtgg tactctgatc actgggtcat cggtggtgga 780
accaagctga ctgtcttggg cgctagcacc acgacgccag cgccgcgacc accaacaccg 840
gcgcccacca tcgcgtcgca gcccctgtcc ctgcgcccag aggcgtgccg gccagcggcg 900
gggggcgcag tgcacacgag ggggctggac ttcgcctgtg atttttgggt gctggtggtg 960
gttggtggag tcctggcttg ctatagcttg ctagtaacag tggcctttat tattttctgg 1020
gtgaggagta agaggagcag gctcctgcac agtgactaca tgaacatgac tccccgccgc 1080
cccgggccca cccgcaagca ttaccagccc tatgccccac cacgcgactt cgcagcctat 1140
cgctccatcg atagagtgaa gttcagcagg agcgcagacg cccccgcgta ccagcagggc 1200
cagaaccagc tctataacga gctcaatcta ggacgaagag aggagtacga tgttttggac 1260
aagagacgtg gccgggaccc tgagatgggg ggaaagccga gaaggaagaa ccctcaggaa 1320
ggcctgtaca atgaactgca gaaagataag atggcggagg cctacagtga gattgggatg 1380
aaaggcgagc gccggagggg caaggggcac gatggccttt accagggtct cagtacagcc 1440
accaaggaca cctacgacgc ccttcacatg caggccctgc cccctcgcta a 1491

<210> SEQ ID NO 12
<211> LENGTH: 496
<212> TYPE: PRT
<213> ORGANISM: Artificial Sequence
<220> FEATURE:
<223> OTHER INFORMATION: Covalent (G54C) DOTA CAR hC825G54C-28z

<400> SEQUENCE: 12

Met Ala Leu Pro Val Thr Ala Leu Leu Leu Pro Leu Ala Leu Leu Leu
1 5 10 15

His Ala Ala Arg Pro Gly Ser His Val Gln Leu Val Glu Ser Gly Gly
20 25 30

-continued

```
Gly Leu Val Gln Pro Gly Gly Ser Leu Arg Leu Ser Cys Ala Ala Ser
        35                  40                  45

Gly Phe Ser Leu Thr Asp Tyr Gly Val His Trp Val Arg Gln Ala Pro
    50                  55                  60

Gly Lys Gly Leu Glu Trp Leu Gly Val Ile Trp Ser Cys Gly Gly Thr
65                  70                  75                  80

Ala Tyr Asn Thr Ala Leu Ile Ser Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Arg Gly Ser Tyr Pro Tyr Asn Tyr
        115                 120                 125

Phe Asp Ala Trp Gly Cys Gly Thr Leu Val Thr Val Ser Ser Gly Gly
    130                 135                 140

Gly Gly Ser Gly Gly Gly Gly Ser Gly Gly Gly Gly Ser Gln Ala Val
145                 150                 155                 160

Val Thr Gln Glu Pro Ser Leu Thr Val Ser Pro Gly Gly Thr Val Thr
                165                 170                 175

Leu Thr Cys Gly Ser Ser Thr Gly Ala Val Thr Ala Ser Asn Tyr Ala
            180                 185                 190

Asn Trp Val Gln Gln Lys Pro Gly Gln Cys Pro Arg Gly Leu Ile Gly
        195                 200                 205

Gly His Asn Asn Arg Pro Pro Gly Val Pro Ala Arg Phe Ser Gly Ser
    210                 215                 220

Leu Leu Gly Gly Lys Ala Ala Leu Thr Leu Leu Gly Ala Gln Pro Glu
225                 230                 235                 240

Asp Glu Ala Glu Tyr Tyr Cys Ala Leu Trp Tyr Ser Asp His Trp Val
                245                 250                 255

Ile Gly Gly Gly Thr Lys Leu Thr Val Leu Gly Ala Ser Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
            340                 345                 350

Tyr Met Asn Met Thr Pro Arg Arg Pro Gly Pro Thr Arg Lys His Tyr
        355                 360                 365

Gln Pro Tyr Ala Pro Pro Arg Asp Phe Ala Ala Tyr Arg Ser Ile Asp
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445
```

-continued

```
Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495


<210> SEQ ID NO 13
<211> LENGTH: 1479
<212> TYPE: DNA
<213> ORGANISM: Artificial Sequence
<220> FEATURE:
<223> OTHER INFORMATION: Covalent (G54C) DOTA CAR hC825G54C-BBz

<400> SEQUENCE: 13

atggccttac cagtgaccgc cttgctcctg ccgctggcct tgctgctcca cgccgccagg      60

ccgggatccc atgttcagtt agtcgagtcc ggtggaggac tggtgcaacc aggaggttct     120

ctgagattgt cctgtgccgc ctctggcttt agtctgacag attacggagt gcactgggtt     180

aggcaggccc ctgggaaagg tttggaatgg ttaggagtta tttggtcctg cggagggaca     240

gcttacaata ccgcactgat ttcaagattc actatctcaa gggataacag caagaacaca     300

ttgtatctgc aaatgaatag cttgagagcc gaggacaccg ctgtctatta ctgtgctaga     360

aggggtagtt atccctacaa ctatttcgac gcatggggct gcggaactct ggtcacagtg     420

tcttccggtg gaggagggag cggtggagga gggagtggtg gaggagggtc tcaggcagtg     480

gtgacacaag aacccagttt gaccgtctct ccaggtggca ctgtgacatt aacctgtggg     540

tcaagcactg gtgctgttac agcaagcaac tacgcaaatt gggtgcagca gaaacctggg     600

cagtgtcctc ggggcctgat tggcgggcat aataacagac ctcctggggt gccagctcgg     660

ttcagcggca gcctgctggg agggaaggca gctctgaccc tgctgggagc acagcctgag     720

gacgaagcag agtactattg cgccctgtgg tactctgatc actgggtcat cggtggtgga     780

accaagctga ctgtcttggg cgctagcacc acgacgccag cgccgcgacc accaacaccg     840

gcgcccacca tcgcgtcgca gcccctgtcc ctgcgcccag aggcgtgccg gccagcggcg     900

gggggcgcag tgcacacgag ggggctggac ttcgcctgtg atatctacat ctgggcgccc     960

ttggccggga cttgtggggt ccttctcctg tcactggtta tcacccttta ctgcaaacgg    1020

ggcagaaaga aactcctgta tatattcaaa caaccattta tgagaccagt acaaactact    1080

caagaggaag atggctgtag ctgccgattt ccagaagaag aagaaggagg atgtgaactg    1140

agagtgaagt tcagcaggag cgcagacgcc cccgcgtaca agcagggcca gaaccagctc    1200

tataacgagc tcaatctagg acgaagagag gagtacgatg ttttggacaa gagacgtggc    1260

cgggaccctg agatgggggg aaagccgaga aggaagaacc ctcaggaagg cctgtacaat    1320

gaactgcaga aagataagat ggcggaggcc tacagtgaga ttgggatgaa aggcgagcgc    1380

cggaggggca aggggcacga tggcctttac cagggtctca gtacagccac caaggacacc    1440

tacgacgccc ttcacatgca ggccctgccc cctcgctaa                           1479


<210> SEQ ID NO 14
<211> LENGTH: 492
<212> TYPE: PRT
<213> ORGANISM: Artificial Sequence
<220> FEATURE:
<223> OTHER INFORMATION: Covalent (G54C) DOTA CAR hC825G54C-BBz

<400> SEQUENCE: 14
```

-continued

```
Met Ala Leu Pro Val Thr Ala Leu Leu Leu Pro Leu Ala Leu Leu Leu
1               5                   10                  15

His Ala Ala Arg Pro Gly Ser His Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Ser Leu Thr Asp Tyr Gly Val His Trp Val Arg Gln Ala Pro
    50                  55                  60

Gly Lys Gly Leu Glu Trp Leu Gly Val Ile Trp Ser Cys Gly Gly Thr
65                  70                  75                  80

Ala Tyr Asn Thr Ala Leu Ile Ser Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Arg Gly Ser Tyr Pro Tyr Asn Tyr
        115                 120                 125

Phe Asp Ala Trp Gly Cys Gly Thr Leu Val Thr Val Ser Ser Gly Gly
    130                 135                 140

Gly Gly Ser Gly Gly Gly Gly Ser Gly Gly Gly Gly Ser Gln Ala Val
145                 150                 155                 160

Val Thr Gln Glu Pro Ser Leu Thr Val Ser Pro Gly Gly Thr Val Thr
                165                 170                 175

Leu Thr Cys Gly Ser Ser Thr Gly Ala Val Thr Ala Ser Asn Tyr Ala
            180                 185                 190

Asn Trp Val Gln Gln Lys Pro Gly Gln Cys Pro Arg Gly Leu Ile Gly
        195                 200                 205

Gly His Asn Asn Arg Pro Pro Gly Val Pro Ala Arg Phe Ser Gly Ser
    210                 215                 220

Leu Leu Gly Gly Lys Ala Ala Leu Thr Leu Leu Gly Ala Gln Pro Glu
225                 230                 235                 240

Asp Glu Ala Glu Tyr Tyr Cys Ala Leu Trp Tyr Ser Asp His Trp Val
                245                 250                 255

Ile Gly Gly Gly Thr Lys Leu Thr Val Leu Gly Ala Ser Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
```

```
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 15
<211> LENGTH: 1041
<212> TYPE: DNA
<213> ORGANISM: Artificial Sequence
<220> FEATURE:
<223> OTHER INFORMATION: Covalent (G54C) DOTA CAR hC825G54C-dz

<400> SEQUENCE: 15

atggccttac cagtgaccgc cttgctcctg ccgctggcct tgctgctcca cgccgccagg     60

ccgggatccc atgttcagtt agtcgagtcc ggtggaggac tggtgcaacc aggaggttct    120

ctgagattgt cctgtgccgc ctctggcttt agtctgacag attacggagt gcactgggtt    180

aggcaggccc ctgggaaagg tttggaatgg ttaggagtta tttggtcctg cggagggaca    240

gcttacaata ccgcactgat ttcaagattc actatctcaa gggataacag caagaacaca    300

ttgtatctgc aaatgaatag cttgagagcc gaggacaccg ctgtctatta ctgtgctaga    360

aggggtagtt atccctacaa ctatttcgac gcatggggct gcggaactct ggtcacagtg    420

tcttccggtg gaggagggag cggtggagga gggagtggtg gaggagggtc tcaggcagtg    480

gtgacacaag aacccagttt gaccgtctct ccaggtggca ctgtgacatt aacctgtggg    540

tcaagcactg gtgctgttac agcaagcaac tacgcaaatt gggtgcagca gaaacctggg    600

cagtgtcctc ggggcctgat tggcgggcat aataacagac ctcctggggt gccagctcgg    660

ttcagcggca gcctgctggg agggaaggca gctctgaccc tgctgggagc acagcctgag    720

gacgaagcag agtactattg cgccctgtgg tactctgatc actgggtcat cggtggtgga    780

accaagctga ctgtcttggg cgctagcacc acgacgccag cgccgcgacc accaacaccg    840

gcgcccacca tcgcgtcgca gcccctgtcc ctgcgcccag aggcgtgccg gccagcggcg    900

gggggcgcag tgcacacgag ggggctggac ttcgcctgtg atttttgggt gctggtggtg    960

gttggtggag tcctggcttg ctatagcttg ctagtaacag tggcctttat tattttctgg   1020

gtgaggagta agaggagcta a                                             1041


<210> SEQ ID NO 16
<211> LENGTH: 346
<212> TYPE: PRT
<213> ORGANISM: Artificial Sequence
<220> FEATURE:
<223> OTHER INFORMATION: Covalent (G54C) DOTA CAR hC825G54C-dz

<400> SEQUENCE: 16

Met Ala Leu Pro Val Thr Ala Leu Leu Leu Pro Leu Ala Leu Leu Leu
1               5                   10                  15

His Ala Ala Arg Pro Gly Ser His Val Gln Leu Val Glu Ser Gly Gly
            20                  25                  30

Gly Leu Val Gln Pro Gly Gly Ser Leu Arg Leu Ser Cys Ala Ala Ser
        35                  40                  45
```

-continued

```
Gly Phe Ser Leu Thr Asp Tyr Gly Val His Trp Val Arg Gln Ala Pro
    50                  55                  60

Gly Lys Gly Leu Glu Trp Leu Gly Val Ile Trp Ser Cys Gly Gly Thr
65                  70                  75                  80

Ala Tyr Asn Thr Ala Leu Ile Ser Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Arg Gly Ser Tyr Pro Tyr Asn Tyr
        115                 120                 125

Phe Asp Ala Trp Gly Cys Gly Thr Leu Val Thr Val Ser Ser Gly Gly
    130                 135                 140

Gly Gly Ser Gly Gly Gly Gly Ser Gly Gly Gly Gly Ser Gln Ala Val
145                 150                 155                 160

Val Thr Gln Glu Pro Ser Leu Thr Val Ser Pro Gly Gly Thr Val Thr
                165                 170                 175

Leu Thr Cys Gly Ser Ser Thr Gly Ala Val Thr Ala Ser Asn Tyr Ala
            180                 185                 190

Asn Trp Val Gln Gln Lys Pro Gly Gln Cys Pro Arg Gly Leu Ile Gly
        195                 200                 205

Gly His Asn Asn Arg Pro Pro Gly Val Pro Ala Arg Phe Ser Gly Ser
    210                 215                 220

Leu Leu Gly Gly Lys Ala Ala Leu Thr Leu Leu Gly Ala Gln Pro Glu
225                 230                 235                 240

Asp Glu Ala Glu Tyr Tyr Cys Ala Leu Trp Tyr Ser Asp His Trp Val
                245                 250                 255

Ile Gly Gly Gly Thr Lys Leu Thr Val Leu Gly Ala Ser Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser
            340                 345
```

<210> SEQ ID NO 17
<211> LENGTH: 45
<212> TYPE: PRT
<213> ORGANISM: Artificial Sequence
<220> FEATURE:
<223> OTHER INFORMATION: CD8a hinge

<400> SEQUENCE: 17

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 18
<211> LENGTH: 135

<212> TYPE: DNA
<213> ORGANISM: Artificial Sequence
<220> FEATURE:
<223> OTHER INFORMATION: CD8a hinge

<400> SEQUENCE: 18
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgat 135

<210> SEQ ID NO 19
<211> LENGTH: 24
<212> TYPE: PRT
<213> ORGANISM: Artificial Sequence
<220> FEATURE:
<223> OTHER INFORMATION: CD8a transmembrane domain

<400> SEQUENCE: 19

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 20
<211> LENGTH: 72
<212> TYPE: DNA
<213> ORGANISM: Artificial Sequence
<220> FEATURE:
<223> OTHER INFORMATION: CD8a transmembrane domain

<400> SEQUENCE: 20
atctacatct gggcgccctt ggccgggact tgtggggtcc ttctcctgtc actggttatc 60
accctttact gc 72

<210> SEQ ID NO 21
<211> LENGTH: 42
<212> TYPE: PRT
<213> ORGANISM: Artificial Sequence
<220> FEATURE:
<223> OTHER INFORMATION: 41BB

<400> SEQUENCE: 21

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 22
<211> LENGTH: 126
<212> TYPE: DNA
<213> ORGANISM: Artificial Sequence
<220> FEATURE:
<223> OTHER INFORMATION: 41BB

<400> SEQUENCE: 22
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

-continued

```
<210> SEQ ID NO 23
<211> LENGTH: 112
<212> TYPE: PRT
<213> ORGANISM: Artificial Sequence
<220> FEATURE:
<223> OTHER INFORMATION: CD3zeta

<400> SEQUENCE: 23

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 24
<211> LENGTH: 336
<212> TYPE: DNA
<213> ORGANISM: Artificial Sequence
<220> FEATURE:
<223> OTHER INFORMATION: CD3zeta

<400> SEQUENCE: 24

agagtgaagt tcagcaggag cgcagacgcc cccgcgtacc agcagggcca gaaccagctc      60

tataacgagc tcaatctagg acgaagagag gagtacgatg ttttggacaa gagacgtggc     120

cgggaccctg agatgggggg aaagccgaga aggaagaacc ctcaggaagg cctgtacaat     180

gaactgcaga aagataagat ggcggaggcc tacagtgaga ttgggatgaa aggcgagcgc     240

cggaggggca aggggcacga tggcctttac cagggtctca gtacagccac caaggacacc     300

tacgacgccc ttcacatgca ggccctgccc cctcgc                               336


<210> SEQ ID NO 25
<211> LENGTH: 112
<212> TYPE: PRT
<213> ORGANISM: Artificial Sequence
<220> FEATURE:
<223> OTHER INFORMATION: CD3zeta Q14K

<400> SEQUENCE: 25

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95
```

```
Thr Lys Asp Thr Tyr Asp Ala Leu His Met Gln Ala Leu Pro Pro Arg
            100                 105                 110


<210> SEQ ID NO 26
<211> LENGTH: 339
<212> TYPE: DNA
<213> ORGANISM: Artificial Sequence
<220> FEATURE:
<223> OTHER INFORMATION: CD3zeta Q14K

<400> SEQUENCE: 26

agagtgaagt tcagcaggag cgcagacgcc cccgcgtaca agcagggcca gaaccagctc      60

tataacgagc tcaatctagg acgaagagag gagtacgatg ttttggacaa gagacgtggc     120

cgggaccctg agatgggggg aaagccgaga aggaagaacc ctcaggaagg cctgtacaat     180

gaactgcaga aagataagat ggcggaggcc tacagtgaga ttgggatgaa aggcgagcgc     240

cggaggggca aggggcacga tggcctttac cagggtctca gtacagccac caaggacacc     300

tacgacgccc ttcacatgca ggccctgccc cctcgctaa                            339


<210> SEQ ID NO 27
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 27

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 28
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 28

ttttgggtgc tggtggtggt tggtggagtc ctggcttgct atagcttgct agtaacagtg      60

gcctttatta ttttctgggt g                                                81


<210> SEQ ID NO 29
<211> LENGTH: 41
<212> TYPE: PRT
<213> ORGANISM: Artificial Sequence
<220> FEATURE:
<223> OTHER INFORMATION: CD28 intracellular domain

<400> SEQUENCE: 29

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 30
<211> LENGTH: 123
<212> TYPE: DNA
```

<213> ORGANISM: Artificial Sequence
<220> FEATURE:
<223> OTHER INFORMATION: CD28 intracellular domain

<400> SEQUENCE: 30
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 31
<211> LENGTH: 14
<212> TYPE: PRT
<213> ORGANISM: Artificial Sequence
<220> FEATURE:
<223> OTHER INFORMATION: LC CDR1

<400> SEQUENCE: 31

Gly Ser Ser Thr Gly Ala Val Thr Ala Ser Asn Tyr Ala Asn
1 5 10

<210> SEQ ID NO 32
<211> LENGTH: 7
<212> TYPE: PRT
<213> ORGANISM: Artificial Sequence
<220> FEATURE:
<223> OTHER INFORMATION: LC CDR2

<400> SEQUENCE: 32

Gly His Asn Asn Arg Pro Pro
1 5

<210> SEQ ID NO 33
<211> LENGTH: 9
<212> TYPE: PRT
<213> ORGANISM: Artificial Sequence
<220> FEATURE:
<223> OTHER INFORMATION: LC CDR3

<400> SEQUENCE: 33

Ala Leu Trp Tyr Ser Asp His Trp Val
1 5

<210> SEQ ID NO 34
<211> LENGTH: 10
<212> TYPE: PRT
<213> ORGANISM: Artificial Sequence
<220> FEATURE:
<223> OTHER INFORMATION: HC CDR1

<400> SEQUENCE: 34

Gly Phe Ser Leu Thr Asp Tyr Gly Val His
1 5 10

<210> SEQ ID NO 35
<211> LENGTH: 16
<212> TYPE: PRT
<213> ORGANISM: Artificial Sequence
<220> FEATURE:
<223> OTHER INFORMATION: HC CDR2 (hC825G54C)

<400> SEQUENCE: 35

Val Ile Trp Ser Cys Gly Gly Thr Ala Tyr Asn Thr Ala Leu Ile Ser
1 5 10 15

<210> SEQ ID NO 36

<211> LENGTH: 16
<212> TYPE: PRT
<213> ORGANISM: Artificial Sequence
<220> FEATURE:
<223> OTHER INFORMATION: HC CDR2

<400> SEQUENCE: 36

Val Ile Trp Ser Gly Gly Gly Thr Ala Tyr Asn Thr Ala Leu Ile Ser
1 5 10 15

<210> SEQ ID NO 37
<211> LENGTH: 11
<212> TYPE: PRT
<213> ORGANISM: Artificial Sequence
<220> FEATURE:
<223> OTHER INFORMATION: HC CDR3

<400> SEQUENCE: 37

Arg Gly Ser Tyr Pro Tyr Asn Tyr Phe Asp Ala
1 5 10

<210> SEQ ID NO 38
<211> LENGTH: 9218
<212> TYPE: DNA
<213> ORGANISM: Artificial Sequence
<220> FEATURE:
<223> OTHER INFORMATION: pELNS-hC825-28Z

<400> SEQUENCE: 38
gagtgggtta catcgaactg gatctcaaca gcggtaagat ccttgagagt tttcgccccg 60
aagaacgttt tccaatgatg agcactttta aagttctgct atgtggcgcg gtattatccc 120
gtattgacgc cgggcaagag caactcggtc gccgcataca ctattctcag aatgacttgg 180
ttgagtactc accagtcaca gaaaagcatc ttacggatgg catgacagta agagaattat 240
gcagtgctgc cataaccatg agtgataaca ctgcggccaa cttacttctg acaacgatcg 300
gaggaccgaa ggagctaacc gcttttttgc acaacatggg ggatcatgta actcgccttg 360
atcgttggga accggagctg aatgaagcca taccaaacga cgagcgtgac accacgatgc 420
ctgtagcaat ggcaacaacg ttgcgcaaac tattaactgg cgaactactt actctagctt 480
cccggcaaca attaatagac tggatggagg cggataaagt tgcaggacca cttctgcgct 540
cggcccttcc ggctggctgg tttattgctg ataaatctgg agccggtgag cgtgggtctc 600
gcggtatcat tgcagcactg gggccagatg gtaagccctc ccgtatcgta gttatctaca 660
cgacggggag tcaggcaact atggatgaac gaaatagaca gatcgctgag ataggtgcct 720
cactgattaa gcattggtaa ctgtcagacc aagtttactc atatatactt tagattgatt 780
taaaacttca tttttaattt aaaaggatct aggtgaagat cctttttgat aatctcatga 840
ccaaaatccc ttaacgtgag ttttcgttcc actgagcgtc agaccccgta gaaaagatca 900
aaggatcttc ttgagatcct ttttttctgc gcgtaatctg ctgcttgcaa acaaaaaaac 960
caccgctacc agcggtggtt tgtttgccgg atcaagagct accaactctt tttccgaagg 1020
taactggctt cagcagagcg cagataccaa atactgtcct tctagtgtag ccgtagttag 1080
gccaccactt caagaactct gtagcaccgc ctacatacct cgctctgcta atcctgttac 1140
cagtggctgc tgccagtggc gataagtcgt gtcttaccgg gttggactca agacgatagt 1200
taccggataa ggcgcagcgg tcgggctgaa cggggggttc gtgcacacag cccagcttgg 1260
agcgaacgac ctacaccgaa ctgagatacc tacagcgtga gctatgagaa agcgccacgc 1320
ttcccgaagg gagaaaggcg gacaggtatc cggtaagcgg cagggtcgga acaggagagc 1380

-continued gcacgaggga gcttccaggg ggaaacgcct ggtatcttta tagtcctgtc gggtttcgcc 1440
acctctgact tgagcgtcga tttttgtgat gctcgtcagg ggggcggagc ctatggaaaa 1500
acgccagcaa cgcggccttt ttacggttcc tggccttttg ctggcctttt gctcacatgt 1560
tctttcctgc gttatcccct gattctgtgg ataaccgtat taccgccttt gagtgagctg 1620
ataccgctcg ccgcagccga acgaccgagc gcagcgagtc agtgagcgag gaagcggaag 1680
agcgcccaat acgcaaaccg cctctccccg cgcgttggcc gattcattaa tgcagctggc 1740
acgacaggtt tcccgactgg aaagcgggca gtgagcgcaa cgcaattaat gtgagttagc 1800
tcactcatta ggcaccccag gctttacact ttatgcttcc ggctcgtatg ttgtgtggaa 1860
ttgtgagcgg ataacaattt cacacaggaa acagctatga ccatgattac gccaagcgcg 1920
caattaaccc tcactaaagg gaacaaaagc tggagctgca agcttaatgt agtcttatgc 1980
aatactcttg tagtcttgca acatggtaac gatgagttag caacatgcct tacaaggaga 2040
gaaaaagcac cgtgcatgcc gattggtgga agtaaggtgg tacgatcgtg ccttattagg 2100
aaggcaacag acgggtctga catggattgg acgaaccact gaattgccgc attgcagaga 2160
tattgtattt aagtgcctag ctcgatacaa taaacgggtc tctctggtta gaccagatct 2220
gagcctggga gctctctggc taactaggga acccactgct taagcctcaa taaagcttgc 2280
cttgagtgct tcaagtagtg tgtgcccgtc tgttgtgtga ctctggtaac tagagatccc 2340
tcagaccctt ttagtcagtg tggaaaatct ctagcagtgg cgcccgaaca gggacctgaa 2400
agcgaaaggg aaaccagagc tctctcgacg caggactcgg cttgctgaag cgcgcacggc 2460
aagaggcgag gggcggcgac tggtgagtac gccaaaaatt ttgactagcg gaggctagaa 2520
ggagagagat gggtgcgaga gcgtcagtat taagcggggg agaattagat cgcgatggga 2580
aaaaattcgg ttaaggccag ggggaaagaa aaaatataaa ttaaaacata tagtatgggc 2640
aagcagggag ctagaacgat tcgcagttaa tcctggcctg ttagaaacat cagaaggctg 2700
tagacaaata ctgggacagc tacaaccatc ccttcagaca ggatcagaag aacttagatc 2760
attatataat acagtagcaa ccctctattg tgtgcatcaa aggatagaga taaaagacac 2820
caaggaagct ttagacaaga tagaggaaga gcaaaacaaa agtaagacca ccgcacagca 2880
agcggccgct gatcttcaga cctggaggag gagatatgag ggacaattgg agaagtgaat 2940
tatataaata taaagtagta aaaattgaac cattaggagt agcacccacc aaggcaaaga 3000
gaagagtggt gcagagagaa aaaagagcag tgggaatagg agctttgttc cttgggttct 3060
tgggagcagc aggaagcact atgggcgcag cctcaatgac gctgacggta caggccagac 3120
aattattgtc tggtatagtg cagcagcaga acaatttgct gagggctatt gaggcgcaac 3180
agcatctgtt gcaactcaca gtctggggca tcaagcagct ccaggcaaga atcctggctg 3240
tggaaagata cctaaaggat caacagctcc tggggatttg gggttgctct ggaaaactca 3300
tttgcaccac tgctgtgcct tggaatgcta gttggagtaa taaatctctg gaacagattg 3360
gaatcacacg acctggatgg agtgggacag agaaattaac aattacacaa gcttaataca 3420
ctccttaatt gaagaatcgc aaaaccagca agaaaagaat gaacaagaat tattggaatt 3480
agataaatgg gcaagtttgt ggaattggtt taacataaca aattggctgt ggtatataaa 3540
attattcata atgatagtag gaggcttggt aggtttaaga atagtttttg ctgtactttc 3600
tatagtgaat agagttaggc agggatattc accattatcg tttcagaccc acctcccaac 3660
cccgagggga cccgacaggc ccgaaggaat agaagaagaa ggtggagaga gagacagaga 3720

-continued

```
cagatccatt cgattagtga acggatctcg acggtatcga ttagactgta gcccaggaat   3780
atggcagcta gattgtacac atttagaagg aaaagttatc ttggtagcag ttcatgtagc   3840
cagtggatat atagaagcag aagtaattcc agcagagaca gggcaagaaa cagcatactt   3900
cctcttaaaa ttagcaggaa gatggccagt aaaaacagta catacagaca atggcagcaa   3960
tttcaccagt actacagtta aggccgcctg ttggtgggcg gggatcaagc aggaatttgg   4020
cattccctac aatccccaaa gtcaaggagt aatagaatct atgaataaag aattaaagaa   4080
aattatagga caggtaagag atcaggctga acatcttaag acagcagtac aaatggcagt   4140
attcatccac aattttaaaa gaaaaggggg gattgggggg tacagtgcag gggaaagaat   4200
agtagacata atagcaacag acatacaaac taaagaatta caaaaacaaa ttacaaaaat   4260
tcaaaatttt cgggtttatt acagggacag cagagatcca gtttggctgc atacgcgtcg   4320
tgaggctccg gtgcccgtca gtgggcagag cgcacatcgc ccacagtccc cgagaagttg   4380
gggggagggg tcggcaattg aaccggtgcc tagagaaggt ggcgcggggt aaactgggaa   4440
agtgatgtcg tgtactggct ccgccttttt cccgagggtg ggggagaacc gtatataagt   4500
gcagtagtcg ccgtgaacgt tctttttcgc aacgggtttg ccgccagaac acaggtaagt   4560
gccgtgtgtg gttcccgcgg gcctggcctc tttacgggtt atggcccttg cgtgccttga   4620
attacttcca cctggctgca gtacgtgatt cttgatcccg agcttcgggt tggaagtggg   4680
tgggagagtt cgaggccttg cgcttaagga gccccttcgc ctcgtgcttg agttgaggcc   4740
tggcctgggc gctggggccg ccgcgtgcga atctggtggc accttcgcgc ctgtctcgct   4800
gctttcgata agtctctagc catttaaaat tttgatgac ctgctgcgac gctttttttc   4860
tggcaagata gtcttgtaaa tgcgggccaa gatctgcaca ctggtatttc ggtttttggg   4920
gccgcgggcg gcgacggggc ccgtgcgtcc cagcgcacat gttcggcgag gcggggcctg   4980
cgagcgcggc caccgagaat cggacggggg tagtctcaag ctggccggcc tgctctggtg   5040
cctggcctcg cgccgccgtg tatcgccccg ccctgggcgg caaggctggc ccggtcggca   5100
ccagttgcgt gagcggaaag atggccgctt cccggccctg ctgcagggag ctcaaaatgg   5160
aggacgcggc gctcgggaga gcgggcgggt gagtcaccca cacaaaggaa aagggccttt   5220
ccgtcctcag ccgtcgcttc atgtgactcc acggagtacc gggcgccgtc caggcacctc   5280
gattagttct cgagcttttg gagtacgtcg tctttaggtt ggggggaggg gttttatgcg   5340
atggagtttc cccacactga gtgggtggag actgaagtta ggccagcttg gcacttgatg   5400
taattctcct tggaatttgc cctttttgag tttggatctt ggttcattct caagcctcag   5460
acagtggttc aaagtttttt tcttccattt caggtgtcgt gagctagacg actagtcgtc   5520
tagctctaga atggccttac cagtgaccgc cttgctcctg ccgctggcct tgctgctcca   5580
cgccgccagg ccgggatccc atgttcagtt agtcgagtcc ggtggaggac tggtgcaacc   5640
aggaggttct ctgagattgt cctgtgccgc ctctggcttt agtctgacag attacggagt   5700
gcactgggtt aggcaggccc ctgggaaagg tttggaatgg ttaggagtta tttggtccgg   5760
cggagggaca gcttacaata ccgcactgat ttcaagattc actatctcaa gggataacag   5820
caagaacaca ttgtatctgc aaatgaatag cttgagagcc gaggacaccg ctgtctatta   5880
ctgtgctaga aggggtagtt atccctacaa ctatttcgac gcatggggct gcggaactct   5940
ggtcacagtg tcttccggtg gaggagggag cggtggagga gggagtggtg gaggagggtc   6000
tcaggcagtg gtgacacaag aacccagttt gaccgtctct ccaggtggca ctgtgacatt   6060
aacctgtggg tcaagcactg gtgctgttac agcaagcaac tacgcaaatt gggtgcagca   6120
```

-continued

```
gaaacctggg cagtgtcctc ggggcctgat tggcgggcat aataacagac ctcctggggt   6180
gccagctcgg ttcagcggca gcctgctggg agggaaggca gctctgaccc tgctgggagc   6240
acagcctgag gacgaagcag agtactattg cgccctgtgg tactctgatc actgggtcat   6300
cggtggtgga accaagctga ctgtcttggg cgctagcacc acgacgccag cgccgcgacc   6360
accaacaccg gcgcccacca tcgcgtcgca gcccctgtcc ctgcgcccag aggcgtgccg   6420
gccagcggcg gggggcgcag tgcacacgag ggggctggac ttcgcctgtg atttttgggt   6480
gctggtggtg gttggtggag tcctggcttg ctatagcttg ctagtaacag tggcctttat   6540
tattttctgg gtgaggagta agaggagcag gctcctgcac agtgactaca tgaacatgac   6600
tccccgccgc cccgggccca cccgcaagca ttaccagccc tatgccccac cacgcgactt   6660
cgcagcctat cgctccatcg atagagtgaa gttcagcagg agcgcagacg cccccgcgta   6720
ccagcagggc cagaaccagc tctataacga gctcaatcta ggacgaagag aggagtacga   6780
tgttttggac aagagacgtg gccgggaccc tgagatgggg ggaaagccga gaaggaagaa   6840
ccctcaggaa ggcctgtaca atgaactgca gaaagataag atggcggagg cctacagtga   6900
gattgggatg aaaggcgagc gccggagggg caaggggcac gatggccttt accagggtct   6960
cagtacagcc accaaggaca cctacgacgc ccttcacatg caggccctgc cccctcgcta   7020
agtcgacaat caacctctgg attacaaaat ttgtgaaaga ttgactggta ttcttaacta   7080
tgttgctcct tttacgctat gtggatacgc tgctttaatg cctttgtatc atgctattgc   7140
ttcccgtatg gctttcattt tctcctcctt gtataaatcc tggttgctgt ctctttatga   7200
ggagttgtgg cccgttgtca ggcaacgtgg cgtggtgtgc actgtgtttg ctgacgcaac   7260
ccccactggt tggggcattg ccaccacctg tcagctcctt tccgggactt tcgctttccc   7320
cctccctatt gccacggcgg aactcatcgc cgcctgcctt gcccgctgct ggacaggggc   7380
tcggctgttg ggcactgaca attccgtggt gttgtcgggg aagctgacgt cctttccatg   7440
gctgctcgcc tgtgttgcca cctggattct gcgcgggacg tccttctgct acgtcccttc   7500
ggccctcaat ccagcggacc ttccttcccg cggcctgctg ccggctctgc ggcctcttcc   7560
gcgtcttcgc cttcgccctc agacgagtcg gatctccctt tgggccgcct ccccgcctgg   7620
aattcgagct cggtaccttt aagaccaatg acttacaagg cagctgtaga tcttagccac   7680
tttttaaaag aaaagggggg actggaaggg ctaattcact cccaacgaag acaagatctg   7740
ctttttgctt gtactgggtc tctctggtta gaccagatct gagcctggga gctctctggc   7800
taactaggga acccactgct taagcctcaa taaagcttgc cttgagtgct tcaagtagtg   7860
tgtgcccgtc tgttgtgtga ctctggtaac tagagatccc tcagaccctt ttagtcagtg   7920
tggaaaatct ctagcagtag tagttcatgt catcttatta ttcagtattt ataacttgca   7980
aagaaatgaa tatcagagag tgagaggaac ttgtttattg cagcttataa tggttacaaa   8040
taaagcaata gcatcacaaa tttcacaaat aaagcatttt tttcactgca ttctagttgt   8100
ggtttgtcca aactcatcaa tgtatcttat catgtctggc tctagctatc ccgcccctaa   8160
ctccgcccag ttccgcccat tctccgcccc atggctgact aatttttttt atttatgcag   8220
aggccgaggc cgcctcggcc tctgagctat tccagaagta gtgaggaggc ttttttggag   8280
gcctagctag gcttttgcgt cgagacgtac ccaattcgcc ctatagtgag tcgtattacg   8340
cgcgctcact ggccgtcgtt ttacaacgtc gtgactggga aaaccctggc gttacccaac   8400
ttaatcgcct tgcagcacat ccccctttcg ccagctggcg taatagcgaa gaggcccgca   8460
```

-continued

```
ccgatcgccc ttcccaacag ttgcgcagcc tgaatggcga atggcgcgac gcgccctgta   8520

gcggcgcatt aagcgcggcg ggtgtggtgg ttacgcgcag cgtgaccgct acacttgcca   8580

gcgccctagc gcccgctcct ttcgctttct tcccttcctt tctcgccacg ttcgccggct   8640

ttccccgtca agctctaaat cgggggctcc ctttagggtt ccgatttagt gctttacggc   8700

acctcgaccc caaaaaactt gattagggtg atggttcacg tagtgggcca tcgccctgat   8760

agacggtttt tcgccctttg acgttggagt ccacgttctt taatagtgga ctcttgttcc   8820

aaactggaac aacactcaac cctatctcgg tctattcttt tgatttataa gggattttgc   8880

cgatttcggc ctattggtta aaaaatgagc tgatttaaca aaaatttaac gcgaatttta   8940

acaaaatatt aacgtttaca atttcccagg tggcactttt cggggaaatg tgcgcggaac   9000

ccctatttgt ttatttttct aaatacattc aaatatgtat ccgctcatga gacaataacc   9060

ctgataaatg cttcaataat attgaaaaag gaagagtatg agtattcaac atttccgtgt   9120

cgcccttatt cccttttttg cggcattttg ccttcctgtt tttgctcacc cagaaacgct   9180

ggtgaaagta aaagatgctg aagatcagtt gggtgcac                           9218


<210> SEQ ID NO 39
<211> LENGTH: 18
<212> TYPE: DNA
<213> ORGANISM: Artificial Sequence
<220> FEATURE:
<223> OTHER INFORMATION: portion of the CD28 intracellular domain

<400> SEQUENCE: 39

aggagtaaga ggagctaa                                                   18


<210> SEQ ID NO 40
<211> LENGTH: 5
<212> TYPE: PRT
<213> ORGANISM: Artificial Sequence
<220> FEATURE:
<223> OTHER INFORMATION: portion of the CD28 intracellular domain

<400> SEQUENCE: 40

Arg Ser Lys Arg Ser
1               5
```

DOTA BINDING CHIMERIC ANTIGEN RECEPTOR FOR CELLULAR THERAPY

CROSS-REFERENCE TO RELATED APPLICATION

The present application is a 35 U.S.C. § 371 national phase application from, and claims priority to, International Application No. PCT/US2020/029576, filed Apr. 23, 2020, and published under PCT Article 21 (2) in English, and is entitled to priority under 35 U.S.C. § 119(e) to U.S. Provisional Patent Application No. 62/837,569 filed Apr. 23, 2019, all of which are incorporated herein by reference in their entireties.

STATEMENT REGARDING FEDERALLY SPONSORED RESEARCH OR DEVELOPMENT

This invention was made with government support under CA168900 awarded by the National Institutes of Health. The government has certain rights in the invention.

BACKGROUND OF THE INVENTION

Adoptive immunotherapy can mediate strong anti-cancer responses in vivo, but it is highly dependent upon the ability to isolate or generate de novo tumor-reactive T cells. One strategy is the chimeric antigen receptor (CAR) approach, which uses genetically programmed, patient-derived lymphocytes transfected with CAR genes to combine the effector functions of T lymphocytes with the ability of antibodies to recognize predefined surface antigens with high specificity in a non-MHC restricted manner and independent of antigen processing. CARs encode an extracellular single chain variable fragment (scFv) antibody domain to bind tumor antigen linked to intracellular TCR and costimulatory signaling domains that mediate robust antigen-driven T cell activation. CAR T cell therapy has striking efficacy in adults and children with treatment refractory CD19+ B cell malignancies and in BCMA+ multiple myeloma.

The promise of CAR T cell therapy for cancer is significant, but several obstacles in the development of CAR T cells, especially for the treatment of solid tumors, are unresolved. One substantial challenge is the difficulty in assessing CAR T cell treatment efficacy, antitumor effects, and therapy-related toxicities, since the fate and localization of the administered cells cannot be assessed directly. As a result, patients are typically evaluated based on indirect measures of response that are acquired months after initiation of treatment, such as changes in tumor size or serum tumor markers. Additionally, many times it is unclear if an adverse event is related to CAR T cell toxicity or other factors. Serial sampling of solid tumors or biopsy of a potential site of toxicity is an option, but it still has the potential for sample bias (both within a lesion and across the entire burden of disease), and it generally carries enough risk that it is not acceptable to patients or their physicians. Thus, in vivo cell-tracking methods are needed to noninvasively monitor the administered cells in target tumors and elsewhere in the body.

A secondary challenge to the achievement of durable complete responses to CAR T cell therapy in solid tumors is based upon the fundamental architecture and activity of the CAR itself. By design, CARs are fixed in their specificity (monospecific). Seldom is a single tumor associated antigen (TAA) expressed ubiquitously across all cancer cells in a patient.

Thus, in principle, the selection of CAR specificity for a patient should be judged individually upon the array of surface antigens that are expressed on the patient's own cancer cells. Further highlighting the need for multiple antigen targeting is the finding that antigen loss has emerged as a major mechanism of tumor escape, even when CAR T cells targeting a single antigen are initially effective. Therefore, the creation of CARs that can adapt and respond to a changing cancer antigen landscape, revealed through companion imaging, has obvious and significant clinical value.

As a further complication to safe and effective CAR T cell therapy in solid tumors, CARs specific for shared TAAs expressed at low levels on healthy tissues can mediate on-target toxicity, which may be fatal. Unfortunately, no methodology exists to adequately screen for risk of toxicity or potential for antitumor response. Even CD19 CAR T cell therapy can provoke an acute cytokine release syndrome (CRS) and long term B cell aplasia, as well as neurotoxicity in some patients.

A need exists for methods that control the level of CAR T cell activity in vivo, and direct T cells specifically to cancer cells. The present invention addresses this need.

SUMMARY OF THE INVENTION

As described herein, the present invention relates to compositions and methods utilizing a DOTA-binding CAR as described elsewhere herein.

The invention provides a modified cell comprising a chimeric immune receptor (CAR), wherein the CAR comprises a DOTA (1,4,7,10-tetraazacyclododecane-1,4,7,10-tetraacetic acid)-binding domain, a transmembrane domain, and an intracellular domain.

In certain embodiments, the DOTA-binding domain of the CAR is selected from the group consisting of an antibody and an scFv. In certain embodiments, the DOTA-binding domain of the CAR is humanized. In certain embodiments, the scFV comprises an amino acid sequence selected from the group consisting of SEQ ID NO: 2 and SEQ ID NO: 4. In certain embodiments, the intracellular domain of the CAR is selected from the group consisting of CD3-zeta, CD27, CD28, CD2, 4-1BB (CD137), OX40 (CD134), CD30, CD40, PD-1, ICOS, lymphocyte function-associated antigen-1 (LFA-1), CD7, LIGHT, NKG2C, B7-H3, a ligand that specifically binds with CD83, a KIR family protein, FcyRIII, FcsRI, a cytoplasmic tail of an Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, CD66d, DAP10, DAP12, CD27, CD5, ICAM-1, Lck, TNFR-I, TNFR-II, Fas, and any combinations thereof.

In certain embodiments, the CAR comprises an amino acid sequence selected from the group consisting of SEQ ID NOs: 6, 8, 10, 12, 14, and 16. In certain embodiments, the CAR is encoded by a nucleic acid sequence selected from the group consisting of SEQ ID NOs: 5, 7, 9, 11, 13, and 15.

In certain embodiments, the cell is selected from the group consisting of a T cell, a macrophage, and an NK cell. In certain embodiments, the cell is an autologous cell.

The invention further provides a Universal Immune Receptor (UnivIR) CAR system comprising a modified T cell comprising a DOTA CAR and a DOTA-conjugated targeting ligand. In certain embodiments, the DOTA CAR comprises a DOTA-binding domain, a transmembrane domain, and an intracellular domain. In certain embodiments, the targeting ligand targets a tumor antigen or a disease-related antigen.

In certain embodiments, the DOTA-binding domain of the CAR is selected from the group consisting of an antibody and an scFv. In certain embodiments, the scFV comprises an amino acid sequence selected from the group consisting of SEQ ID NO: 2 and SEQ ID NO: 4. In certain embodiments, the intracellular domain of the CAR is selected from the group consisting of CD3-zeta, CD27, CD28, CD2, 4-1BB, OX40, CD30, CD40, PD-1, ICOS, lymphocyte function-associated antigen-1 (LFA-1), CD7, LIGHT, NKG2C, B7-H3, a ligand that specifically binds with CD83, a KIR family protein, FcγRIII, FcsRI, a cytoplasmic tail of an Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, CD66d, DAP10, DAP12, CD27, CD5, ICAM-1, Lck, TNFR-I, TNFR-II, Fas, and any combinations thereof.

In certain embodiments, the CAR comprises an amino acid sequence selected from the group consisting of SEQ ID NOs: 6, 8, 10, 12, 14, and 16. In certain embodiments, the CAR is encoded by a nucleic acid sequence selected from the group consisting of SEQ ID NOs: 5, 7, 9, 11, 13, and 15. In certain embodiments, the tumor antigen is selected from the group consisting of Her2/neu, folate receptor alpha (FRa), EGFR, CD20, CD37, CD123, glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, folate receptor beta (FRβ), CD19, TCRVb, TCRBCI, BCMA, Claudin 4, Claudin 6, FSHR, EPCAM, EGFRvIII, GD2, PCSA, CD2, CD5, CD7, CD3, CD4, CD30, and mesothelin.

In certain embodiments, the system comprises more than one targeting ligand and each targeting ligand targets a different tumor antigen or disease-related antigen.

In certain embodiments, the DOTA is covalently conjugated to the targeting ligand. In certain embodiments, the DOTA is covalently conjugated to a chelator capable of chelating a metal.

In certain embodiments, the targeting ligand is selected from the group consisting of an antibody, an scFv, a DARPin, a Fab, and a small molecule. In certain embodiments, the small molecule comprises folic acid. In certain embodiments, the targeting ligand is selected from the group consisting of Trastuzumab, Mov18, Cetuximab, and Rituximab. In certain embodiments, the antibody is labeled with $^{89}$Zr-desferrioxamine chelate (DFO). In certain embodiments, the targeting ligand is labeled with trans-cyclooctene (TCO).

The invention further provides a method for treating a disease or disorder in a subject in need thereof. In certain embodiments, the method comprises administering to the subject any UnivIR CAR system contemplated herein.

In certain embodiments, the disease is cancer. In certain embodiments, the disease is an autoimmune disease. In certain embodiments, distinct antigens are targeted sequentially or simultaneously.

The invention further provides a method for carrying a payload to the tumor microenvironment in a subject in need thereof. In certain embodiments, the method comprises administering to the subject any UnivIR CAR system contemplated herein.

In certain embodiments, the method further comprises administering to the subject a second CAR comprising an antigen binding domain, a transmembrane domain, and an intracellular domain.

The invention further provides a method of tracking CAR T cells in a subject in vivo. In certain embodiments, the method comprises administering to the subject a composition comprising a population of DOTA CAR T cells and a population of DOTA-conjugated targeting ligands. In certain embodiments, each DOTA CAR comprises a DOTA-binding domain. In certain embodiments, each DOTA CAR comprises a transmembrane domain. In certain embodiments, each DOTA CAR comprises an intracellular domain. In certain embodiments, each targeting ligand comprises a labeled antibody that targets an antigen, wherein the label on the antibody is detectable in vivo. In certain embodiments, the method comprises imaging the cells in the subject.

The invention further provides a method of treating a disease or disorder in a subject in need thereof. In certain embodiments, the method comprises administering to the subject a composition comprising a population of DOTA CAR T cells, a population of DOTA-conjugated targeting ligands, and a population of radiolabeled DOTA-comprising compounds. In certain embodiments, each DOTA CAR comprises a DOTA-binding domain. In certain embodiments, each DOTA CAR comprises a transmembrane domain. In certain embodiments, each DOTA CAR comprises an intracellular domain. In certain embodiments, each targeting ligand comprises a labeled antibody that targets a tumor antigen or disease-related antigen, wherein the label on the antibody is detectable in vivo. In certain embodiments, the method comprises imaging the cells in the subject. In certain embodiments, the method comprises administering a treatment based on the imaging results and/or based on analysis of target antigen expression using tumor or blood biomarkers.

In certain embodiments, the DOTA-binding domain comprises an amino acid sequence selected from the group consisting of SEQ ID NO: 2 and SEQ ID NO: 4. In certain embodiments, the disease is cancer. In certain embodiments, the disease is autoimmunity. In certain embodiments, the antibody is labeled with $^{89}$Zr-desferrioxamine chelate (DFO). In certain embodiments, the antibody is labeled with trans-cyclooctene (TCO). In certain embodiments, the method further comprises administering an $^{18}$F-containing tetrazine or derivative thereof to the subject after the composition is administered to the subject. I In certain embodiments, the administered cells are non-invasively monitored in target tumors and/or elsewhere in the body. In certain embodiments, the imaging comprises positron-emission tomography (PET) and/or computed tomography (CT or CAT) scanning. In certain embodiments, the antigen specificity is determined from a patient's own cells. In certain embodiments, the population of DOTA-conjugated targeting ligands comprises ligands that target different antigens. In certain embodiments, the different antigens are targeted sequentially or simultaneously. In certain embodiments, the composition is administered over a period of time, and the antigen specificity of the targeting ligands are changed based on the imaging results and/or based on analysis of target antigen expression using tumor or blood biomarkers. In certain embodiments, the antigen specificity of the targeting ligands is changed based on on-target toxicity, off-target toxicity, and/or cytokine release syndrome (CRR).

In certain embodiments, the method further comprises controlling the level of CAR T cell activity in vivo based on the imaging results. In certain embodiments, the method further comprises increasing or decreasing the number of DOTA molecules per targeting ligand.

The invention further provides a DOTA-comprising compound comprising DOTA (1,4,7,10-tetraazacyclododecane-1,4,7,10-tetraacetic acid), and/or its complex with a metal ion, conjugated to a linker comprising formula (I):

$$*—X^1—(CH_2)_{m1}—(\text{phenylene})_{0\text{-}1}—X^2—[CH_2—(CH_2)_y—X^3]_{m2}—(CH_2)_{m3}—X^4, \qquad (I)$$

wherein in (I): the bond marked as * indicates the attachment point to the DOTA; m1 is selected from the group consisting of 0, 1, 2, 3, 4, 5, 6, 7, 8, 9, 11, 12, 13, 14, 15, 16, 17, 18, 19, and 20; m2 is selected from the group consisting of 0, 1, 2, 3, 4, 5, 6, 7, 8, 9, 10, 11, 12, 13, 14, 15, 16, 17, 18, 19, and 20; m3 is selected from the group consisting of 0, 1, 2, 3, 4, 5, 6, 7, 8, 9, 10, 11, 12, 13, 14, 15, 16, 17, 18, 19, and 20; $X^1$ is selected from the group consisting of absent (a bond), 0, and N($R^3$); each $X^2$ and $X^3$ is independently selected from the group consisting of absent (a bond), —O—, —C(=O)N$R^3$—, —N($R^3$)C(=O)—, —C(=S)N$R^3$—, —N($R^3$)C(=S)—, —NHC(=S)NH—, —N($R^3$)—, —CH($R^3$)—, —NHC(=O)CH=CH—, —NHC(=O)CH=CH—$CH_2$N(R)—, —NHC(=O)CH=CH—$CH_2$—(N-linked heterocyclylene)-, —NHC(=O)C≡C—, —NHC(=S)CH=CH—, —NHC(=S)CH=CH—$CH_2$N(R)—, —NHC(=S)CH=CH—$CH_2$—(N-linked heterocyclylene)-, —NHC(=S)C≡C—, —NHS(=O)CH=CH—, —NHS(=O)CH=CH—$CH_2$N(R)—, —NHS(=O)CH=CH—$CH_2$—(N-linked heterocyclylene)-, —NHS(=O)C≡C—, —NHS(=O)$_2$CH=CH—, —NHS(=O)$_2$CH=CH—$CH_2$N(R)—, —NHS(=O)$_2$CH=CH—$CH_2$—(N-linked heterocyclylene)-, —NHS(=O)$_2$C≡C—, —C(=O)CH=CH—, —C(=O)CH=CH—$CH_2$N(R)—, —C(=O)CH=CH—$CH_2$—(N-linked heterocyclylene)-, —C(=O)C≡C—, —S(=O)CH=CH—, —S(=O)CH=CH—$CH_2$N(R)—, —S(=O)CH=CH—$CH_2$—(N-linked heterocyclylene)-, —S(=O)C≡C—, —S(=O)$_2$CH=CH—, —S(=O)$_2$CH=CH—$CH_2$N(R)—, —S(=O)$_2$CH=CH—$CH_2$—(N-linked heterocyclylene)-, and —S(=O)$_2$C≡C—; each occurrence of y is independently 0 or 1; $X^4$ is selected from the group consisting of H, halogen, —OH, —$NH_2$, —$R^3$, —C(=O)OH, —C(=O)N($R^3$)($CH_2$)$_{2\text{-}10}$$NH_2$, —NH-folate, —C(=O)N($R^3$)($CH_2$)$_{2\text{-}10}$NH-folate, —NH-phenylene-$CH_2$-DOTA (and/or its complex with a metal ion), —NHC(=S)NH-phenylene-$CH_2$-DOTA (and/or its complex with a metal ion), a carboxylic ester, an alkyne, and maleimido; each $R^3$ is independently selected from the group consisting of H, -folate, —$CH_2CH_2$NH-folate, —C(=O)$CH_2CH_2$NH-folate, —C(=O)NH$CH_2CH_2$NH-folate, -phenylene-$CH_2$-DOTA (and/or its complex with a metal ion), —C(=O)NH-phenylene-$CH_2$-DOTA (and/or its complex with a metal ion), —NHC(=S)NH-phenylene-$CH_2$-DOTA (and/or its complex with a metal ion), —C(=O)CH=$CH_2$, —C(=O)CH=CH—$CH_2NR_2$, —C(=S)CH=$CH_2$, —C(=S)CH=CH—$CH_2NR_2$, —S(=O)CH=$CH_2$, —S(=O)CH=CH—$CH_2NR_2$, —S(=O)$_2$CH=$CH_2$, —S(=O)$_2$CH=CH—$CH_2NR_2$, —C(=O)C≡CR, —S(=O)C≡CR, —S(=O)$_2$C≡CR, optionally substituted $C_1$-$C_6$ alkyl, optionally substituted $C_3$-$C_8$ cycloalkyl, and optionally substituted $C_3$-$C_8$ cycloheteroalkyl; each occurrence of R is independently H, optionally substituted $C_1$-$C_6$ alkyl, optionally substituted $C_3$-$C_8$ cycloalkyl, or optionally substituted $C_3$-$C_8$ cycloheteroalkyl, or two R bound to the same N atom can combine to form an optionally substituted 3-8-membered heterocyclyl; or a salt, metal ion complex, solvate, enantiomer, or diastereoisomer thereof.

In certain embodiments, the metal ion comprises Y, Ca, Lu, Gd, In, Ga, Mg, Ni, Cu, Zn, Tc, or Fe. In certain embodiments, the DOTA is coupled to the linker through an amide or ester linkage. In certain embodiments, the DOTA is coupled to the linker through a carbon-carbon bond. In certain embodiments, each phenylene, if present, is independently selected from the group consisting of 1,2-phenylene, 1,3-phenylene, and 1,4-phenylene. In certain embodiments, at least one of the $X^1$, $X^2$, $X^3$, $X^4$, and $R^3$ groups comprises a reactive group that is capable of forming a covalent bond with a thiol group (thio-reactive group). In certain embodiments, the thio-reactive group is present in the $R^3$ group attached to $X^1$, $X^2$, $X^3$, or $X^4$. In certain embodiments, the thio-reactive group is —C(=O)CH=$CH_2$, —C(=O)CH=CH—$CH_2NR_2$, —S(=O)CH=$CH_2$, —S(=O)CH=CH—$CH_2NR_2$, —S(=O)$_2$CH=$CH_2$, —S(=O)$_2$CH=CH—$CH_2NR_2$, —C(=O)C≡CR, —S(=O)C≡CR, —S(=O)$_2$C≡CR, —NHC(=O)CH=CH—, —NHC(=O)CH=CH—$CH_2$N(R)—, —NHC(=O)CH=CH—$CH_2$—(N-linked heterocyclylene)-, —NHC(=O)C≡C—, —NHC(=S)CH=CH—, —NHC(=S)CH=CH—$CH_2$N(R)—, —NHC(=S)CH=CH—$CH_2$—(N-linked heterocyclylene)-, —NHC(=S)C≡C—, —NHS(=O)CH=CH—, —NHS(=O)CH=CH—$CH_2$N(R)—, —NHS(=O)CH=CH—$CH_2$—(N-linked heterocyclylene)-, —NHS(=O)C≡C—, —NHS(=O)$_2$CH=CH—, —NHS(=O)$_2$CH=CH—$CH_2$N(R)—, —NHS(=O)$_2$CH=CH—$CH_2$—(N-linked heterocyclylene)-, —NHS(=O)$_2$C≡C—, —C(=O)CH=CH—, —C(=O)CH=CH—$CH_2$N(R)—, —C(=O)CH=CH—$CH_2$—(N-linked heterocyclylene)-, —C(=O)C≡C—, —S(=O)CH=CH—, —S(=O)CH=CH—$CH_2$N(R)—, —S(=O)CH=CH—$CH_2$—(N-linked heterocyclylene)-, —S(=O)C≡C—, —S(=O)$_2$CH=CH—, —S(=O)$_2$CH=CH—$CH_2$N(R)—, —S(=O)$_2$CH=CH—$CH_2$—(N-linked heterocyclylene)-, or —S(=O)$_2$C≡C—.

In certain embodiments, at least one of the $R^3$ groups is substituted with $^{18}$F. In certain embodiments, at least one of the $R^3$ groups is substituted with at least one of an azido group, —$CH_2CH_2$NH-folate, —C(=O)$CH_2CH_2$NH-folate, —C(=O)NH$CH_2CH_2$NH-folate, -phenylene-$CH_2$-DOTA (and/or its complex with a metal ion), and —C(=O)NH-phenylene-$CH_2$-DOTA (and/or its complex with a metal ion).

In certain embodiments, the azido group is further reacted with a molecule comprising difluorooctyne (DIFO) or dibenzocyclooctyne (DBCO) group. In certain embodiments, the molecule further comprises desferrioxamine or a trans-cycloctene group. In certain embodiments, the desferrioxamine is further complexed with $^{89}$Zr. In certain embodiments, the trans-cycloctene group is further reacted with a $^{18}$F-comprising tetrazine. In certain embodiments, $X^4$ is —C(═O)OH, an activated carboxylic ester, NH-folate, —NH-phenylene-$CH_2$-DOTA (and/or its complex with a metal ion), or —NHC(═S)NH-phenylene-$CH_2$-DOTA (and/or its complex with a metal ion). In certain embodiments, the activated carboxylic ester is a polyhalophenyl ester, mono- or di-nitrophenyl ester, thioester, N-hydroxysuccinimido ester, or hydroxybenzotriazole ester. In certain embodiments, $X^4$ is an alkyne, which is optionally strained.

In certain embodiments, the compound comprises:

$$[\mathrm{DOTA}—X^1—(CH_2)_{m1}—(\mathrm{phenylene})_{0\text{-}1}—X^2—[CH_2—(CH_2)_y—X^3]_{m2}—(CH_2)_{m3}—X^4—]_{m4}X^5 \quad \text{(II)}$$

wherein: m4 is 2, 3, or 4; $X^5$ is a polyvalent group such that: m4=2 and $X^5$ is A or $A(X^6)(X^6)$, wherein A is $CH_2$, NH, O, S, S(═O), or $S(═O)_2$; m4=3 and $X^5$ is A or $A(X^6)(X^6)(X^6)$, wherein A is CH or N; m4=4 and $X^5$ is A or $A(X^6)(X^6)(X^6)(X^6)$, wherein A is C; each occurrence of $X^6$ is independently a bond, $—(CH_2)_{1\text{-}12}—*$, $—(CH_2)_{0\text{-}11}C(═O)OH$, $—(CH_2)_{1\text{-}11}NH_2$, or $—(CH_2)_{1\text{-}12}OH$, wherein the bond marked as * indicates the attachment point to the $X^4$ and wherein the functional group marked in bold is chemically conjugated to the $X^4$.

In certain embodiments, the compound is at least one of

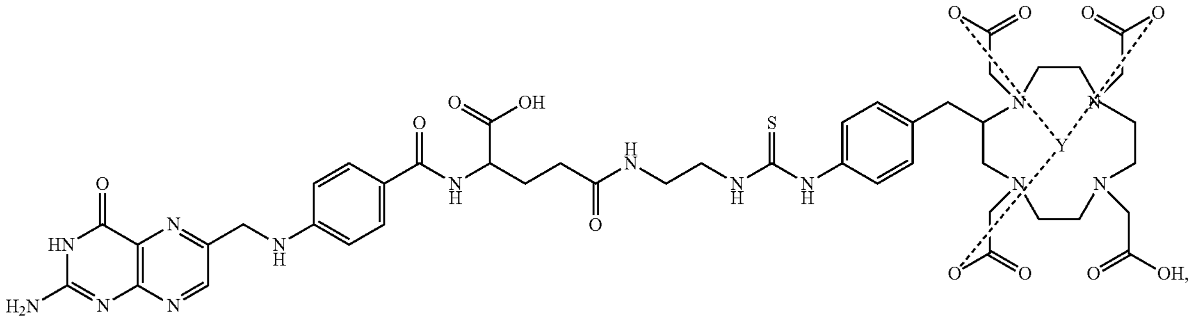

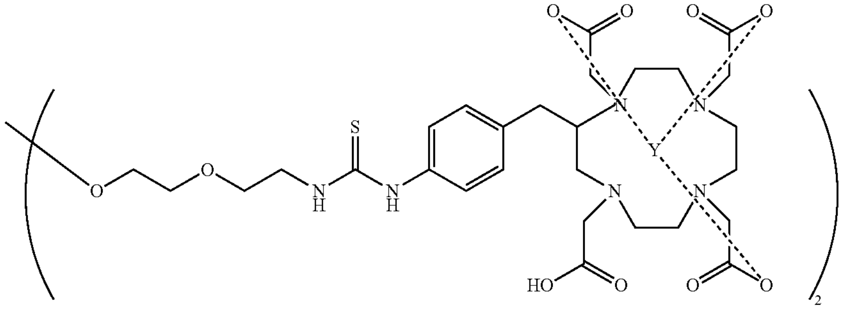

,

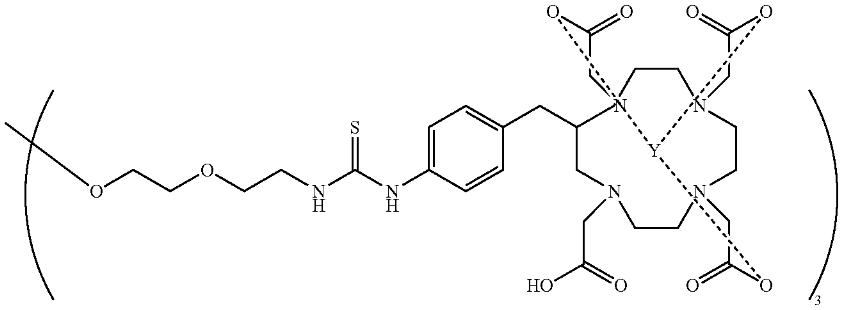

,

-continued

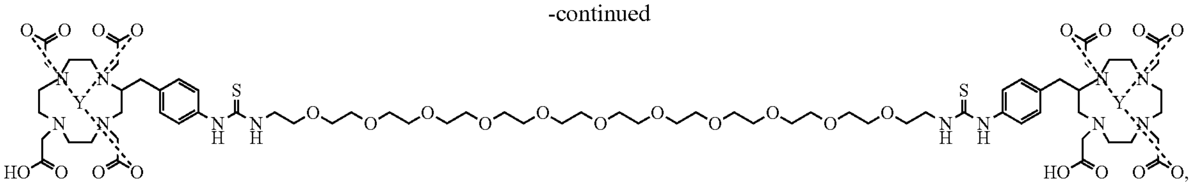

,

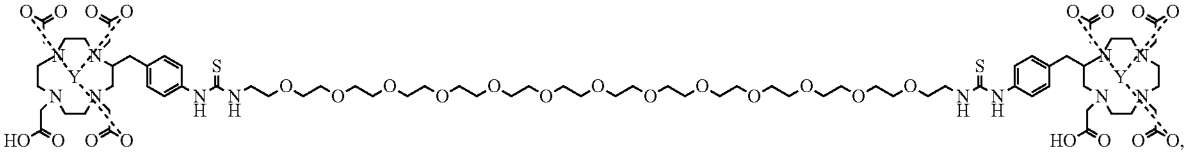

,

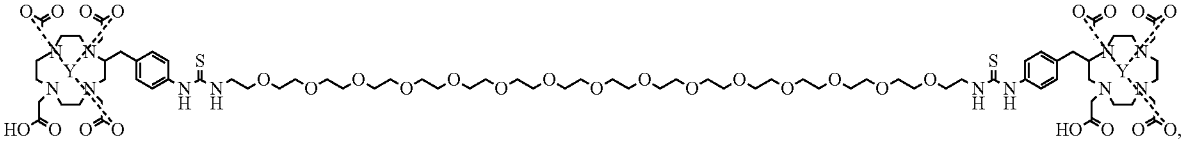

,

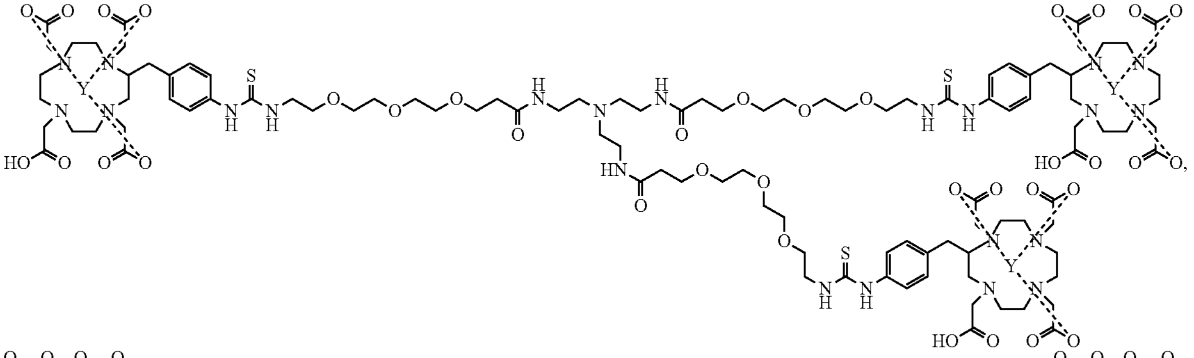

,

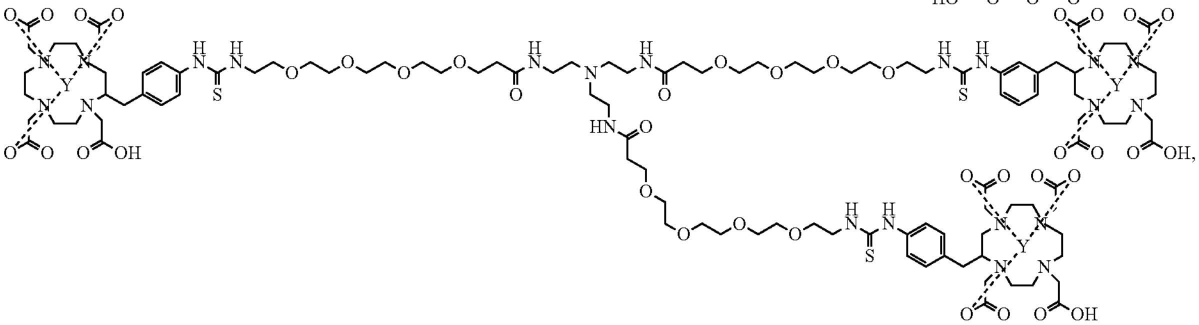

,

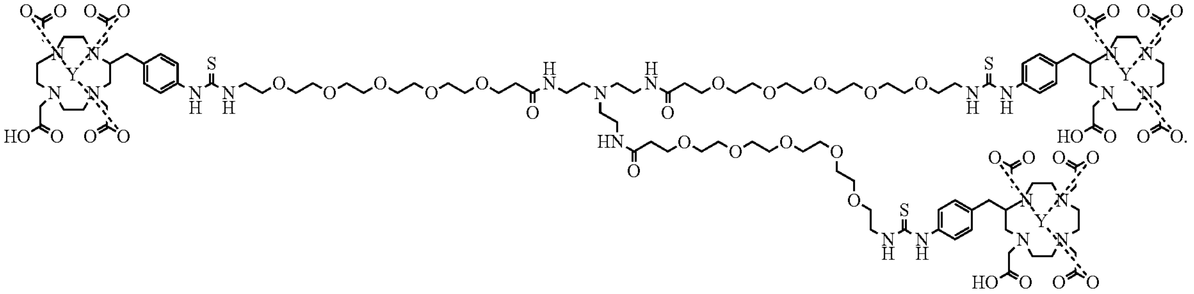

.

The invention further provides an adduct compound of an antibody with any DOTA-comprising compound contemplated herein, wherein a covalent bond is formed between at least one surface group of the antibody and the $X^4$ group of the DOTA-comprising compound.

In certain embodiments, the antibody is selected from the group consisting of Trastuzumab, Mov18, Cetuximab, and Rituximab. In certain embodiments, the DOTA-comprising compound is bound to an anti-metal ion-DOTA scFv. In certain embodiments, the DOTA-comprising compound is further bound to an anti-metal ion-DOTA scFv through a covalent bond formed between a surface accessible cysteine residue in the anti-metal ion-DOTA scFv and at least one $R^3$ group comprising a thio-reactive group.

In certain embodiments, the thio-reactive group is present at least one of the $X^1$, $X^2$, $X^3$, $X^4$, and $R^3$ groups $R^3$ group attached to $X^1$ or $X^2$. In certain embodiments, the thio-reactive group is $—C(═O)CH═CH_2$, $—C(═O)CH═CH—CH_2NR_2$, $—S(═O)CH═CH_2$, $—S(═O)CH═CH—CH_2NR_2$, $—S(═O)_2CH═CH_2$, —S $(=O)_2CH=CH-CH_2NR_2$, $-C(=O)C\equiv CR$, $-S(=O)C\equiv CR$, $-S(=O)_2C\equiv CR$, $-NHC(=O)CH=CH-$, $-NHC(=O)CH=CH-CH_2N(R)-$, $-NHC(=O)CH=CH-CH_2-$(N-linked heterocyclylene)-, $-NHC(=O)C\equiv C-$, $-NHS(=O)CH=CH-$, $-NHS(=O)CH=CH-CH_2N(R)-$, $-NHS(=O)CH=CH-CH_2-$(N-linked heterocyclylene)-, $-NHS(=O)C\equiv C-$, $-NHS(=O)_2CH=CH-$, $-NHS(=O)_2CH=CH-CH_2N(R)-$, $-NHS(=O)_2CH=CH-CH_2-$(N-linked heterocyclylene)-, $-NHS(=O)_2C\equiv C-$, $-C(=O)CH=CH-$, $-C(=O)CH=CH-CH_2N(R)-$, $-C(=O)CH=CH-CH_2-$(N-linked heterocyclylene)-, $-C(=O)C\equiv C-$, $-S(=O)CH=CH-$, $-S(=O)CH=CH-CH_2N(R)-$, $-S(=O)CH=CH-CH_2-$(N-linked heterocyclylene)-, $-S(=O)C\equiv C-$, $-S(=O)_2CH=CH-$, $-S(=O)_2CH=CH-CH_2N(R)-$, $-S(=O)_2CH=CH-CH_2-$(N-linked heterocyclylene)-, or $-S(=O)_2C\equiv C-$.

In certain embodiments, the surface group of the antibody comprises a primary amine, a thiol, or an azide. In certain embodiments, the number of the DOTA-comprising compounds conjugated to the antibody can be varied so as to modulate the biological efficacy of the adduct compound.

The invention further provides a method of tracking CAR T cells in a subject in vivo. In certain embodiments, the method comprises administering to the subject a composition comprising a population of any DOTA CAR T cells contemplated herein and a population of any radiolabeled DOTA-comprising compounds contemplated herein. In certain embodiments, the compounds are labelled with a traceable radiolabel. In certain embodiments, each DOTA CAR comprises a DOTA-binding domain, a transmembrane domain, and an intracellular domain. In certain embodiments, the method further comprises imaging the cells in the subject.

The invention further provides a method of treating a disease or disorder in a subject in need thereof. In certain embodiments, the method comprises administering to the subject a composition comprising a population of any DOTA CAR T cells contemplated herein and a population of any radiolabeled DOTA-comprising compounds contemplated herein. In certain embodiments, the compounds are labelled with a traceable radiolabel. In certain embodiments, each DOTA CAR comprises a DOTA-binding domain, a transmembrane domain, and an intracellular domain. In certain embodiments, the method comprises imaging the cells in the subject. In certain embodiments, the method comprises administering a treatment based on the imaging results and/or based on analysis of target antigen expression using tumor or blood biomarkers.

In certain embodiments, the traceable radiolabel comprises $^{18}F$. In certain embodiments, the DOTA-binding domain comprises an amino acid sequence selected from the group consisting of SEQ ID NO: 2 and SEQ ID NO: 4. In certain embodiments, the disease is cancer. In certain embodiments, the disease is autoimmunity. In certain embodiments, the administered cells are noninvasively monitored in target tumors and/or elsewhere in the body. In certain embodiments, the imaging comprises positron-emission tomography (PET) and/or computed tomography (CT or CAT) scanning. In certain embodiments, the method comprises controlling the level of CAR T cell activity in vivo based on the imaging results. In certain embodiments, the method comprises increasing or decreasing the number of DOTA molecules per targeting ligand.

BRIEF DESCRIPTION OF THE DRAWINGS

The following detailed description of specific embodiments of the invention will be better understood when read in conjunction with the appended drawings. For the purpose of illustrating the invention, exemplary embodiments are shown in the drawings. It should be understood, however, that the invention is not limited to the precise arrangements and instrumentalities of the embodiments shown in the drawings.

FIG. 1A is a schematic comparing and contrasting UnivIR T cells to conventional CAR T cells. FIG. 1B is a schematic of a universal immune receptor comprised of an anti-DOTA scFv linked to classical CAR intracellular signaling domains. T cells are engineered to exert immune responses toward multiple tumor associated antigens (TAAs) with introduction of specific DOTA-labeled targeting ligands.

FIG. 2A is a schematic of the anti-DOTA scFv CAR T cell expression plasmid. FIG. 2B illustrates the various anti-DOTA scFv CAR T cell expression vectors with various combinations of intracellular signaling domains: Delta z (dz): lacks an intracellular signaling domain, Zeta: comprised of a CD3ζ intracellular domain, BBz: comprised of 4-1BB and CD3ζ, 28z: comprised of CD28 and CD3ζ, and 28BBz: comprised of CD28, 4-1BB, and CD3ζ intracellular domains. FIG. 2C shows representative flow cytometry plots from primary human T cells transduced with recombinant CAR lentiviruses. Expression of the DOTA CAR on their cell surface is shown on the y-axis; GFP, a marker of CAR vector transduction efficiency, is shown on the x-axis.

FIG. 3A shows hC8.2.5 DOTA CAR T cells secrete IFNγ in response to immobilized Yttrium-DOTA in a dose dependent manner. DOTA-NHS or Y-DOTA-Sarcosine-Biotin were incubated at various concentrations in a 96-well plate and allowed to passively adhere overnight at 4° C. Plates were washed 2× with PBS and 50,000 immune receptor expressing T cells were added to each well. Plates were incubated at 37° C. and 5% $CO_2$ for 16 hours. Supernatants were harvested and analyzed for IFNγ secretion using a standard IFNγ ELISA kit. Y-DOTA was superior to non-chelated DOTA. FIG. 3B shows MALDI-TOF MS data for Herceptin before and after labeling with DOTA-NHS-ester. The average number of DOTA's per antibody was determined using the difference in mass between labeled and unlabeled antibody; in this example there are ~9.3 DOTAs per antibody.

FIGS. 3C-3D show anti-DOTA immune receptor T cells exhibit cytokine secretion in the presence of immobilized DOTA-Y labeled antibodies. In FIG. 3C, Herceptin, Herceptin-Streptavidin, or Herceptin-Streptavidin+biotin-DOTA-Y were incubated at various concentrations in a 96-well plate and allowed to passively adhere overnight at 4° C. Plates were washed 2× with PBS and 50,000 immune receptor expressing T cells were added to each well. Plates were incubated at 37° C. and 5% $CO_2$ for 16 hours. Supernatants were harvested and analyzed for IFNγ secretion using a standard IFNγ ELISA kit. FIG. 3D was run in a similar manner to FIG. 3C, but used Herceptin directly conjugated to either DOTA or DOTA-Y. FIG. 3E shows addition of DOTA-conjugated targeting ligands leads to dose-dependent lysis of antigen positive cells. FIG. 3F shows a schematic for "on-demand" redirection of DOTA T cells with Y-DOTA-Herceptin and their redirection against HER2+ cancer cells. FIG. 3G depicts HER2+ cancer cell lysis by DOTA CAR T cells upon addition of Y-DOTA-Herceptin (arrow shows time of addition of Y-DOTA-Herceptin). CAR T cell activity is precisely controlled by antibody arming dose. FIG. 3H shows that signaling-deficient DOTA CAR T cells (DOTA-dz) do not kill cancer cells, even when combined with high concentrations of Y-DOTA-Herceptin.

FIG. 4A illustrates the pre-loading protocol. 4D5 is a humanized Herceptin antibody. FIGS. 4B-4C shows representative flow cytometry plots showing loading of Herceptin-DOTA-Y antibody to CAR T cells. Plots are gated on live cells and show GFP expression (x-axis) versus Herceptin-DOTA-Y antibody binding (APC, y-axis). Results show that a dose dependent low level loading of DOTA T cells with herceptin-DOTA-Y is achieved, with full loss of loading by 72 hours.

FIG. 5A is an experimental schematic illustrating anti-DOTA immune receptor T cells lyse multiple tumor cells with introduction of specific DOTA-Y labeled antibodies. Herceptin-DOTA-Y (Her2-specific), Mov18-DOTA-Y (Folate receptor-specific), and Cetuximab-DOTA-Y (EGFR-specific) antibodies are combined with various DOTA CAR T cells and added to SKBR3 (Her2+), T47D (FR+), SKOV3 (Her2+) or MDA468 (EGFR+) cell lines and efficiency of targeted killing determined. FIG. 5B shows targeted cell lysis of either SKBR3 cells by Herceptin-DOTA-Y-CAR T cells (left) or T47D cells by Mov18-DOTA-Y-CAR T cells (right) at 16 hours post-addition of CAR T cells. xCellegence plates were seeded with $1\times10^4$ SKBR3 or $1\times10^4$ T47D cells/well and a baseline reading was allowed to establish overnight, with measurement intervals set at 20 minutes. DOTA CAR T cells were added to wells at a density of $0.5\times10^5$ receptor positive cells/well. Measurements were continued for 4 days. xCellegence software was used to normalize readings and calculate lysis values compared to tumor only control. Lysis (%) of Her2+ SKBR3 cells (left) and of FRα+ T47D cells (right) 16 hours post T cell addition is shown. FIG. 5C shows the dose-dependent lysis of SKOV3 cells by Herceptin-DOTA-Y-CAR T cells. CAR T cells lacking intracellular signaling domains do not elicit target cell lysis. xCellegence plates were seeded with $1\times10^4$ SKOV3 cells/well and a baseline reading was allowed to establish overnight, with measurement intervals set at 20 minutes. DOTA T cells (70% receptor positive) were added to wells at a density of $0.5\times10^5$ cells/well, along with varying amounts of Herceptin-DOTA-Y. Measurements were continued for 4 days. xCellegence software was used to normalize readings and calculate lysis values compared to tumor only control. T cells added at T=0. FIG. 5D shows the dose-dependent lysis of MDA468 cells by Cetuximab-DOTA-Y-CAR T cells. CAR T cells lacking intracellular signaling domains do not elicit target cell lysis. xCellegence plates were seeded with $1\times10^4$ MDA-468 cells/well (EGFR+, $Her2^-$) and a baseline reading was allowed to establish overnight, with measurement intervals set at 20 minutes. DOTA T cells (70% receptor positive) were added to wells at a density of $0.5\times10^5$ cells/well, along with varying amounts of either Cetuximab-DOTA-Y or Herceptin-DOTA-Y (non-targeting control). Measurements were continued for 4 days. xCellegence software was used to normalize readings and calculate lysis values compared to tumor only control. T cells added at T=0. FIG. 5E illustrates the specificity of cell lysis of EGFR+ tumor cells by Cetuximab-DOTA-Y, but not Herceptin-DOTA-Y, CAR T cells. FIG. 5F illustrates a DOTA CAR is capable of lysing CD20+ cells through Rituximab-Bn-DOTA and Rituximab-Bn-DOTA-Y. SKOV3 cells serve as an antigen negative control.

FIG. 6A shows the chemical structure of DOTA-NHS-ester (left) or P-SCN-Bn-DOTA chelators (right), in which the linker arises from one of the carboxylic acids (DOTA) or the cyclen ring (Bn-DOTA), respectively. FIG. 6B shows target-cell lysis in response to CAR T cells combined with Herceptin-DOTA or Herceptin-Bn-DOTA antibodies±yttrium (Y). Herceptin-DOTA-CAR T cells bound to chelating metal ions have a higher affinity for the CAR receptor and elicit greater target cell killing at lower doses, and the Bn-DOTA derivative has markedly increased affinity relative to the DOTA derivative. FIG. 6C shows dose-dependent lysis of antigen positive cells is observed with various chelated metal ions.

FIG. 11A shows images of NSG mice with injected I.P. with $1\times10^6$ SKOV3 tumor cells on day 0. Herceptin-DOTA-Y was injected I.P. on day 6, with subsequent dosing every 6 days. DOTA-CAR T cells were injected on day 7 I.P. FIGS. 11B-11C illustrate the average tumor cell radiance following administration of DOTA-CAR T cells. Both a high and medium dose of CAR T cells are able to control tumor cell growth. CAR T cells lacking an intracellular signaling domain (Dz) fail to control tumor growth. FIG. 11D displays survival curves for mice treated with various DOTA CAR T cells. FIG. 11E shows T cell counts and % CD8+ cells.

DETAILED DESCRIPTION

Definitions

Figure 1A:
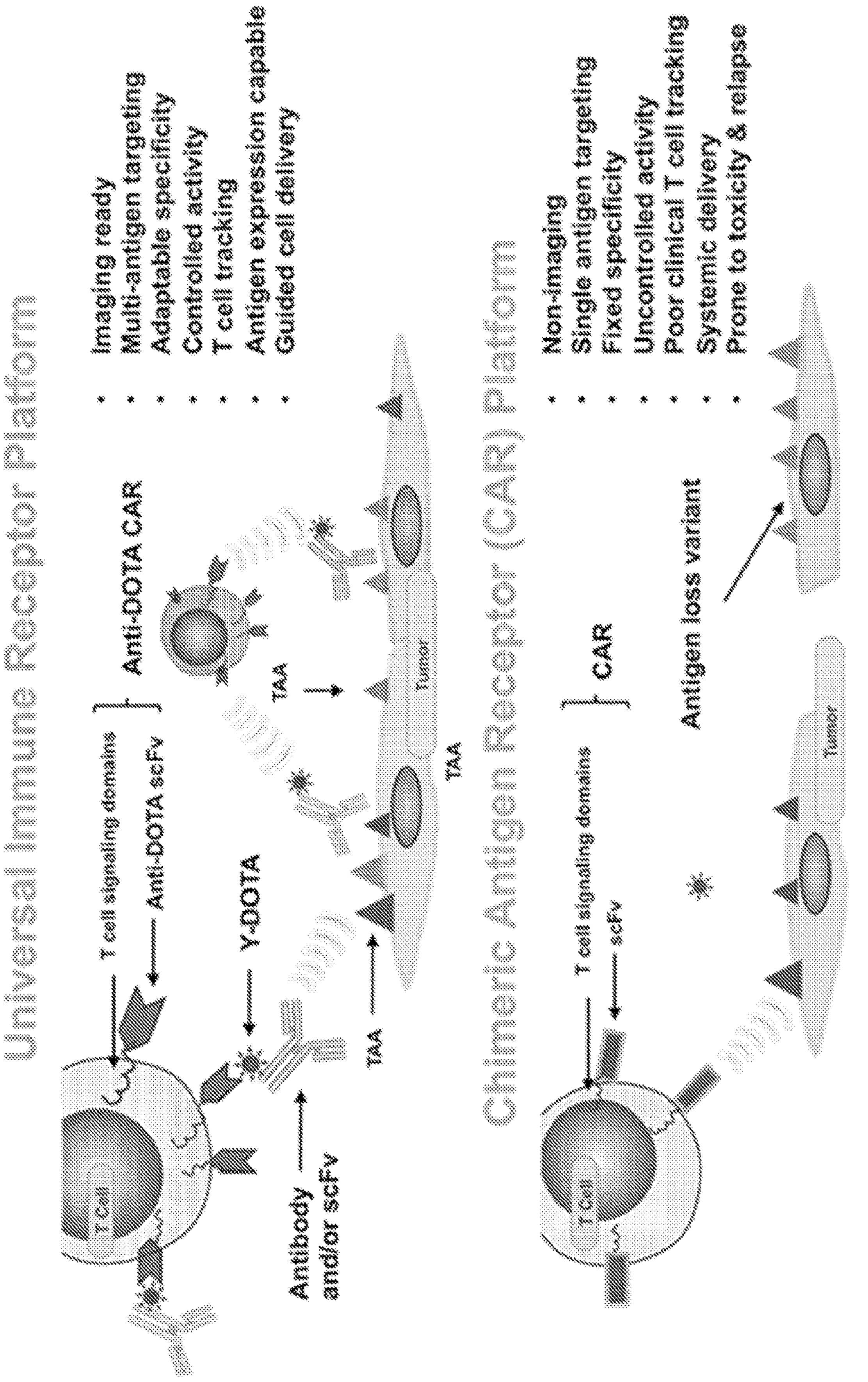
FIGS. 1A-1B illustrate the Universal Immune Receptor (UnivIR) platform.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or 10%, more preferably +5%, even more preferably +1%, and still more preferably +0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, NY; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. Kappa and lambda light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

"Xenogeneic" refers to any material derived from an animal of a different species.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs has specificity to a selected target, for example a B cell surface receptor. CARs may also comprise an intracellular activation domain, a transmembrane domain and an extracellular domain comprising a tumor associated antigen binding region. In some aspects, CARs comprise an extracellular domain comprising an anti-B cell binding domain fused to CD3-zeta transmembrane and intracellular domain.

"Cetuximab" is a monoclonal antibody that targets Epidermal Growth Factor Receptor (EGFR). Cetuximab is the generic name for the trade name drug ERBITUX® and is also referred to as (C225. Cetuximab is an anti-cancer ("anti-neoplastic") targeted therapy.

The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "DARPin", which is an acronym for "designed ankyrin repeat protein", is a genetically engineered antibody mimetic protein typically exhibiting highly specific and high-affinity target protein binding.

As used herein, "DOTA" refers to the chelating agent 1,4,7,10-tetraazacyclododecane-1,4,7,10-tetraacetic acid, also referred to as tetra-azacyclododecanetetra-acetic acid, and any salts, solvates, derivatives, or isoforms thereof. Also included are labeled forms of DOTA, for example DOTA labeled with the beta-emitting radioisotope yttrium Y90.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

As used herein, the term "folic acid" or "folate" refers to (2S)-2-[[4-[(2-amino-4-oxo-1H-pteridin-6-yl)methylamino]benzoyl]amino]pentanedioic acid, also known as (4-(((2-amino-4-oxo-3,4-dihydropteridin-6-yl)methyl)amino)benzoyl)-L-glutamic acid, or any salt, solvate, enantiomer, racemate, derivative, analogue, biologically equivalent analogue, or any mixture thereof:

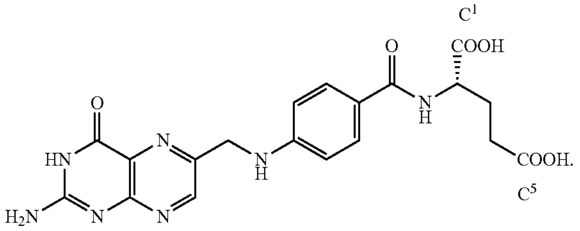 [SMILES: Nc1nc2ncc(CNc3ccc(C(=O)N[C@@H](CCC(=O)O)C(=O)O)cc3)nc2c(=O)[nH]1]

When incorporated within a compound or construct contemplated within the invention, the folic acid or folate can be attached through any of its atoms or groups, such as but not limited one or more of its carboxylic acids. In a non-limiting example, —NH-folate refers to a —NH group conjugated with a folic acid as an amide through one of its carboxylic acid groups. In a non-limiting example, —NH-folate refers to a —NH group conjugated with a folic acid as an amide through the folate's $C^1$ carboxylic acid group. In a non-limiting example, —NH-folate refers to a —NH group conjugated with a folic acid as an amide through the folate's $C^5$ carboxylic acid group.

"Herceptin" or "HERCEPTIN®" refers to a monoclonal antibody that targets the HER2/neu protein. HERCEPTIN® is the trade name for the generic drug Trastuzumab. HERCEPTIN® is used to treat metastatic breast cancer. It is effective against tumors that overexpress the HER2/neu protein.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence.

The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

When "an immunologically effective amount," "an autoimmune disease-inhibiting effective amount," or "therapeutic amount" is indicated, the precise amount of the compositions of the present invention to be administered can be determined by a physician or researcher with consideration of individual differences in age, weight, tumor size, extent of infection or metastasis, and condition of the patient (subject).

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Mov18" refers to the commercially available folate receptor a monoclonal antibody. Folate receptor (FR) is overexpressed in human ovarian carcinoma cells. Mov18 is used as a cancer therapeutic.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Rituximab" is a monoclonal antibody that binds CD20. Rituximab is the generic drug name for RITUXAN®. It is used for the treatment of certain types of non-Hodgkin's lymphoma and chronic lymphocytic leukemia (CLL).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genonic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Herein, a set of new molecular imaging tools were developed that are applicable to cellular therapy. At the same time, a Universal Immune Receptor (UnivIR) CAR T cell system comprised of a modified T cell comprising a DOTA CAR and DOTA-conjugated targeting ligand, was developed. This system challenges the current paradigm in gene therapy of fixed specificity vector design, which is restricted in antigen specificity, patient accessibility, and tumor type. The UnivIR CAR T cell system allows for a combination of flexibility in targeted antigen-specificity by re-directed T cells, simplified CAR manufacturing, modulation of T cell survival and function, and a suite of companion diagnostic tools for guiding T cell delivery, monitoring therapy, predicting response to therapy, and assessing the potential for on-target toxicity.

DOTA Chimeric Antigen Receptor (CAR)

The present invention provides compositions and methods for modified cells or precursor cells thereof (e.g., modified T cells, macrophages, or NK cells) comprising a chimeric antigen receptor (CAR) having affinity for DOTA. A subject CAR of the invention, which is referred to as a DOTA CAR or DOTA-binding CAR or anti-DOTA immune receptor, comprises a DOTA-binding domain, a transmembrane domain, and an intracellular signaling domain. A subject CAR of the invention may optionally comprise a hinge domain. Accordingly, a subject CAR of the invention comprises a DOTA-binding domain, a hinge domain, a transmembrane domain, and an intracellular signaling domain. In some embodiments, each of the domains of a subject CAR is separated by a linker.

The extracellular domain of the subject CAR specifically binds to DOTA. The DOTA-binding domain can include any domain that binds to the DOTA including but not limited to, a monoclonal antibody, a polyclonal antibody, a synthetic antibody, a human antibody, a humanized antibody, a non-human antibody, and any fragment thereof, including an antigen binding fragment (Fab), and a single-chain variable fragment (scFv). Preferably, the DOTA-binding domain is an scFv that binds to DOTA. In certain embodiments, the DOTA-binding domain comprises a DOTA-specific VH domain, a spacer sequence, and a DOTA-specific VL domain.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker or spacer, which connects the N-terminus of the VH with the C-terminus of the VL, or the C-terminus of the VH with the N-terminus of the VL. The terms "linker" and "spacer" are used interchangeably herein. In some embodiments, the DOTA-binding domain comprises an scFv having the configuration from N-terminus to C-terminus, VH—linker—VL. In some embodiments, the DOTA-binding domain comprises an scFv having the configuration from N-terminus to C-terminus, VL—linker—VH. Those of skill in the art would be able to select the appropriate configuration for use in the present invention.

In certain embodiments, the scFv comprises a high affinity anti-Y-DOTA scFv (C8.2.5). In certain embodiments, the scFv comprises a modified form of C8.2.5, e.g. the scFv comprises a substitution of a cysteine for the glycine at amino acid position 54 (G54C). Without wishing to be bound by specific theory, the G54C mutation places a cysteine near the DOTA binding pocket of the scFv that can react with a variety of DOTA-comprising compounds and form a covalent bond. The invention should be construed to include any scFv variant that is capable of forming a covalent linkage. Examples of such variants include, but are not limited to, thiols such as G55C and C56C (Corneillie™, et al. (2004) Bioconjug Chem.; 15(6):1392-402), and primary amines such as G54K, G55K, and G56K (Marquez B V, et al. (2012) Bioconjug Chem. May 16; 23(5):1080-9.)

In certain aspects, the DOTA-binding domain comprises a humanized scFv. In certain embodiments, the C8.2.5 scFv is humanized. In certain embodiments, the G54C scFv is humanized.

In one aspect, the DOTA-binding domain is encoded by a nucleotide sequence comprising SEQ ID NO: 1. In another aspect, the DOTA-binding domain comprises the amino acid sequence of SEQ ID NO: 2. In yet another aspect, the DOTA-binding domain comprises a sequence that has been mutated from its wild-type form to increase its affinity to DOTA. In yet another aspect, the DOTA-binding domain is encoded by a nucleotide sequence comprising SEQ ID NO: 3. In still another aspect, the DOTA-binding domain comprises the amino acid sequence of SEQ ID NO: 4.

In certain embodiments, the DOTA-binding domain comprises a light chain complementarity determining region comprising an amino acid sequence selected from the group consisting of SEQ ID NOs: 31, 32, and 33. In certain embodiments, the DOTA-binding domain consists of the light chain complementarity determining regions of SEQ ID NOs: 31, 32, and 33. In certain embodiments, the DOTA-binding domain comprises a heavy chain complementarity determining region comprising an amino acid sequence selected from the group consisting of SEQ ID NOs: 34, 35, 36 and 37. In certain embodiments, the DOTA-binding domain consists of the heavy chain complementarity determining regions of SEQ ID NOs: 34, 35, 36 and 37.

In certain embodiments, the CAR comprises a CD8a hinge domain. In certain embodiments, the hinge domain comprises the amino acid sequence of SEQ ID NO: 17. In certain embodiments, the hinge domain is encoded by the nucleic acid sequence of SEQ ID NO: 18.

The DOTA-binding domain may be operably linked to another domain of the CAR, such as the transmembrane domain, or the intracellular signaling domain, each described elsewhere herein, for expression in the cell. In one embodiment, a first nucleic acid sequence encoding the DOTA-binding domain is operably linked to a second nucleic acid encoding a transmembrane domain, and further operably linked to a third nucleic acid sequence encoding an intracellular domain.

The DOTA-binding domains described herein can be combined with any of the transmembrane domains, any of the intracellular signaling domains, or any of the other domains described herein that may be included in a CAR of the present invention.

Transmembrane Domain

With respect to the transmembrane domain, the DOTA CAR can be designed to comprise a transmembrane domain that is fused to the DOTA-binding domain. In one embodiment, the transmembrane domain that naturally is associated with one of the domains in the DOTA CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the DOTA CAR. A glycine-serine doublet provides a particularly suitable linker.

In certain embodiments, the transmembrane domain comprises a CD8α transmembrane domain, or a portion thereof. In certain embodiments, the transmembrane domain comprises the amino acid sequence of SEQ ID NO: 19. In certain embodiments, the transmembrane domain is encoded by the nucleotide sequence of SEQ ID NO: 20. In certain embodiments, the transmembrane domain comprises a CD28 transmembrane domain, or a portion thereof. In certain embodiments, the transmembrane domain comprises the amino acid sequence of SEQ ID NO: 27. In certain embodiments, the transmembrane domain is encoded by the nucleotide sequence of SEQ ID NO: 28.

Intracellular Domain

The "intracellular domain" or otherwise the "intracellular signaling domain" or "cytoplasmic domain" of the DOTA CAR of the invention is responsible for activation of at least one of the normal effector functions of the immune cell in which the DOTA CAR has been placed in. The term "effector function" refers to a specialized function of a cell. Effector function of a T cell, for example, may be cytolytic activity or helper activity including the secretion of cytokines. Thus the term "intracellular domain" refers to the portion of a protein which transduces the effector function signal and directs the cell to perform a specialized function. While usually the entire intracellular domain can be employed, in many cases it is not necessary to use the entire chain. To the extent that a truncated portion of the intracellular domain is used, such truncated portion may be used in place of the intact chain as long as it transduces the effector function signal. The term intracellular domain is thus meant to include any truncated portion of the intracellular domain sufficient to transduce the effector function signal.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular domain include, without limitation, the ζ chain of the T cell receptor complex or any of its homologs, e.g., η chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular domain may be human CD3 zeta chain, FcyRIII, FcsRI, cytoplasmic tails of Fc receptors, an immunoreceptor tyrosine-based activation motif (ITAM) bearing cytoplasmic receptors, and combinations thereof.

In one embodiment, the intracellular domain of the CAR includes any portion of one or more co-stimulatory molecules, such as at least one signaling domain from CD2, CD3, CD8, CD27, CD28, ICOS, 4-1BB, PD-1, any derivative or variant thereof, any synthetic sequence thereof that has the same functional capability, and any combination thereof.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon RIb), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CDlib, ITGAX, CD11c, ITGBl, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAMI, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the DOTA CAR of the invention comprises a cytoplasmic signaling sequence derived from CD3 zeta.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular domain is derived from FCER1G (also known as FCRG; Fc epsilon receptor I gamma chain; Fc receptor gamma-chain; fc-epsilon RI-gamma; fcRgamma; fceR1 gamma; high affinity immunoglobulin epsilon receptor subunit gamma; immunoglobulin E receptor, high affinity, gamma chain; etc.). In one embodiment, the intracellular domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular domain is derived from T-cell surface glycoprotein CD3 gamma chain (also known as CD3G, T-cell receptor T3 gamma chain, CD3-GAMMA, T3G, gamma polypeptide (TiT3 complex), etc.).

In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, and so forth). In one embodiment, the intracellular domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in an FN3 CAR of the present disclosure includes a DAP10/CD28 type signaling chain. In one embodiment, an intracellular signaling domain suitable for use in an FN3 CAR of the present disclosure includes a ZAP70 polypeptide.

In certain embodiments, the intracellular domain includes at least one mutated ITAM domain, for example in CD28 (Feucht et al. (2019) *Nature Medicine* 25, 82-88).

In a preferred embodiment, the intracellular domain of the DOTA CAR can be designed to comprise the CD3-zeta signaling domain by itself or combined with any other desired cytoplasmic domain(s) useful in the context of the DOTA CAR of the invention. For example, the intracellular domain of the DOTA CAR can comprise a CD3 zeta chain portion and a costimulatory signaling region. The costimulatory signaling region refers to a portion of the DOTA CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD28 and 4-1BB as the co-stimulatory signaling element, other costimulatory elements are within the scope of the invention.

Multiple intracellular domain sequences (e.g. CD3, CD28, and 4-1BB) within the DOTA CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In certain embodiments, the intracellular domain is designed to comprise the signaling domain of CD3-zeta. In certain embodiments, the intracellular domain is designed to comprise 4-1BB and CD3-zeta. In certain embodiments, the intracellular domain is designed to comprise CD28 and CD3-zeta. In certain embodiments, the intracellular domain is designed to comprise CD28, 4-1BB and CD3-zeta. In certain embodiments, the intracellular domain comprise any combination of CD3-zeta, CD28, 4-1BB, and the like. In certain embodiments, the intracellular domain comprises one or more amino acid sequences selected from the group consisting of SEQ ID NOs: 21, 23, 25, and 29. In certain embodiments, the intracellular domain is encoded by one or more nucleic acid sequences selected from the group consisting of SEQ ID NOs: 22, 24, 26, and 30.

In certain embodiments, the DOTA CAR comprises a portion of the CD28 intracellular domain. In certain embodiments, the intracellular domain comprises the amino acid sequence of RSKRS (SEQ ID NO: 40), which may be encoded by the nucleic acid sequence of aggagtaagaggagctaa (SEQ ID NO: 39). This segment allows for stable surface resident expression of the extracellular and transmembrane domains but does not elicit T cell function upon receptor binding, as shown herein in the Experimental Examples.

In one aspect, the invention includes an isolated DOTA CAR comprising a DOTA-binding domain, a transmembrane domain, and a CD28 intracellular domain. In another aspect, the invention includes an isolated nucleic acid encoding a DOTA CAR, wherein the CAR comprises a DOTA-binding domain, a transmembrane domain, and a CD28 intracellular domain. Another aspect of the invention includes an isolated polypeptide comprising a DOTA-binding domain, a transmembrane domain, and a CD28 intracellular domain.

In another aspect, the invention includes an isolated DOTA CAR comprising a DOTA-binding domain, a transmembrane domain, and a CD3ζ intracellular domain. In another aspect, the invention includes an isolated nucleic acid encoding a DOTA CAR, wherein the CAR comprises a DOTA-binding domain, a transmembrane domain, and a CD3ζ intracellular domain. Another aspect of the invention includes an isolated polypeptide comprising a DOTA-binding domain, a transmembrane domain, and a CD3ζ intracellular domain.

In another aspect, the invention includes an isolated DOTA CAR comprising a DOTA-binding domain, a transmembrane domain, a CD28 intracellular domain, and a CD3ζ intracellular domain. In another aspect, the invention includes an isolated nucleic acid encoding a DOTA CAR, wherein the CAR comprises a DOTA-binding domain, a transmembrane domain, a CD28 intracellular domain, and a CD3ζ intracellular domain. Another aspect of the invention includes an isolated polypeptide comprising a DOTA-binding domain, a transmembrane domain, a CD28 intracellular domain, and a CD3ζ intracellular domain.

In yet another aspect, the invention includes an isolated DOTA CAR comprising a DOTA-binding domain, a transmembrane domain, a 4-1BB intracellular domain, and a CD3ζ intracellular domain. In another aspect, the invention includes an isolated nucleic acid encoding a DOTA CAR, wherein the CAR comprises a DOTA-binding domain, a transmembrane domain, a 4-1BB intracellular domain, and a CD3ζ intracellular domain. Another aspect of the invention includes an isolated polypeptide comprising a DOTA-binding domain, a transmembrane domain, a 4-1BB intracellular domain, and a CD3ζ intracellular domain.

In another aspect, the invention includes an isolated DOTA CAR comprising a DOTA-binding domain, a transmembrane domain, a CD28 intracellular domain, a 4-1BB intracellular domain, and a CD3ζ intracellular domain. In another aspect, the invention includes an isolated nucleic acid encoding a DOTA CAR, wherein the CAR comprises a DOTA-binding domain, a transmembrane domain, a CD28 intracellular domain, a 4-1BB intracellular domain, and a CD3ζ intracellular domain. Another aspect of the invention includes an isolated polypeptide comprising a DOTA-binding domain, a transmembrane domain, a CD28 intracellular domain, a 4-1BB intracellular domain, and a CD3ζ intracellular domain.

Another aspect of the invention includes a DOTA CAR comprising a DOTA-binding domain comprising an hC825G54C scFv, a hinge domain, a transmembrane domain, and an intracellular domain comprising a 5 amino acid portion of the CD28 domain. An isolated nucleic acid and isolated polypeptide of the DOTA CAR are also embodiments of the invention.

In certain embodiments of the invention, the CAR is encoded by the nucleic acid sequence of any one of SEQ ID NOs: 5, 7, 9, 11, 13, and 15. In other embodiments, the CAR comprises the amino acid sequence of any one of SEQ ID NOs: 6, 8, 10, 12, 14, and 16.

In certain embodiments, the modified cell is a T cell. In certain embodiments, the modified cell is a macrophage. In certain embodiments, the modified cell is an NK cell. In certain embodiments, the modified cell is an autologous cell.

Sequences of the CARs and their individual domains are found in Table 1.

TABLE 1

| SEQ ID NO: | Description | Sequence |
|---|---|---|
| 1 | Humanized DOTA-binding scFV (hC825) nucleotide sequence | catgttcagttagtcgagtccggtggaggactggtgcaaccaggaggt tctctgagattgtcctgtgccgcctctggctttagtctgacagattac ggagtgcactgggttaggcaggcccctgggaaaggtttggaatggtta ggagttatttggtccggcggagggacagcttacaataccgcactgatt tcaagattcactatctcaagggataacagcaagaacacattgtatctg caaatgaatagcttgagagccgaggacaccgctgtctattactgtgct agaaggggtagttatccctacaactatttcgacgcatggggctgcgga |

TABLE 1-continued

| SEQ ID NO: | Description | Sequence |
|---|---|---|
| | | actctggtcacagtgtcttccggtggaggagggagcggtggaggaggg<br>agtggtggaggagggtctcaggcagtggtgacacaagaacccagtttg<br>accgtctctccaggtggcactgtgacattaacctgtgggtcaagcact<br>ggtgctgttacagcaagcaactacgcaaattgggtgcagcagaaacct<br>gggcagtgtcctcggggcctgattggcgggcataataacagacctcct<br>ggggtgccagctcggttcagcggcagcctgctgggagggaaggcagct<br>ctgaccctgctgggagcacagcctgaggacgaagcagagtactattgc<br>gccctgtggtactctgatcactgggtcatcggtggtggaaccaagctg<br>actgtcttgggc |
| 2 | Humanized DOTA-binding scFV (hC825) amino acid sequence | HVQLVESGGGLVQPGGSLRLSCAASGFSLTDYGVHWVRQAPGKGLEWL<br>GVIWSGGGTAYNTALISRFTISRDNSKNTLYLQMNSLRAEDTAVYYCA<br>RRGSYPYNYFDAWGCGTLVTVSSGGGGSGGGGSGGGGSQAVVTQEPSL<br>TVSPGGTVTLTCGSSTGAVTASNYANWVQQKPGQCPRGLIGGHNNRPP<br>GVPARFSGSLLGGKAALTLLGAQPEDEAEYYCALWYSDHWVIGGGTKL<br>TVLG |
| 3 | Humanized DOTA-binding scFV (hC825/G54C) nucleotide sequence | catgttcagttagtcgagtccggtggaggactggtgcaaccaggaggt<br>tctctgagattgtcctgtgccgcctctggctttagtctgacagattac<br>ggagtgcactgggttaggcaggcccctgggaaaggtttggaatggtta<br>ggagttatttggtcctgcggagggacagcttacaataccgcactgatt<br>tcaagattcactatctcaagggataacagcaagaacacattgtatctg<br>caaatgaatagcttgagagccgaggacaccgctgtctattactgtgct<br>agaaggggtagttatccctacaactatttcgacgcatggggctgcgga<br>actctggtcacagtgtcttccggtggaggagggagcggtggaggaggg<br>agtggtggaggagggtctcaggcagtggtgacacaagaacccagtttg<br>accgtctctccaggtggcactgtgacattaacctgtgggtcaagcact<br>ggtgctgttacagcaagcaactacgcaaattgggtgcagcagaaacct<br>gggcagtgtcctcggggcctgattggcgggcataataacagacctcct<br>ggggtgccagctcggttcagcggcagcctgctgggagggaaggcagct<br>ctgaccctgctgggagcacagcctgaggacgaagcagagtactattgc<br>gccctgtggtactctgatcactgggtcatcggtggtggaaccaagctg<br>actgtcttgggc |
| 4 | Humanized DOTA-binding scFV (hC825/G54C) amino acid sequence | HVQLVESGGGLVQPGGSLRLSCAASGFSLTDYGVHWVRQAPGKGLEWL<br>GVIWSCGGTAYNTALISRFTISRDNSKNTLYLQMNSLRAEDTAVYYCA<br>RRGSYPYNYFDAWGCGTLVTVSSGGGGSGGGGSGGGGSQAVVTQEPSL<br>TVSPGGTVTLTCGSSTGAVTASNYANWVQQKPGQCPRGLIGGHNNRPP<br>GVPARFSGSLLGGKAALTLLGAQPEDEAEYYCALWYSDHWVIGGGTKL<br>TVLG |
| 5 | DOTA CAR hC825-28z nucleotide sequence | atggccttaccagtgaccgccttgctcctgccgctggccttgctgctc<br>cacgccgccaggccgggatcccatgttcagttagtcgagtccggtgga<br>ggactggtgcaaccaggaggttctctgagattgtcctgtgccgcctct<br>ggctttagtctgacagattacggagtgcactgggttaggcaggcccct<br>gggaaaggtttggaatggttaggagttatttggtccggcggagggaca<br>gcttacaataccgcactgatttcaagattcactatctcaagggataac<br>agcaagaacacattgtatctgcaaatgaatagcttgagagccgaggac<br>accgctgtctattactgtgctagaaggggtagttatccctacaactat<br>ttcgacgcatggggctgcggaactctggtcacagtgtcttccggtgga<br>ggagggagcggtggaggagggagtggtggaggagggtctcaggcagtg<br>gtgacacaagaacccagtttgaccgtctctccaggtggcactgtgaca<br>ttaacctgtgggtcaagcactggtgctgttacagcaagcaactacgca<br>aattgggtgcagcagaaacctgggcagtgtcctcggggcctgattggc<br>gggcataataacagacctcctggggtgccagctcggttcagcggcagc<br>ctgctgggagggaaggcagctctgaccctgctgggagcacagcctgag<br>gacgaagcagagtactattgcgccctgtggtactctgatcactgggtc<br>atcggtggtggaaccaagctgactgtcttgggcgctagcaccacgacg<br>ccagcgccgcgaccaccaacaccggcgcccaccatcgcgtcgcagccc<br>ctgtccctgcgcccagaggcgtgccggccagcggcggggggcgcagtg<br>cacacgagggggctggacttcgcctgtgatttttgggtgctggtggtg<br>gttggtggagtcctggcttgctatagcttgctagtaacagtggccttt<br>attattttctgggtgaggagtaagaggagcaggctcctgcacagtgac<br>tacatgaacatgactccccgccgccccgggcccacccgcaagcattac<br>cagccctatgccccaccacgcgacttcgcagcctatcgctccatcgat<br>agagtgaagttcagcaggagcgcagacgcccccgcgtaccagcagggc<br>cagaaccagctctataacgagctcaatctaggacgaagagaggagtac<br>gatgttttggacaagagacgtggccgggaccctgagatgggggaaag<br>ccgagaaggaagaaccctcaggaaggcctgtacaatgaactgcagaaa<br>gataagatggcggaggcctacagtgagattgggatgaaaggcgagcgc<br>cggaggggcaaggggcacgatggcctttaccagggtctcagtacagcc<br>accaaggacacctacgacgcccttcacatgcaggccctgccccctcgc<br>taa |

TABLE 1-continued

| SEQ ID NO: | Description | Sequence |
|---|---|---|
| 6 | DOTA CAR hC825-28z amino acid sequence | MALPVTALLLPLALLLHAARPGSHVQLVESGGGLVQPGGSLRLSCAAS<br>GFSLTDYGVHWVRQAPGKGLEWLGVIWSGGGTAYNTALISRFTISRDN<br>SKNTLYLQMNSLRAEDTAVYYCARRGSYPYNYFDAWGCGTLVTVSSGG<br>GGSGGGGSGGGGSQAVVTQEPSLTVSPGGTVTLTCGSSTGAVTASNYA<br>NWVQQKPGQCPRGLIGGHNNRPPGVPARFSGSLLGGKAALTLLGAQPE<br>DEAEYYCALWYSDHWVIGGGTKLTVLGASTTTPAPRPPTPAPTIASQP<br>LSLRPEACRPAAGGAVHTRGLDFACDFWVLVVVGGVLACYSLLVTVAF<br>IIFWVRSKRSRLLHSDYMNMTPRRPGPTRKHYQPYAPPRDFAAYRSID<br>RVKFSRSADAPAYQQGQNQLYNELNLGRREEYDVLDKRRGRDPEMGGK<br>PRRKNPQEGLYNELQKDKMAEAYSEIGMKGERRRGKGHDGLYQGLSTA<br>TKDTYDALHMQALPPR |
| 7 | DOTA CAR hC825-BBz nucleotide sequence | atggccttaccagtgaccgccttgctcctgccgctggccttgctgctc<br>cacgccgccaggccgggatcccatgttcagttagtcgagtccggtgga<br>ggactggtgcaaccaggaggttctctgagattgtcctgtgccgcctct<br>ggctttagtctgacagattacggagtgcactgggttaggcaggcccct<br>gggaaaggtttggaatggttaggagttatttggtccggcggagggaca<br>gcttacaataccgcactgatttcaagattcactatctcaagggataac<br>agcaagaacacattgtatctgcaaatgaatagcttgagagccgaggac<br>accgctgtctattactgtgctagaaggggtagttatccctacaactat<br>ttcgacgcatggggctgcggaactctggtcacagtgtcttccggtgga<br>ggagggagcggtggaggagggagtggtggaggagggtctcaggcagtg<br>gtgacacaagaacccagtttgaccgtctctccaggtggcactgtgaca<br>ttaacctgtgggtcaagcactggtgctgttacagcaagcaactacgca<br>aattgggtgcagcagaaacctgggcagtgtcctcggggcctgattggc<br>gggcataataacagacctcctggggtgccagctcggttcagcggcagc<br>ctgctgggagggaaggcagctctgaccctgctgggagcacagcctgag<br>gacgaagcagagtactattgcgccctgtggtactctgatcactgggtc<br>atcggtggtggaaccaagctgactgtcttgggcgctagcaccacgacg<br>ccagcgccgcgaccaccaacaccggcgcccaccatcgcgtcgcagccc<br>ctgtccctgcgcccagaggcgtgccggccagcggcgggggcgcagtg<br>cacacgagggggctggacttcgcctgtgatatctacatctgggcgccc<br>ttggccgggacttgtggggtccttctcctgtcactggttatcaccctt<br>tactgcaaacggggcagaaagaaactcctgtatatattcaaacaacca<br>tttatgagaccagtacaaactactcaagaggaagatggctgtagctgc<br>cgatttccagaagaagaagaaggaggatgtgaactgagagtgaagttc<br>agcaggagcgcagacgcccccgcgtacaagcagggccagaaccagctc<br>tataacgagctcaatctaggacgaagagaggagtacgatgttttggac<br>aagagacgtggccgggaccctgagatggggggaaagccgagaaggaag<br>aaccctcaggaaggcctgtacaatgaactgcagaaagataagatggcg<br>gaggcctacagtgagattgggatgaaaggcgagcgccggaggggcaag<br>gggcacgatggcctttaccagggtctcagtacagccaccaaggacacc<br>tacgacgcccttcacatgcaggccctgccccctcgctaa |
| 8 | DOTA CAR hC825-BBz amino acid sequence | MALPVTALLLPLALLLHAARPGSHVQLVESGGGLVQPGGSLRLSCAAS<br>GFSLTDYGVHWVRQAPGKGLEWLGVIWSGGGTAYNTALISRFTISRDN<br>SKNTLYLQMNSLRAEDTAVYYCARRGSYPYNYFDAWGCGTLVTVSSGG<br>GGSGGGGSGGGGSQAVVTQEPSLTVSPGGTVTLTCGSSTGAVTASNYA<br>NWVQQKPGQCPRGLIGGHNNRPPGVPARFSGSLLGGKAALTLLGAQPE<br>DEAEYYCALWYSDHWVIGGGTKLTVLGASTTTPAPRPPTPAPTIASQP<br>LSLRPEACRPAAGGAVHTRGLDFACDIYIWAPLAGTCGVLLLSLVITL<br>YCKRGRKKLLYIFKQPFMRPVQTTQEEDGCSCRFPEEEEGGCELRVKF<br>SRSADAPAYKQGQNQLYNELNLGRREEYDVLDKRRGRDPEMGGKPRRK<br>NPQEGLYNELQKDKMAEAYSEIGMKGERRRGKGHDGLYQGLSTATKDT<br>YDALHMQALPPR |
| 9 | DOTA CAR hC825-8z nucleotide sequence | atggccttaccagtgaccgccttgctcctgccgctggccttgctgctc<br>cacgccgccaggccgggatcccatgttcagttagtcgagtccggtgga<br>ggactggtgcaaccaggaggttctctgagattgtcctgtgccgcctct<br>ggctttagtctgacagattacggagtgcactgggttaggcaggcccct<br>gggaaaggtttggaatggttaggagttatttggtccggcggagggaca<br>gcttacaataccgcactgatttcaagattcactatctcaagggataac<br>agcaagaacacattgtatctgcaaatgaatagcttgagagccgaggac<br>accgctgtctattactgtgctagaaggggtagttatccctacaactat<br>ttcgacgcatggggctgcggaactctggtcacagtgtcttccggtgga<br>ggagggagcggtggaggagggagtggtggaggagggtctcaggcagtg<br>gtgacacaagaacccagtttgaccgtctctccaggtggcactgtgaca<br>ttaacctgtgggtcaagcactggtgctgttacagcaagcaactacgca<br>aattgggtgcagcagaaacctgggcagtgtcctcggggcctgattggc<br>gggcataataacagacctcctggggtgccagctcggttcagcggcagc<br>ctgctgggagggaaggcagctctgaccctgctgggagcacagcctgag<br>gacgaagcagagtactattgcgccctgtggtactctgatcactgggtc<br>atcggtggtggaaccaagctgactgtcttgggcgctagcaccacgacg<br>ccagcgccgcgaccaccaacaccggcgcccaccatcgcgtcgcagccc<br>ctgtccctgcgcccagaggcgtgccggccagcggcgggggcgcagtg<br>cacacgagggggctggacttcgcctgtgattttgggtgctggtggtg |

TABLE 1-continued

| SEQ ID NO: | Description | Sequence |
|---|---|---|
| | | gttggtggagtcctggcttgctatagcttgctagtaacagtggccttt<br>attattttctgggtgaggagtaagaggagctaa |
| 10 | DOTA CAR hC825-5z amino acid sequence | MALPVTALLLPLALLLHAARPGSHVQLVESGGGLVQPGGSLRLSCAAS<br>GFSLTDYGVHWVRQAPGKGLEWLGVIWSGGGTAYNTALISRFTISRDN<br>SKNTLYLQMNSLRAEDTAVYYCARRGSYPYNYFDAWGCGTLVTVSSGG<br>GGSGGGGSGGGGSQAVVTQEPSLTVSPGGTVTLTCGSSTGAVTASNYA<br>NWVQQKPGQCPRGLIGGHNNRPPGVPARFSGSLLGGKAALTLLGAQPE<br>DEAEYYCALWYSDHWVIGGGTKLTVLGASTTTPAPRPPTPAPTIASQP<br>LSLRPEACRPAAGGAVHTRGLDFACDFWVLVVVGGVLACYSLLVTVAF<br>IIFWVRSKRS |
| 11 | Covalent (G54C) DOTA CAR hC825G54C-28z nucleotide sequence | atggccttaccagtgaccgccttgctcctgccgctggccttgctgctc<br>cacgccgccaggccgggatcccatgttcagttagtcgagtccggtgga<br>ggactggtgcaaccaggaggttctctgagattgtcctgtgccgcctct<br>ggctttagtctgacagattacggagtgcactgggttaggcaggcccct<br>gggaaaggtttggaatggttaggagttatttggtcctgcggagggaca<br>gcttacaataccgcactgatttcaagattcactatctcaagggataac<br>agcaagaacacattgtatctgcaaatgaatagcttgagagccgaggac<br>accgctgtctattactgtgctagaaggggtagttatccctacaactat<br>ttcgacgcatggggctgcggaactctggtcacagtgtcttccggtgga<br>ggagggagcggtggaggagggagtggtggaggagggtctcaggcagtg<br>gtgacacaagaacccagtttgaccgtctctccaggtggcactgtgaca<br>ttaacctgtgggtcaagcactggtgctgttacagcaagcaactacgca<br>aattgggtgcagcagaaacctgggcagtgtcctcggggcctgattggc<br>gggcataataacagacctcctggggtgccagctcggttcagcggcagc<br>ctgctgggagggaaggcagctctgaccctgctgggagcacagcctgag<br>gacgaagcagagtactattgcgccctgtggtactctgatcactgggtc<br>atcggtggtggaaccaagctgactgtcttgggcgctagcaccacgacg<br>ccagcgccgcgaccaccaacaccggcgcccaccatcgcgtcgcagccc<br>ctgtccctgcgcccagaggcgtgccggccagcggcggggggcgcagtg<br>cacacgagggggctggacttcgcctgtgatttttgggtgctggtggtg<br>gttggtggagtcctggcttgctatagcttgctagtaacagtggccttt<br>attattttctgggtgaggagtaagaggagcaggctcctgcacagtgac<br>tacatgaacatgactccccgccgccccgggcccacccgcaagcattac<br>cagccctatgccccaccacgcgacttcgcagcctatcgctccatcgat<br>agagtgaagttcagcaggagcgcagacgcccccgcgtaccagcagggc<br>cagaaccagctctataacgagctcaatctaggacgaagagaggagtac<br>gatgttttggacaagagacgtggccgggaccctgagatggggggaaag<br>ccgagaaggaagaaccctcaggaaggcctgtacaatgaactgcagaaa<br>gataagatggcggaggcctacagtgagattgggatgaaaggcgagcgc<br>cggaggggcaaggggcacgatggcctttaccagggtctcagtacagcc<br>accaaggacacctacgacgcccttcacatgcaggccctgccccctcgc<br>taa |
| 12 | Covalent (G54C) DOTA CAR hC825G54C-28z amino acid sequence | MALPVTALLLPLALLLHAARPGSHVQLVESGGGLVQPGGSLRLSCAAS<br>GFSLTDYGVHWVRQAPGKGLEWLGVIWSCGGTAYNTALISRFTISRDN<br>SKNTLYLQMNSLRAEDTAVYYCARRGSYPYNYFDAWGCGTLVTVSSGG<br>GGSGGGGSGGGGSQAVVTQEPSLTVSPGGTVTLTCGSSTGAVTASNYA<br>NWVQQKPGQCPRGLIGGHNNRPPGVPARFSGSLLGGKAALTLLGAQPE<br>DEAEYYCALWYSDHWVIGGGTKLTVLGASTTTPAPRPPTPAPTIASQP<br>LSLRPEACRPAAGGAVHTRGLDFACDFWVLVVVGGVLACYSLLVTVAF<br>IIFWVRSKRSRLLHSDYMNMTPRRPGPTRKHYQPYAPPRDFAAYRSID<br>RVKFSRSADAPAYQQGQNQLYNELNLGRREEYDVLDKRRGRDPEMGGK<br>PRRKNPQEGLYNELQKDKMAEAYSEIGMKGERRRGKGHDGLYQGLSTA<br>TKDTYDALHMQALPPR |
| 13 | Covalent (G54C) DOTA CAR hC825G54C-BBz nucleotide sequence | atggccttaccagtgaccgccttgctcctgccgctggccttgctgctc<br>cacgccgccaggccgggatcccatgttcagttagtcgagtccggtgga<br>ggactggtgcaaccaggaggttctctgagattgtcctgtgccgcctct<br>ggctttagtctgacagattacggagtgcactgggttaggcaggcccct<br>gggaaaggtttggaatggttaggagttatttggtcctgcggagggaca<br>gcttacaataccgcactgatttcaagattcactatctcaagggataac<br>agcaagaacacattgtatctgcaaatgaatagcttgagagccgaggac<br>accgctgtctattactgtgctagaaggggtagttatccctacaactat<br>ttcgacgcatggggctgcggaactctggtcacagtgtcttccggtgga<br>ggagggagcggtggaggagggagtggtggaggagggtctcaggcagtg<br>gtgacacaagaacccagtttgaccgtctctccaggtggcactgtgaca<br>ttaacctgtgggtcaagcactggtgctgttacagcaagcaactacgca<br>aattgggtgcagcagaaacctgggcagtgtcctcggggcctgattggc<br>gggcataataacagacctcctggggtgccagctcggttcagcggcagc<br>ctgctgggagggaaggcagctctgaccctgctgggagcacagcctgag<br>gacgaagcagagtactattgcgccctgtggtactctgatcactgggtc<br>atcggtggtggaaccaagctgactgtcttgggcgctagcaccacgacg<br>ccagcgccgcgaccaccaacaccggcgcccaccatcgcgtcgcagccc<br>ctgtccctgcgcccagaggcgtgccggccagcggcggggggcgcagtg |

TABLE 1-continued

| SEQ ID NO: | Description | Sequence |
|---|---|---|
| | | cacacgagggggctggacttcgcctgtgatatctacatctgggcgccc ttggccgggacttgtggggtccttctcctgtcactggttatcaccctt tactgcaaacggggcagaaagaaactcctgtatatattcaaacaacca tttatgagaccagtacaaactactcaagaggaagatggctgtagctgc cgatttccagaagaagaagaaggaggatgtgaactgagagtgaagttc agcaggagcgcagacgcccccgcgtacaagcagggccagaaccagctc tataacgagctcaatctaggacgaagagaggagtacgatgttttggac aagagacgtggccgggaccctgagatgggggggaaagccgagaaggaag aaccctcaggaaggcctgtacaatgaactgcagaaagataagatggcg gaggcctacagtgagattgggatgaaaggcgagcgccggaggggcaag gggcacgatggcctttaccagggtctcagtacagccaccaaggacacc tacgacgcccttcacatgcaggccctgccccctcgctaa |
| 14 | Covalent (G54C) DOTA CAR hC825G54C-BBz amino acid sequence | MALPVTALLLPLALLLHAARPGSHVQLVESGGGLVQPGGSLRLSCAAS GFSLTDYGVHWVRQAPGKGLEWLGVIWSCGGTAYNTALISRFTISRDN SKNTLYLQMNSLRAEDTAVYYCARRGSYPYNYFDAWGCGTLVTVSSGG GGSGGGGSGGGGSQAVVTQEPSLTVSPGGTVTLTCGSSTGAVTASNYA NWVQQKPGQCPRGLIGGHNNRPPGVPARFSGSLLGGKAALTLLGAQPE DEAEYYCALWYSDHWVIGGGTKLTVLGASTTTPAPRPPTPAPTIASQP LSLRPEACRPAAGGAVHTRGLDFACDIYIWAPLAGTCGVLLLSLVITL YCKRGRKKLLYIFKQPFMRPVQTTQEEDGCSCRFPEEEEGGCELRVKF SRSADAPAYKQGQNQLYNELNLGRREEYDVLDKRRGRDPEMGGKPRRK NPQEGLYNELQKDKMAEAYSEIGMKGERRRGKGHDGLYQGLSTATKDT YDALHMQALPPR |
| 15 | Covalent (G54C) DOTA CAR hC825G54C-δz nucleotide sequence | atggccttaccagtgaccgccttgctcctgccgctggccttgctgctc cacgccgccaggccgggatcccatgttcagttagtcgagtccggtgga ggactggtgcaaccaggaggttctctgagattgtcctgtgccgcctct ggctttagtctgacagattacggagtgcactgggttaggcaggcccct gggaaaggtttggaatggttaggagttatttggtcctgcggagggaca gcttacaataccgcactgatttcaagattcactatctcaagggataac agcaagaacacattgtatctgcaaatgaatagcttgagagccgaggac accgctgtctattactgtgctagaaggggtagttatccctacaactat ttcgacgcatggggctgcggaactctggtcacagtgtcttccggtgga ggagggagcggtggaggagggagtggtggaggagggtctcaggcagtg gtgacacaagaacccagtttgaccgtctctccaggtggcactgtgaca ttaacctgtgggtcaagcactggtgctgttacagcaagcaactacgca aattgggtgcagcagaaacctgggcagtgtcctcggggcctgattggc gggcataataacagacctcctggggtgccagctcggttcagcggcagc ctgctgggagggaaggcagctctgaccctgctgggagcacagcctgag gacgaagcagagtactattgcgccctgtggtactctgatcactgggtc atcggtggtggaaccaagctgactgtcttgggcgctagcaccacgacg ccagcgccgcgaccaccaacaccggcgcccaccatcgcgtcgcagccc ctgtccctgcgcccagaggcgtgccggccagcggcggggggcgcagtg cacacgagggggctggacttcgcctgtgatttttgggtgctggtggtg gttggtggagtcctggcttgctatagcttgctagtaacagtggccttt attattttctgggtgaggagtaagaggagctaa |
| 16 | Covalent (G54C) DOTA CAR hC825G54C-δz amino acid sequence | MALPVTALLLPLALLLHAARPGSHVQLVESGGGLVQPGGSLRLSCAAS GFSLTDYGVHWVRQAPGKGLEWLGVIWSCGGTAYNTALISRFTISRDN SKNTLYLQMNSLRAEDTAVYYCARRGSYPYNYFDAWGCGTLVTVSSGG GGSGGGGSGGGGSQAVVTQEPSLTVSPGGTVTLTCGSSTGAVTASNYA NWVQQKPGQCPRGLIGGHNNRPPGVPARFSGSLLGGKAALTLLGAQPE DEAEYYCALWYSDHWVIGGGTKLTVLGASTTTPAPRPPTPAPTIASQP LSLRPEACRPAAGGAVHTRGLDFACDFWVLVVVGGVLACYSLLVTVAF IIFWVRSKRS |
| 17 | CD8α hinge amino acid sequence | TTTPAPRPPTPAPTIASQPLSLRPEACRPAAGGAVHTRGLDFACD |
| 18 | CD8α hinge nucleic acid sequence | accacgacgccagcgccgcgaccaccaacaccggcgcccaccatcgcg tcgcagcccctgtccctgcgcccagaggcgtgccggccagcggcgggg ggcgcagtgcacacgagggggctggacttcgcctgtgat |
| 19 | CD8α transmembrane domain amino acid sequence | IYIWAPLAGTCGVLLLSLVITLYC |
| 20 | CD8α transmembrane domain nucleic acid sequence | atctacatctgggcgcccttggccgggacttgtggggtccttctcctg tcactggttatcaccctttactgc |

TABLE 1-continued

| SEQ ID NO: | Description | Sequence |
|---|---|---|
| 21 | 4-1BB amino acid sequence | KRGRKKLLYIFKQPFMRPVQTTQEEDGCSCRFPEEEEGGCEL |
| 22 | 4-1BB nucleic acid sequence | aaacggggcagaaagaaactcctgtatatattcaaacaaccatttatg agaccagtacaaactactcaagaggaagatggctgtagctgccgattt ccagaagaagaagaaggaggatgtgaactg |
| 23 | CD3 zeta domain amino acid sequence | RVKFSRSADAPAYQQGQNQLYNELNLGRREEYDVLDKRRGRDPEMGGK PRRKNPQEGLYNELQKDKMAEAYSEIGMKGERRRGKGHDGLYQGLSTA TKDTYDALHMQALPPR |
| 24 | CD3 zeta domain nucleic acid sequence | agagtgaagttcagcaggagcgcagacgcccccgcgtaccagcagggc cagaaccagctctataacgagctcaatctaggacgaagagaggagtac gatgttttggacaagagacgtggccgggaccctgagatggggggaaag ccgagaaggaagaaccctcaggaaggcctgtacaatgaactgcagaaa gataagatggcggaggcctacagtgagattgggatgaaaggcgagcgc cggaggggcaaggggcacgatggcctttaccagggtctcagtacagcc accaaggacacctacgacgcccttcacatgcaggccctgccccctcgc |
| 25 | CD3 zeta Q14K domain amino acid sequence | RVKFSRSADAPAYKQGQNQLYNELNLGRREEYDVLDKRRGRDPEMGGK PRRKNPQEGLYNELQKDKMAEAYSEIGMKGERRRGKGHDGLYQGLSTA TKDTYDALHMQALPPR |
| 26 | CD3 zeta Q14K domain nucleic acid sequence | agagtgaagttcagcaggagcgcagacgcccccgcgtacaagcagggc cagaaccagctctataacgagctcaatctaggacgaagagaggagtac gatgttttggacaagagacgtggccgggaccctgagatggggggaaag ccgagaaggaagaaccctcaggaaggcctgtacaatgaactgcagaaa gataagatggcggaggcctacagtgagattgggatgaaaggcgagcgc cggaggggcaaggggcacgatggcctttaccagggtctcagtacagcc accaaggacacctacgacgcccttcacatgcaggccctgccccctcgc taa |
| 27 | CD28 transmembrane domain amino acid sequence | FWVLVVVGGVLACYSLLVTVAFIIFWV |
| 28 | CD28 transmembrane domain nucleic acid sequence | ttttgggtgctggtggtggttggtggagtcctggcttgctatagcttg ctagtaacagtggcctttattattttctgggtg |
| 29 | CD28 intracellular domain amino acid sequence | RSKRSRLLHSDYMNMTPRRPGPTRKHYQPYAPPRDFAAYRS |
| 30 | CD28 intracellular domain nucleic acid sequence | aggagtaagaggagcaggctcctgcacagtgactacatgaacatgact ccccgccgccccgggcccacccgcaagcattaccagccctatgcccca ccacgcgacttcgcagcctatcgctcc |
| 31 | LC CDR1 | GSSTGAVTASNYAN |
| 32 | LC CDR2 | GHNNRPP |
| 33 | LC CDR3 | ALWYSDHWV |
| 34 | HC CDR1 | GFSLTDYGVH |
| 35 | HC CDR2 (hC825G54C) | VIWSCGGTAYNTALIS |
| 36 | HC CDR2 | VIWSGGGTAYNTALIS |
| 37 | HC CDR3 | RGSYPYNYFDA |
| 38 | pELNS-hC825-28Z | gagtgggttacatcgaactggatctcaacagcggtaagatccttgaga gttttcgccccgaagaacgttttccaatgatgagcacttttaaagttc tgctatgtggcgcggtattatcccgtattgacgccgggcaagagcaac tcggtcgccgcatacactattctcagaatgacttggttgagtactcac cagtcacagaaaagcatcttacggatggcatgacagtaagagaattat gcagtgctgccataaccatgagtgataacactgcggccaacttacttc tgacaacgatcggaggaccgaaggagctaaccgcttttttgcacaaca tgggggatcatgtaactcgccttgatcgttgggaaccggagctgaatg aagccataccaaacgacgagcgtgacaccacgatgcctgtagcaatgg |

TABLE 1-continued

| SEQ ID NO: | Description | Sequence |
|---|---|---|
| | | caacaacgttgcgcaaactattaactggcgaactacttactctagctt cccggcaacaattaatagactggatggaggcggataaagttgcaggac cacttctgcgctcggcccttccggctggctggtttattgctgataaat ctggagccggtgagcgtgggtctcgcggtatcattgcagcactggggc cagatggtaagccctcccgtatcgtagttatctacacgacggggagtc aggcaactatggatgaacgaaatagacagatcgctgagataggtgcct cactgattaagcattggtaactgtcagaccaagtttactcatatatac tttagattgatttaaaacttcatttttaatttaaaaggatctaggtga agatcctttttgataatctcatgaccaaaatcccttaacgtgagtttt cgttccactgagcgtcagaccccgtagaaaagatcaaaggatcttctt gagatcctttttttctgcgcgtaatctgctgcttgcaaacaaaaaaac caccgctaccagcggtggtttgtttgccggatcaagagctaccaactc tttttccgaaggtaactggcttcagcagagcgcagataccaaatactg tccttctagtgtagccgtagttaggccaccacttcaagaactctgtag caccgcctacatacctcgctctgctaatcctgttaccagtggctgctg ccagtggcgataagtcgtgtcttaccgggttggactcaagacgatagt taccggataaggcgcagcggtcgggctgaacggggggttcgtgcacac agcccagcttggagcgaacgacctacaccgaactgagatacctacagc gtgagctatgagaaagcgccacgcttcccgaagggagaaaggcggaca ggtatccggtaagcggcagggtcggaacaggagagcgcacgagggagc ttccagggggaaacgcctggtatctttatagtcctgtcgggtttcgcc acctctgacttgagcgtcgatttttgtgatgctcgtcaggggggcgga gcctatggaaaaacgccagcaacgcggcctttttacggttcctggcct tttgctggccttttgctcacatgttctttcctgcgttatcccctgatt ctgtggataaccgtattaccgcctttgagtgagctgataccgctcgcc gcagccgaacgaccgagcgcagcgagtcagtgagcgaggaagcggaag agcgcccaatacgcaaaccgcctctccccgcgcgttggccgattcatt aatgcagctggcacgacaggtttcccgactggaaagcgggcagtgagc gcaacgcaattaatgtgagttagctcactcattaggcaccccaggctt tacactttatgcttccggctcgtatgttgtgtggaattgtgagcggat aacaatttcacacaggaaacagctatgaccatgattacgccaagcgcg caattaaccctcactaaagggaacaaaagctggagctgcaagcttaat gtagtcttatgcaatactcttgtagtcttgcaacatggtaacgatgag ttagcaacatgccttacaaggagagaaaaagcaccgtgcatgccgatt ggtggaagtaaggtggtacgatcgtgccttattaggaaggcaacagac gggtctgacatggattggacgaaccactgaattgccgcattgcagaga tattgtatttaagtgcctagctcgatacaataaacgggtctctctggt tagaccagatctgagcctgggagctctctggctaactagggaacccac tgcttaagcctcaataaagcttgccttgagtgcttcaagtagtgtgtg cccgtctgttgtgtgactctggtaactagagatccctcagaccctttt agtcagtgtggaaaatctctagcagtggcgcccgaacagggacctgaa agcgaaagggaaaccagagctctctcgacgcaggactcggcttgctga agcgcgcacggcaagaggcgaggggcggcgactggtgagtacgccaaa aattttgactagcggaggctagaaggagagagatgggtgcgagagcgt cagtattaagcgggggagaattagatcgcgatgggaaaaaattcggtt aaggccagggggaaagaaaaaatataaattaaaacatatagtatgggc aagcagggagctagaacgattcgcagttaatcctggcctgttagaaac atcagaaggctgtagacaaatactgggacagctacaaccatcccttca gacaggatcagaagaacttagatcattatataatacagtagcaaccct ctattgtgtgcatcaaaggatagagataaaagacaccaaggaagcttt agacaagatagaggaagagcaaaacaaaagtaagaccaccgcacagca agcggccgctgatcttcagacctggaggaggagatatgagggacaatt ggagaagtgaattatataaatataaagtagtaaaaattgaaccattag gagtagcacccaccaaggcaaagagaagagtggtgcagagagaaaaaa gagcagtgggaataggagctttgttccttgggttcttgggagcagcag gaagcactatgggcgcagcctcaatgacgctgacggtacaggccagac aattattgtctggtatagtgcagcagcagaacaatttgctgagggcta ttgaggcgcaacagcatctgttgcaactcacagtctggggcatcaagc agctccaggcaagaatcctggctgtggaaagatacctaaaggatcaac agctcctggggatttggggttgctctggaaaactcatttgcaccactg ctgtgccttggaatgctagttggagtaataaatctctggaacagattg gaatcacacgacctggatggagtgggacagagaaattaacaattacac aagcttaatacactccttaattgaagaatcgcaaaaccagcaagaaaa gaatgaacaagaattattggaattagataaatgggcaagtttgtggaa ttggtttaacataacaaattggctgtggtatataaaattattcataat gatagtaggaggcttggtaggtttaagaatagtttttgctgtactttc tatagtgaatagagttaggcagggatattcaccattatcgtttcagac ccacctcccaaccccgaggggacccgacaggcccgaaggaatagaaga agaaggtggagagagagacagagacagatccattcgattagtgaacgg atctcgacggtatcgattagactgtagcccaggaatatggcagctaga ttgtacacatttagaaggaaaagttatcttggtagcagttcatgtagc cagtggatatatagaagcagaagtaattccagcagagacagggcaaga aacagcatacttcctcttaaaattagcaggaagatggccagtaaaaac agtacatacagacaatggcagcaatttcaccagtactacagttaaggc cgcctgttggtgggcggggatcaagcaggaatttggcattccctacaa tccccaaagtcaaggagtaatagaatctatgaataaagaattaaagaa |

TABLE 1-continued

| SEQ ID NO: | Description | Sequence |
|---|---|---|
| | | aattataggacaggtaagagatcaggctgaacatcttaagacagcagt |
| | | acaaatggcagtattcatccacaattttaaaagaaaaggggggattgg |
| | | ggggtacagtgcaggggaaagaatagtagacataatagcaacagacat |
| | | acaaactaaagaattacaaaaacaaattacaaaaattcaaaattttcg |
| | | ggtttattacagggacagcagagatccagtttggctgcatacgcgtcg |
| | | tgaggctccggtgcccgtcagtgggcagagcgcacatcgcccacagtc |
| | | cccgagaagttggggggaggggtcggcaattgaaccggtgcctagaga |
| | | aggtggcgcggggtaaactgggaaagtgatgtcgtgtactggctccgc |
| | | ctttttcccgagggtgggggagaaccgtatataagtgcagtagtcgcc |
| | | gtgaacgttctttttcgcaacgggtttgccgccagaacacaggtaagt |
| | | gccgtgtgtggttcccgcgggcctggcctctttacgggttatggccct |
| | | tgcgtgccttgaattacttccacctggctgcagtacgtgattcttgat |
| | | cccgagcttcgggttggaagtgggtgggagagttcgaggccttgcgct |
| | | taaggagccccttcgcctcgtgcttgagttgaggcctggcctgggcgc |
| | | tggggccgccgcgtgcgaatctggtggcaccttcgcgcctgtctcgct |
| | | gctttcgataagtctctagccatttaaaatttttgatgacctgctgcg |
| | | acgctttttttctggcaagatagtcttgtaaatgcgggccaagatctg |
| | | cacactggtatttcggtttttggggccgcgggcggcgacggggcccgt |
| | | gcgtcccagcgcacatgttcggcgaggcggggcctgcgagcgcggcca |
| | | ccgagaatcggacgggggtagtctcaagctggccggcctgctctggtg |
| | | cctggcctcgcgccgccgtgtatcgccccgccctgggcggcaaggctg |
| | | gcccggtcggcaccagttgcgtgagcggaaagatggccgcttcccggc |
| | | cctgctgcagggagctcaaaatggaggacgcggcgctcgggagagcgg |
| | | gcgggtgagtcacccacacaaaggaaaagggcctttccgtcctcagcc |
| | | gtcgcttcatgtgactccacggagtaccgggcgccgtccaggcacctc |
| | | gattagttctcgagcttttggagtacgtcgtctttaggttggggggag |
| | | gggttttatgcgatggagtttccccacactgagtgggtggagactgaa |
| | | gttaggccagcttggcacttgatgtaattctccttggaatttgccctt |
| | | tttgagtttggatcttggttcattctcaagcctcagacagtggttcaa |
| | | agtttttttcttccatttcaggtgtcgtgagctagacgactagtcgtc |
| | | tagctctagaatggccttaccagtgaccgccttgctcctgccgctggc |
| | | cttgctgctccacgccgccaggccgggatcccatgttcagttagtcga |
| | | gtccggtggaggactggtgcaaccaggaggttctctgagattgtcctg |
| | | tgccgcctctggctttagtctgacagattacggagtgcactgggttag |
| | | gcaggcccctgggaaaggtttggaatggttaggagttatttggtccgg |
| | | cggagggacagcttacaataccgcactgatttcaagattcactatctc |
| | | aagggataacagcaagaacacattgtatctgcaaatgaatagcttgag |
| | | agccgaggacaccgctgtctattactgtgctagaaggggtagttatcc |
| | | ctacaactatttcgacgcatggggctgcggaactctggtcacagtgtc |
| | | ttccggtggaggagggagcggtggaggagggagtggtggaggagggtc |
| | | tcaggcagtggtgacacaagaacccagtttgaccgtctctccaggtgg |
| | | cactgtgacattaacctgtgggtcaagcactggtgctgttacagcaag |
| | | caactacgcaaattgggtgcagcagaaacctgggcagtgtcctcgggg |
| | | cctgattggcgggcataataacagacctcctggggtgccagctcggtt |
| | | cagcggcagcctgctgggagggaaggcagctctgaccctgctgggagc |
| | | acagcctgaggacgaagcagagtactattgcgccctgtggtactctga |
| | | tcactgggtcatcggtggtggaaccaagctgactgtcttgggcgctag |
| | | caccacgacgccagcgccgcgaccaccaacaccggcgcccaccatcgc |
| | | gtcgcagcccctgtccctgcgcccagaggcgtgccggccagcggcggg |
| | | gggcgcagtgcacacgagggggctggacttcgcctgtgatttttgggt |
| | | gctggtggtggttggtggagtcctggcttgctatagcttgctagtaac |
| | | agtggcctttattattttctgggtgaggagtaagaggagcaggctcct |
| | | gcacagtgactacatgaacatgactccccgccgccccgggcccacccg |
| | | caagcattaccagccctatgccccaccacgcgacttcgcagcctatcg |
| | | ctccatcgatagagtgaagttcagcaggagcgcagacgcccccgcgta |
| | | ccagcagggccagaaccagctctataacgagctcaatctaggacgaag |
| | | agaggagtacgatgttttggacaagagacgtggccgggaccctgagat |
| | | ggggggaaagccgagaaggaagaaccctcaggaaggcctgtacaatga |
| | | actgcagaaagataagatggcggaggcctacagtgagattgggatgaa |
| | | aggcgagcgccggaggggcaaggggcacgatggcctttaccagggtct |
| | | cagtacagccaccaaggacacctacgacgcccttcacatgcaggccct |
| | | gccccctcgctaagtcgacaatcaacctctggattacaaaatttgtga |
| | | aagattgactggtattcttaactatgttgctccttttacgctatgtgg |
| | | atacgctgctttaatgcctttgtatcatgctattgcttcccgtatggc |
| | | tttcattttctcctccttgtataaatcctggttgctgtctctttatga |
| | | ggagttgtggcccgttgtcaggcaacgtggcgtggtgtgcactgtgtt |
| | | tgctgacgcaacccccactggttggggcattgccaccacctgtcagct |
| | | cctttccgggactttcgctttccccctccctattgccacggcggaact |
| | | catcgccgcctgccttgcccgctgctggacaggggctcggctgttggg |
| | | cactgacaattccgtggtgttgtcggggaagctgacgtcctttccatg |
| | | gctgctcgcctgtgttgccacctggattctgcgcgggacgtccttctg |
| | | ctacgtcccttcggccctcaatccagcggaccttccttcccgcggcct |
| | | gctgccggctctgcggcctcttccgcgtcttcgccttcgccctcagac |
| | | gagtcggatctccctttgggccgcctccccgcctggaattcgagctcg |
| | | gtacctttaagaccaatgacttacaaggcagctgtagatcttagccac |
| | | tttttaaaagaaaaggggggactggaagggctaattcactcccaacga |

TABLE 1-continued

| SEQ ID NO: | Description | Sequence |
|---|---|---|
| | | agacaagatctgcttttttgcttgtactgggtctctctggttagaccag<br>atctgagcctgggagctctctggctaactagggaacccactgcttaag<br>cctcaataaagcttgccttgagtgcttcaagtagtgtgtgcccgtctg<br>ttgtgtgactctggtaactagagatccctcagacccttttagtcagtg<br>tggaaaatctctagcagtagtagttcatgtcatcttattattcagtat<br>ttataacttgcaaagaaatgaatatcagagagtgagaggaacttgttt<br>attgcagcttataatggttacaaataaagcaatagcatcacaaatttc<br>acaaataaagcatttttttcactgcattctagttgtggtttgtccaaa<br>ctcatcaatgtatcttatcatgtctggctctagctatcccgcccctaa<br>ctccgcccagttccgcccattctccgccccatggctgactaattttttt<br>ttatttatgcagaggccgaggccgcctcggcctctgagctattccaga<br>agtagtgaggaggcttttttggaggcctagctaggcttttgcgtcgag<br>acgtacccaattcgccctatagtgagtcgtattacgcgcgctcactgg<br>ccgtcgttttacaacgtcgtgactgggaaaaccctggcgttacccaac<br>ttaatcgccttgcagcacatccccctttcgccagctggcgtaatagcg<br>aagaggcccgcaccgatcgcccttcccaacagttgcgcagcctgaatg<br>gcgaatggcgcgacgcgccctgtagcggcgcattaagcgcggcgggtg<br>tggtggttacgcgcagcgtgaccgctacacttgccagcgccctagcgc<br>ccgctcctttcgctttcttcccttcctttctcgccacgttcgccggct<br>ttccccgtcaagctctaaatcgggggctccctttagggttccgattta<br>gtgctttacggcacctcgaccccaaaaaacttgattagggtgatggtt<br>cacgtagtgggccatcgccctgatagacggtttttcgccctttgacgt<br>tggagtccacgttctttaatagtggactcttgttccaaactggaacaa<br>cactcaaccctatctcggtctattcttttgatttataagggattttgc<br>cgatttcggcctattggttaaaaaatgagctgatttaacaaaaattta<br>acgcgaattttaacaaaatattaacgtttacaatttcccaggtggcac<br>ttttcggggaaatgtgcgcggaacccctatttgtttatttttctaaat<br>acattcaaatatgtatccgctcatgagacaataaccctgataaatgct<br>tcaataatattgaaaaaggaagagtatgagtattcaacatttccgtgt<br>cgcccttattcccttttttgcggcattttgccttcctgtttttgctca<br>cccagaaacgctggtgaaagtaaaagatgctgaagatcagttgggtgc<br>ac |

DOTA-Conjugated Targeting Ligands In certain aspects, the invention provides a Universal Immune Receptor (UnivIR) CAR system comprising a modified T cell comprising a DOTA CAR and a DOTA-conjugated targeting ligand. In certain embodiments, the targeting ligand comprises an antibody. In certain embodiments, the targeting ligand targets a tumor antigen.

Tumor antigens are proteins that are produced by tumor cells that elicit an immune response, particularly T-cell mediated immune responses. The selection of the DOTA-conjugated antibody of the invention will depend on the particular type of cancer to be treated. Tumor antigens are well known in the art and include, for example, a Her2/neu, EGFR, EpCAM, folate receptor alpha (FRa), CD20, CD37, glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, folate receptor beta (FRβ), and mesothelin. In a preferred embodiment, the tumor antigen is selected from the group consisting of CD20, CD37, EpCAM, folate receptor (FRa), mesothelin, and EGFR, HER2, and any combination thereof.

In certain embodiments, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and is not expressed in other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding proteincyclophilin C-associated protein, TAAL6, TAG72, TLP, and TPS.

In certain embodiments, the targeting ligand targets a disease-related antigen. For example, the targeting ligand can target an antigen involved in autoimmunity. Autoimmune antigens can include, but are not limited to, Dsg1, Dsg3, CEA, La/SSB, TCRs, MOG, GP2, paraneoplastic antigens (e.g. PNMA-3, Jo-1, SRP-54, CARP VIII, etc) and cognate epitopes of autoantibodies (e.g. anti-Hu, anti-Ri, anti-Tr, etc).

In certain embodiments, the UnivIR CAR system includes multiple DOTA-conjugated antibodies with multiple antigen specificities. For example, the UnivIR CAR system may include a first DOTA-conjugated antibody that is specific for a first tumor antigen (e.g. Her2) and a second DOTA-conjugated antibody that is specific for a second tumor antigen (e.g. EGFR). The UnivIR CAR system may optionally comprise a third DOTA-conjugated antibody that is specific for a third tumor antigen (e.g. FRa), and so on and so forth.

DOTA-Comprising Compounds

In certain aspects, the invention provides a DOTA-comprising compound, which further comprises a linker, or a salt, solvate, enantiomer, or diastereoisomer thereof. In certain embodiments, the linker comprises one or more functionalities that allow for attachment of the DOTA-comprising compound to other compounds of interest. The invention includes the DOTA-comprising compounds, as well as the adducts of those DOTA-comprising compounds with other molecules of interest, such as antibodies, scFv's, imaging reagents, and so forth, as described herein.

In certain embodiments, the DOTA-comprising compound comprises DOTA (1,4,7,10-tetraazacyclododecane-1,4,7,10-tetraacetic acid), and/or its complex with a metal ion. Non-limiting examples of metals that can be chelated by DOTA include Y, Ca, Lu, Gd, In, Ga, Mg, Ni, Cu, Zn, and Fe, and also include radioactive metals for imaging such as Y-86, In-111, Ga-68, Cu-64, Cu-60, or Tc-99m. The DOTA can be covalently attached to the linker through any chemistry known in the art. In one example, the DOTA can be covalently attached to the linker through at least one of the DOTA's carboxylic acid: in this particular case, the attachment can be achieved through formation of an amide or ester bond between the DOTA and the linker. In another example, the DOTA can be covalently attached to the linker through at least one of the carbon atoms in the tetraazacyclododecane ring and/or through at least one of the methylene groups of at least one of the four carboxylic acid groups in DOTA.

In certain embodiments, the linker can be any linker known in the art, as long as the presence of the linker does not significantly disturb the DOTA's ability to complex a metal ion and/or to bind to the anti-metal ion-DOTA scFv.

In certain embodiments, the compound and/or linker comprises the formula (I), or a salt, metal ion complex, solvate, enantiomer, or diastereoisomer thereof:

$$*—X^1—(CH_2)_{m1}—(phenylene)_{0\text{-}1}—X^2—[CH_2—(CH_2)_y—X^3]_{m2}—(CH_2)_{m3}—X^4 \quad (I)$$

In certain embodiments, the targeting ligand comprises a commercially available monoclonal antibody specific for a tumor antigen. Examples of such antibodies include but are not limited to HERCEPTIN®, Mov18, Cetuximab, and Rituximab (RITUXAN®).

In certain embodiments, the targeting ligand is selected from the group consisting of an scFv, a DARPin, a Fab, and a small molecule.

In certain embodiments, the small molecule comprises folic acid. In certain embodiments, the small molecule is folic acid.

In certain embodiments, the DOTA is conjugated to the targeting ligand (e.g. antibody) by a covalent linkage. In certain embodiments, the CAR affinity for DOTA-labeled targeting ligands is tuned by changing the linker (e.g. NHS-DOTA vs. SCN-DOTA) and/or addition of a chelated metal ion (metals such as Y, Ca, Lu, Gd, In, Ga, Mg, Ni, Cu, Zn, or Fe). In certain embodiments, the antibody is labeled with $^{89}$Zr-desferrioxamine chelate (DFO). In certain embodiments, the antibody is labeled with trans-cyclooctene (TCO). In certain embodiments, the DOTA CAR is mutated to contain a cysteine or lysine that is capable of forming a covalent bond with a DOTA-conjugated antibody that has a thiol-reactive or amine-reactive group (e.g. irr-Y-DOTA-$N_3$-TFP).

wherein:

the bond marked as * indicates the attachment point to the DOTA;

m1 is selected from the group consisting of 0, 1, 2, 3, 4, 5, 6, 7, 8, 9, 11, 12, 13, 14, 15, 16, 17, 18, 19, and 20;

m2 is selected from the group consisting of 0, 1, 2, 3, 4, 5, 6, 7, 8, 9, 10, 11, 12, 13, 14, 15, 16, 17, 18, 19, and 20;

m3 is selected from the group consisting of 0, 1, 2, 3, 4, 5, 6, 7, 8, 9, 10, 11, 12, 13, 14, 15, 16, 17, 18, 19, and 20;

$X^1$ is selected from the group consisting of absent (a bond), O, and $N(R^3)$; each $X^2$ and $X^3$ is independently selected from the group consisting of absent (a bond), —O—, —C(=O)$NR^3$—, —$N(R^3)$C(=O)—, —C(=S)$NR^3$—, —$N(R^3)$C(=S)—, —NHC(=S)NH—, —$N(R^3)$—, —$CH(R^3)$—, —NHC(=O)CH=CH—, —NHC(=O)CH=CH—$CH_2$N(R)—, —NHC(=O)CH=CH—$CH_2$—(N-linked heterocyclylene)-, —NHC(=O)C≡C—, —NHC(=S)CH=CH—, —NHC(=S)CH=CH—$CH_2$N(R)—, —NHC(=S)CH=CH—$CH_2$—(N-linked heterocyclylene)-, —NHC(=S)C≡C—, —NHS(=O)CH=CH—, —NHS(=O)CH=CH—$CH_2$N(R)—, —NHS(=O)CH=CH—$CH_2$—(N-linked heterocyclylene)-, —NHS(=O)C≡C—, —NHS(=O)$_2$CH=CH—, —NHS(=O)$_2$CH=CH—$CH_2$N(R)—, —NHS(=O)$_2$CH=CH—$CH_2$—(N-linked heterocyclylene)-, —NHS(=O)$_2$C≡C—, —C(=O)CH=CH—, —C(=O)CH=CH—$CH_2$N(R)—, —C(=O)CH=CH—$CH_2$—(N-linked heterocyclylene)-, —C(=O)C≡C—, —S(=O)CH=CH—, —S(=O)CH=CH—$CH_2$N(R)—, —S(=O)CH=CH—$CH_2$—(N-linked heterocyclylene)-, —S(=O)C≡C—, —S(=O)$_2$CH=CH—, —S(=O)$_2$CH=CH—$CH_2$N(R)—, —S(=O)$_2$CH=CH—$CH_2$—(N-linked heterocyclylene)-, and —S(=O)$_2$C≡C—;

each occurrence of y is independently 0 or 1;

$X^4$ is selected from the group consisting of H, —OH, —$NH_2$, halogen (including Cl, Br, I, and F, such as but not limited to $^{18}$F, or any other isotope thereof), —$R^3$, —C(=O)OH, a carboxylic ester, C(=O)N($R^3$)($CH_2$)$_{2-10}$$NH_2$, —NH-folate, —C(=O)N($R^3$)($CH_2$)$_{2-10}$NH-folate, —NH-phenylene-$CH_2$-DOTA (and/or its complex with a metal ion), —NHC(=S)NH-phenylene-$CH_2$-DOTA (and/or its complex with a metal ion), an alkyne (including a strained alkyne), and maleimido;

each $R^3$ is independently selected from the group consisting of H, -folate, —$CH_2CH_2$NH-folate, —C(=O)$CH_2CH_2$NH-folate, —C(=O)NH$CH_2CH_2$NH-folate, -phenylene-$CH_2$-DOTA (and/or its complex with a metal ion), —C(=O)NH-phenylene-$CH_2$-DOTA (and/or its complex with a metal ion), —NHC(=S)NH-phenylene-$CH_2$-DOTA (and/or its complex with a metal ion), —C(=O)CH=$CH_2$, —C(=O)CH=CH—$CH_2NR_2$, —C(=S)CH=$CH_2$, —C(=S)CH=CH—$CH_2NR_2$, —S(=O)CH=$CH_2$, —S(=O)CH=CH—$CH_2NR_2$, —S(=O)$_2$CH=$CH_2$, —S(=O)$_2$CH=CH—$CH_2NR_2$, —C(=O)C≡CR, —S(=O)C≡CR, —S(=O)$_2$C≡CR, optionally substituted $C_1$-$C_6$ alkyl, optionally substituted $C_3$-$C_8$ cycloalkyl, and optionally substituted $C_3$-$C_8$ cycloheteroalkyl;

each occurrence of R is independently H, optionally substituted $C_1$-$C_6$ alkyl, optionally substituted $C_3$-$C_8$ cycloalkyl, or optionally substituted $C_3$-$C_8$ cycloheteroalkyl, or two R bound to the same N atom can combine to form an optionally substituted 3-8-membered heterocyclyl.

The invention contemplates that the compound and/or linker can comprise one or more functional groups that allow for their covalent coupling(s)/conjugation(s) to one or more other molecules. In certain embodiments, the compound and/or linker comprises an amino group, which can be coupled through an amide bond to another molecule comprising a carboxylic acid (carboxylate) group. In certain embodiments, the compound and/or linker comprises a carboxylic acid (carboxylate) group, which can be coupled through an amide bond to another molecule comprising an amine group. In certain embodiments, the compound and/or linker comprises a hydroxyl group, which can be coupled through an ester bond to another molecule comprising a carboxylic acid (carboxylate) group. In certain embodiments, the compound and/or linker comprises a carboxylic acid (carboxylate) group, which can be coupled through an ester bond to another molecule comprising a hydroxyl group. In certain embodiments, the compound and/or linker comprises a leaving group (such as but not limited to a halogen, tosylate, mesylate, triflate, and the like), which can be coupled through nucleophilic displacement to another molecule comprising a nucleophilic group (such as but not limited to a thiol, hydroxyl, amine, or carboxylic acid). In certain embodiments, the compound and/or linker comprises a nucleophilic group (such as but not limited to a thiol, hydroxyl, amine, or carboxylic acid), which can be coupled through nucleophilic displacement to another molecule comprising a leaving group (such as but not limited to a halogen, tosylate, mesylate, triflate, and the like). In certain embodiments, the compound and/or linker comprises a group that is represented with an open valency (such as the generic alkyl group R—$CH_2$—), and that group can be linked through a single covalent bond to another molecule. This list is not exhausting and it means to be illustrative only. Any other reactions and reagents known to promote intermolecular coupling are incorporated herein. Any of these compounds and the corresponding conjugates are contemplated within the invention.

In certain embodiments, the compound and/or linker contemplated in the invention), or a salt, metal ion complex, solvate, enantiomer, or diastereoisomer thereof, comprises:

$$[\text{DOTA-}X^1\text{—}(CH_2)_{m1}\text{-(phenylene)}_{0\text{-}1}\text{-}X^2\text{—}[CH_2\text{—}(CH_2)_y\text{—}X^3]_{m2}\text{—}(CH_2)_{m3}\text{—}X^4\text{—}]_{m4}X^5 \quad \text{(II)}$$

wherein:

m4 is 2, 3, or 4;

$X^5$ is a polyvalent group such that:

m4=2 and $X^5$ is A or A($X^6$)($X^6$), wherein A is $CH_2$, NH, O, S, S(=O), or S(=O)$_2$;

m4=3 and $X^5$ is A or A($X^6$)($X^6$)($X^6$), wherein A is CH or N;

m4=4 and $X^5$ is A or A($X^6$)($X^6$)($X^6$)($X^6$), wherein A is C;

wherein each occurrence of $X^6$ is independently a bond, —($CH_2$)$_{1-12}$—*, —($CH_2$)$_{0-11}$C(=O)OH, —($CH_2$)$_{1-11}$$NH_2$, or —($CH_2$)$_{1-12}$OH, wherein the bond marked as * indicates the attachment point to the $X^4$ and wherein the functional group marked in bold is chemically conjugated to the $X^4$.

One skilled in the art would contemplate that each pairing of $X^4$ and $X^5$ is conjugated through chemistry that is compatible with and appropriate for the chemical groups involved. In a non-limiting embodiment, in the cases where $X^4$ comprises a carboxylic group and $X^5$ comprises an amine group, the conjugation can take place through formation of an amide bond. In a non-limiting embodiment, in the cases where $X^4$ comprises a leaving group (such as but not limited to a halogen) and $X^5$ comprises an amine or hydroxyl group, the conjugation can take place through formation of an amine or ether bond, respectively. In a non-limiting embodiment, in the cases where $X^4$ comprises an amine group and $X^5$ comprises a carboxylic group, the conjugation can take place through formation of an amide bond.

In certain embodiments, $X^1$ is absent (a bond). In certain embodiments, $X^1$ is O. In certain embodiments, $X^1$ is N($R^3$).

In certain embodiments, $X^2$ is absent (a bond). In certain embodiments, $X^2$ is —O—. In certain embodiments, $X^2$ is —C(=O)N$R^3$—. In certain embodiments, $X^2$ is —N($R^3$)C(=O)—. In certain embodiments, $X^2$ is —C(=S)N$R^3$—. In certain embodiments, $X^2$ is —N($R^3$)C(=S)—. In certain embodiments, $X^2$ is —NHC(=S)NH—. In certain embodiments, $X^2$ is —N($R^3$)—. In certain embodiments, $X^2$ is —CH($R^3$)—. In certain embodiments, $X^2$ is —NHC(=O)CH=CH—. In certain embodiments, $X^2$ is —NHC(=O)CH=CH—$CH_2$N(R)—. In certain embodiments, $X^2$ is —NHC(=O)CH=CH—$CH_2$—(N-linked heterocyclylene)-. In certain embodiments, $X^2$ is —NHC(=O)C≡C—. In certain embodiments, $X^2$ is —NHC(=S)CH=CH—. In certain embodiments, $X^2$ is —NHC(=S)CH=CH—$CH_2$N(R)—. In certain embodiments, $X^2$ is —NHC(=S)CH=CH—$CH_2$—(N-linked heterocyclylene)-. In certain embodiments, $X^2$ is —NHC(=S)C≡C—. In certain embodiments, $X^2$ is —NHS(=O)CH=CH—. In certain embodiments, $X^2$ is —NHS(=O)CH=CH—$CH_2$N(R)—. In certain embodiments, $X^2$ is —NHS(=O)CH=CH—$CH_2$—(N-linked heterocyclylene)-. In certain embodiments, $X^2$ is —NHS(=O)C≡C—. In certain embodiments, $X^2$ is —NHS(=O)$_2$CH=CH—. In certain embodiments, $X^2$ is —NHS(=O)$_2$CH=CH—$CH_2$N(R)—. In certain embodiments, $X^2$ is —NHS(=O)$_2$CH=CH—$CH_2$—(N-linked heterocyclylene)-. In certain embodiments, $X^2$ is —NHS(=O)$_2$C≡C—. In certain embodiments, $X^2$ is —C(=O)CH=CH—. In certain embodiments, $X^2$ is —C(=O)CH=CH—$CH_2$N(R)—. In certain embodiments, $X^2$ is —C(=O)CH=CH—$CH_2$—(N-linked heterocyclylene)-. In certain embodiments, $X^2$ is —C(=O)C≡C—, —S(=O)CH=CH—. In certain embodiments, $X^2$ is —S(=O)CH=CH—$CH_2$N(R)—. In certain embodiments, $X^2$ is —S(=O)CH=CH—$CH_2$—(N-linked heterocyclylene)-. In certain embodiments, $X^2$ is —S(=O)C≡C—. In certain embodiments, $X^2$ is —S(=O)$_2$CH=CH—. In certain embodiments, $X^2$ is —S(=O)$_2$CH=CH—$CH_2$N(R)—. In certain embodiments, $X^2$ is —S(=O)$_2$CH=CH—$CH_2$—(N-linked heterocyclylene)-. In certain embodiments, $X^2$ is —S(=O)$_2$C≡C—.

In certain embodiments, $X^3$ is absent (a bond). In certain embodiments, $X^3$ is —O—. In certain embodiments, $X^3$ is —C(=O)N$R^3$—. In certain embodiments, $X^3$ is —N($R^3$)C(=O)—. In certain embodiments, $X^3$ is —C(=S)N$R^3$—. In certain embodiments, $X^3$ is —N($R^3$)C(=S)—. In certain embodiments, $X^3$ is —NHC(=S)NH—. In certain embodiments, $X^3$ is —N($R^3$)—. In certain embodiments, $X^3$ is —CH($R^3$)—. In certain embodiments, $X^3$ is —NHC(=O)CH=CH—. In certain embodiments, $X^3$ is —NHC(=O)CH=CH—$CH_2$N(R)—. In certain embodiments, $X^3$ is —NHC(=O)CH=CH—$CH_2$—(N-linked heterocyclylene)-. In certain embodiments, $X^3$ is —NHC(=O)C≡C—. In certain embodiments, $X^3$ is —NHC(=S)CH=CH—. In certain embodiments, $X^3$ is —NHC(=S)CH=CH—$CH_2$N(R)—. In certain embodiments, $X^3$ is —NHC(=S)CH=CH—$CH_2$—(N-linked heterocyclylene)-. In certain embodiments, $X^3$ is —NHC(=S)C≡C—. In certain embodiments, $X^3$ is —NHS(=O)CH=CH—. In certain embodiments, $X^3$ is —NHS(=O)CH=CH—$CH_2$N(R)—. In certain embodiments, $X^3$ is —NHS(=O)CH=CH—$CH_2$—(N-linked heterocyclylene)-. In certain embodiments, $X^3$ is —NHS(=O)C≡C—. In certain embodiments, $X^3$ is —NHS(=O)$_2$CH=CH—. In certain embodiments, $X^3$ is —NHS(=O)$_2$CH=CH—$CH_2$N(R)—. In certain embodiments, $X^3$ is —NHS(=O)$_2$CH=CH—$CH_2$—(N-linked heterocyclylene)-. In certain embodiments, $X^3$ is —NHS(=O)$_2$C≡C—. In certain embodiments, $X^3$ is —C(=O)CH=CH—. In certain embodiments, $X^3$ is —C(=O)CH=CH—$CH_2$N(R)—. In certain embodiments, $X^3$ is —C(=O)CH=CH—$CH_2$—(N-linked heterocyclylene)-. In certain embodiments, $X^3$ is —C(=O)C≡C—, —S(=O)CH=CH—. In certain embodiments, $X^3$ is —S(=O)CH=CH—$CH_2$N(R)—. In certain embodiments, $X^3$ is —S(=O)CH=CH—$CH_2$—(N-linked heterocyclylene)-. In certain embodiments, $X^3$ is —S(=O)C≡C—. In certain embodiments, $X^3$ is —S(=O)$_2$CH=CH—. In certain embodiments, $X^3$ is —S(=O)$_2$CH=CH—$CH_2$N(R)—. In certain embodiments, $X^3$ is —S(=O)$_2$CH=CH—$CH_2$—(N-linked heterocyclylene)-. In certain embodiments, $X^3$ is —S(=O)$_2$C≡C—.

In certain embodiments, y is 0. In certain embodiments, y is 1.

In certain embodiments, $X^4$ is H. In certain embodiments, $X^4$ is F. In certain embodiments, $X^4$ is Cl. In certain embodiments, $X^4$ is Br. In certain embodiments, $X^4$ is I. In certain embodiments, $X^4$ is —OH. In certain embodiments, $X^4$ is —$NH_2$. In certain embodiments, $X^4$ is —$R^3$. In certain embodiments, $X^4$ is —C(=O)OH. In certain embodiments, $X^4$ is —C(=O)N($R^3$)($CH_2$)$_{2\text{-}10}$$NH_2$. In certain embodiments, $X^4$ is —NH-folate. In certain embodiments, $X^4$ is —C(=O)N($R^3$)($CH_2$)$_{2\text{-}10}$NH-folate. In certain embodiments, $X^4$ is —NH— phenylene-$CH_2$-DOTA (and/or its complex with a metal ion). In certain embodiments, $X^4$ is —NHC(=S)NH-phenylene-$CH_2$-DOTA (and/or its complex with a metal ion). In certain embodiments, $X^4$ is a carboxylic ester. In certain embodiments, $X^4$ is an alkyne. In certain embodiments, $X^4$ is maleimido.

In certain embodiments, $R^3$ is H. In certain embodiments, $R^3$ is -folate. In certain embodiments, $R^3$ is —$CH_2CH_2$NH-folate. In certain embodiments, $R^3$ is —C(=O)$CH_2CH_2$NH-folate. In certain embodiments, $R^3$ is —C(=O)NH$CH_2CH_2$NH-folate. In certain embodiments, $R^3$ is -phenylene-$CH_2$-DOTA (and/or its complex with a metal ion). In certain embodiments, $R^3$ is —C(=O)NH-phenylene-$CH_2$-DOTA (and/or its complex with a metal ion). In certain embodiments, $R^3$ is —NHC(=S)NH-phenylene-$CH_2$-DOTA (and/or its complex with a metal ion). In certain embodiments, $R^3$ is —C(=O)CH=$CH_2$. In certain embodiments, $R^3$ is —C(=O)CH=CH—$CH_2NR_2$. In certain embodiments, $R^3$ is —C(=S)CH=$CH_2$. In certain embodiments, $R^3$ is —C(=S)CH=CH—$CH_2NR_2$. In certain embodiments, $R^3$ is —S(=O)CH=$CH_2$. In certain embodiments, $R^3$ is —S(=O)CH=CH—$CH_2NR_2$. In certain embodiments, $R^3$ is —S(=O)$_2$CH=$CH_2$. In certain embodiments, $R^3$ is —S(=O)$_2$CH=CH—$CH_2NR_2$. In certain embodiments, $R^3$ is —C(=O)C≡CR, —S(=O)C≡CR. In certain embodiments, $R^3$ is —S(=O)$_2$C≡CR. In certain embodiments, $R^3$ is optionally substituted $C_1$-$C_6$ alkyl. In certain embodiments, $R^3$ is optionally substituted $C_3$-$C_8$ cycloalkyl. In certain embodiments, $R^3$ is optionally substituted $C_3$-$C_8$ cycloheteroalkyl.

In certain embodiments, R is H. In certain embodiments, R is optionally substituted $C_1$-$C_6$ alkyl. In certain embodiments, R is optionally substituted $C_3$-$C_8$ cycloalkyl. In certain embodiments, R is optionally substituted $C_3$-$C_8$ cycloheteroalkyl. In certain embodiments, two R bound to the same N atom can combine to form an optionally substituted 3-8-membered heterocyclyl.

In certain embodiments, m4 is 2. In certain embodiments, m4 is 3. In certain embodiments, m4 is 4.

In certain embodiments, $X^5$ is A. In certain embodiments, $X^5$ is A($X^6$)($X^6$). In certain embodiments, $X^5$ is A($X^6$)($X^6$)($X^6$). In certain embodiments, $X^5$ is A($X^6$)($X^6$)($X^6$)($X^6$). In certain embodiments, A is $CH_2$. In certain embodiments, A is NH. In certain embodiments, A is O. In certain embodiments, A is S. In certain embodiments, A is S(=O). In certain embodiments, A is or S(=O)$_2$. In certain embodiments, A is CH. In certain embodiments, A is N. In certain embodiments, A is C. In certain embodiments, $X^6$ is a bond. In certain embodiments, $X^6$ is $-(CH_2)_{1-12}-*$. In certain embodiments, $X^6$ is $-(CH_2)_{1-11}NH_2$. In certain embodiments, $X^6$ is $-(CH_2)_{0-11}C(=O)OH$. In certain embodiments, $X^6$ is $-(CH_2)_{1-12}OH$. In certain embodiments, the bond marked as * indicates the attachment point to the $X^4$ and wherein the functional group marked in bold is chemically conjugated to the $X^4$.

In certain embodiments, at least one $R^3$ is substituted with at least one $^{18}F$.

In certain embodiments, the N-linked heterocyclyl comprises one of the following:

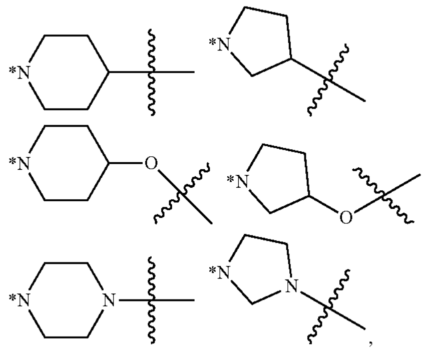

wherein the *N is bound to $NHC(=O)CH=CH-CH_2-$.

In certain embodiments, each phenylene is independently selected from the group consisting of 1,2-phenylene, 1,3-phenylene, and 1,4-phenylene. In certain embodiments, at least one phenylene is 1,2-phenylene. In certain embodiments, at least one phenylene is 1,3-phenylene. In certain embodiments, at least one phenylene is 1,4-phenylene.

In certain embodiments, at least one of the $X^1$, $X^2$, $X^3$, $X^4$, and $R^3$ groups comprises a group that is capable of forming a covalent bond with a thiol group (a thio-reactive group), such as the thiol group in a cysteine residue, or an amine group (an amine-reactive group) such as the amine group in a lysine residue. For example, a cysteine or lysine group can be engineered on the surface of the anti-Y-DOTA scFv, in proximity of the binding site of the Y-DOTA to the anti-Y-DOTA scFv. In that case, once the DOTA-comprising compound binds to the anti-Y-DOTA scFv, the linker comprising the thio-reactive or amine-reactive group is brought in close proximity to the scFv surface cysteine or lysine group, allowing for formation of a covalent bond between the linker and the scFv (i.e., the thiol group of the cysteine residue reacts with the thio-reactive group, or the amine group of the lysine reacts with the amine-reactive group). In certain embodiments, the thio-reactive or amine-reactive group is present in the $R^3$ group attached to $X^1$. In other embodiments, the thio-reactive or amine-reactive group is present in the $R^3$ group attached to $X^2$. In other embodiments, the thio-reactive or amine-reactive group is present in $X^2$. In yet other embodiments, the thio-reactive or amine-reactive group is present in the $R^3$ group attached to $X^3$. In other embodiments, the thio-reactive or amine-reactive group is present in $X^3$. In other embodiments, the thio-reactive or amine-reactive group is present in the $R^3$ group attached to $X^4$. In yet other embodiments, the thio-reactive or amine-reactive group is present in $X^4$.Non-limiting examples of such thio-reactive or amine-reactive groups are $-C(=O)CH=CH_2$, $-S(=O)CH=CH_2$, $-S(=O)_2CH=CH_2$, $-C(=O)CH=CH-CH_2NR_2$, $-S(=O)CH=CH-CH_2NR_2$, $-S(=O)_2CH=CH-CH_2NR_2$, $C(=O)C\equiv CH$, $S(=O)C\equiv CH$, $S(=O)_2C\equiv CH$, α,β-unsaturated ketones, α,β-unsaturated esters, α,β-unsaturated amides, α,β-unsaturated sulfones, α,β-unsaturated sulfoxides, α,β-unsaturated sulfonamides, propargyl ketones, propargyl esters, propargyl amides, propargyl sulfones, propargyl sulfoxides, propargyl sulfonamides, maleimides, α-chloro amides, disulfides, 5-fluoro-2,4-dinitrobenzene, and so forth.

In certain embodiments, at least one of the $R^3$ groups comprises a group that allows for imaging of the DOTA-comprising compound and its adducts with biological compounds. Non-limiting examples of such detectable $R^3$ groups include $^{18}F$, $^{11}C$, $^{89}Zr$, $^{68}Ga$, $^{68}Y$, $^{64}Cu$, $^{60}Cu$, $^{123}I$, $^{124}I$, $^{125}I$ $^{111}In$, $^{99m}Tc$.

In certain embodiments, at least one of the $R^3$ groups comprises an azido group, which allows for covalent attachment to other molecules through a click reaction. For example, the azido group can react with an alkyne in the presence of copper ions to form a 5-membered heteroatom ring: a Cu(I)-catalyzed azide-alkyne cycloaddition (CuAAC). For example, the azido group can react with a strained difluorooctyne (DIFO) or a strained dibenzocyclooctyne (DBCO, which comprises the group

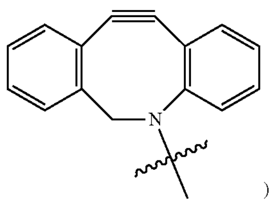 [SMILES: *N1Cc2ccccc2C#Cc2ccccc21]

)

in copper-free conditions: strain-promoted azide-alkyne cycloaddition (SPAAC). For example, the azido group can react with activated alkenes, such as oxanorbomadiene, to form triazoles. The invention contemplates the use of any reaction involving the azido group.

In certain embodiments, the azido group of the DOTA-comprising compound is reacted with a compound comprising DBCO or an analogue thereof. In other embodiments, the DBCO-comprising compound further comprises deferoxamine (or desferrioxamine). In that case, the resulting molecule will have the DOTA covalently linked through a linker to the DFO, which can be used for imaging, using for example $^{89}Zr$. In other embodiments, the DBCO-comprising compound further comprises a metal ion chelator such as but not limited to DOTA, NOTA, NODAGA, or DTPA, which can be used for imaging, using for example $^{68}Ga$, $^{64}Cu$, $^{60}Cu$, $^{111}In$, $^{68}Y$, or $^{99m}Tc$.

DFO

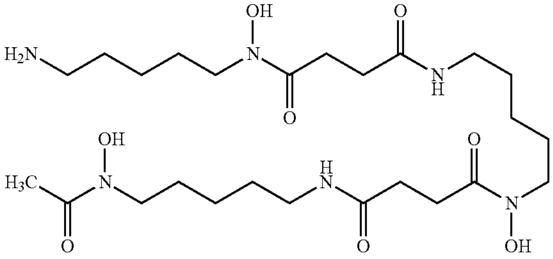

In certain embodiments, the azido group of the DOTA-comprising compound is reacted with a compound comprising DBCO or an analogue thereof. In other embodiments, the DBCO-comprising compound further comprises a trans-cycloctene group (TCO, which comprises the group

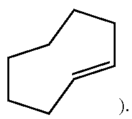

).

In that case, the resulting molecule will have the DOTA covalently linked through a linker to the TCO, which is activated towards Diels-Alder reactions as a dienophile and is capable of reacting accordingly with the diene tetrazine (such as methyltetrazine), or an analogue thereof, as illustrated in a non-limiting manner below. In certain embodiments, the tetrazine further comprises a label, such as but not limited to $^{18}F$, $^{11}C$, $^{123}I$, $^{124}I$, $^{125}I$, $^{89}Zr$, $^{68}Ga$, $^{68}Y$, $^{64}Cu$, $^{60}Cu$, $^{111}In$, or $^{99m}Tc$ which allows for PET or SPECT imaging.

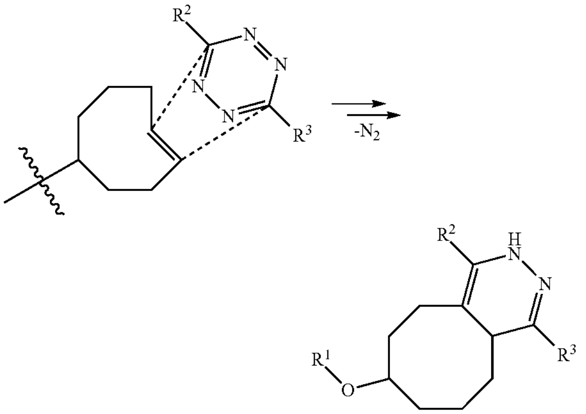

In certain embodiments, $X^4$ is H. In other embodiments, $X^4$ is —OH. In yet other embodiments, $X^4$ is —$NH_2$. In yet other embodiments, $X^4$ is —C(═O)OH. In yet other embodiments, $X^4$ is —C(═O)N($R^3$)$(CH_2)_{2-10}NH_2$. In yet other embodiments, $X^4$ is —NH-folate. In yet other embodiments, $X^4$ is —C(═O)N($R^3$)$(CH_2)_{2-10}$NH-folate. In yet other embodiments, $X^4$ is —NH-phenylene-$CH_2$-DOTA (and/or its complex with a metal ion). In yet other embodiments, $X^4$ is —NHC(═S)NH-phenylene-$CH_2$-DOTA (and/or its complex with a metal ion), In yet other embodiments, $X^4$ is a carboxylic ester, such as $C_1$-$C_6$ alkyl ester or $C_3$-$C_8$ cycloalkyl ester. In yet other embodiments, $X^4$ is an activated carboxylic ester, which is capable of reacting with an amine, such as an amine side chain in a protein, to form a corresponding amide bond. Non-limiting example of activated esters include polyhalophenyl esters (wherein the phenyl ring is substituted with 2, 3, 4, or 5 independently selected halogen atoms), mono- or di-nitrophenyl esters, thioesters, N-hydroxysuccinimido esters, hydroxybenzotriazole esters, and so forth. In yet other embodiments, $X^4$ is an isothiocyanate. In certain embodiments, the DOTA-comprising compound comprising the activated carboxylic ester or isothiocyanate is contacted with a protein (such as, but not limited to, an antibody), wherein at least one surface amino group in the protein will react with the activated carboxylic ester or isothiocyanate, thus attaching the DOTA-comprising compound to the protein. The number of DOTA-comprising compounds attached to the protein will depend on reaction conditions, contact time between the reagents, reactivity of the surface amino group(s), reactivity of the activated ester group or isothiocyanate, and may be manipulated in order to control the number of DOTA-comprising compounds attached to the protein, as known in the art. The number of DOTA-comprising compounds attached to the protein can be determined as known in the art using, for example, any method demonstrated herein or known by one skilled in the art.

In certain embodiments, $X^4$ is an alkyne or strained alkyne, which allows for covalent attachment to other molecules through a click reaction. For example, the alkyne can react with an azide in the presence of copper ions to form a 5-membered heteroatom ring: a Cu(I)-catalyzed azide-alkyne cycloaddition (CuAAC). For example, the strained alkyne can react with an azide in copper-free conditions: a strain-promoted azide-alkyne cycloaddition (SPAAC). Non-limiting examples of strained alkynes include dibenzocyclooctyne (DBCO), bicyclononyne (BCN), monofluorooctyne (MOFO), and difluorocyclooctyne (DIFO). The invention contemplates the use of any reaction involving the alkyne group. In certain embodiments, the antibody can be site-specifically labeled with an azide, which can subsequently be coupled with the DOTA-comprising compound via the alkyne or strained alkyne. Methods of introducing azido groups in a protein (such as, but not limited to, an antibody). Non-limiting examples of such methods include the GlyClick method, which allows for introducing two azido groups of the Fc portion of the antibody (see, for example, Wagner et al., (2015) *Methods Mol. Biol.* 1337: 109-27.

Alternatively, $X^4$ is a thiol-reactive group, which can react with a surface cysteine residue of the protein to form a covalent bond. In that case, the surface cysteine residue can exist in the wild-type form of the protein and/or can be introduced by mutation, using for example site-directed mutagenesis. Non-limiting examples of $X^4$ contemplated include, but are not limited to, maleimido and iodoacetamido.

Methods of Treatment

Certain aspects of the invention provide methods for treating cancer in a subject in need thereof. Certain aspects of the invention provide methods for treating a disease or disorder in a subject in need thereof. In certain embodiments, the method comprises administering to the subject a UnivIR CAR system of the present invention. The UnivIR CAR system can be designed to target a single antigen (e.g. tumor antigen) or multiple antigens and distinct antigens can be targeted sequentially or simultaneously. The antigen specificity (e.g. tumor antigen specificity) can be determined from a patient's own cells (e.g. tumor cells).

In certain aspects, the method of treating cancer comprises administering to the subject a composition comprising a population of DOTA CAR T cells, a population of DOTA-conjugated targeting ligands, and a population of radiolabeled DOTA-comprising compounds. Each DOTA CAR comprises a DOTA-binding domain, a transmembrane domain, and an intracellular domain, and each targeting ligand comprises a labeled antibody that targets a tumor antigen. The cells are imaged in the subject, and a treatment is administered based on the imaging results. In certain embodiments, the antigen specificity of the targeting ligands can be changed based on analysis of target antigen expression using tumor or blood biomarkers.

In certain aspects, the method of treating a disease or disorder comprises administering to the subject a composition comprising a population of DOTA CAR T cells, a population of DOTA-conjugated targeting ligands, and a population of radiolabeled DOTA-comprising compounds. Each DOTA CAR comprises a DOTA-binding domain, a transmembrane domain, and an intracellular domain, and each targeting ligand comprises a labeled antibody that targets a disease-related antigen. The cells are imaged in the subject, and a treatment is administered based on the imaging results and/or based on analysis of target antigen expression using tumor or blood biomarkers.

In certain embodiments, the antigen specificity of the targeting ligands can be changed based on analysis of target antigen expression using tumor or blood biomarkers. Tumor or blood biomarkers can be analyzed by standard methods known to one of ordinary skill in the art. Examples of such method include but are not limited to, microarrays, ELISAs, mass spectrometry, IHC, fluorescence in situ hybridization (FISH), PCR, next generation sequencing, and "liquid biopsies" including assays for circulating free DNA (cfDNA) and circulating tumor DNA (ctDNA).

The antibody can be labeled with any compound suitable for imaging. In certain embodiments, the antibody is labeled with $^{89}$Zr-desferrioxamine chelate (DFO). In certain embodiments, the antibody is labeled with trans-cyclooctene (TCO).

Imaging can be performed by any technique known to one of ordinary skill in the art. For example, imaging can be performed by positron-emission tomography (PET), single-photon emission computed tomography (SPECT) and/or computed tomography (CT or CAT) scanning.

Administering and imaging the cells allows for noninvasively monitoring in target tumors and/or elsewhere in the body. For example, cells may be imaged in the tumor itself, providing information on the efficacy of the CAR T cell therapy, and/or the cells can be imaged at a site distal to the tumor to determine whether any off-tumor effects are present.

The population of DOTA-conjugated targeting ligands may comprise antibodies that are specific for a single tumor antigen. Alternatively the population may comprise antibodies that are specific for multiple, distinct tumor antigens. The distinct tumor antigens can be targeted sequentially or simultaneously. The types of antibodies chosen will depend on the type of cancer to be treated. The antigen specificity can be determined from a patient's own cells.

The composition can be administered as a single dose or as multiple doses over a period of time. The method provides a means of collecting imaging results over time and adjusting the tumor antigen specificity of the targeting ligands based on these results.

The tumor antigen specificity of the targeting ligands can be changed based on on-target toxicity, off-target toxicity, cytokine release syndrome (CRR), or other factors that are determined based on the results of the imaging. The level of CAR T cell activity in vivo may also be controlled based on the imaging results. For example, the number of cells, or the dosing of the antibody can be adjusted accordingly.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the UnivIR CAR system of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Other types of diseases or disorders that may be treated with the compositions and methods of the invention include, but are not limited to, autoimmune diseases and chronic viral infections.

In certain embodiments, the disease treated is chronic viral infections. For example, the UnivIR CAR system described herein can be used to target viral envelope proteins or viral surface proteins (e.g. bNAb scFv (HIV), HA protein (influenza), etc).

In certain embodiments, the disease to be treated is an autoimmune disease. For example, the UnivIR CAR system described herein can be used to target a self protein (e.g. CEA, MOG, or GP2 targeted Treg cells via hC825-6z CAR) to suppress autoimmunity, or to target an immunopathogenic cells (e.g. autoimmune B cell targeting through cognate epitopes of autoantibodies or autoimmune T cell targeting via TCR) as a means of abrogating autoimmunity.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., RITUXAN®. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described for example in U.S. Pat. No. 6,120,766).

In certain embodiments, the number of DOTA molecules per targeting ligand (e.g. per antibody) can be varied (increased or decreased) in order to tune the efficacy of the CAR T cells.

Imaging Tools

A set of complementary molecular imaging tools was developed herein that is applicable to CAR T cell therapy. Radiolabeled antibodies, pretargeted imaging, direct radiolabeling of cells for tracking via PET imaging, and the use of PET imaging reporter genes for cell tracking have all been employed as diagnostic tools relatively independently of each other in various settings. A multifunctional Y-DOTA reagent was synthesized herein that is capable of taking advantage of the many molecular imaging methods that currently exist. This unified approach to imaging CAR T cells has the potential to yield insights that wouldn't have been evident with the use of a single molecular imaging biomarker.

The new clinical tools and approaches developed herein merge imaging and cell therapy technologies in order to guide CAR T cells to tumor sites; readily identify risks for toxicity; mitigate CRS and/or on-target toxicity, predict responses to therapy; track infused T cells; and provide a longstanding standardized bioorthogonal platform to the healthcare community.

Tagged and imaging-enabled targeting ligands covalently attached to a universal immune receptor on the T cell surface create on demand CAR T cells. This will dramatically transform the expanding CAR/UnivIR field. The image-guided Y-DOTA-based covalent-linking UnivIR approach stands to provide a useful platform for assembly line-like production of CAR T cells of virtually any specificity. Furthermore, this form of synthetic biology is also poised to permit exquisite control of CAR T cell activity based upon prescribed tagged-antibody dosing. Redirected antigen specificity and image-based tracking can be conferred specifically to UnivIR transduced T cells in vivo, and unlike a bispecific antibody which links TAAs to TCR alone, the UnivIR platform also permits the inclusion of costimulatory signaling to bolster T cell function, proliferation and survival in vivo.

In certain aspects, the invention includes a method of tracking CAR T cells in a subject in vivo. In certain embodiments, the method comprises administering to the subject a composition comprising a population of DOTA CAR T cells and a population of DOTA-conjugated targeting ligands. In certain embodiments, the method comprises administering to the subject a composition comprising a population of DOTA CAR T cells and a population of radiolabeled DOTA-comprising compounds. Each DOTA CAR comprises a DOTA-binding domain, a transmembrane domain, and an intracellular domain, and each targeting ligand comprises a labeled antibody that targets an antigen (e.g. a tumor antigen) and is detectable in vivo. The cells are then imaged in the subject in vivo. In certain embodiments, the covalent (G54C) DOTA CAR hC825G54C-δz is used to image and/or track engineered T cells in vivo. In one non-limiting example, an F-18 labeled DOTA-comprising compound would allow for PET imaging of the T cells upon infusion into a patient. Radiolabeled covalent and non-covalent DOTA-comprising compounds could both be used to image the cells.

In certain embodiments, $^{18}F$ labeled DOTA-comprising compounds (covalent or reversible) can be used to image and or track DOTA CAR T cells. Other imaging radioisotopes (besides $^{18}F$) could also be used including but not limited to $^{11}C$, $^{89}Zr$, $^{68}G$, $^{86}Y$ $^{64}Cu$, $^{60}Cu$, $^{123}I$, $^{124}I$, $^{125}I$, $^{111}In$ $^{99m}Tc$. Other metal ions could also be chelated to DOTA, which comprise Y, Ca, Lu, Gd, In, Ga, Mg, Ni, Cu, Zn, Tc, and/or Fe.

Additional Uses of DOTA CAR

In certain embodiments, a subject DOTA CAR of the present invention (e.g. the covalent (G54C) DOTA CAR comprising a hC825G54C scFv) can be used as a means to direct, accumulate, and retain cells to different organs (e.g. T regs for autoimmunity). This can be done through the covalent attachment of a DOTA-conjugated targeting ligand to the CAR that directs the cells to the organ, with additional dosing of targeting ligand as needed to prolong retention.

In certain embodiments, covalent (G54C) DOTA CAR hC825G54C-δz can also be used as a means to carry a payload to the tumor microenvironment. The receptor can be used to covalently link proteins and/or small molecules that are tagged with DOTA. A T cell co-expressing both the hC825G54C-δz and a standard CAR would be able to target a tumor while also carrying these additional molecules to help bolster efficacy. Payload molecules can include, but are not limited to, small molecule drugs, checkpoint blockade antibodies (PD1, CTLA-4, etc), nanoparticles, matrix degrading enzymes, cytokines, and decoy binding proteins (Fas, PD-1, etc).

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as “gene guns” (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine (“DMPC”) can be obtained from Sigma, St. Louis, MO; dicetyl phosphate (“DCP”) can be obtained from K & K Laboratories (Plainview, NY); cholesterol (“Choi”) can be obtained from Calbiochem-Behring; dimyristyl phosphatidylglycerol (“DMPG”) and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. “Liposome” is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the expanded T cells, transfecting the expanded T cells, and electroporating the expanded T cells. One nucleic acid may be introduced by one method and another nucleic acid may be introduced into the T cell by a different method.

RNA

In one embodiment, the nucleic acids introduced into the T cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain derived from an antibody to a co-stimulatory molecule, and an intracellular domain derived from a portion of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In certain embodiments, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. 5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MEDPULSER™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

In certain embodiments, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Expansion of T Cells

As demonstrated by the data disclosed herein, expanding the T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

Pharmaceutical Compositions

Pharmaceutical compositions of the present invention may comprise the modified T cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the invention to be administered may be autologous, allogeneic or xenogeneic with respect to the subject undergoing therapy.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It can generally be stated that a pharmaceutical composition comprising the modified T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified T cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The results of the experiments are now described.

Example 1: The Anti-DOTA Universal Immune Receptor (UnivIR) Platform

Herein, the current paradigm of randomly circulating, non-trackable, and uncontrollable CAR T cells of single antigen specificity, which restricts patient access to otherwise safe and effective CAR T cell therapy, is challenged (FIG. 1A). An innovative bioorthogonal image-guided Universal Immune Receptor (UnivIR) CAR system was developed that incorporates rationally designed clinically-actionable linking strategies and unique architectures in order to enable unprecedented coupling with a suite of new companion diagnostic imaging tools for (i) image-guided delivery of T cells, (ii) T cell tracking in vivo, (iii) companion tumor antigen expression analyses, (iv) controlled and tumor-localized T cell activity for heightened safety, (v) simultaneous multi-antigen targeting, (vi) simple standardized and rapid CAR-like manufacturing and performance via reversible and irreversible linkage systems, and (vii) adaptable antigen specificity to address antigen heterogeneity and loss (FIGS. 1A-1B).

Figure 1B:
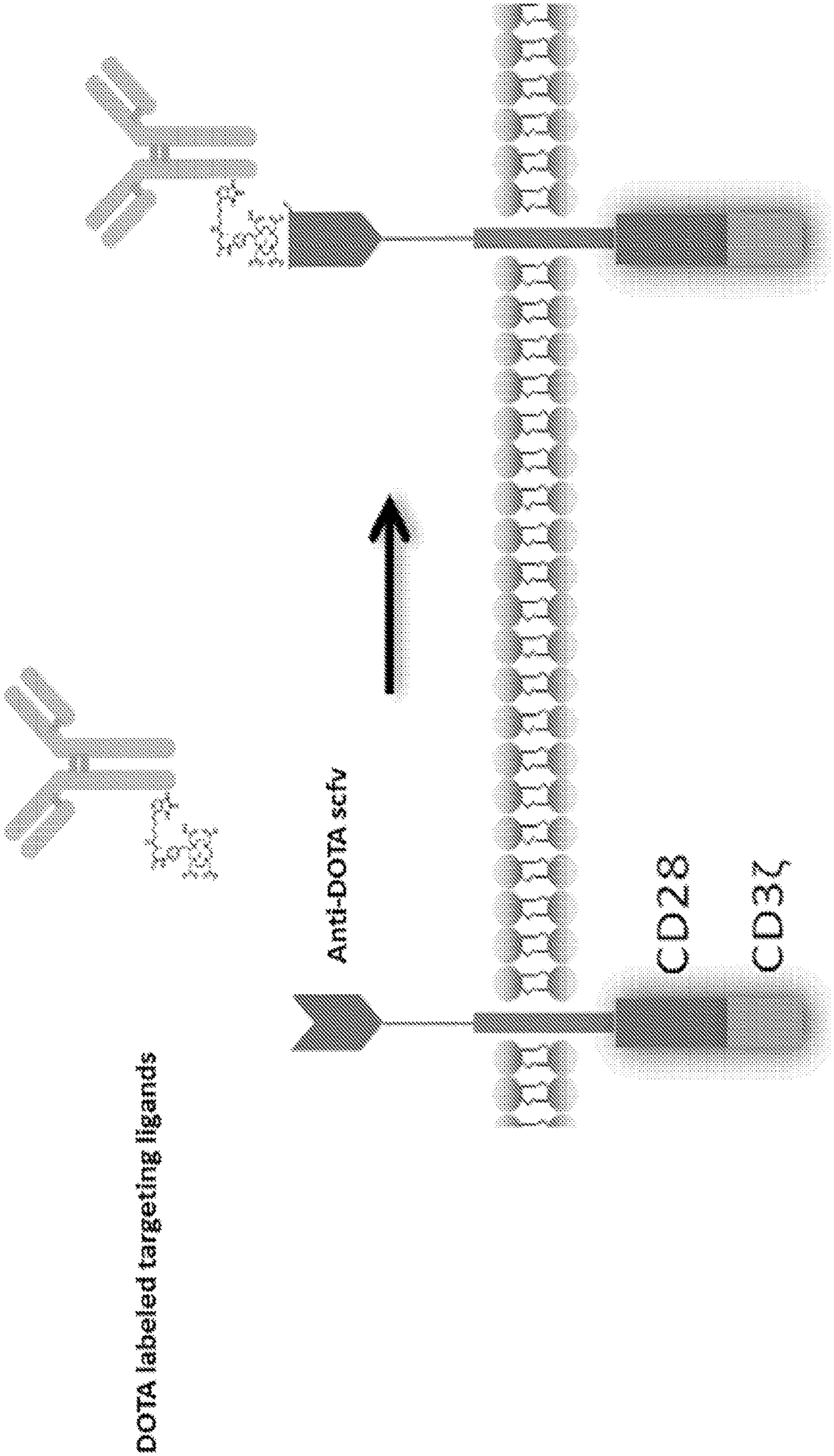

The chelating agent, 1,4,7,10-tetraazacyclododecane-1,4,7,10-tetraacetic acid (DOTA), acts as a unifying functional keystone between pretargeted imaging and CAR T cell therapy to enable image-guided CAR T cell delivery (FIGS. 1A-1B). DOTA-gadolinium (DOTA-Gd) has extensive clinical history as a magnetic resonance imaging (MRI) contrast agent and has an excellent safety profile in humans. A bioorthogonal image-guided T cell delivery (IGTD) method was developed herein using a yttrium(Y)-DOTA-based Universal Immune Receptor (UnivIR) system that is readily standardized and designed to address the most significant challenges in the field of cellular immunotherapy, including focused delivery, controlled activity, patient safety and durability of response.

The UnivIR platform capitalizes on a picomolar affinity anti-Y-DOTA scFv, which binds to antibodies labeled with Y-DOTA (FIG. 1B) (Orcutt et al., *Nucl Med Biol* 38, 223-233 (2011)). This non-covalent system is capable of mediating antigen-specific re-direction and activation of anti-DOTA UnivIR CAR T cells. In the present application, this high affinity non-covalent system was converted into a novel high affinity covalent system. At the same time, a set of molecular imaging tools based on the Y-DOTA system were developed that can be used as companion diagnostic agents in the setting of cellular immunotherapy.

This theranostic IGTD platform provides a useful, adaptable, standardized and simple platform for on-demand production of CAR T cells of virtually any specificity through a covalent linking of immune receptor and targeting ligand. This innovative platform can be used in tandem with a suite of molecular imaging tools for guided T cell delivery, monitoring therapy, predicting response to therapy, and assessing the potential for on-target toxicity.

Figure 2A:
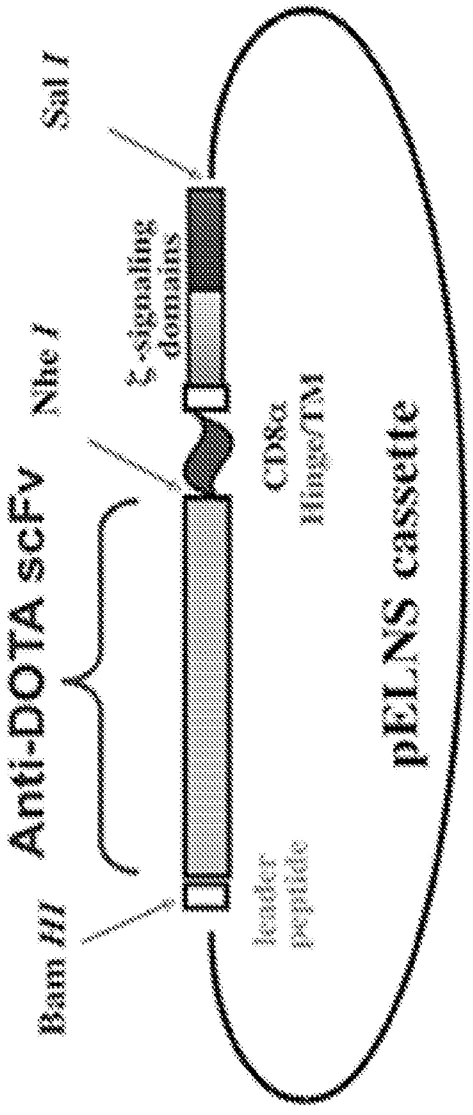
FIGS. 2A-2C illustrate anti-DOTA Universal Immune Receptor constructs and their expression in primary T cells.
Figure 2B:
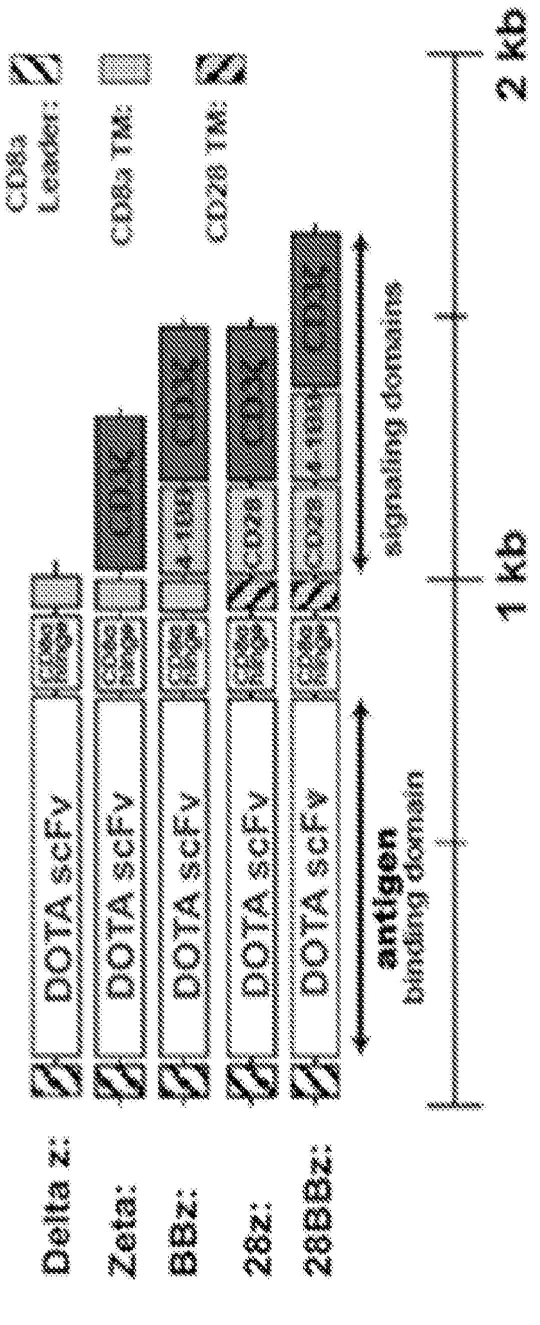
Figure 2C:
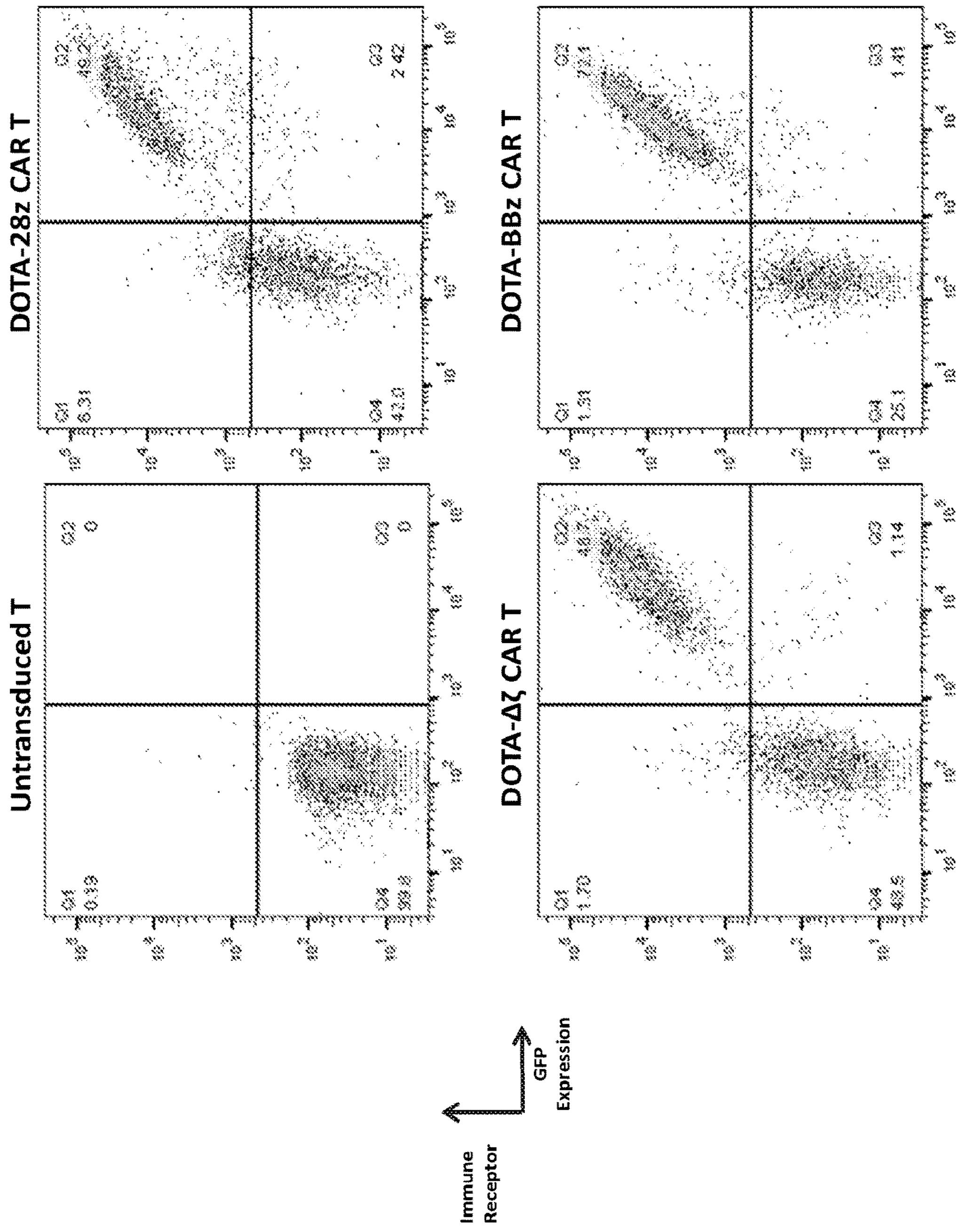

Example 2: Anti-DOTA Universal Immune Receptor Expression, Binding, and Redirected Killing Multiple high affinity, non-covalent anti-Y-DOTA CAR constructs, which incorporated the C8.2.5 scFv for DOTA specificity (Orcutt et al., *Nucl Med Biol* 38, 223-233 (2011)), were developed by retrofitting CAR lentivirus vectors containing various intracellular signaling domains (FIG. 2A-2B). Primary human T cells were transduced with lentivirus containing GFP and these anti-Y-DOTA CAR constructs (FIG. 2C). At 14 days post-transduction, T cells were labeled with polyclonal anti-human IgG antibody to detect CAR expression. Staining of cells was determined by flow cytometric analysis. High efficiency recombinant CAR lentiviral transduction of primary human T cells resulted in hC8.2.5 DOTA CAR expression in >48% of all T cells (FIG. 2C). The DOTA-BBz-CAR was the most highly expressed and was detected in >70% of T cells (FIG. 2C).

Figure 3A:
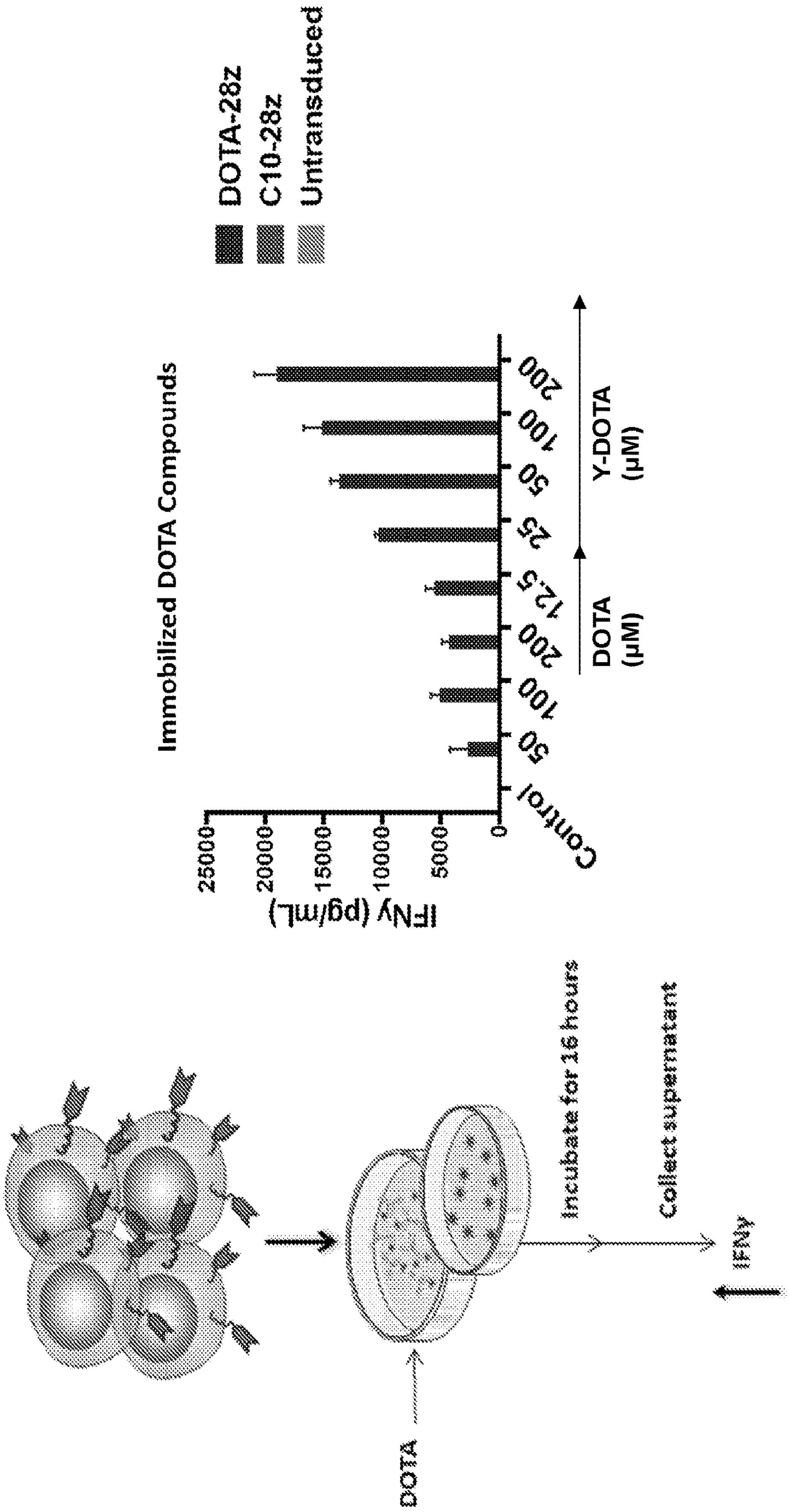
FIGS. 3A-3H illustrate Anti-DOTA Universal Immune Receptor binding and redirected killing.

When stimulated with immobilized non-chelated DOTA, the hC8.2.5 DOTA CAR T cells produced low levels of IFNγ, an effect that was saturating at 100 uM (FIG. 3A). By contrast, stimulation of the same hC8.2.5 DOTA CAR T cells with immobilized Y-DOTA induced a dose-defined activation of T cells that was non-saturating and dramatically heightened at higher concentrations, consistent with the binding affinity of the anti-Y-DOTA scFv to Y-DOTA being several orders of magnitude higher than to DOTA (Orcutt et al., *Nucl Med Biol* 38, 223-233 (2011)).

Figure 3B:
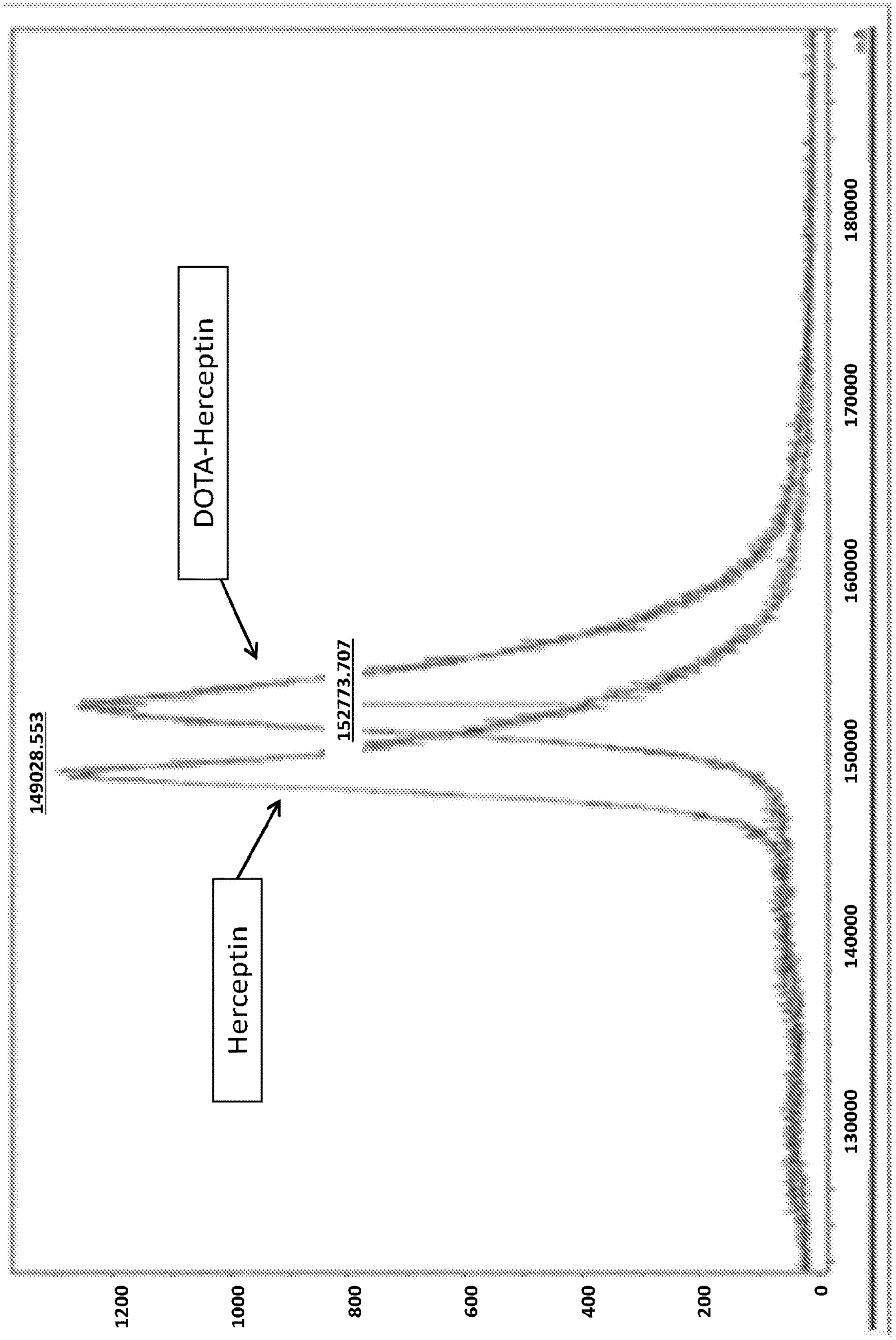
Figure 3C:
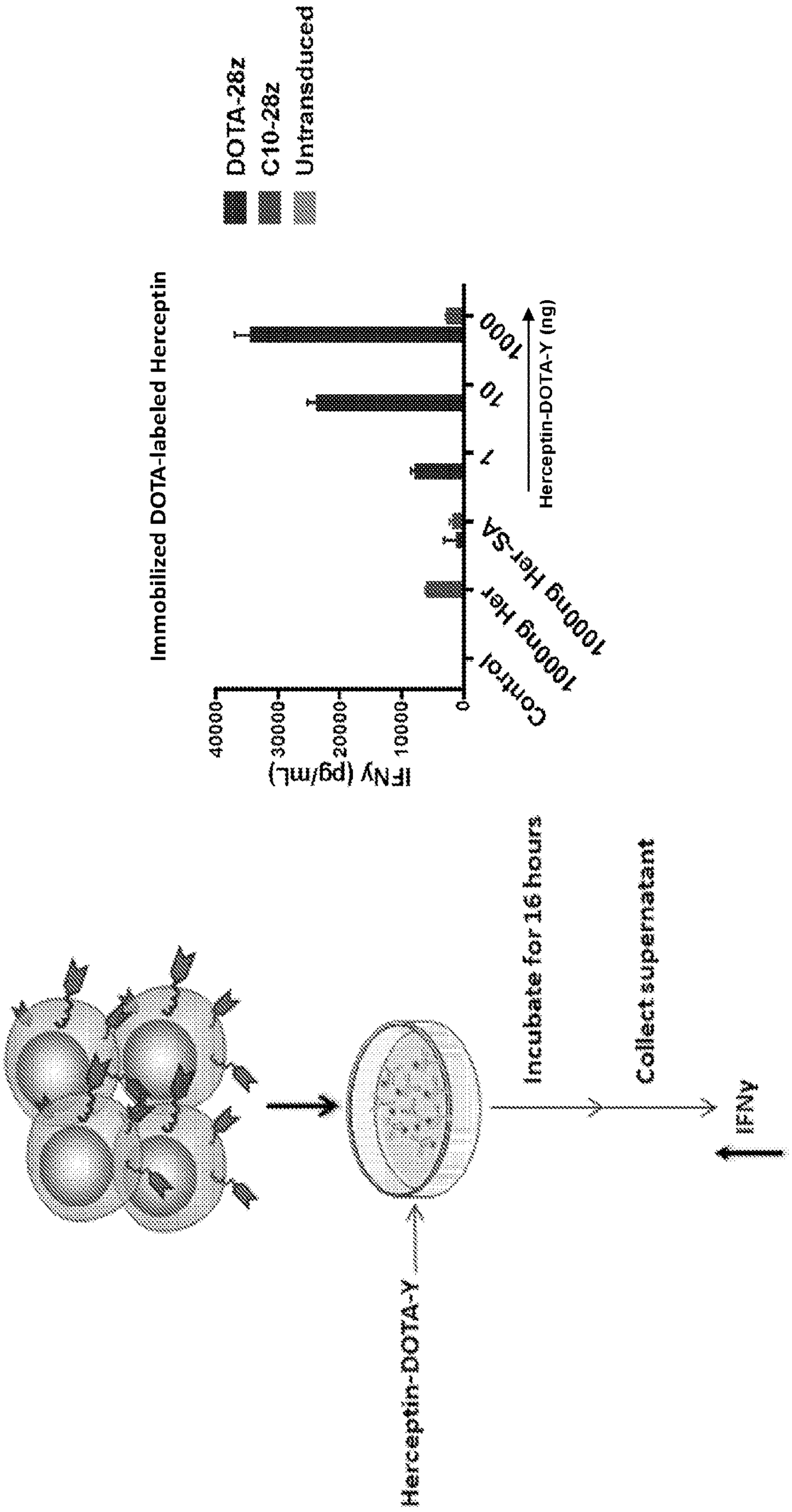

To test whether DOTA CAR T cells can be redirected "on demand" against TAAs expressed on cancer cells, Herceptin was labeled with DOTA using the commercially available DOTA-NHS-ester, and the number of DOTA's per antibody was determined via MALDI-TOF mass spectrometry (FIG. 3B). Incubating the DOTA-conjugated antibodies with yttrium chloride (YCl3) yielded Y-DOTA-conjugated Herceptin Antibodies. Herceptin, Herceptin-Streptavidin, or Herceptin-Streptavidin+Biotin-DOTA-Y antibodies were incubated at various concentrations in a 96-well plate and allowed to passively adhere overnight at 4° C. Plates were washed 2× with PBS and 50,000 immune receptor expressing T cells were added to each well. Plates were incubated at 37° C. and 5% $CO_2$ for 16 hours. Supernatants were harvested and analyzed for IFNγ secretion using a standard IFNγ ELISA kit. Results showed that anti-DOTA immune receptor T cells exhibit cytokine secretion in the presence of immobilized DOTA-Y labeled antibodies (FIG. 3C).

Figure 3D:
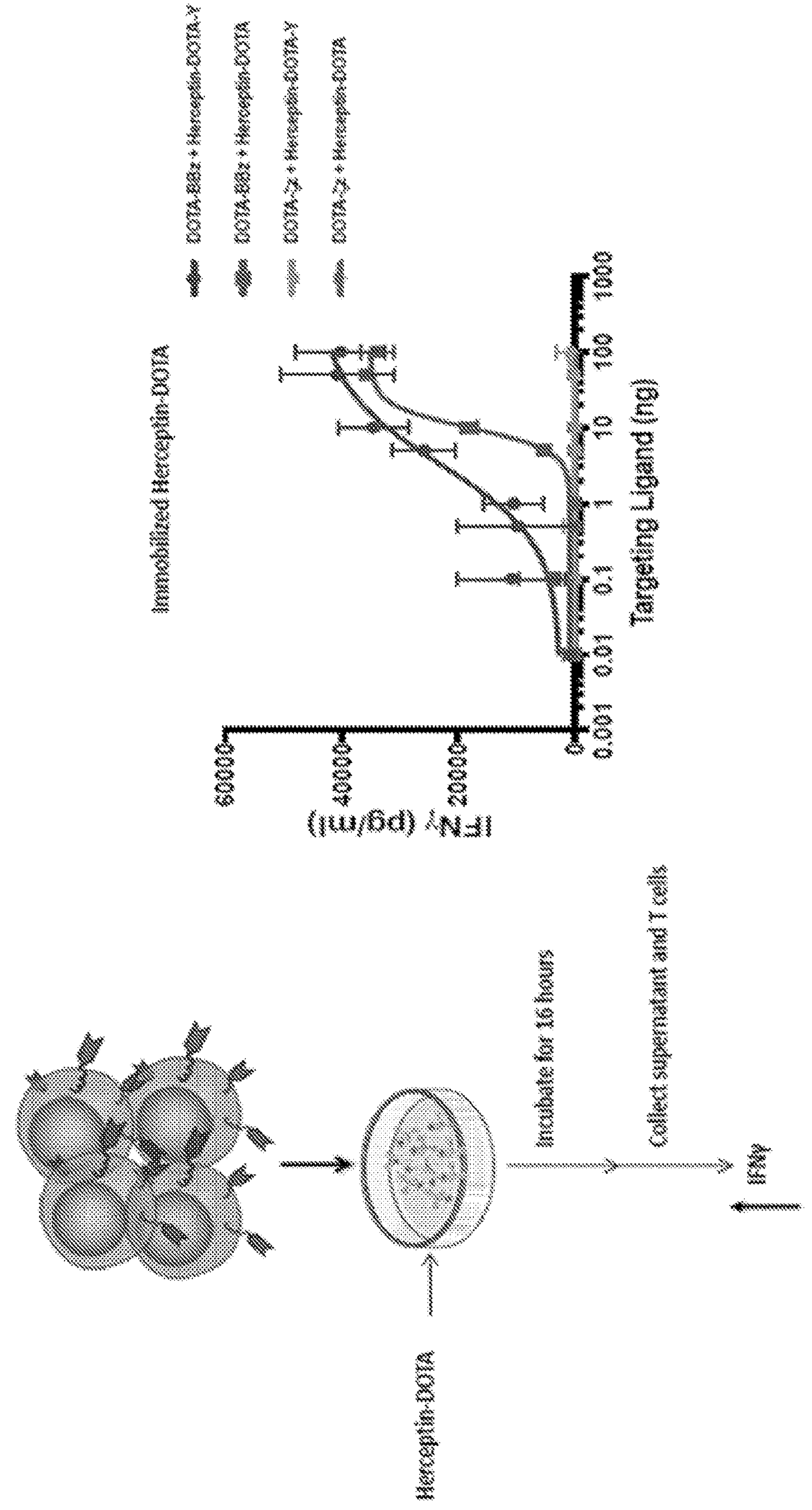
Figure 3E:
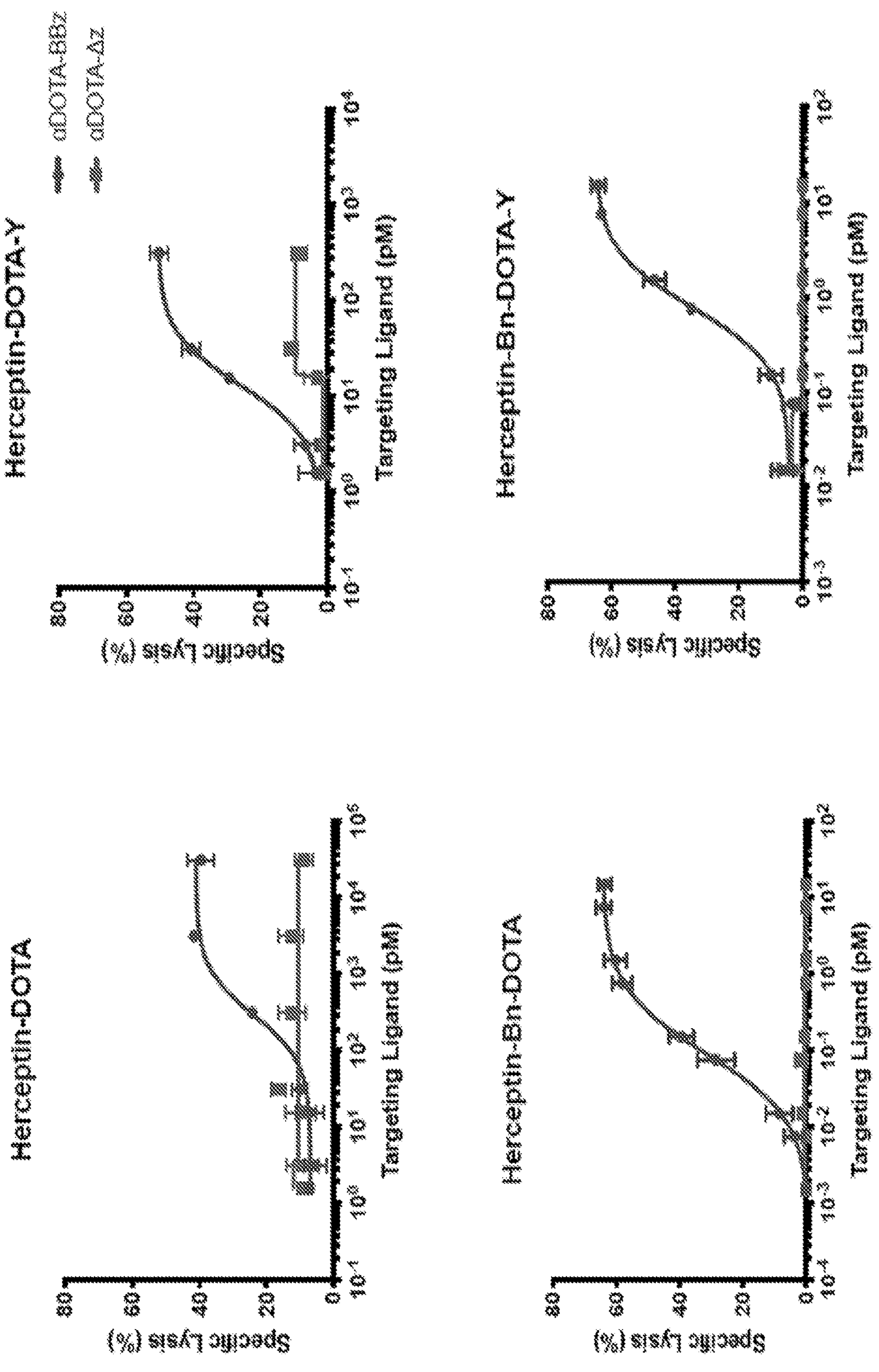
Figure 3F:
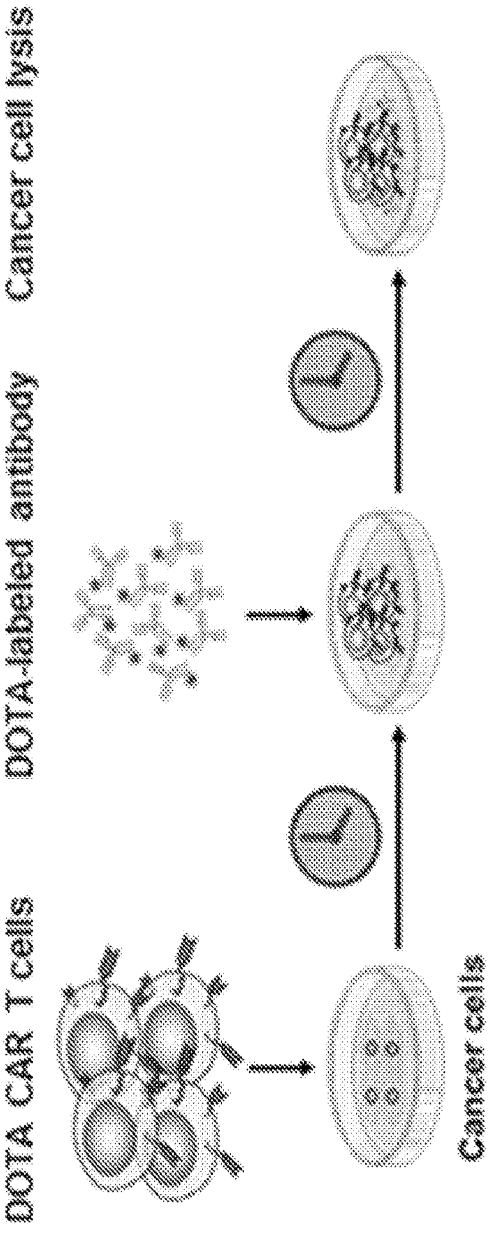
Figure 6A:
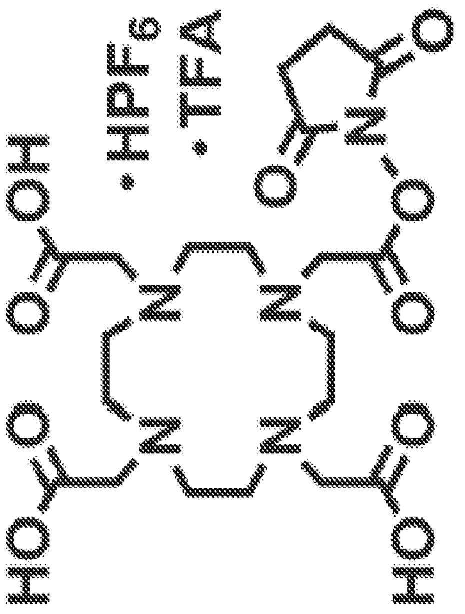
FIGS. 6A-6C illustrate the effects of different DOTA derivatives and the addition of chelating metal ions to receptor-ligand interactions.
Figure 6A:
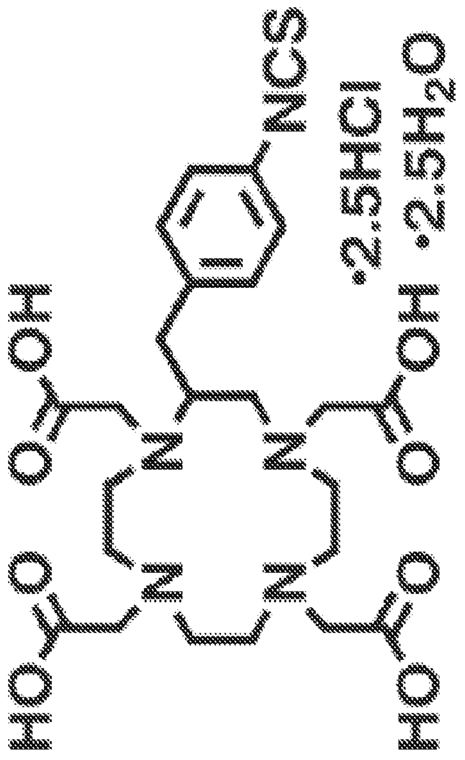
Figure 6B:
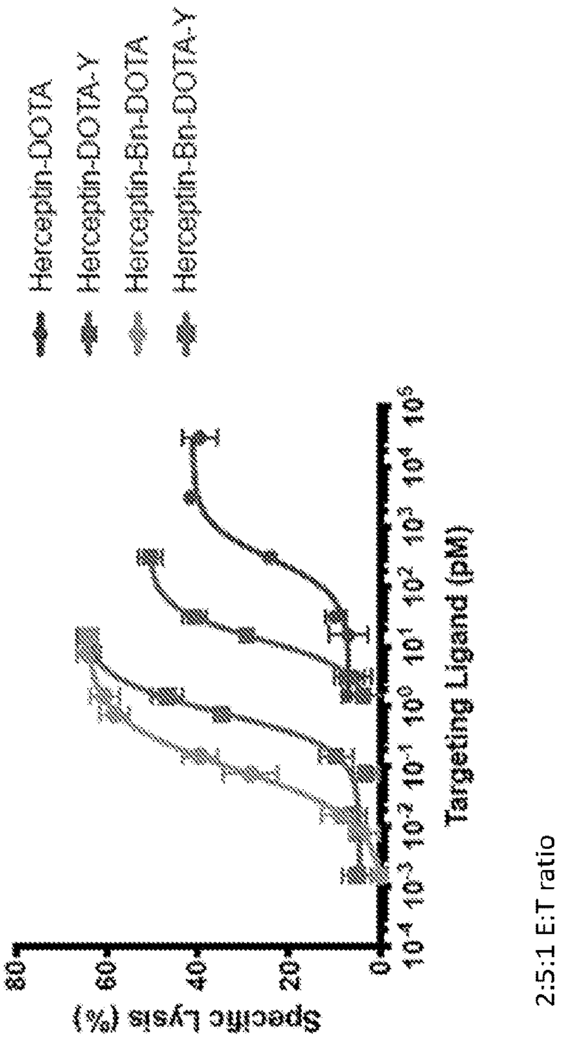

To investigate the ability of DOTA-linked antibodies to trigger effector function in CAR T cells, CAR T cells were incubated with varying amounts of the Her2-specific Herceptin-conjugated DOTA antibody for 16 hours (FIG. 3D). Following this incubation, the supernatant was collected and IFNγ production was measured. The DOTA-BBz-CAR T cells produced IFNγ (FIG. 3D). Results showed that addition of DOTA-conjugated targeting ligands leads to dose-dependent lysis of antigen positive cells (FIG. 3E). Addition of chelated metal ion or altered linker allowed for affinity tuning of the receptor-targeting ligand interaction (FIGS. 3E & 6B).

Figure 3G:
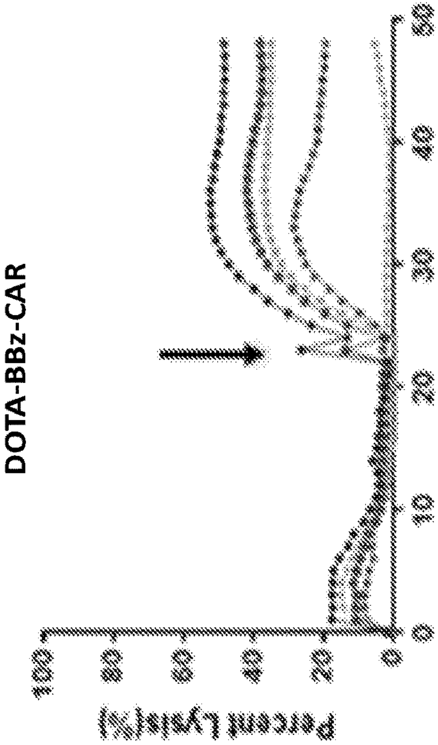
Figure 3H:
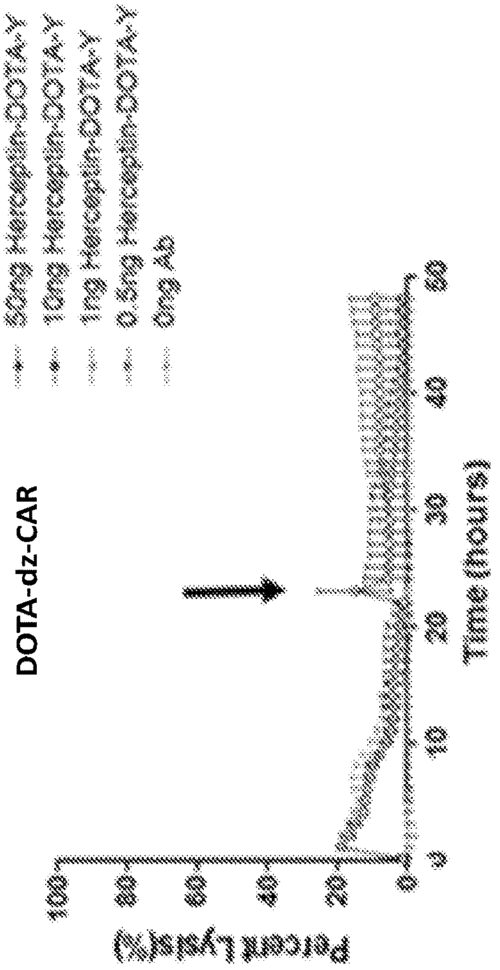

To investigate the ability of DOTA-Y-CAR T cell complexes to lyse target cells, HER2-specific Herceptin-DOTA-Y-CAR T cell complexes were co-cultured with $Her2^+$ SKBR3 breast cancer cells (FIG. 3G). Cancer cell killing was not detectable in co-cultures of DOTA CAR T cells and cancer cells until Y-DOTA-labeled Herceptin Ab was added to culture at various doses. Cancer cell killing was rapid and "on demand" upon provision of the Y-DOTA-Ab (FIG. 3H), and DOTA CAR T cell activity was precisely controlled by antibody dose. Importantly, hC8.2.5 DOTA CAR based killing was dependent upon T cell signaling since CD3 signaling-deficient hC8.2.5 DOTA CAR T cells (DOTA-dz) did not lyse HER2+ cancer cells even at the highest Ab concentrations (FIG. 3I). Similar results were noted when targeting EGFR+ MDA-468 cells with Y-DOTA-Cetuximab.

These results show that a high affinity non-covalent DOTA CAR can be expressed on T cell surfaces to functionally redirect T cell-mediated killing of human cancer cells by the simple provision of DOTA-labeled-antibodies specific for different antigens. Additionally, the cytolytic activity of DOTA CAR T cells can be precisely controlled by the dose of Y-DOTA-antibody, by alteration to the DOTA linker, and/or by chelation of different metal ions to DOTA.

Figure 4A:
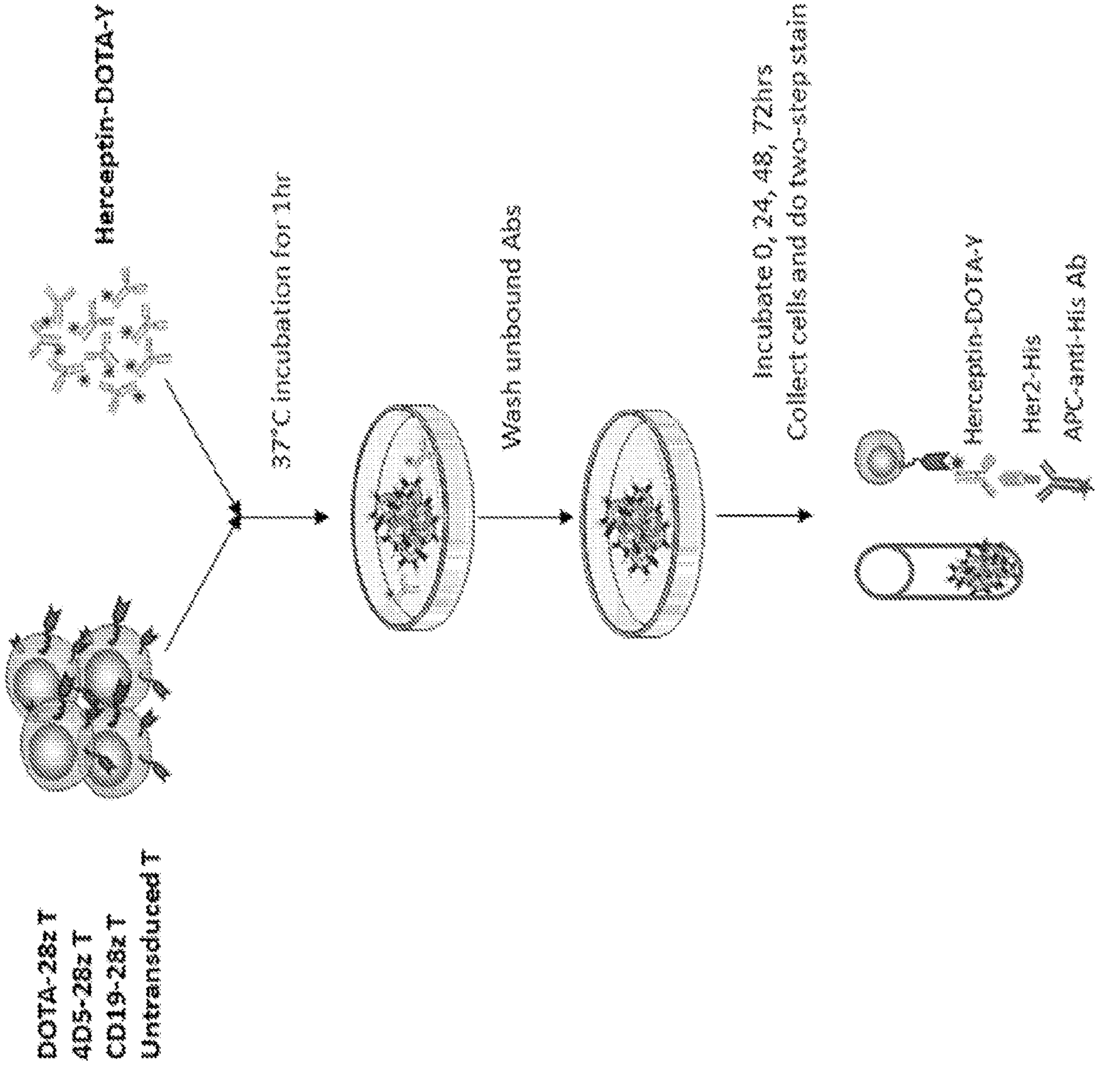
FIGS. 4A-4C illustrate that anti-DOTA immune receptor T cells permit pre-loading of DOTA-Y labeled targeting ligands.
Figure 4B:
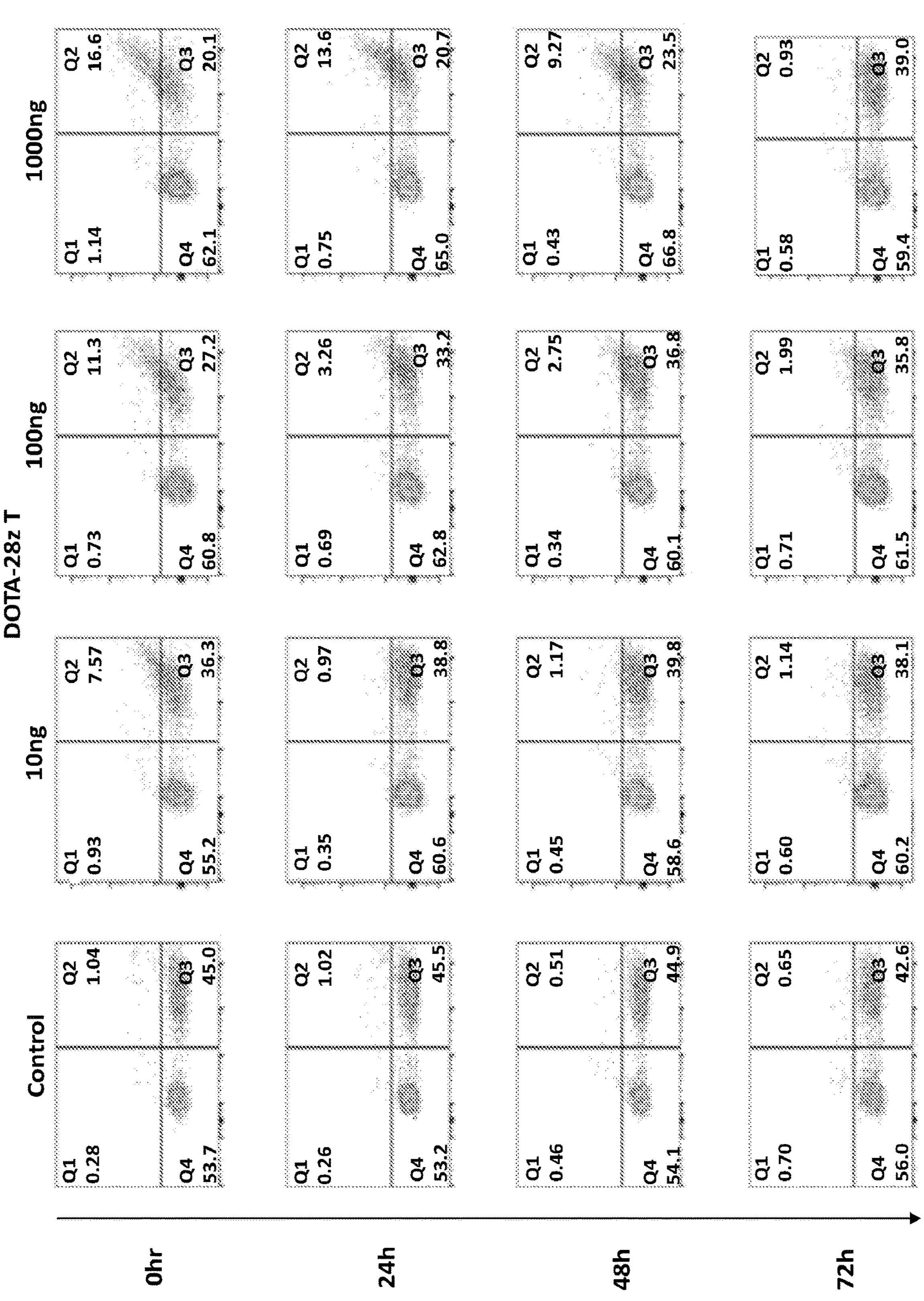
Figure 4C:
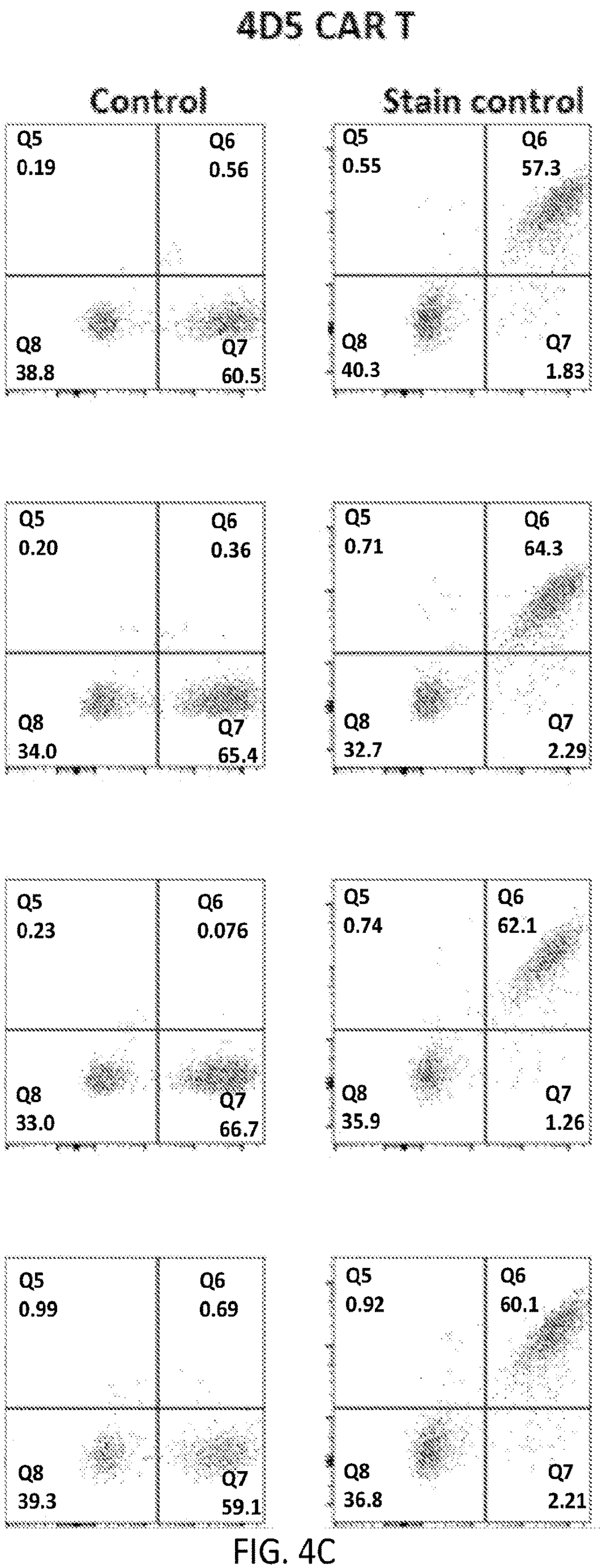

Example 3: Anti-DOTA Immune Receptor T Cells Permit Pre-Loading of DOTA-Y Labeled Targeting Ligands One key feature of the present invention is the ability to alter the specificity of the DOTA-Y by loading the DOTA with target-specific ligands/antibodies. A protocol for pre-labeling the antibodies was optimized and tested. Primary human T cells were transduced with lentivirus containing GFP and DOTA immune receptor (FIG. 4A). At 14 days post-activation, T cells were incubated with Herceptin-DOTA-Y antibody for 1 hour at 37° C. Excess antibody was washed and, at various time points post-antibody addition, cells were stained with soluble recombinant Her2-His, followed by PE anti-His APC antibody and analyzed by flow cytometry, gating on live cells. Results showed that dose-dependent, low level loading is achieved, with full loss of loading by 72 hours (FIG. 4B).

Figure 5A:
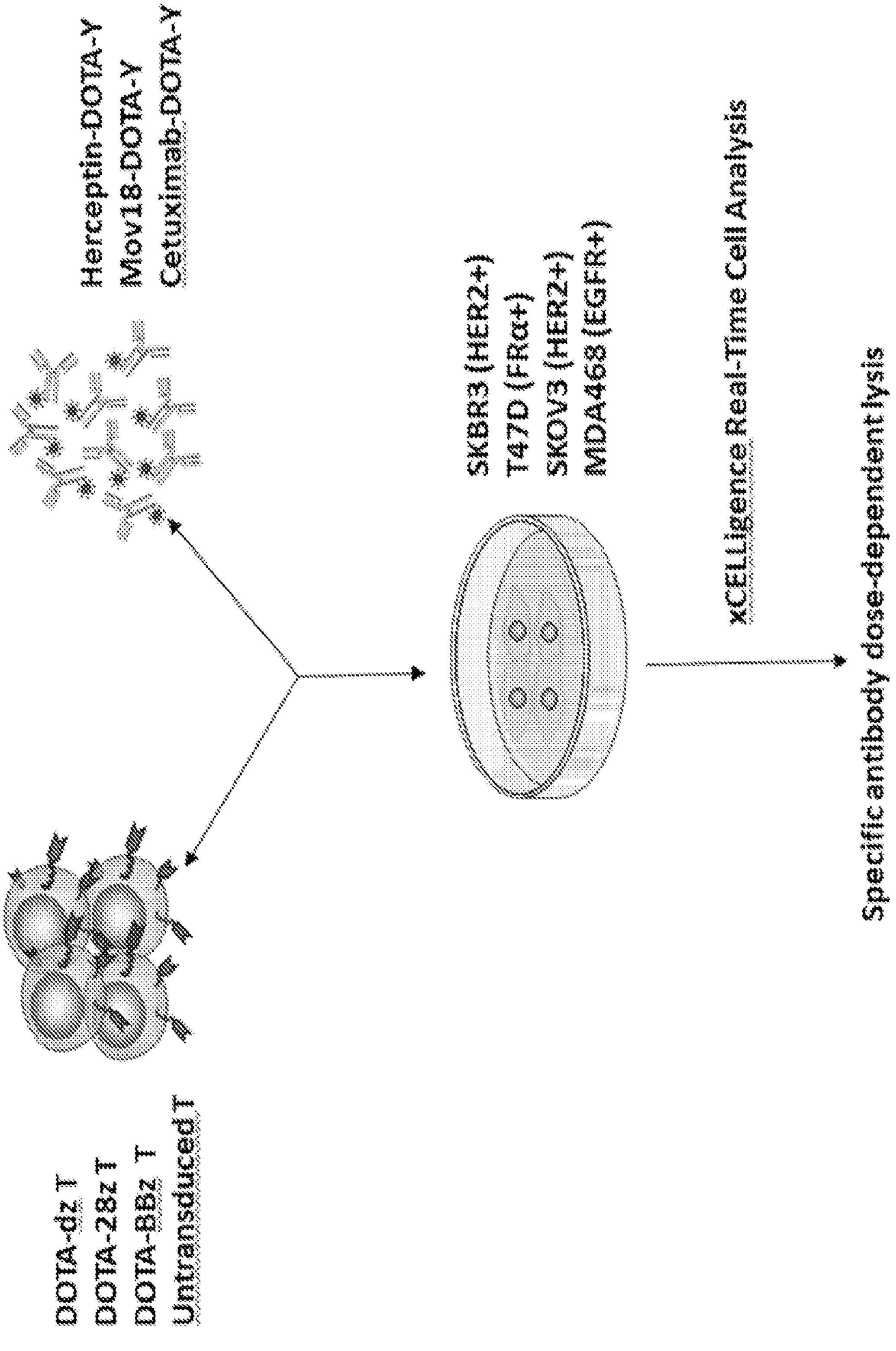
FIGS. 5A-5F illustrate the ability to change the DOTA-Y antibody specificity to target CAR T cells against various cell surface antigens.
Figure 5B:
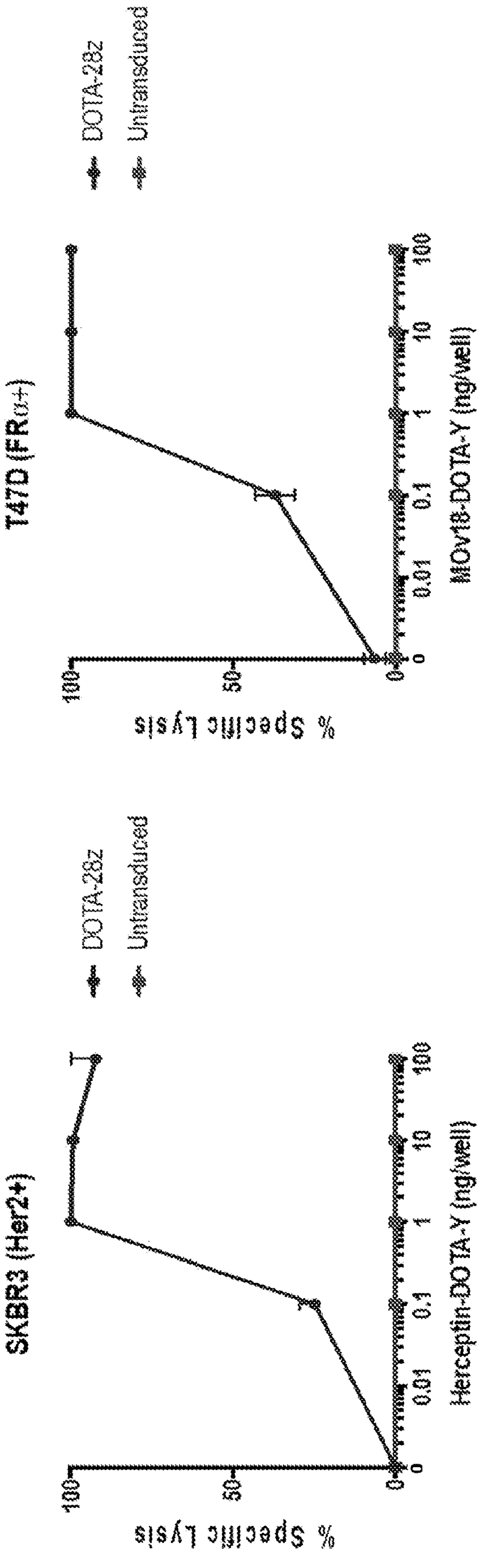
Figure 5C:
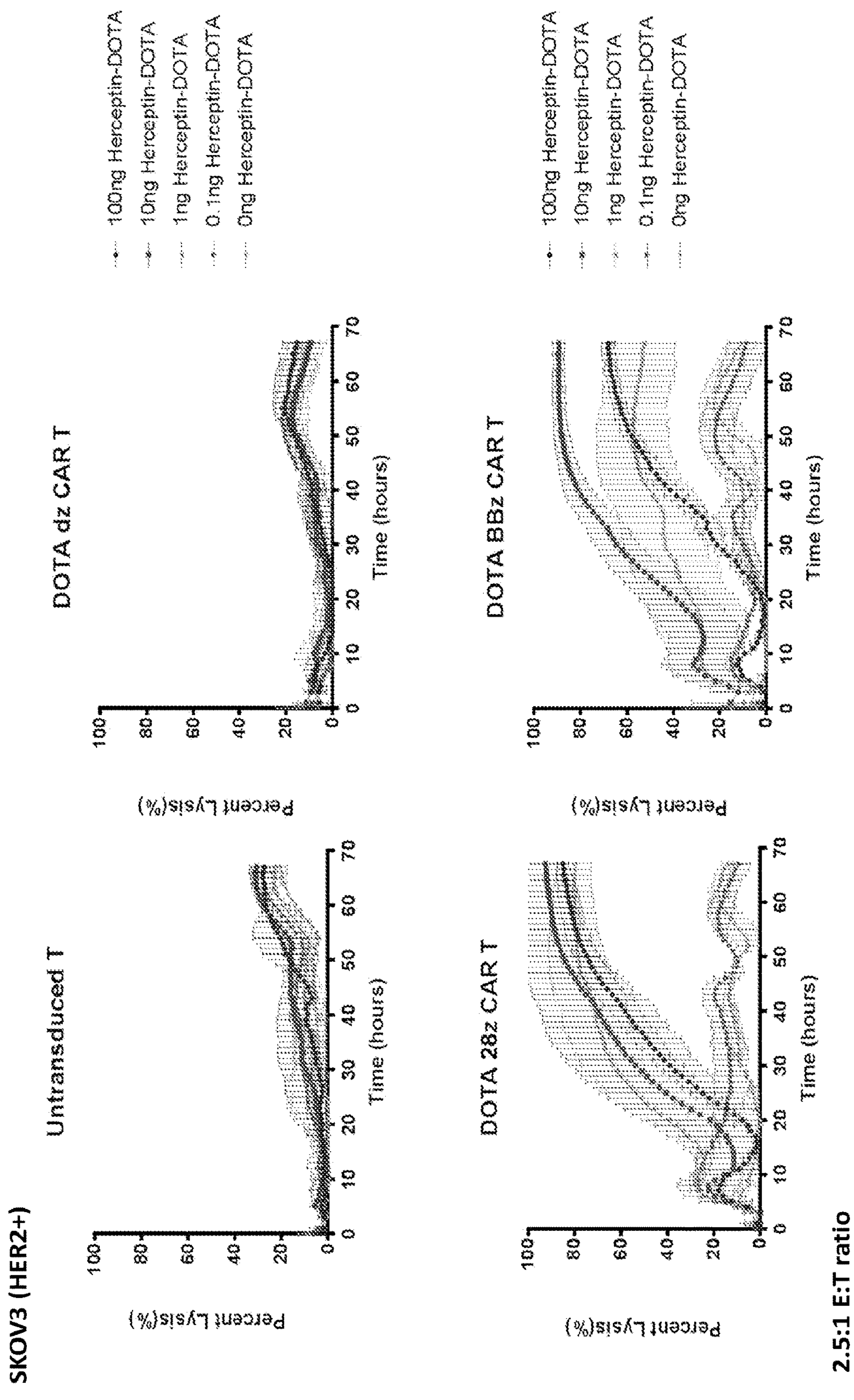
Figure 5D:
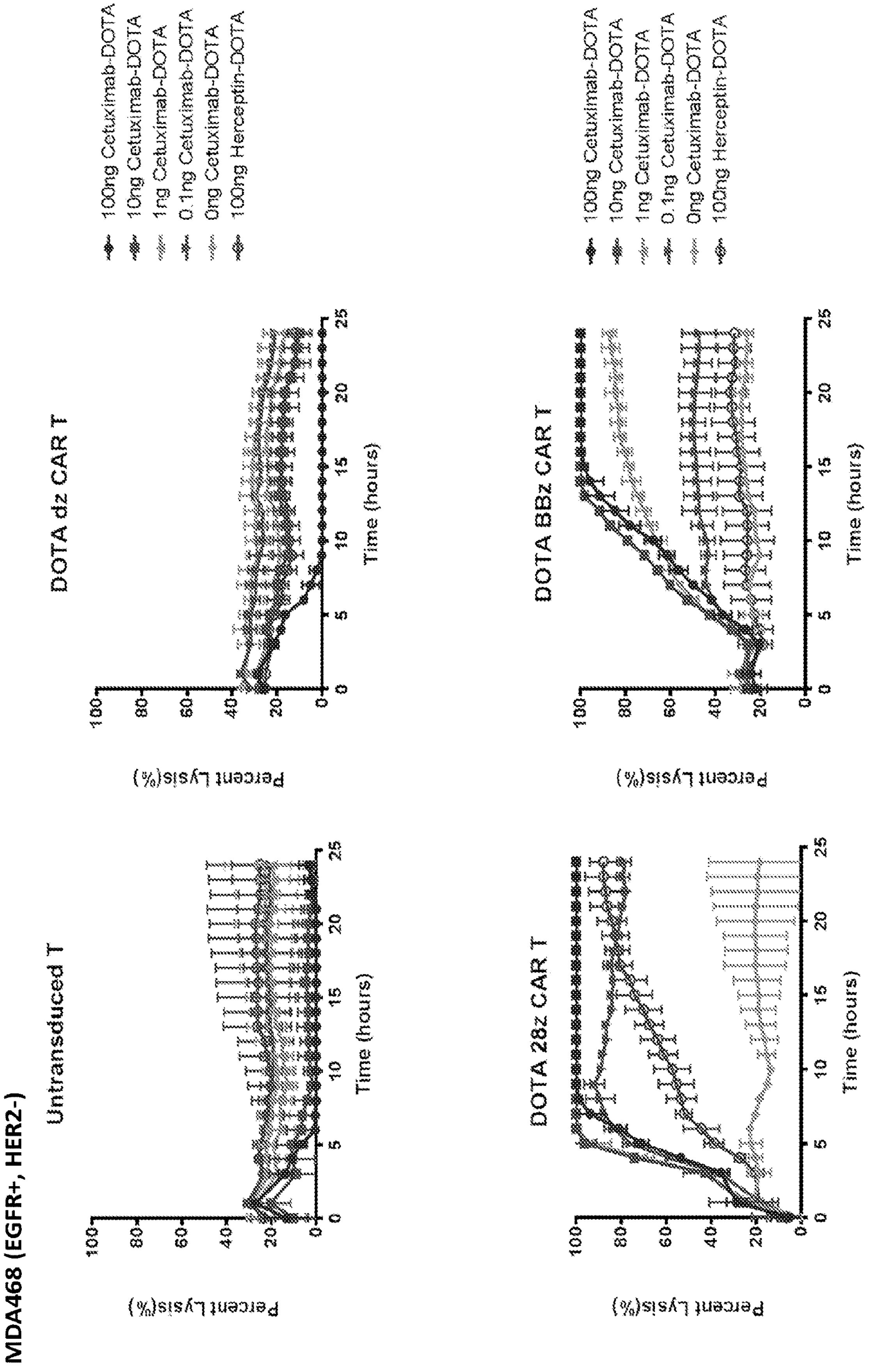
Figure 5E:
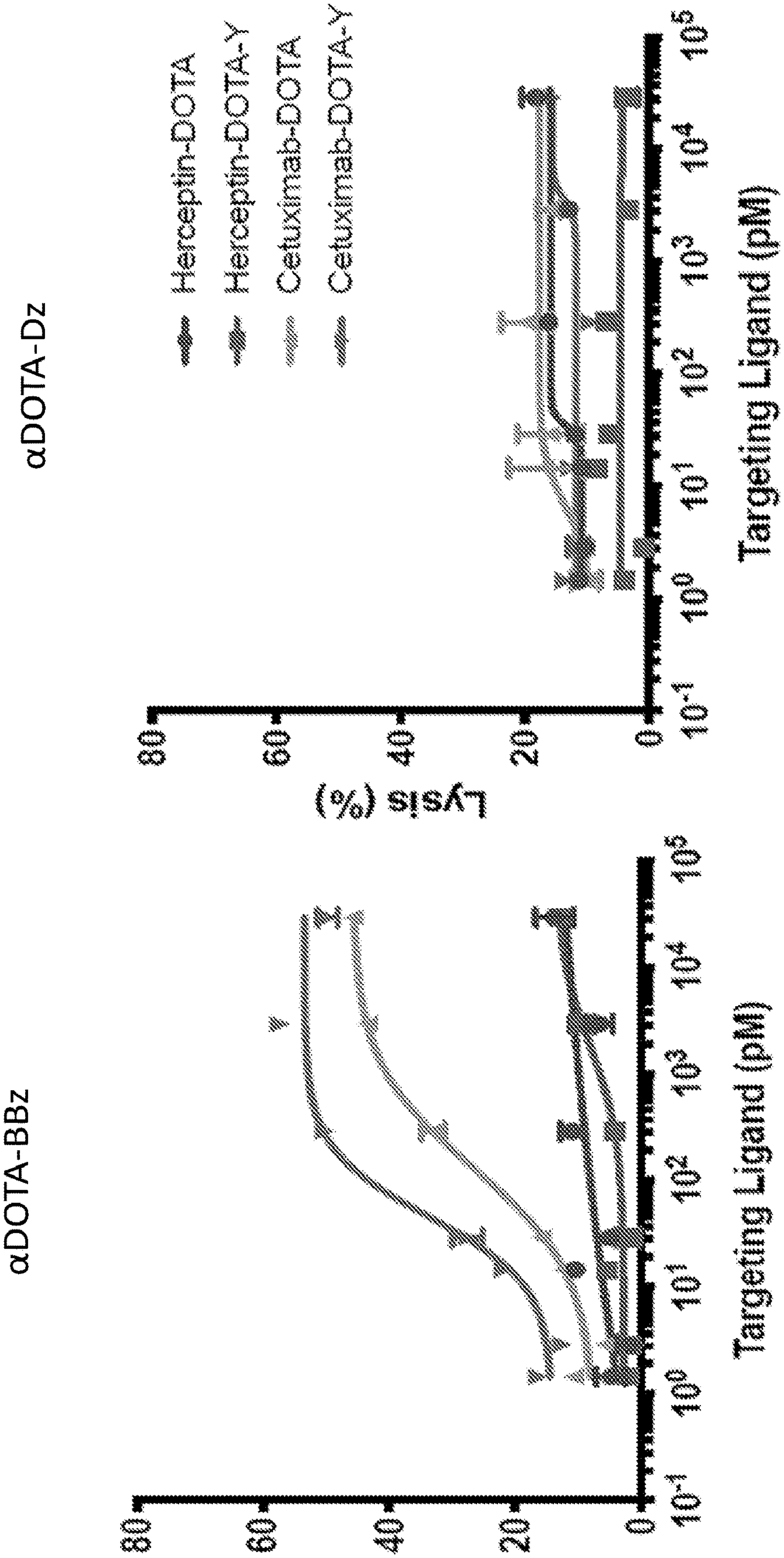
Figure 5F:
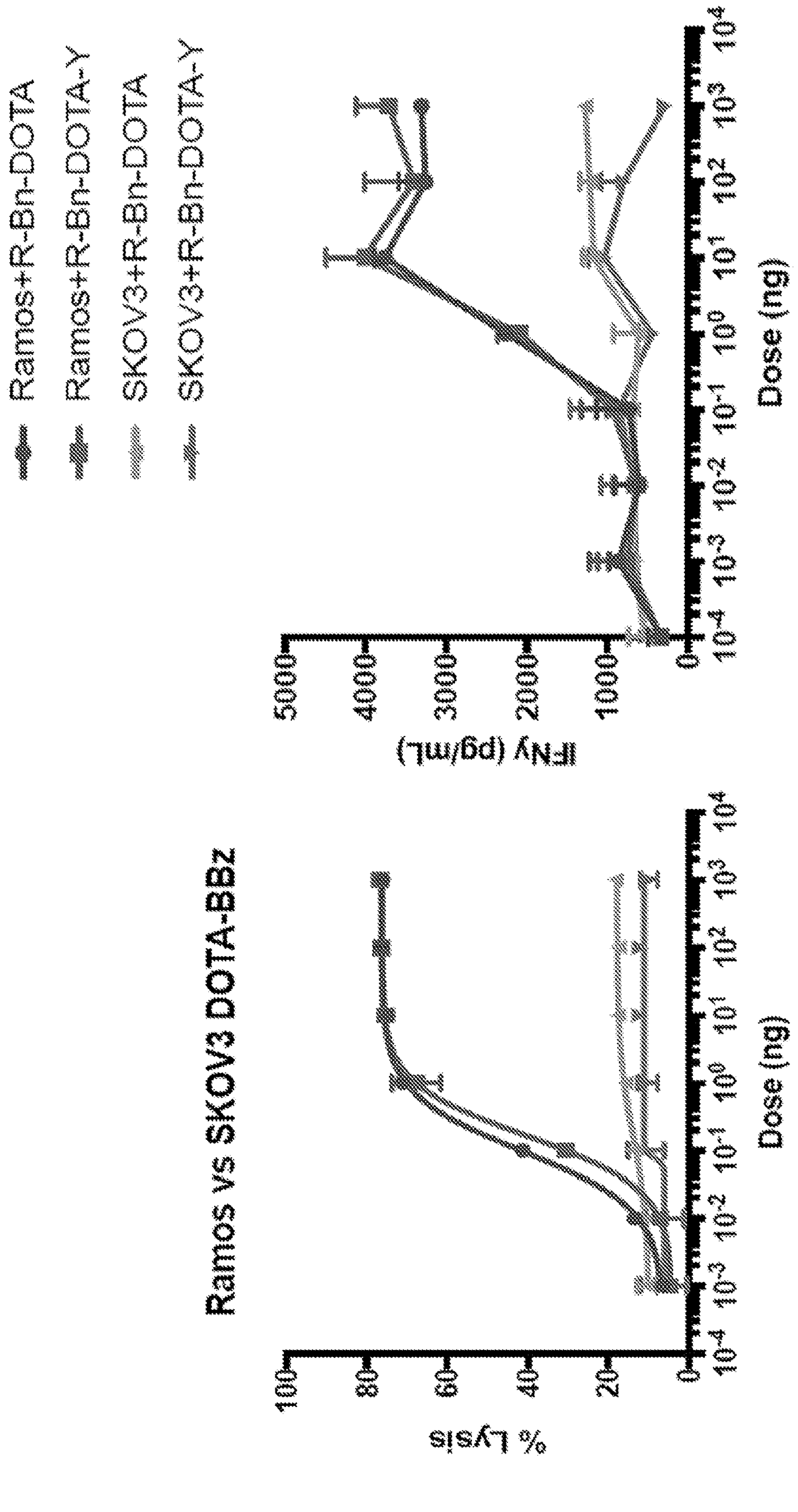

Example 4: DOTA-Y Antibody-CAR T Cell Complexes Target Specific Antigen-Bearing Cell Targets The specificity of pre-loaded DOTA-Y antibodies was tested. Antibodies specific for the cell surface receptors Her2 (Herceptin), Folate receptor (Mov18), or EGFR (Cetuximab), which were conjugated to DOTA-Y, were combined with CAR T cells expressing various intracellular domains and incubated with multiple cell lines, including SKBR3 (Her2+), T47D ($Fra_+$), SKOV3 ($Her2^+$), and MDA468 ($EGFR^+$) cells (FIG. 5A). DOTA-28z-CAR T cells combined with Herceptin or Mov18 antibodies were able to lyse SKBR3 and T47D cells, respectively (FIG. 5B). Additionally, various amounts of Herceptin or Cetuximab antibody was tested in SKOV3 or MDA468 cells, respectively (FIGS. 5C and 5D, respectively). Cell lysis was not observed in CARs lacking an intracellular binding domain (top rows), however there was a dose-dependent and time-dependent correlation between these factors and overall cell killing (FIGS. 5C and 5D, bottom). When Herceptin- or Cetuximab-DOTA-Y antibody and CAR T cells were mixed with $EGFR^+$ MDA468 cells, only the EGFR-specific Cetuximab-loaded CAR was able to lyse the MDA468 cells (FIG. 5E). Additionally, CD20+ cells were specifically lysed by a DOTA CAR armed with a rituximab-Bn-DOTA antibody (FIG. 5F). Taken together, these data demonstrated that DOTA-Y conjugated antibodies can be generated against multiple types of tumor antigens and combined with DOTA CAR T cells, to target and eliminate multiple types of tumor antigen-bearing cells.

Figure 6C:
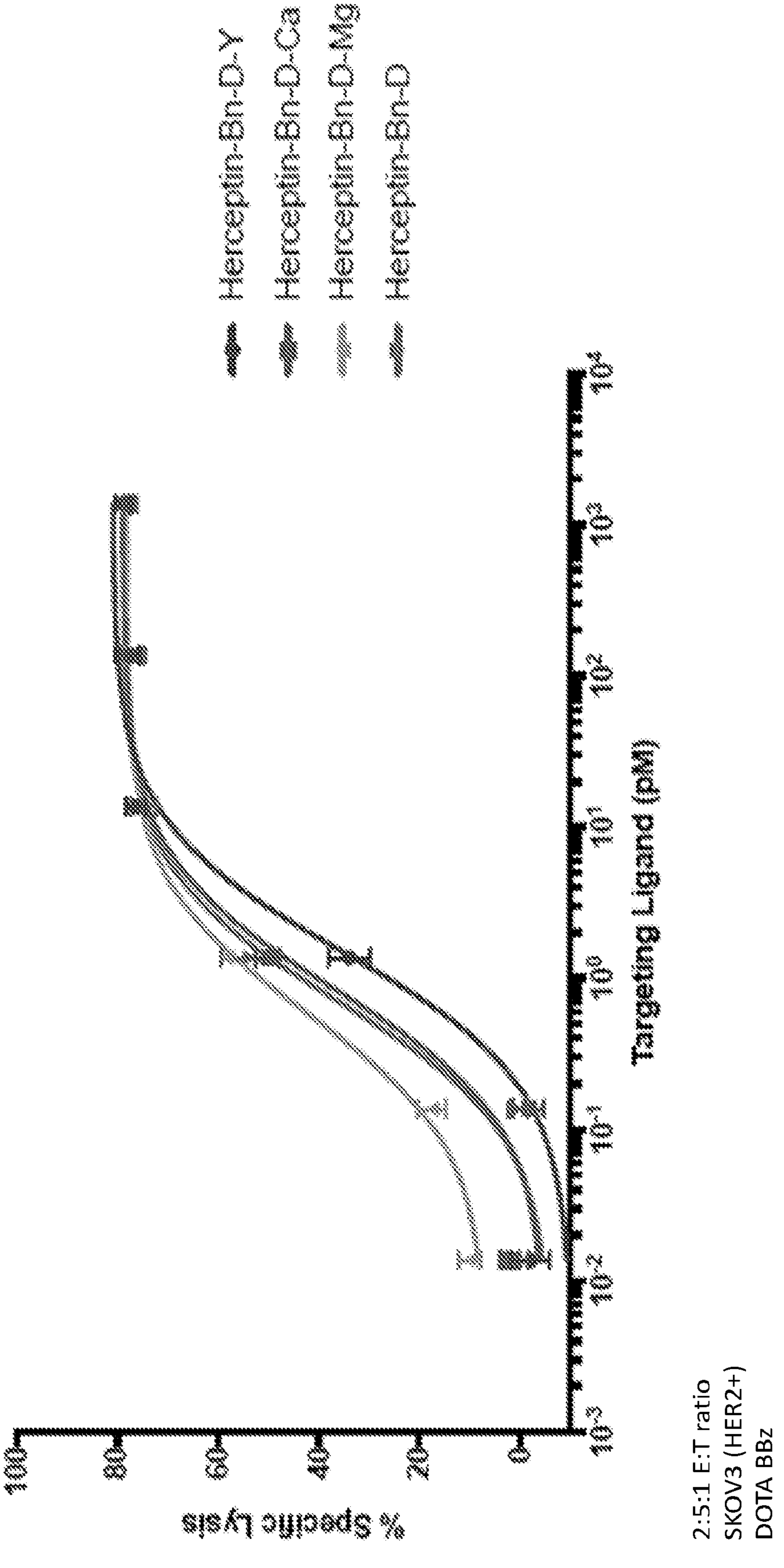

Example 5: Addition of Chelated Metal Ions to DOTA-Conjugated Antibodies or Altered DOTA Linkers Enables Modification of CAR Receptor-Targeting Ligand Interactions Addition of chelated metal ions to a DOTA-conjugated antibody changes the conformation of the DOTA moiety and modifies its affinity for the DOTA CAR. Herceptin antibodies were conjugated to DOTA, various metal ions were chelated, and the ability of DOTA CAR T cells to kill their targets was evaluated. Compared to the Herceptin-DOTA-CAR T cells, the addition of Y or modification of the DOTA linker to Bn increased target cell lysis at increasingly lower DOTA-ligand concentrations (FIG. 6B). Addition of Y, Ca, and Mg, to Herceptin-Bn-DOTA antibody-complexes also slightly increased SKOV3 cell lysis at a lower dose compared to Herceptin-Bn-DOTA alone (FIG. 6C).

Figure 7:
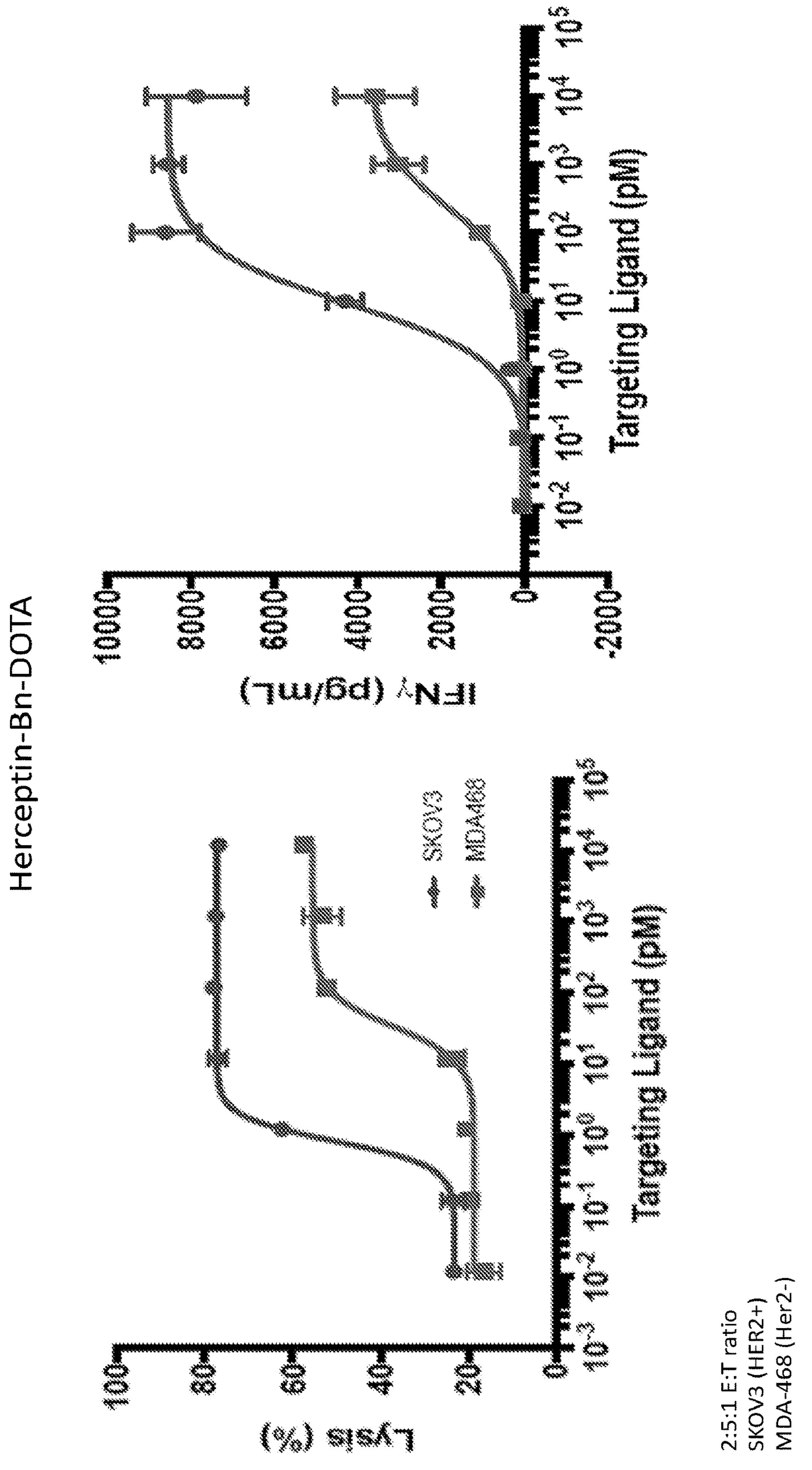
FIG. 7 illustrates that addition of a large excess of targeting ligands causes non-specific tumor cell lysis.
Figure 8:
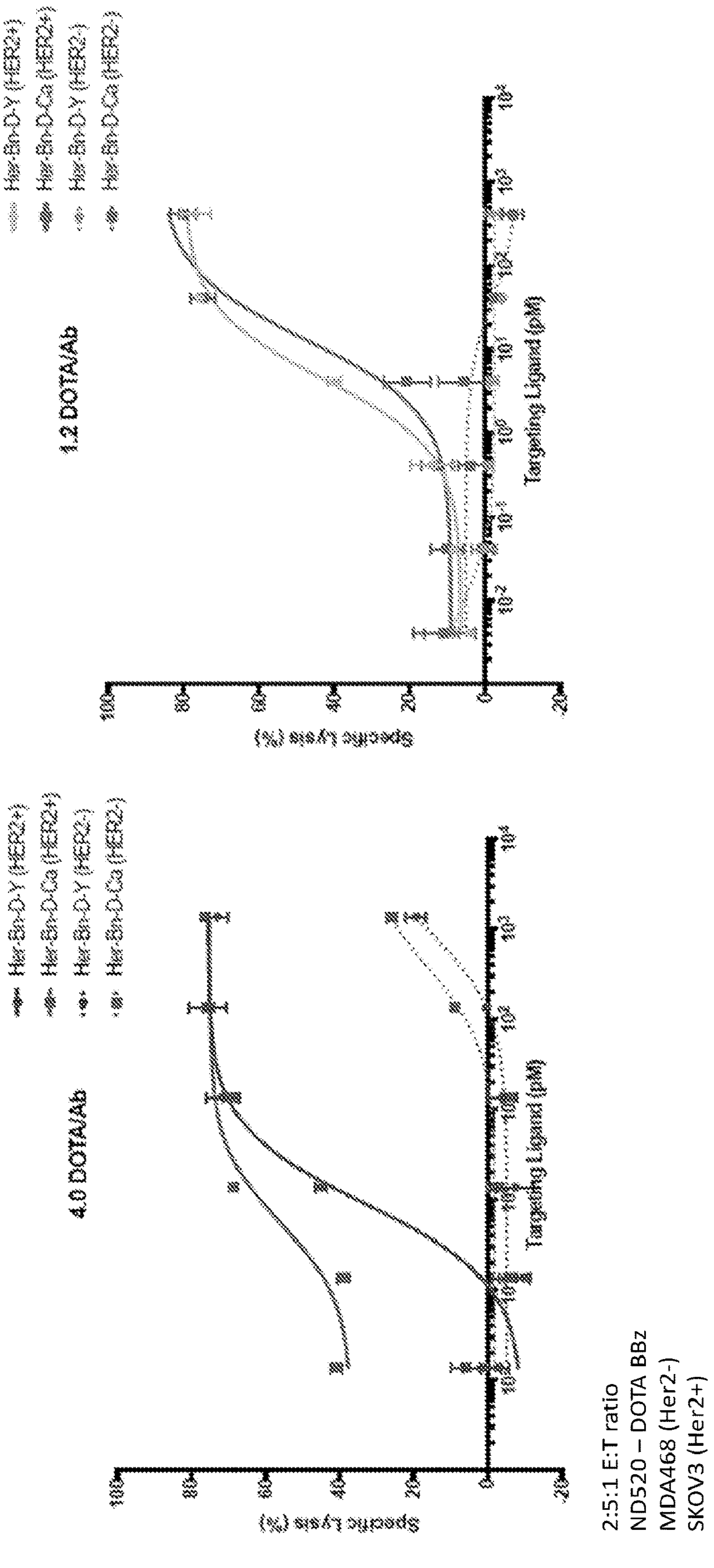
FIG. 8 illustrates that varying the number of chelators per antibody allows for reduced non-specific cell lysis while maintaining strong lytic function in SKOV3 (HER2+) and MDA468 (HER2-) cells.
Figure 9:
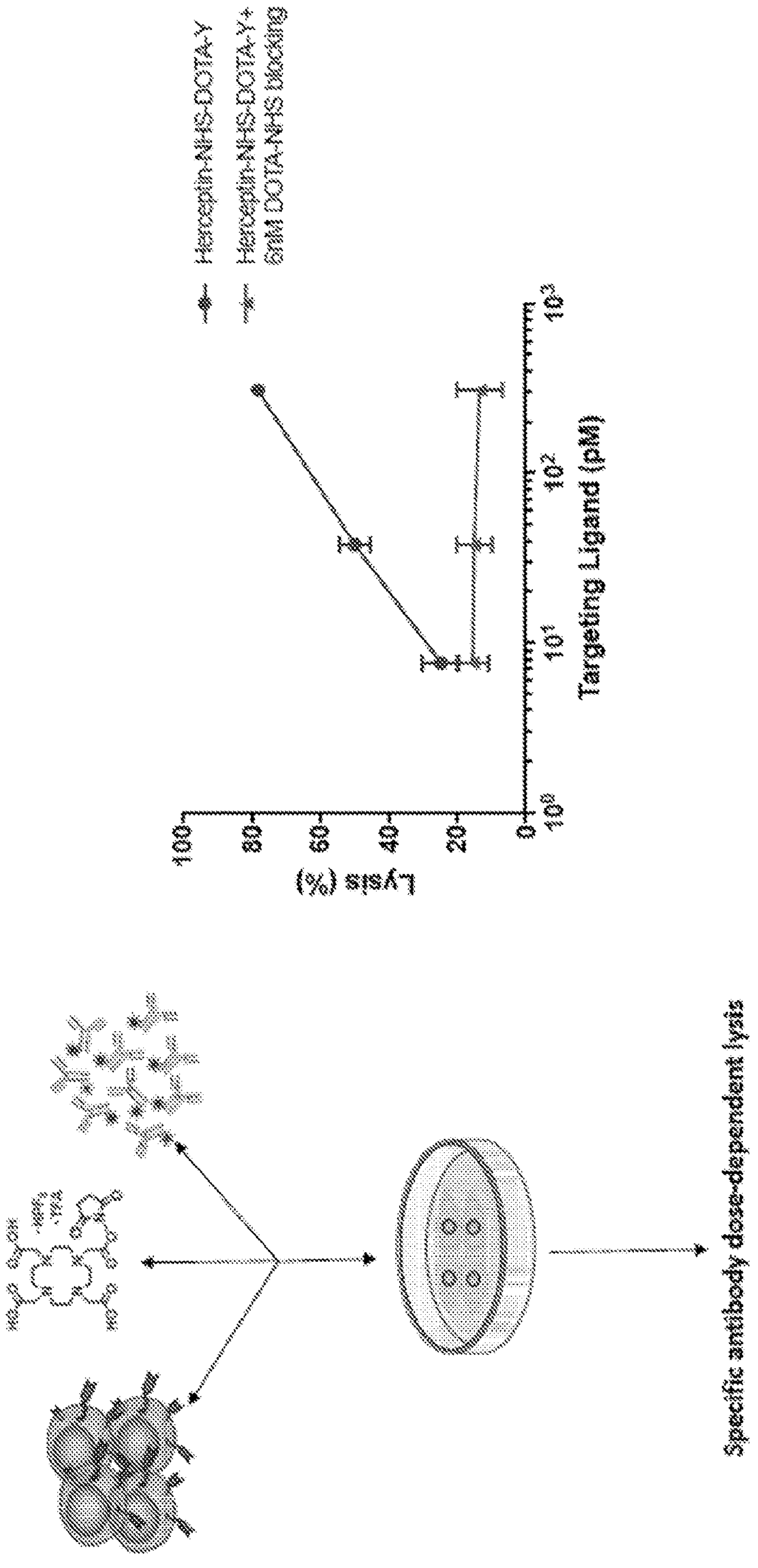
FIG. 9 shows that the addition of free monomeric DOTA (6 nM DOTA-NHS blocking) leads to the blockade of lytic function by Herceptin-NHS-DOTA-Y-CAR T cells.

To test the specificity of high-affinity DOTA-conjugated antibodies, Herceptin-Bn-DOTA antibody complexes were incubated with CAR T cells and SKOV3 (Her2+) and MDA468 (Her2) cells. Non-specific lysis of MDA468 cells by Herceptin-Bn-DOTA CAR T cells occurs at high concentrations of the targeting ligands (FIG. 7). Varying the number of chelators per antibody allows for reduced non-specific cell lysis while maintaining strong lytic function (FIG. 8)

Taken together, these data suggest that the addition of chelated metal ions to DOTA-conjugated antibodies allows for administration of lower concentrations of the target ligand to achieve comparable levels of DOTA-CAR-mediated cell lysis.

Example 6: In Vivo Efficacy of DOTA-CAR T Cells

Figure 10:
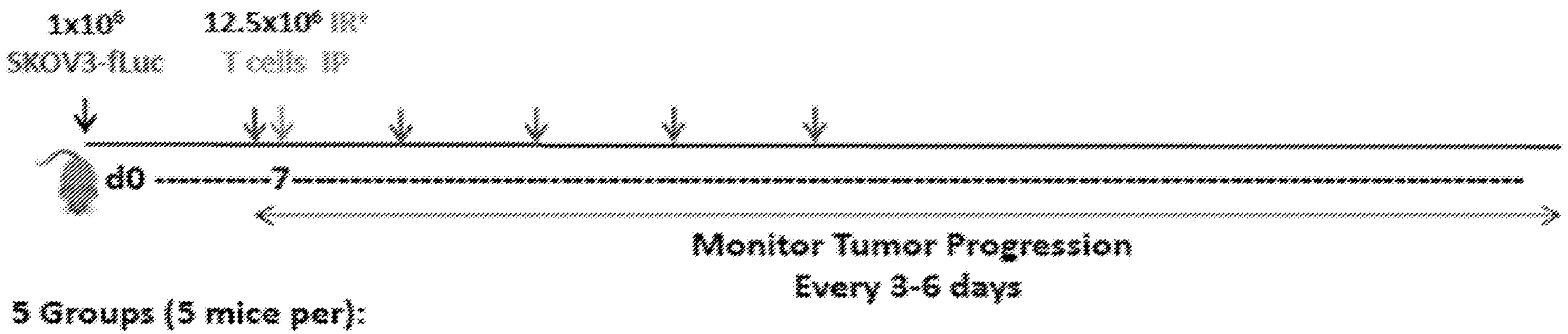
FIG. 10 is the experimental design of a pilot study investigating the in vivo efficacy of anti-DOTA immune receptor CAR T cells.
Figure 11A:
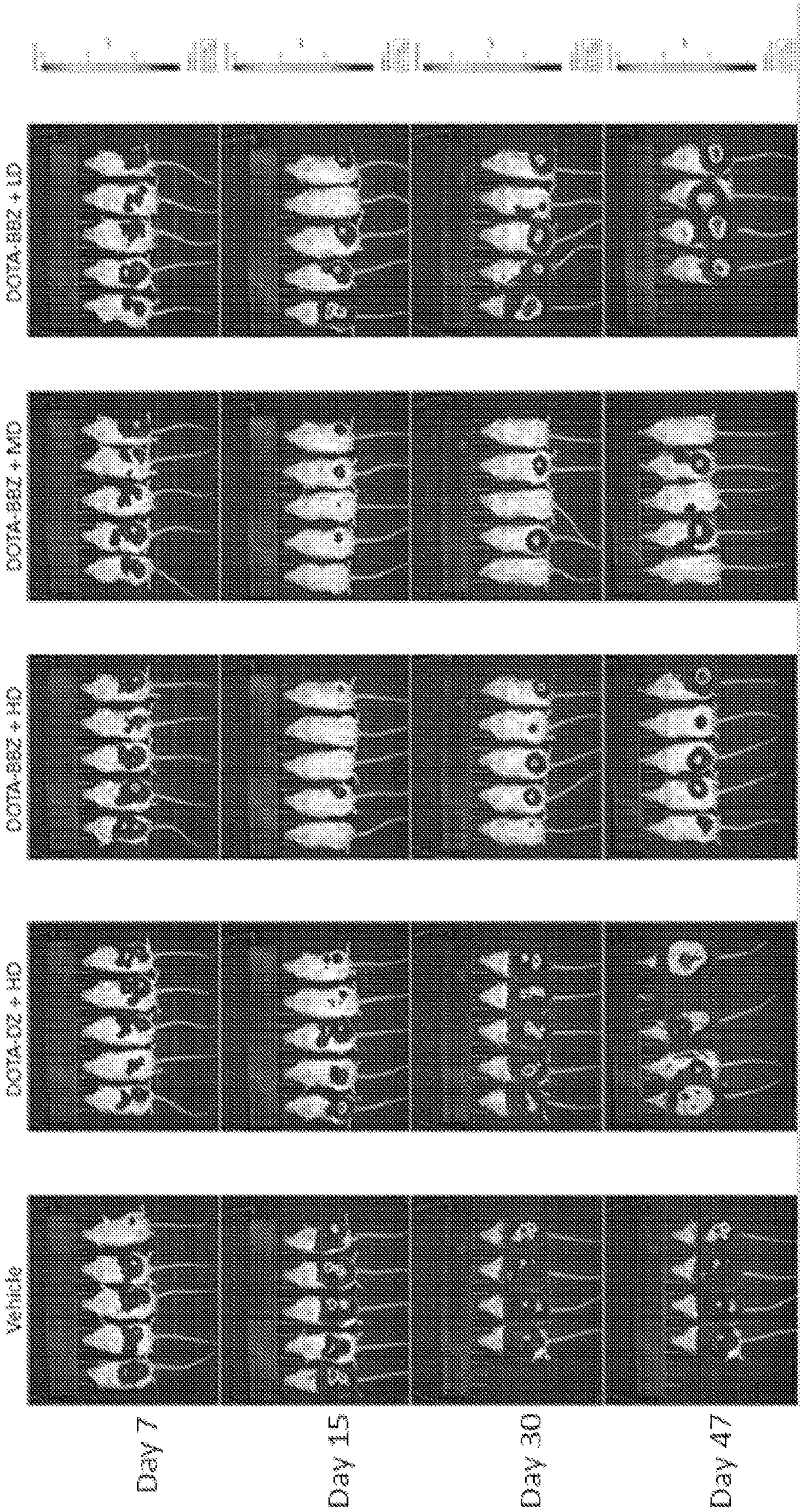
FIGS. 11A-11E illustrate the in vivo efficacy of DOTA CAR T cells.
Figure 11B:
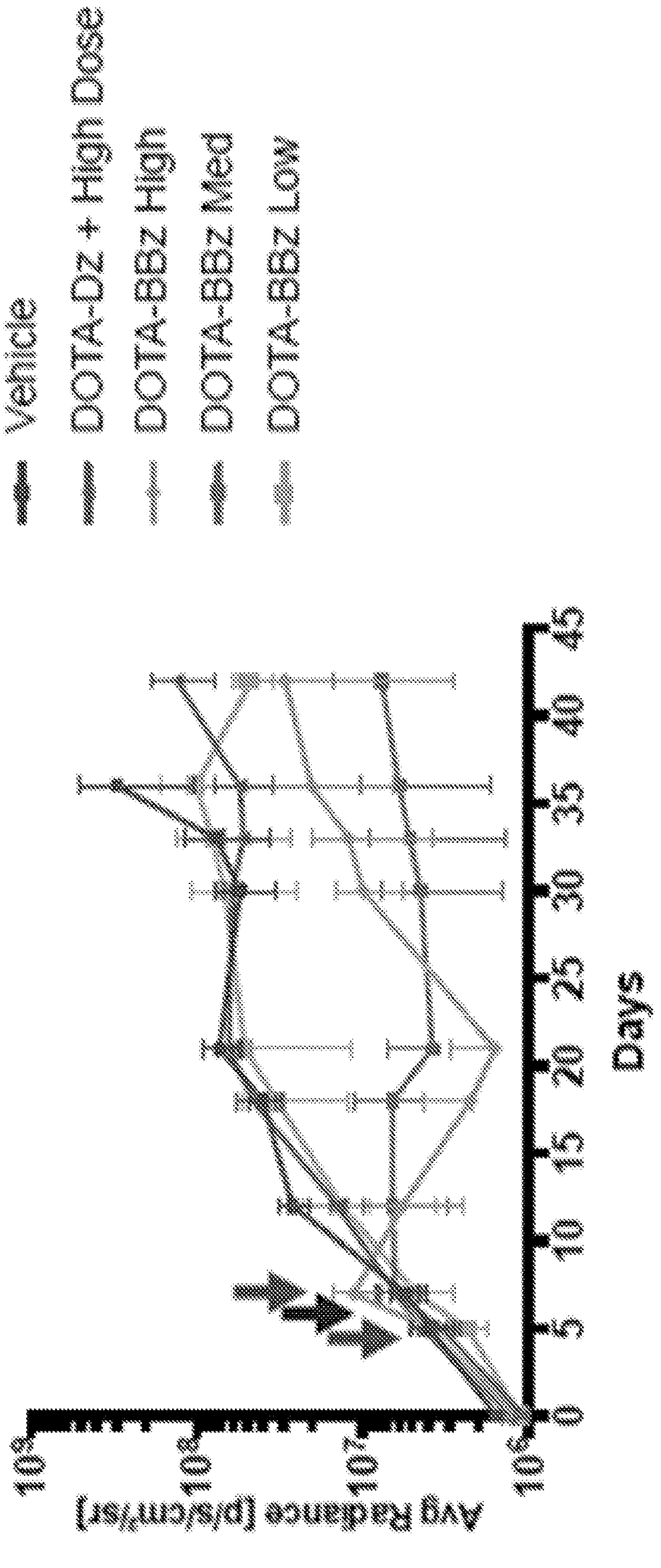
Figure 11C:
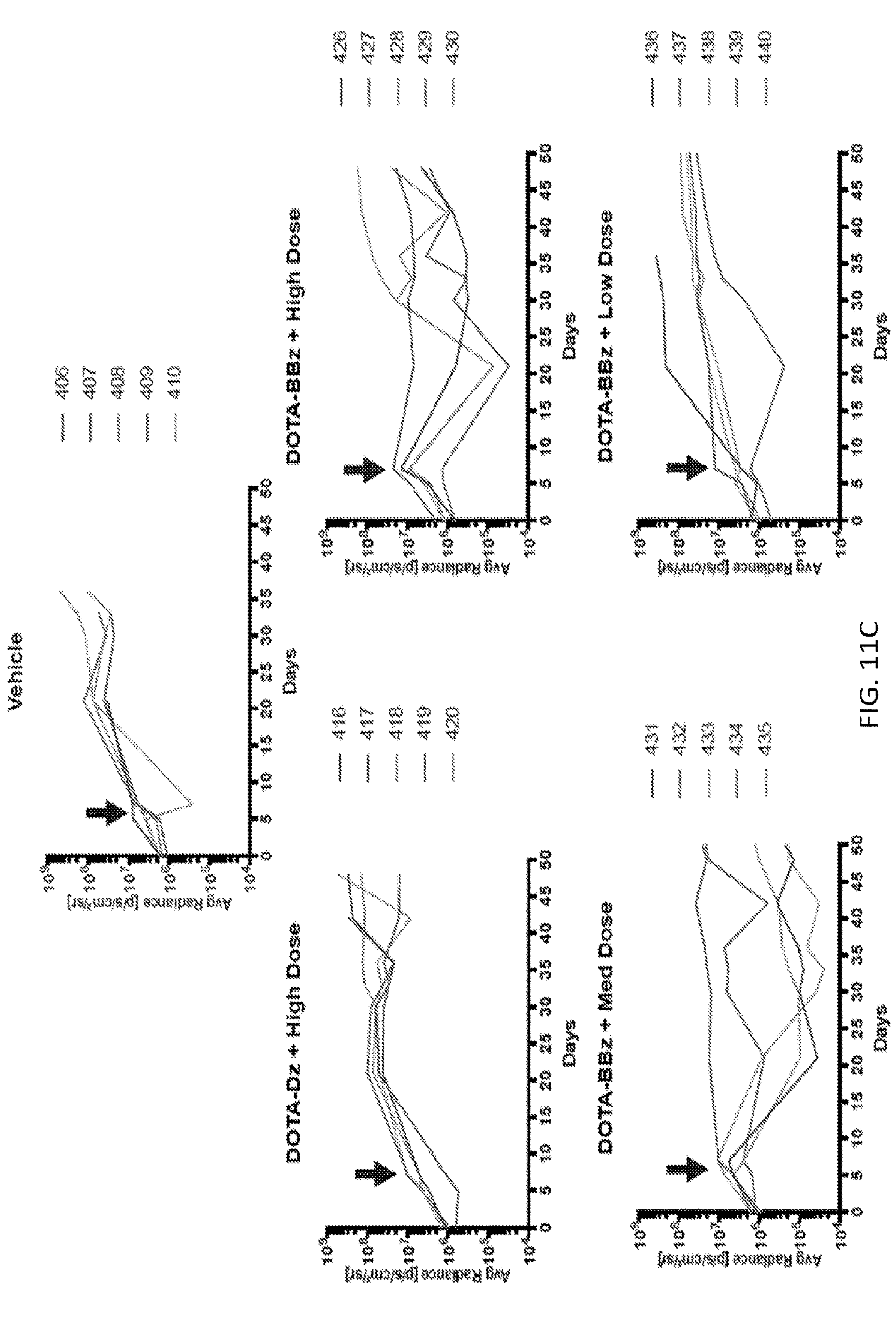
Figure 11D:
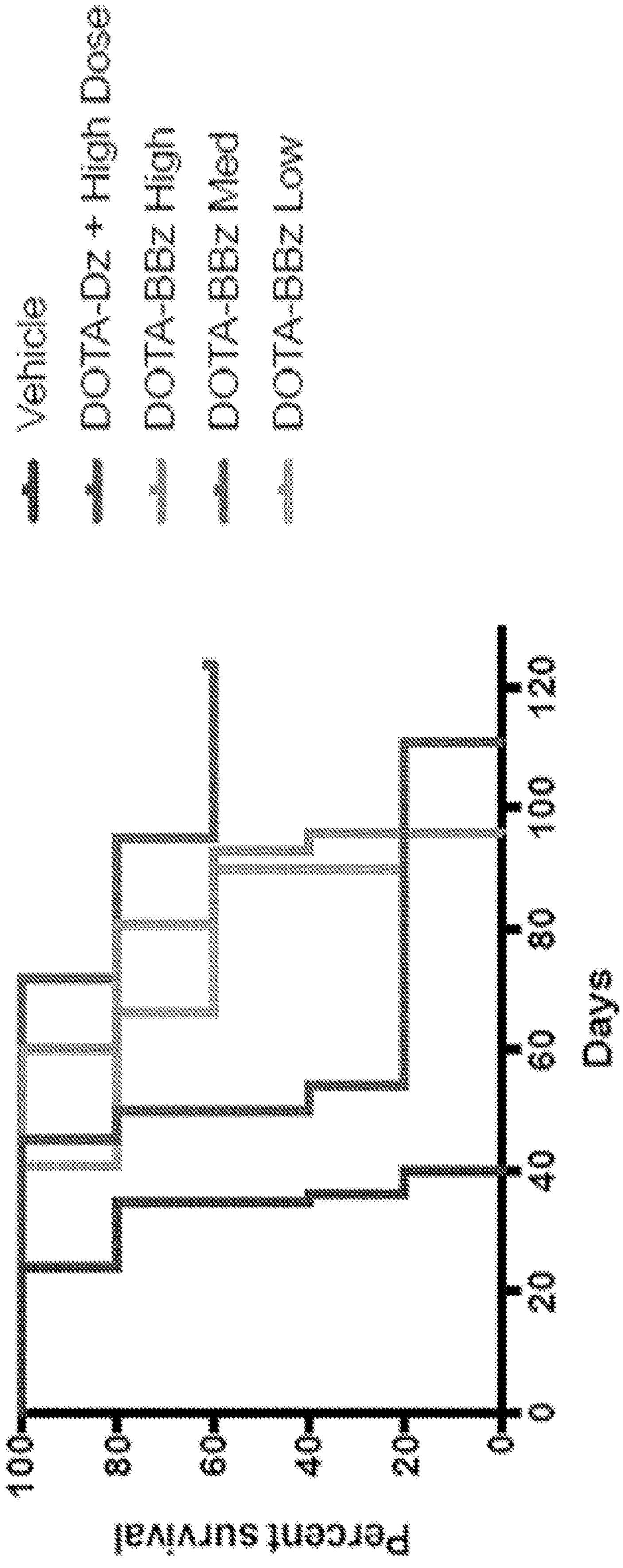
Figure 11E:
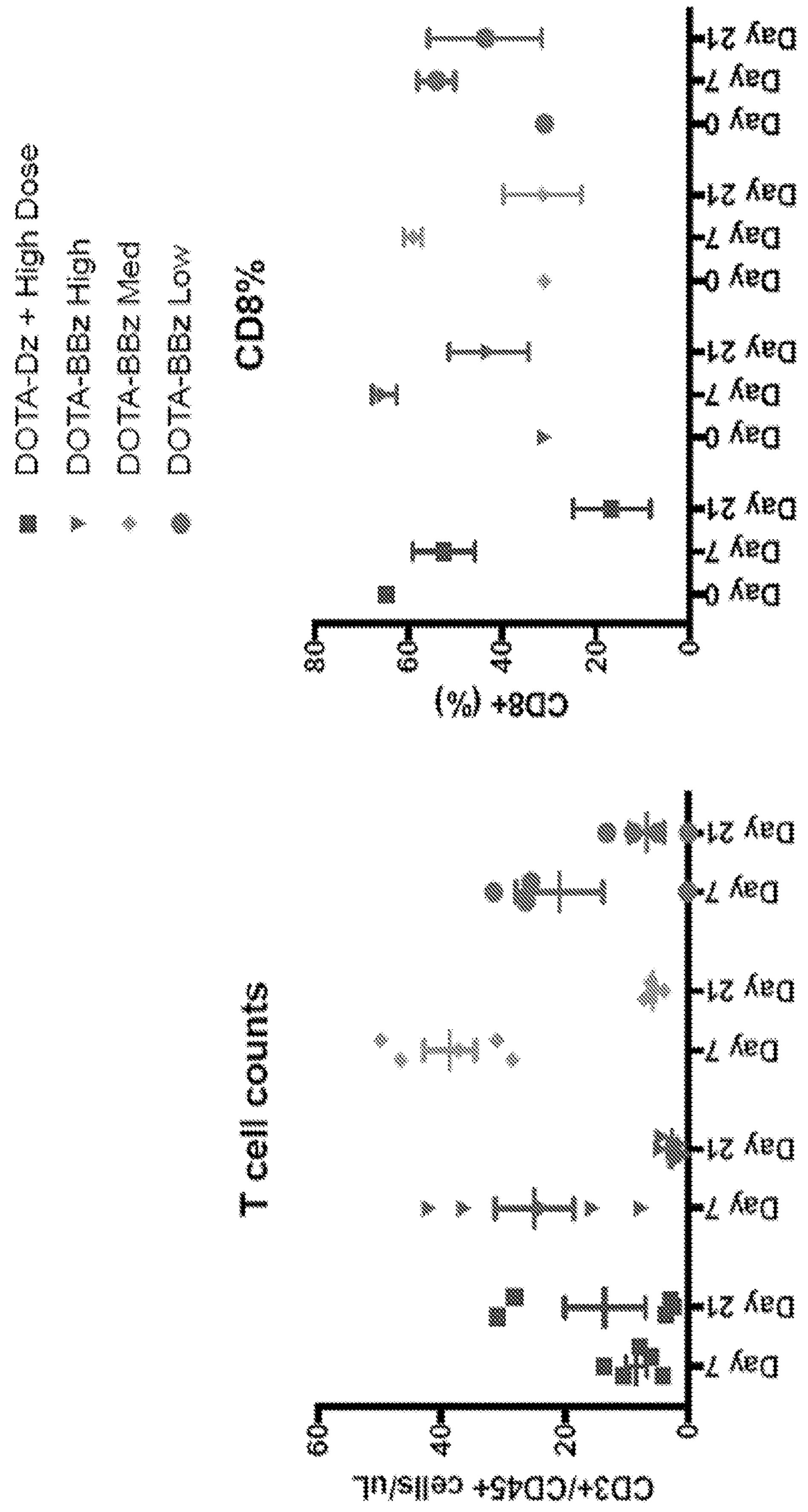

To test the in vivo effects of the DOTA-Y antibody-CAR T cell system, SKOV3-Luciferase reporter tumor mice were injected with $12.5\times10^6$ DOTA CAR expressing T cells and various concentrations of Herceptin-DOTA-Y. Herceptin-DOTA-Y was continually administered every 6 days throughout the experiment and tumor progression and overall survival of mice were measured (FIG. 10). Mice that received either DOTA-BBz CAR T cells in high or medium doses had overall lower tumor radiance compared to control animals, as well as those receiving a low dose of CAR T cells or CAR T cells lacking an intracellular domain (FIGS. 11A-11C). Further, 60% of mice that received a medium dose of DOTA-BBz CAR T cells were still alive at day 120 compared to all other groups who had no survivors (FIG. 11D). T cell counts and percent of CD8+ cells are shown in FIG. 11E. Taken together, these data demonstrate that DOTA-CAR T cells are effective at controlling tumor growth and, thus, promoting mouse survival.

Figure 12:
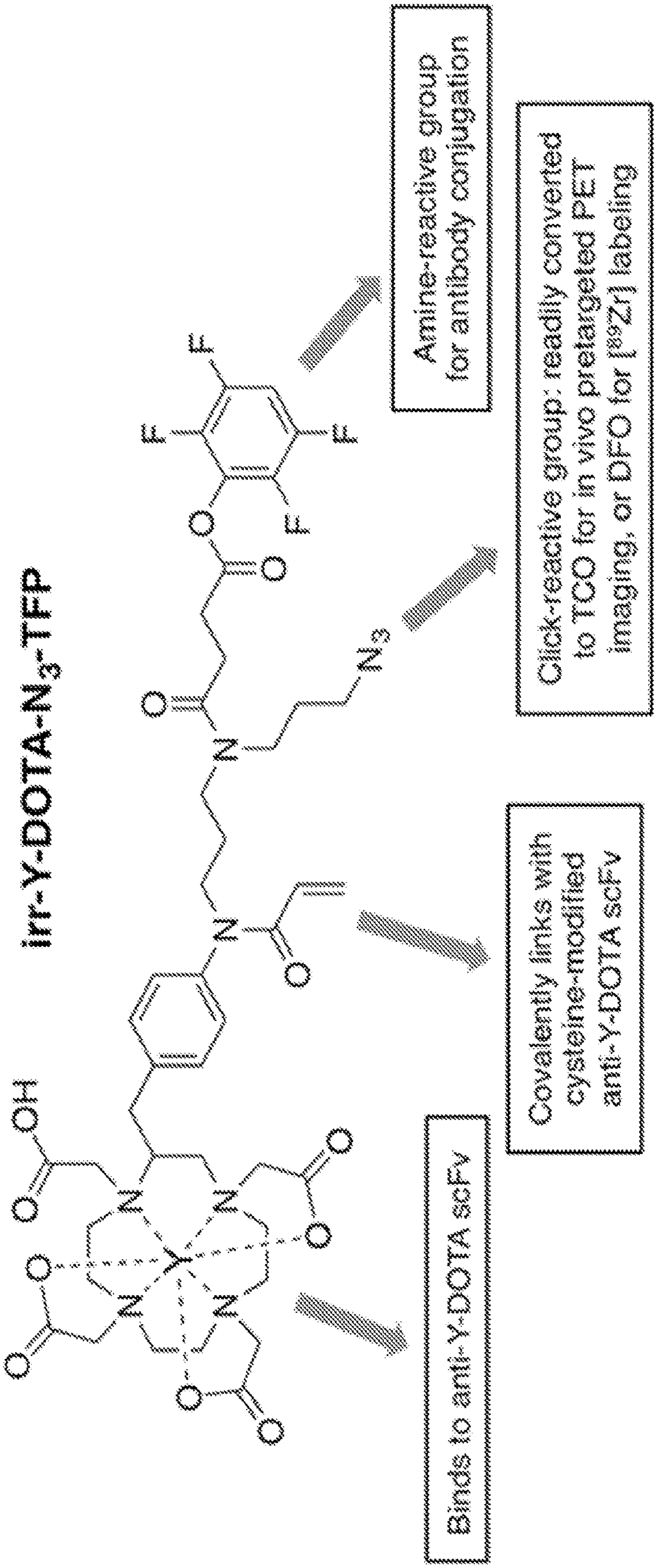
FIG. 12 shows the structure of irr-Y-DOTA-$N_3$-TFP. This multifunctional Y-DOTA reagent has different domains that permit (1) binding to anti-Y-DOTA scFv with high affinity, (2) covalent linking with a cysteine-modified anti-Y-DOTA scFv, (3) click chemistry via a terminal azide, and (4) antibody conjugation via primary amines.
Figure 18:
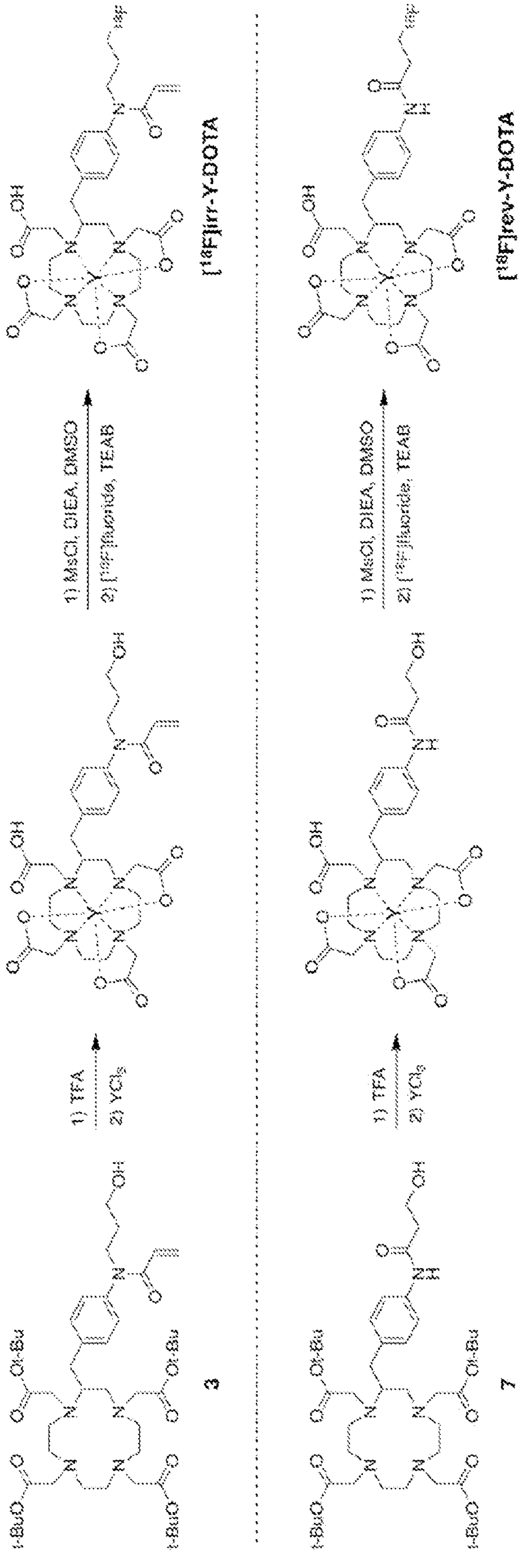
FIG. 18 illustrates the proposed synthesis of [$^{18}$F]irr-Y-DOTA and [$^{18}$F]rev-Y-DOTA.

Example 7: A Covalent-Linking UnivIR CAR T Cell System and Companion Diagnostic Imaging Tools A set of companion diagnostic imaging tools is developed herein that is applicable to cellular immunotherapy and capable of monitoring therapy, predicting response to therapy, and assessing the potential for on-target toxicity. Additionally, a covalent-linking UnivIR CAR T cell system is developed and tested herein that allows a combination of flexibility in targeted antigen-specificity by re-directed T cells, simplified CAR manufacturing, and modulation of T cell survival and function. To achieve these goals, a novel covalent-linking Y-DOTA-based reagent is synthesized, irr-Y-DOTA-$N_3$-TFP, which contains several different functional domains (FIG. 12). A non-covalent Y-DOTA-based reagent (rev-Y-DOTA-$N_3$-TFP) is synthesized for comparison. Next, a covalent-linking high affinity anti-Y-DOTA scFv, in which a glycine near the Y-DOTA binding pocket has been mutated to a cysteine, is generated (hC8.2.5/G54C scFv). This modified scFv is capable of forming a covalent bond with the Y-DOTA reagent via an intramolecular Michael addition between the cysteine on the scFv and the vinyl amide on the Y-DOTA reagent. UnivIR CAR T cells are engineered to express this modified scFv as a component of the CAR, and their ability to engage irr-Y-DOTA-$N_3$-Herceptin, form a covalent bond, and mediate antigen-specific cell killing under different treatment conditions is tested. The ability of UnivIR CAR T cells to effect multi-antigen targeting is explored (using anti-HER2 and anti-EGFR antibodies), and CAR constructs with different costimulatory domains are engineered and tested for functional activity. Tumor antigen expression is evaluated using irr-Y-DOTA-$N_3$-Herceptin as a common precursor for the synthesis of a [$^{89}$Zr]-labeled antibody for PET imaging, or TCO-labeled antibody for pretargeted PET imaging using [$^{18}$F]-tetrazine as the probe (Altai M, et al. J Nucl Med. 2017; 58(10):1553-9; Denk C, et al. Angew Chem Int Ed Engl. 2014; 53(36):9655-9). The ability of tumor uptake to predict response to therapy is evaluated, and evidence of target engagement by UnivIR CAR T cells is assessed. One of the advantages of a pretargeted approach in this setting is that it can predict response to concurrent therapy, since imaging can be performed following therapeutic doses of antibody. The capacity of PET imaging to monitor UnivIR CAR T cell trafficking in vivo is tested using two different methods: (a) UnivIR CAR T cells that have been directly labeled (pre-armed) with [$^{89}$Zr]DFO-irr-Y-DOTA-Herceptin and (b) a reporter gene method, in which UnivIR CAR T cells (which express the anti-Y-DOTA scFv reporter as a component of the CAR construct) are tracked with novel reversible and irreversible [$^{18}$F]-Y-DOTA small molecule PET probes (FIG. 18).

Figure 13A:
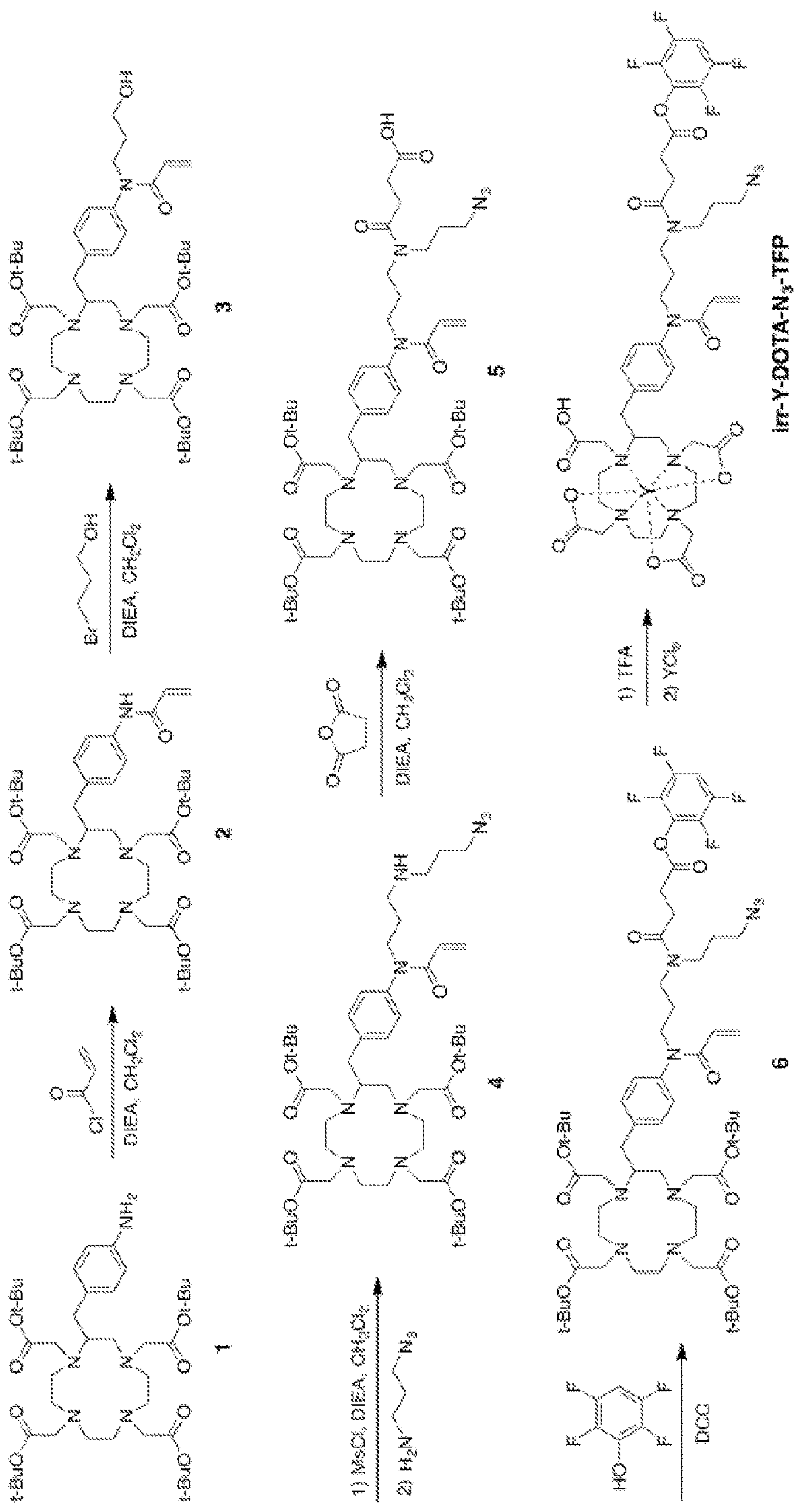
FIGS. 13A-13B illustrate the proposed synthesis of irr-Y-DOTA-$N_3$-TFP (FIG. 13A) and rev-Y-DOTA-$N_3$-TFP (FIG. 13B).
Figure 13B:
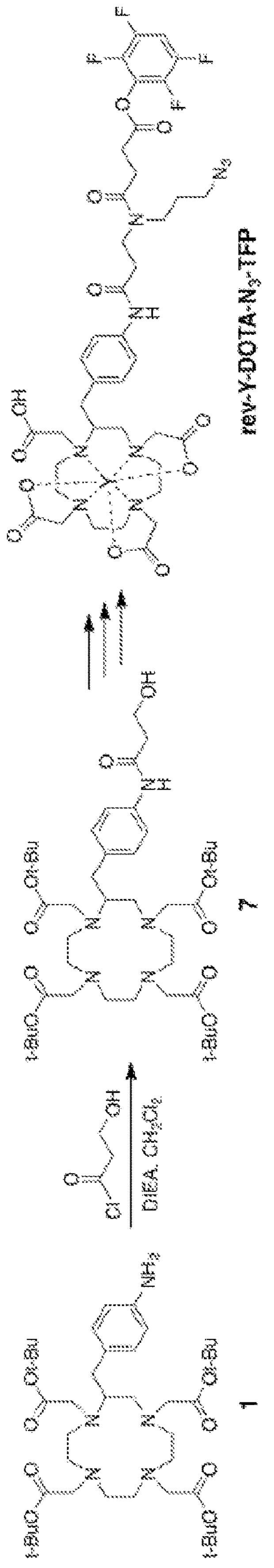

Example 8: Development of a Covalent-Linking Y-DOTA-Based Immune Receptor System as a Theranostic Agent Capable of Tailored Antigen Specificity Novel reversible (rev-Y-DOTA-$N_3$-TFP) and irreversible (irr-Y-DOTA-$N_3$-TFP) Y-DOTA-based reagents (FIGS. 13A-13B) are synthesized from commercially available DOTA-tetra(t-butyl ester)-Bn-$NH_2$ (FIGS. 13A-13B, compound 1). All synthetic intermediates and final products are characterized by HPLC, NMR, and LCMS.

Figure 14:
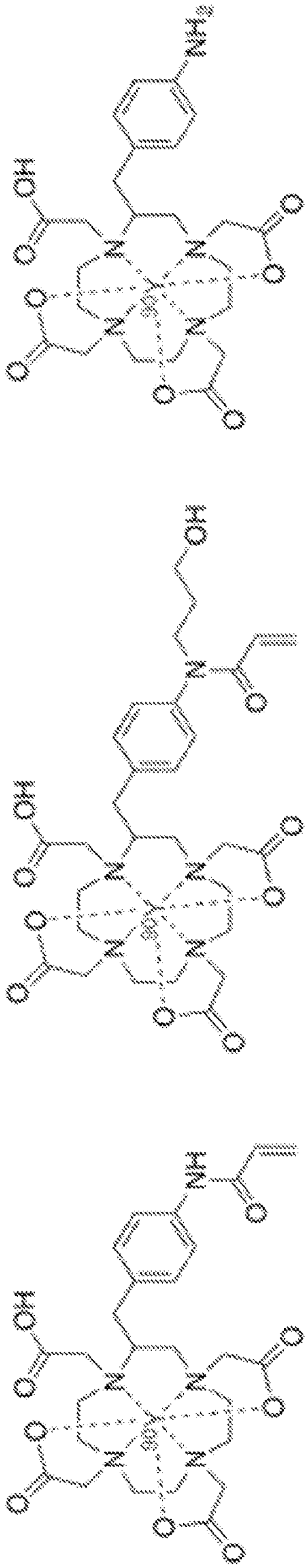
FIG. 14 illustrates the structures of $[^{90}Y]$AABD, irr-$[^{90}Y]$DOTA, and $[^{90}Y]$DOTA-Bn-$NH_2$.

Compounds 2 and 3 are deprotected with trifluoroacetic acid (TFA), and labeled with [$^{90}$Y] to furnish the covalent-linking probes [$^{90}$Y]AABD and irr-[$^{90}$Y]DOTA (a compound structurally similar to the final multifunctional Y-DOTA reagents), respectively (FIG. 14). Commercially available DOTA-Bn-$NH_2$ is labeled with [$^{90}$Y] and used as a non-covalent probe for comparison (FIG. 14), since the affinity of Y-DOTA-Bn-$NH_2$ for the anti-Y-DOTA scFv is known ($K_D$=8.2 pM) (Orcutt et al., *Nucl Med Biol* 38, 223-233 (2011)). The equilibrium dissociation constants ($K_D$) for irr-[$^{90}$Y]DOTA and [$^{90}$Y]DOTA-Bn-$NH_2$ are measured using saturation binding experiments in which increasing concentrations of radioligand are incubated with UnivIR CAR T cells that express the high affinity anti-Y-DOTA scFv (C8.2.5) or the modified hC8.2.5/G54C scFv. Cold (nonradioactive) Y-DOTA is used for blocking experiments, to determine nonspecific binding. To confirm that the probes and modified scFv (hC8.2.5/G54C) are capable of forming a covalent attachment, [$^{90}$Y]AABD and irr-[$^{90}$Y]DOTA are incubated with the hC8.2.5/G54C scFv for 2 hours. Samples are denatured and reduced for SDS-PAGE analysis (so only permanently bound complexes remain attached to the antibody), and imaged on a phosphor plate. Blocking experiments are performed with cold Y-DOTA, and the non-covalent probe, [$^{90}$Y]DOTA-Bn-$NH_2$ is used as a control. All experiments are performed in triplicate, and standard deviations are calculated for each sample.

Figure 19:
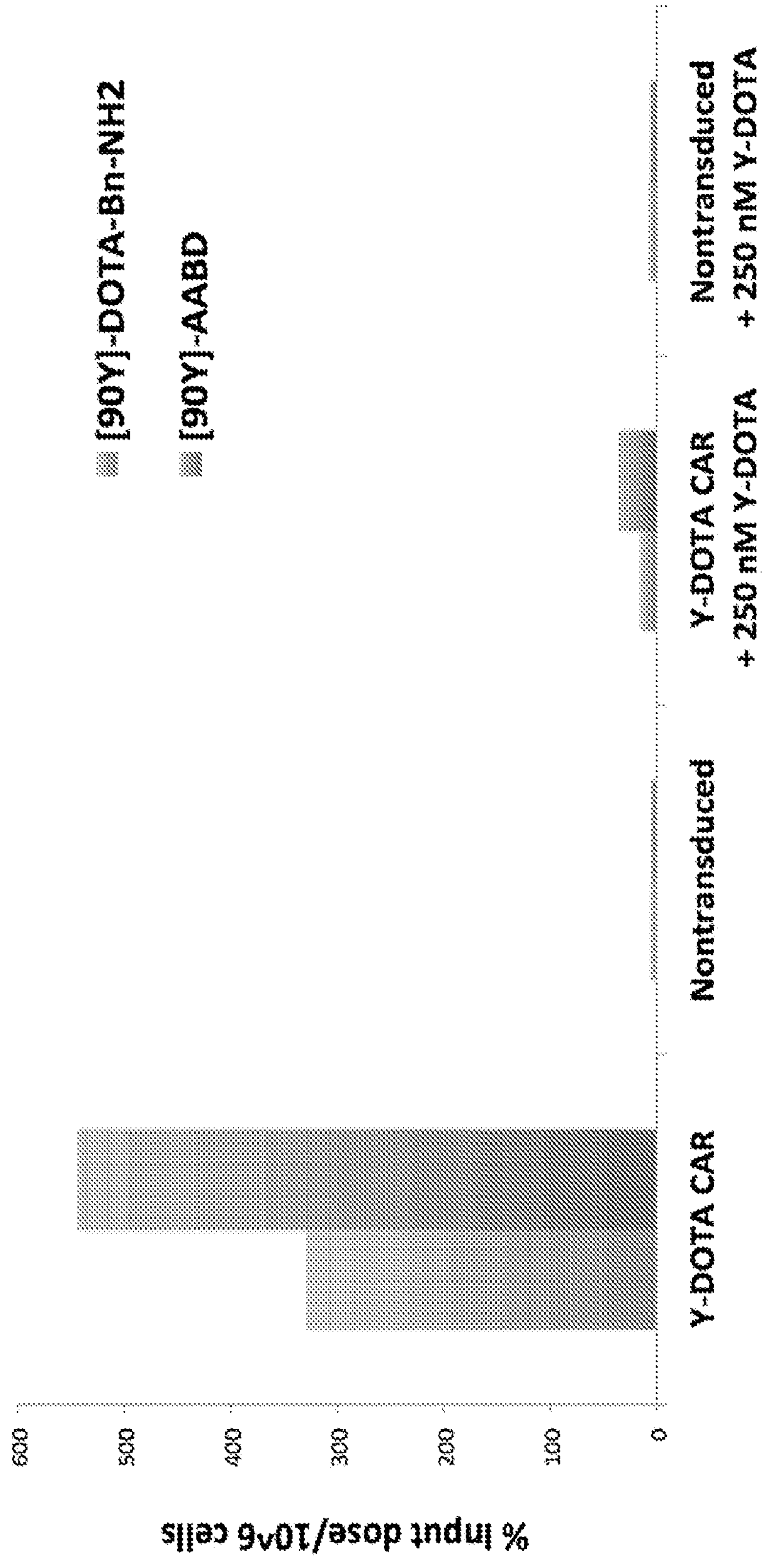
FIG. 19 is a histogram illustrating [9° Y]DOTA-Bn-$NH_2$ and [$^{90}$Y]AABD uptake in SKOV3 cells transduced with the DOTA CAR. The uptake can be blocked by an excess of Y-DOTA-Bn-$NH_2$ (250 nM), and nontransduced cells do not take up either probe, thus the nonspecific binding is low.

[$^{90}$Y]DOTA-Bn-NH2 and [$^{90}$Y]AABD (FIG. 14) were synthesized by incubating 0.6 mCi of Y-90 with DOTA-Bn-NH2 or AABD at 80° C. for 30 min. The radiochemical purity of [$^{90}$Y]DOTA-Bn-NH2 and [$^{90}$Y]AABD was >95% as analyzed by ITLC (instant thin-layer chromatography). Cell uptake studies were performed with SKOV3 cells transduced with the DOTA CAR, with untransduced SKOV3 cells as a control; excess Y-DOTA-Bn-NH2 (250 nM) was used as a blocking agent. DOTA CAR SKOV3 cells demonstrated marked uptake of both probes with >300% input/10^6 cells at 30 min, with substantially less uptake in the untransduced cells and the blocking experiment (FIG. 19).

Figure 20:
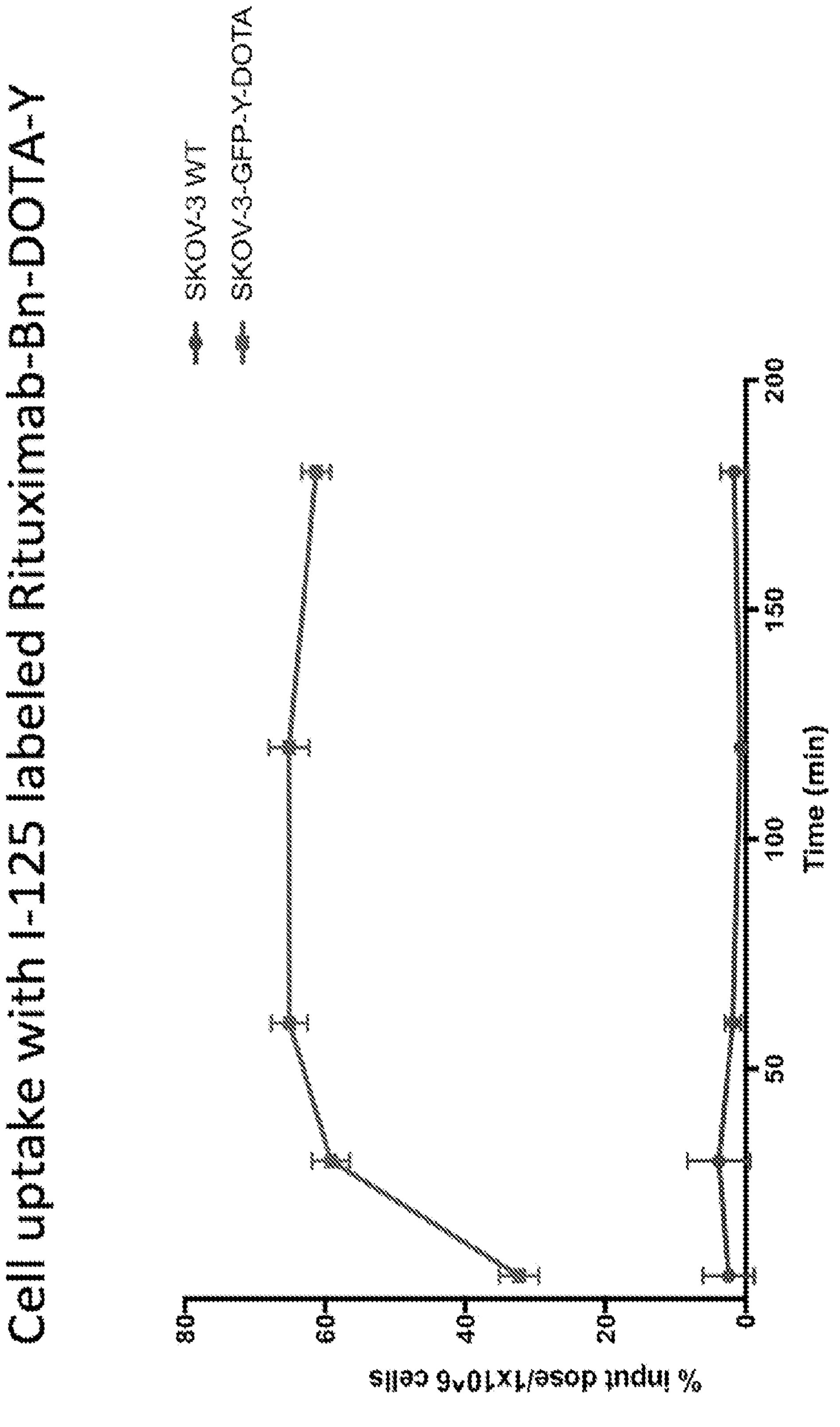
FIG. 20 is a graph illustrating [$^{15}$I]Rituximab-Bn-DOTA-Y uptake in SKOV3 cells transduced with the DOTA CAR. The cells bind to [$^{125}$I]Rituximab-Bn-DOTA-Y rapidly, with maximum uptake at 60 min. Nontransduced cells (SKOV3 WT) demonstrate minimal to no binding to the Y-DOTA labeled antibody.

Rituxumab-Bn-DOTA-Y was radiolabeled with 1-125 using Pierce Pre-Coated Iodination Tubes. The radiochemical purity of [$^{125}$I]Rituximab-Bn-DOTA-Y was >99% based on ITLC (instant thin-layer chromatography). Cell uptake studies with [$^{125}$I]Rituximab-Bn-DOTA-Y were performed with SKOV3 cells that were transduced with the DOTA CAR, with untransduced SKOV3 cells as a control. DOTA CAR SKOV3 cells demonstrated [$^{125}$I]Rituximab-Bn-DOTA-Y uptake of 65% input/10^6 cells, at 60 min, with minimal to no uptake in untransduced cells (FIG. 20). This experiment confirmed that Y-DOTA labeled antibodies are capable of binding to cells that express the DOTA CAR, with minimal nonspecific binding.

Herceptin is conjugated with rev-Y-DOTA-$N_3$-TFP, irr-Y-DOTA-$N_3$-TFP, and p-SCN-Bn-DOTA via primary amines on the antibody. The number of labels per antibody is calculated using MALDI-TOF mass spectrometry. Immunoreactivity is determined using a [$^{89}$Zr]-labeled antibody. The ability of UnivIR CAR T cells to mediate antigen-specific killing of HER2-positive tumor cells after treatment with rev-Y-DOTA-TCO-Herceptin, irr-Y-DOTA-TCO-Herceptin, or Y-DOTA-Herceptin is assessed.

A high affinity covalent-linking anti-Y-DOTA UnivIR CAR system is developed by performing site-directed mutagenesis on the high affinity non-covalent anti-DOTA hC8.2.5 scFv portion of the hC8.2.5 DOTA CAR construct to introduce a G54C amino acid substitution near the Y-DOTA binding pocket. The G54C mutation confers covalent reactivity to the low affinity parental 2D12.5 scFv, from which the C8.2.5 scFv was derived (Corneillie™, et al. Bioconjug Chem. 2004; 15(6):1392-402; Corneillie™, et al. Bioconjug Chem. 2004; 15(6):1389-91). Non-covalent hC8.2.5 and covalent hC8.2.5/G54C Y-DOTA-based CARs comprised of the extracellular picomolar affinity anti-Y-DOTA scFvs and intracellular CD3-(and CD28 costimulatory signaling modules, are designed, constructed and tested (FIG. 2A). hC8.2.5scFv:Y-DOTA binding on the T cell surface was already demonstrated herein. CD28 provides robust effector function but poor in vivo persistence, while 4-1BB confers a greater ability to persist in vivo with reduced function on the per cell basis. Given these differential attributes, the impact of these different costimulatory domains is tested. High titer lentivirus is produced using standardized procedures (Carpenito C, et al. Proc Natl Acad Sci USA. 2009; $10^6$(9):3360-5), that reproducibly results in ~70-90% transduction efficiency in human T cells (Lanitis E, et al. Mol Ther. 2012; 20(3):633-43; Song D G, et al. Blood. 2012; 119(3):696-706; Song D, et al. Cancer Res. 2011). In all assays, lentiviral transduction of T cells is performed under conditions of optimal transduction efficiency with control green fluorescent protein (GFP) lentiviral transduction performed in parallel cultures.

The tetrafluorophenyl ester TFP ester was selected as the amine-reactive domain for the Y-DOTA reagent because its increased stability relative to the NHS ester permits chelation of yttrium to the DOTA reagent, in sodium acetate buffer at pH 5, without hydrolysis of the TFP ester (Calderon Sanchez O, et al. Bioconjug Chem. 2003; 14(6):1209-13; Mier W, et al. Bioconjug Chem. 2005; 16(1):237-40). However, if hydrolysis of the TFP ester proves to be a problem, then less reactive esters are explored, such as p-nitrophenyl ester. Alternatively, DOTA is first conjugated to the antibody, and then yttrium chelation is performed.

If there is a substantial drop in affinity of the hC8.2.5/G54C scFv for Y-DOTA-Bn-$NH_2$, or lack of covalent reactivity, alternative sites for incorporation of cysteine can be tested, such as G55C and C56C, which were reported to be capable of forming covalent linkages in the 2D12.5 scFv (Comeillie™, et al. Bioconjug Chem. 2004; 15(6):1392-402). If the G54C, G55C, and G56C mutants all demonstrate low affinity or lack of covalent reactivity, the existing lower affinity anti-Y-DOTA covalent system, 2D12.5/G54C scFv, that has been used successfully as a CAR T cell reporter gene (Krebs S, et al. J Nucl Med. 2018; 59(12):1894-1900; Wei L H, et al. J Nucl Med. 2008; 49(11):1828-35) is used.

Figure 15:
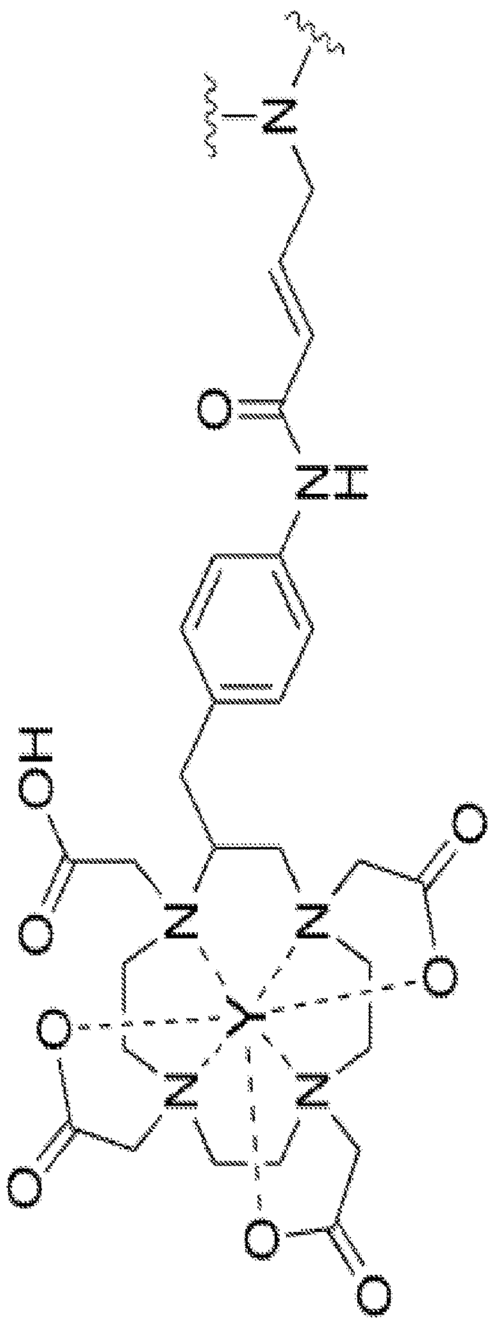
FIG. 15 shows the general structure of alternative non-limiting covalent Y-DOTA probes.

If the irreversible multifunctional Y-DOTA reagent irr-Y-DOTA-$N_3$-TFP, and its radiolabeled precursor, irr-[$^{90}$Y]DOTA are not able to form a covalent linkage with the modified hC8.2.5/G54C scFv, alternative probes are explored. These alternatives include molecules with a disulfide or a γ-amino-α,β-unsaturated amide (FIG. 15), since both have been shown to form covalent linkages with cysteine-containing proteins with reactivity that is similar to a terminal vinyl amide (such as [$^{90}$Y]AABD). Given their self-assembling covalent binding, the recently described SpyCatcher:SpyTag system may also be used (Moon H, et al. Chemical communications. 2016; 52(97):14051-4).

Alternatively, site-directed mutagenesis is performed on the high affinity non-covalent anti-DOTA hC8.2.5 scFv portion of the hC8.2.5 DOTA CAR construct to introduce a G54K, G55K, or G56K amino acid substitution near the Y-DOTA binding pocket. The introduced lysine is capable of forming a covalent linkage with thiol-reactive and amine-reactive DOTA-comprising compounds described herein (e.g. DOTA compounds containing α,β-unsaturated amides and 5-fluoro-2,4-dinitrobenzene).

Example 9: Testing the Ability of Multifunctional Y-DOTA Labeled Antibodies to Engage UnivIR CAR T Cells and Mediate Antigen-Specific Cell Killing In Vitro DOTA-specific UnivIR CAR T cells armed with TAA-specific antibodies recognize and exert robust effector functions in response to imaging-defined, antigen positive cancer cells (FIGS. 3A-3I). The multifunctional Y-DOTA reagents developed herein are used to synthesize reversible and irreversible Y-DOTA conjugated Herceptin labeled with either [$^{89}$Zr] or TCO for imaging (FIG. 16). [$^{89}$Zr]-labeled Herceptin is used to measure the immunoreactivity of the labeled antibodies, and to confirm that [$^{89}$Zr]DFO-irr-Y-DOTA-Herceptin is capable of forming a covalent linkage with UnivIR CAR T cells. [$^{89}$Zr]-labeled Herceptin is also used for biodistribution studies and PET imaging in tumor-bearing mice, to confirm successful tumor targeting by the labeled antibodies, and assess if tumor uptake is predictive of response to therapy. In addition, [$^{89}$Zr]-labeled Herceptin is used to measure anti-Y-DOTA receptor availability on UnivIR CAR T cells. TCO-labeled Herceptin is used for pretargeted PET imaging studies, and is imaged with the click-reactive probe [$^{18}$F]tetrazine. The ability of tumor uptake to predict response to concurrent therapy is evaluated, and evidence of target engagement by UnivIR CAR T cells is assessed.

Data presented herein show that DOTA-specific UnivIR CAR T cell activity can be controlled through Y-DOTA-Herceptin antibody dosing. New imaging antibodies are tested. Multi-antigen targeting, either simultaneously or sequentially, is also evaluated. The loadable specificity of the UnivIR CAR T cell system predicts that CAR T cells undergoing cell division are likely to maintain high level expression of the anti-Y-DOTA receptor, but dilute the covalently-linked antibody load equally among its two daughter cells. As a secondary objective, the impact of T cell proliferation on antibody dilution and effector function is tested in pharmacokinetic assays, the dose of loaded antibody required to instill T cell sensitivity/function in vitro is evaluated, and receptor turnover and the effect of repeat antibody-loading on anti-tumor T cell function is assessed.

Figure 16:
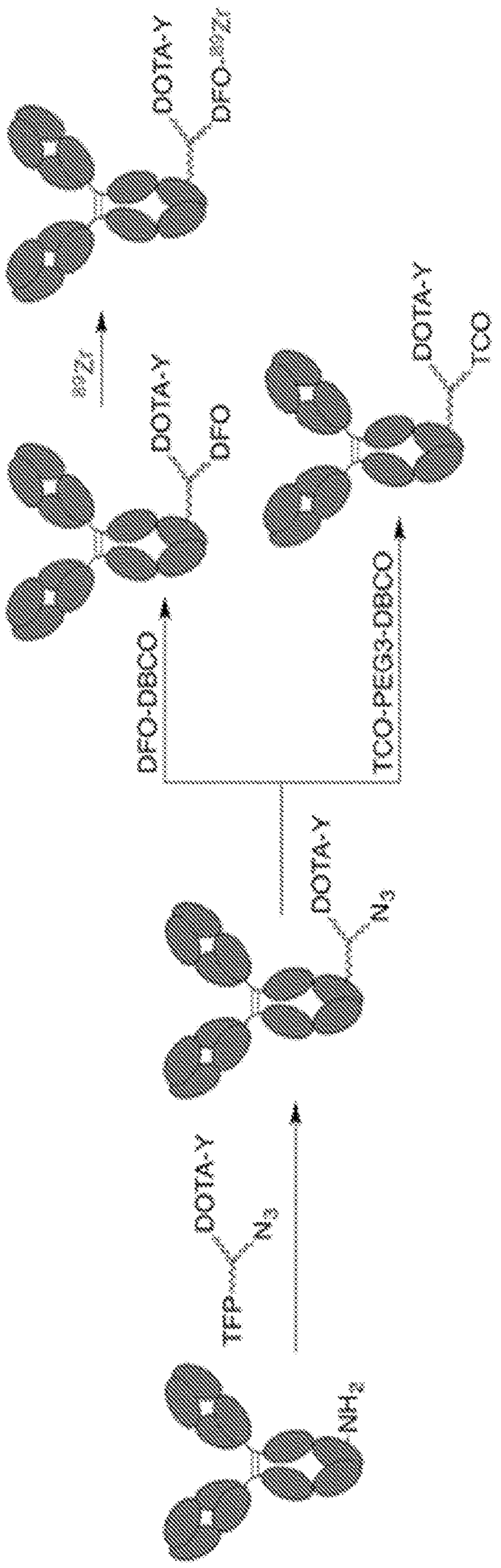
FIG. 16 illustrates the scheme for generating antibodies labeled with Y-DOTA and either $^{89}$Zr-DFO or TCO. Primary amines on antibodies will react with the tetrafluorophenyl ester (TFP) on the multifunctional Y-DOTA reagent, forming a stable amide bond. The terminal azide on the Y-DOTA reagent will then be converted to a desferrioxamine chelate (DFO) via click chemistry, and labeled with $[^{89}Zr]$. Alternatively, the terminal azide will be reacted with a reagent that allows for introduction of trans-cyclooctene (TCO) into the molecule; the TCO is a substrate for click chemistry and useful for in vivo pre-targeted PET imaging.

Herceptin is labeled with rev-Y-DOTA-$N_3$-TFP and irr-Y-DOTA-$N_3$-TFP. These azide-labeled antibodies serve as a common precursor for the synthesis of both [$^{89}$Zr] and TCO-labeled antibodies (FIG. 16). For the [$^{89}$Zr]-labeled antibody, commercially available desferrioxamine (DFO)-dibenzocyclooctyne (DBCO) is coupled to the azide-labeled antibody via a strain-promoted azide-alkyne cycloaddition reaction. The resulting DFO-labeled antibody is then incubated with [$^{89}$Zr] to produce [$^{89}$Zr]DFO-rev-Y-DOTA-Herceptin or [$^{89}$Zr]DFO-irr-Y-DOTA-Herceptin. The immunoreactivity of the labeled antibodies is determined by incubating [$^{89}$Zr] labeled antibody with HER2-positive (SKOV3) or HER2-negative cells (CEM) for 1 hour; after centrifugation, the immunoreactive fraction is calculated as % cell-bound activity/total activity. [$^{89}$Zr]DFO-irr-Y-DOTA-Herceptin is incubated with covalent hC8.2.5/G54C CAR T cells, and the presence of a covalent linkage is assessed via washout experiments. [$^{89}$Zr]DFO-rev-Y-DOTA-Herceptin and non-covalent hC8.2.5 CAR T cells are used as controls, and a blocking study is performed with Y-DOTA-Bn-$NH_2$. Both [$^{89}$Zr]-labeled antibodies are imaged via PET/CT in mice bearing HER2 positive and negative tumors; PET/CT imaging is performed at 24, 48, 72, and 120 hours following injection of radiotracer via the tail vein. The maximum and mean SUV is measured within each tumor, and the ratio of uptake for positive and negative tumors is calculated. 5 mice are imaged for each experiment. Tissue harvesting and biodistribution analysis are performed following the 120 hour PET imaging. Tumor tissue is obtained for pathologic evaluation and autoradiography, to assess the distribution of radiolabeled antibody within the tumor compared to the distribution of HER2 expression. Increased radiotracer uptake in antigen positive tumors is predictive of response to UnivIR CAR T cell therapy.

Figure 17:
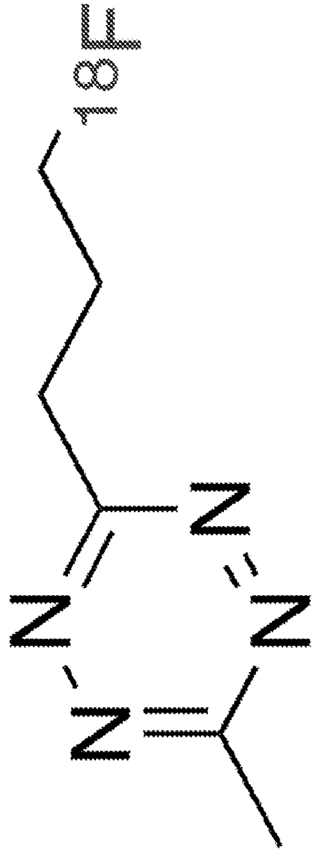
FIG. 17 illustrates the structure of [$^{18}$F]tetrazine.

TCO-labeled antibody is synthesized using commercially available TCO-PEG3-DBCO, which is coupled to the azide-labeled antibody via a strain-promoted azide-alkyne cycloaddition reaction (FIG. 16). [$^{18}$F]Tetrazine (FIG. 17), which undergoes a rapid click reaction with TCO, is synthesized in three steps from commercially available starting material, as previously described (Denk C, et al. Angew Chem Int Ed Engl. 2014; 53(36): 9655-9). Both reversible and irreversible TCO-labeled Herceptin is imaged via PET/CT in mice bearing HER2 positive and negative tumors. PET/CT imaging is performed at 1, 2, and 4 hours following injection of [$^{18}$F]tetrazine via the tail vein. Mice are imaged 24 hours or 48 hours after administration of a single therapeutic dose of antibody. Five mice are used for each imaging experiment; image analysis is performed as described elsewhere herein. Tissue harvesting and biodistribution analysis is performed following the 120 hour PET imaging; tumor tissue are obtained for pathologic evaluation and autoradiography. Increased radiotracer uptake in antigen positive tumors is predictive of response to UnivIR CAR T cell therapy. This PET/CT imaging experiment is then repeated in tumor bearing mice treated with the reversible system (rev-Y-DOTA-TCO-Herceptin followed by hC8.2.5 CAR T cells) or irreversible system (irr-Y-DOTA-TCO-Herceptin followed by hC8.2.5/G54C CAR T cells). Mice are treated with antibody on day 0, and then imaged with [$^{18}$F]tetrazine PET on day 1 (at 4 hours following radiotracer injection, or the optimal time point based on previous studies). Mice are then treated with antibody again on day 3, and imaged with [$^{18}$F]tetrazine PET on day 4. Unlabeled Herceptin and nontransduced cells are used for controls. Seven mice per imaging experiment are used. Tissue harvesting and biodistribution analysis are performed following the last PET imaging experiment. Tumor tissue is obtained for pathologic evaluation and autoradiography. The imaging data is analyzed for predictiveness of response and evidence of target engagement.

Primary human T cells are transduced to express the hC8.2.5 or hC8.2.5/G54C CARs using methods established herein for clinical application (FIG. 2C). Flow cytometric analysis using Protein-L or goat anti-mouse Ig as detection agent is used to confirm surface expression of the CARs and determine relative transduction efficiencies. To initially validate the capacity of the non-covalent hC8.2.5 and covalent hC8.2.5/G54C CARs to bind to a Y-DOTA-labeled antibody (Y-DOTA-Ab), DOTA CAR T cells are stained with rev-Y-DOTA-TCO-Herceptin, irr-Y-DOTA-TCO-Herceptin, and Y-DOTA-Herceptin Y-DOTA Herceptin, washed and then secondarily stained with fluorochrome-labeled recombinant HER2 protein, using a sandwich flow cytometry assay. The stability of the interaction between the various Y-DOTA-Abs and the hC8.2.5 or hC8.2.5/G54C CAR constructs expressed by T cells are then serially assessed by flow cytometry in surface protein dissociation assays. The expected covalent bond between the hC8.2.5/G54C and modified irr-Y-DOTA-Ab predicts more stable binding of the irr-Y-DOTA-$N_3$-Herceptin to the surface of hC8.2.5/G54C CAR T cells, compared to the parental hC8.2.5 CAR. To further test for covalent binding between the hC8.2.5/G54C CAR and irr-Y-DOTA-$N_3$-Herceptin, hC8.2.5 and hC8.2.5/G54C CAR T cells are armed with rev-Y-DOTA-$N_3$-Herceptin, irr-Y-DOTA-$N_3$-Herceptin, or Y-DOTA-Herceptin and serially assessed for covalent CAR formation by CD3z Western blot analysis under denaturing conditions where unbound CARs and antibody-bound CARs can easily be distinguished by size. All assays are performed at least thrice in triplicate and relative statistical comparisons made by paired 2-tailed Students t-test.

Next, using HER2 and EGFR as model target tumor antigens, the DOTA CAR T cells are armed with rev-Y-DOTA-TCO-Herceptin, irr-Y-DOTA-TCO-Herceptin, or Y-DOTA-Herceptin (or control antibodies) and co-cultured with the established human cancer lines that express HER2 (SKOV3 and SKBR3) or EGFR (MDA-468, SKOV3, A1847, A2780) or lines that do not express (CEM and AE17), and antigen-driven effector function is assessed. Armed DOTA CAR T cells are tested for the capacity to respond to antigen bearing tumor cells, through measurement of cytokine secretion (ELISA, cytokine bead array), T cell proliferation (CFSE dilution) and specific lysis ($Cr^{51}$ release and/or xCELLigence assay). The impact of costimulatory modules (CD28 or 4-1BB; FIG. 2B) on antigen-stimulated T cell proliferation, survival and cytokine secretion by DOTA CAR T cells is determined using CFSE dilution and cytokine bead array, respectively (IFN-g, TNF-α, GM-CSF, MIP1a, IL-2, IL-4 and IL-10). Polyfunctionality is measured by intracellular cytokine secretion assay. The impact of antigen expression level by target tumor cells on the magnitude of response is assessed using antigen-negative AE17 cells engineered to express surface HER2 or EGFR at high, intermediate or low levels. Similar assays are performed using a series of Y-DOTA-Cetuximab antibodies for EGFR targeting, and simultaneous or sequential multi-antigen targeting is tested.

Covalent binding of the irr-Y-DOTA-TCO-Herceptin to hC8.2.5/G54C CARs provides the unique opportunity to robustly evaluate CAR turnover, i.e. whether cell division results in dilution of the Ab on the CAR T cell, with each daughter cell retaining half of the starting Y-DOTA Ab quantity, and to determine whether these cells are amenable to secondary arming with an Y-DOTA-Ab of different specificity to broaden reactivity, thus addressing emerging antigen loss variants. A flow-based monitoring system is used to detect and distinguish Ab-armed DOTA CAR T and empty CAR T cells. Using multiparameter flow cytometry, CFSE-labeled hC8.2.5/G54C or hC8.2.5 CARs T cells that have undergone antigen-induced proliferation are measured for (i) cell division with CFSE, (ii) retained irr-Y-DOTA-TCO-Herceptin surface expression, and (iii) "empty" CAR T units with fluorchrome-labeled Y-DOTA. With each cell division cycle, divided daughter cells will undergo progressive dilution of detectable surface Y-DOTA-Ab while the presence of empty CAR complexes will increase and facilitate opportunities for secondary Y-DOTA-Ab arming and redirected function. CFSE diluted T cells of different division cycles are sorted and re-armed with a different Y-DOTA-Ab to determine the impact of cell division on secondary response and to test the hypothesis that after a focused primary immune response, the secondary response can be diversified to limit tumor immune escape.

Stem cells, naïve T cells or T cells with a stem cell memory phenotype with a propensity for long life can be considered as a T cell source. Beyond the current scope, the DOTA CAR T approach might also be utilized for directed T cell homing or delivery; e.g. loading of signaling deficient DOTA CAR T cells with tumor-specific integrin receptors or immunomodulatory payloads to enable T cell retention and delivery to tumor sites.

Example 10: Evaluating UnivIR CAR T Cell Tracking Methods as a Companion Diagnostic Imaging Tool The effect of a variety of therapeutic regimens on UnivIR CAR T cell function are evaluated in vivo, and two different cell tracking methods are applied to the in vivo studies in order to better understand differences in response. [$^{89}$Zr]DFO-irr-Y-DOTA-Herceptin is used to label (and pre-arm) hC8.2.5/G54C CAR T cells via a covalent linkage. Washout of [$^{89}$Zr] is measured over several days to evaluate the stability of the cell labeling. The proliferation and antigen-specific cytolytic activity of radiolabeled cells is compared to unlabeled cells. For PET imaging, [$^{89}$Zr] labeled CAR T cells are administered (on day 0) to mice bearing HER2 positive and negative tumors via the tail vein. PET/CT imaging is performed on day 1, 2, 4, and 7. Cohorts of mice are treated with rev-Y-DOTA-TCO-Herceptin or irr-Y-DOTA-TCO-Herceptin on a q1, q2, or q3 day schedule. Another cohort of mice is treated with pre-armed CAR T cells incubated with irr-Y-DOTA-TCO-Herceptin, and then treated with irr-Y-DOTA-TCO-Herceptin on a daily schedule. Control experiments include treatment with no antibody, Herceptin, or non-transduced T cells. Seven mice are used per imaging experiment. Tumor uptake is measured and compared with response. Tissue harvesting and biodistribution analysis is performed following the last PET imaging experiment; tumor tissue is obtained for pathologic evaluation and autoradiography.

Two [$^{18}$F]-labeled Y-DOTA derivatives, [$^{18}$F]rev-Y-DOTA and [$^{18}$F]irr-Y-DOTA (FIG. 18), are synthesized using compounds 3 and 7 from (FIGS. 13A-13B). All synthetic intermediates and final products are characterized by HPLC, NMR, and LCMS. Biodistribution data for both radiotracers are collected at 5 min, 30 min, 1 h, and 2 h post injection of radiotracer, with 5 mice per time point. Organs are harvested and counted using a well gamma counter. PET/CT imaging is performed with both radiotracers using mice injected subcutaneously with varying amounts of hC8.2.5 CAR T cells or hC8.2.5/G54C CAR T cells, and the sensitivity for detecting the cells is determined. A set of PET/CT imaging experiments is then performed using 4 different treatment regimens (utilizing both the reversible and irreversible UnivIR CAR T cell systems) that produced varying degrees of response based on prior in vivo data. Dynamic PET imaging is acquired for 2 hours following injection of [$^{18}$F]rev-Y-DOTA or [$^{18}$F]irr-Y-DOTA on day 1, 2, 4, and 7 post administration of CAR T cells. The difference in uptake/sensitivity between cells directly labeled with [$^{89}$Zr] and the reporter gene approach using [$^{18}$F]rev-Y-DOTA and [$^{18}$F]irr-Y-DOTA is compared.

Assays of in vivo function: Preclinical experiments are performed to determine the ability of non-covalent hC8.2.5 and covalent hC8.2.5/G54C UnivIR CAR T cells armed with the [$^{89}$Zr]DFO-irr-Y-DOTA-Herceptin to attenuate growth or reject human cancer in vivo using established human ovarian and breast cancer xenograft models in NSG mice wherein the cancer cell lines are transfected to express firefly luciferase (fLuc) for tumor growth monitoring. The impact of Y-DOTA-Ab dosing schedule and concentration is assessed. Also tested is the ability of the DOTA CAR T cells armed with various [$^{89}$Zr]DFO-irr-Y-DOTA-Herceptin or [$^{89}$Zr]DFO-irr-Y-DOTA-Cetuximab to treat mice bearing large, established s.c. fLuc+ HER2+ (SKOV3 and SKBR3) or EGFR+(MDA-468, A1847) tumor. Results are confirmed in other tumor model systems, including breast cancer (HER2, EGFR), and ALL (CD19, CD123). Impact of route of infusion and armed UnivIR CAR T cell dose is investigated, as is the impact of Y-DOTA-Ab maintenance post T cell transfer. Naked Ab without DOTA, and Y-DOTA-Abs with irrelevant antigen specificity, serve as controls.

In pre-diagnostic imaging experiments, tumor-bearing mice are pretreated with the [$^{89}$Zr]DFO-irr-Y-DOTA-Herceptin or [$^{89}$Zr]DFO-rev-Y-DOTA-Herceptin to pre-target the tumor, imaged and subsequently infused i.v. with DOTA CAR T cells to determine their capacity recognize and respond against the different Y-DOTA-Abs immobilized on the tumor cell surface. Tumor monitoring is performed routinely by luciferase bioluminescence imaging and caliper sizing. To determine whether Y-DOTA-Ab dosing can induce and regulate DOTA CAR T cell anti-tumor activity in vivo, unarmed CAR T cells are infused into tumor-bearing mice and [$^{89}$Zr]DFO-rev-Y-DOTA-Herceptin subsequently administered at titered doses and with varied dosing schedules. UnivIR CAR T cells are assayed for their capacity to control the outgrowth of tumors with heterogeneous antigen expression or antigen loss through simultaneous or sequential HER2/EGFR targeting.

This new set of molecular imaging tools enables unique exploration of the mechanism of action of UnivIR CAR T cells, and CAR T cells in general, by interrogating the various components that are relevant to the UnivIR CAR T cell system, including tumor antigen expression, antibody deposition in tumor, trafficking of CAR T cells, and target engagement by UnivIR CAR T cells within the tumor microenvironment. These imaging tools also allow exploration of the impact of a number of variables in UnivIR CAR T cell activity, such as antibody dose, timing between antibody dosing and CAR T infusion, pre-arming UnivIR CAR T cells with antibody versus infusing them unarmed (which requires that they find anti-DOTA labeled antibody in vivo), use of an irreversible (covalent-linking) UnivIR CAR T cell system versus a reversible system, affinity tuning (by changing the metal ion-DOTA complex in order to modify its affinity for the anti-DOTA scFv), and treatment with reversible vs. irreversible cold Y-DOTA as a means of controlling CAR T cell function.

Example 11

Figure 21:
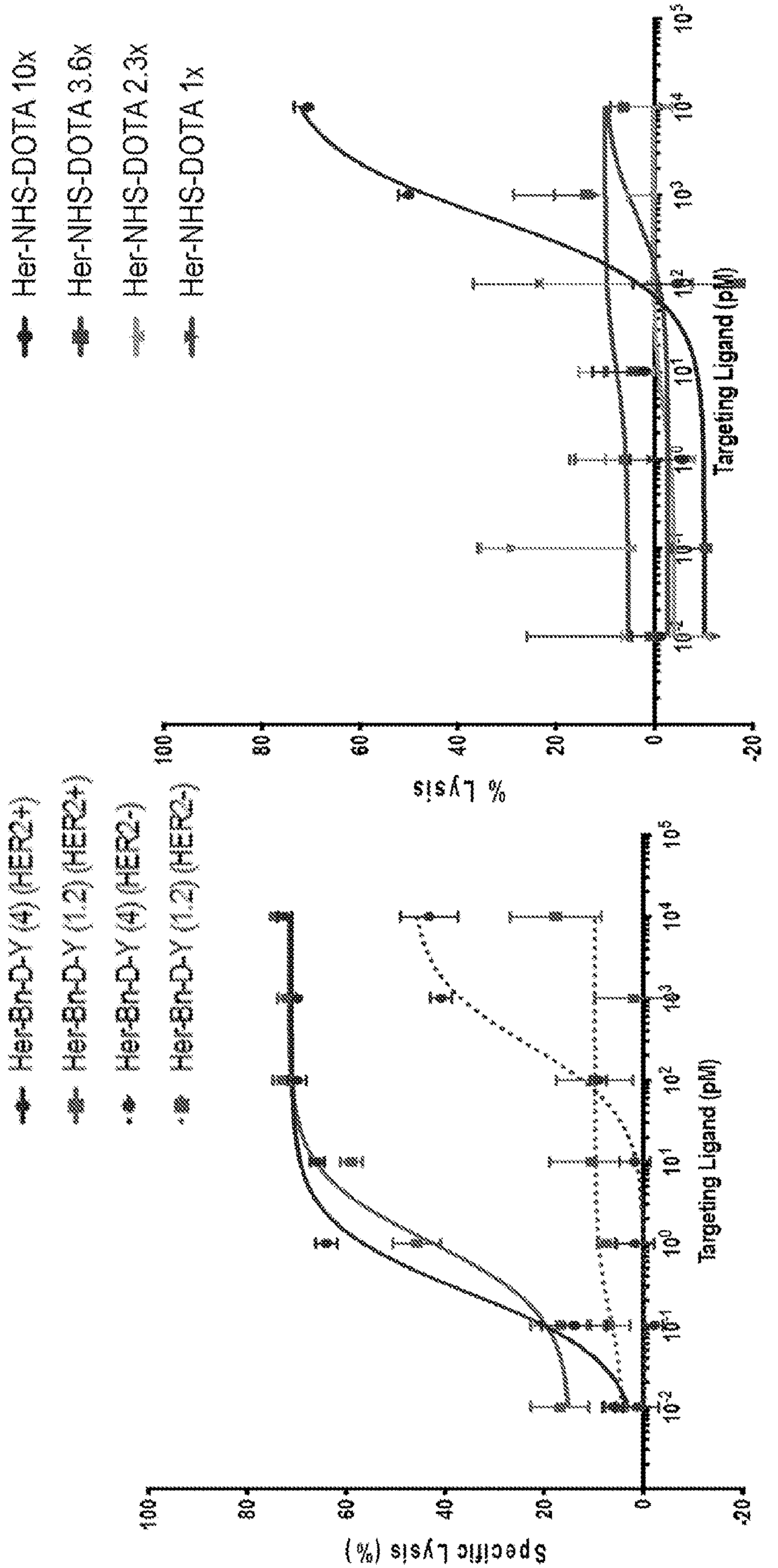
FIG. 21 illustrates the finding that lowering valency of targeting ligands allows for affinity tuning of the receptor-targeting ligand interaction. 2.5:1 E:T ratio.

Previous data showed that Herceptin-Bn-DOTA targeting ligands with lower valency reduced off-target lysis while maintaining efficacy against antigen-expressing cells (FIG. 21, left panel). Herceptin was conjugated to DOTA-NHS molecules at varying molar ratios in order to create targeting ligands with lower valency. Skov3 (HER2+) cells expressing firefly luciferase (fLuc) were incubated for 16 hours with DOTA CAR T cells at a 2.5:1 E:T ratio and targeting ligands at a range of concentrations. Each condition was run in triplicate. Luminescence was measured after co-culture and used to calculate specific lysis (FIG. 21, right panel). The Herceptin-NHS-DOTA system, which has lower affinity, required a higher valency to effectively lyse target cells.

Figure 22:
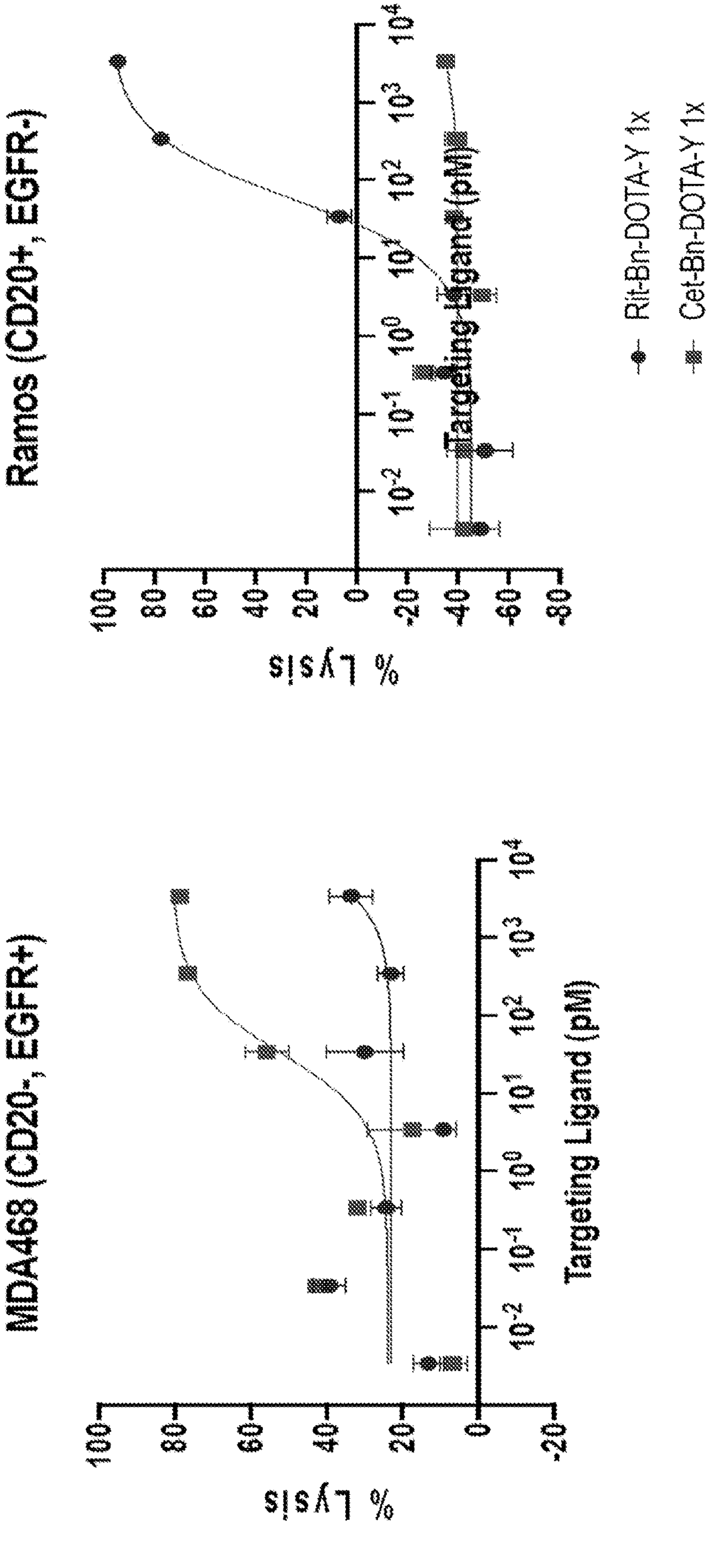
FIG. 22 illustrates the finding that lower valency targeting ligands specific for other markers selectively lyse target cells. DOTA BBz. 2.5:1 E:T ratio.

Cetuximab and Rituximab were conjugated to Bn-DOTA to create targeting ligands with an average of 1 DOTA molecule per antibody, confirmed by MALDI TOF. MDA468 (CD20-/EGFR+) cells and Ramos (CD20+/EGFR−) cells expressing fLuc were incubated for 16 hours with DOTA CAR T cells at a 2.5:1 E:T ratio and targeting ligands at a range of concentrations. Each condition was run in triplicate. Luminescence was measured after co-culture and used to calculate lysis. Lower valency Cetuximab-Bn-DOTA and Rituximab-Bn-DOTA targeting ligands were able to specifically lyse their respective target cell lines (FIG. 22).

Figure 23:
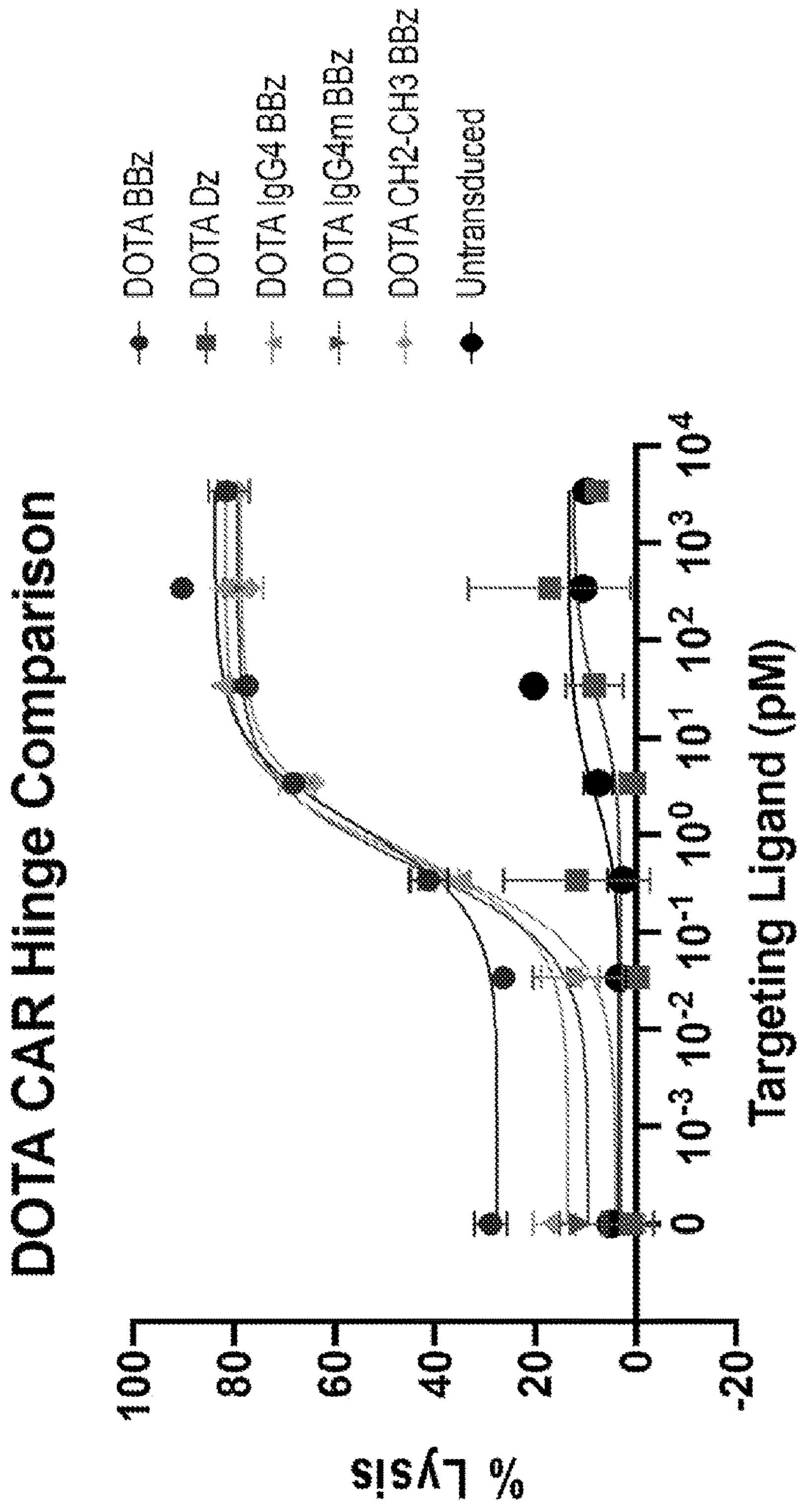
FIG. 23 illustrates anti-DOTA CARs with varying hinge lengths function with the Herceptin-DOTA system and may be useful for other types of targeting ligands. CD8a: 135 bp, IgG4: 36 bp, CH2CH3: 648 bp. 2.5:1 E:T ratio. SKOV3 target cell line.

DOTA CARs with varying hinge lengths were created to allow the possibility of optimizing physical interactions at the cell surface (FIG. 23). The standard DOTA CAR uses a CD8a hinge (45 AA). DOTA CARs with a shorter IgG4 hinge (12 AA) and a longer IgG4-$CH_2CH_3$ hinge (216 AA) were created. The IgG4 hinge was inserted with and without an amino acid change that allows cross-linking. To assess their function, Skov3 (HER2+) cells expressing fLuc were incubated for 16 hours with DOTA CAR T cells at a 2.5:1 E:T ratio and targeting ligand at a range of concentrations. Each condition was run in triplicate. Luminescence was measured after co-culture and used to calculate lysis. Although no significant differences were observed with this system, in certain non-limiting embodiments these constructs can play a role in optimizing interactions between other targeting ligands and antigens (FIG. 23).

Figure 24:
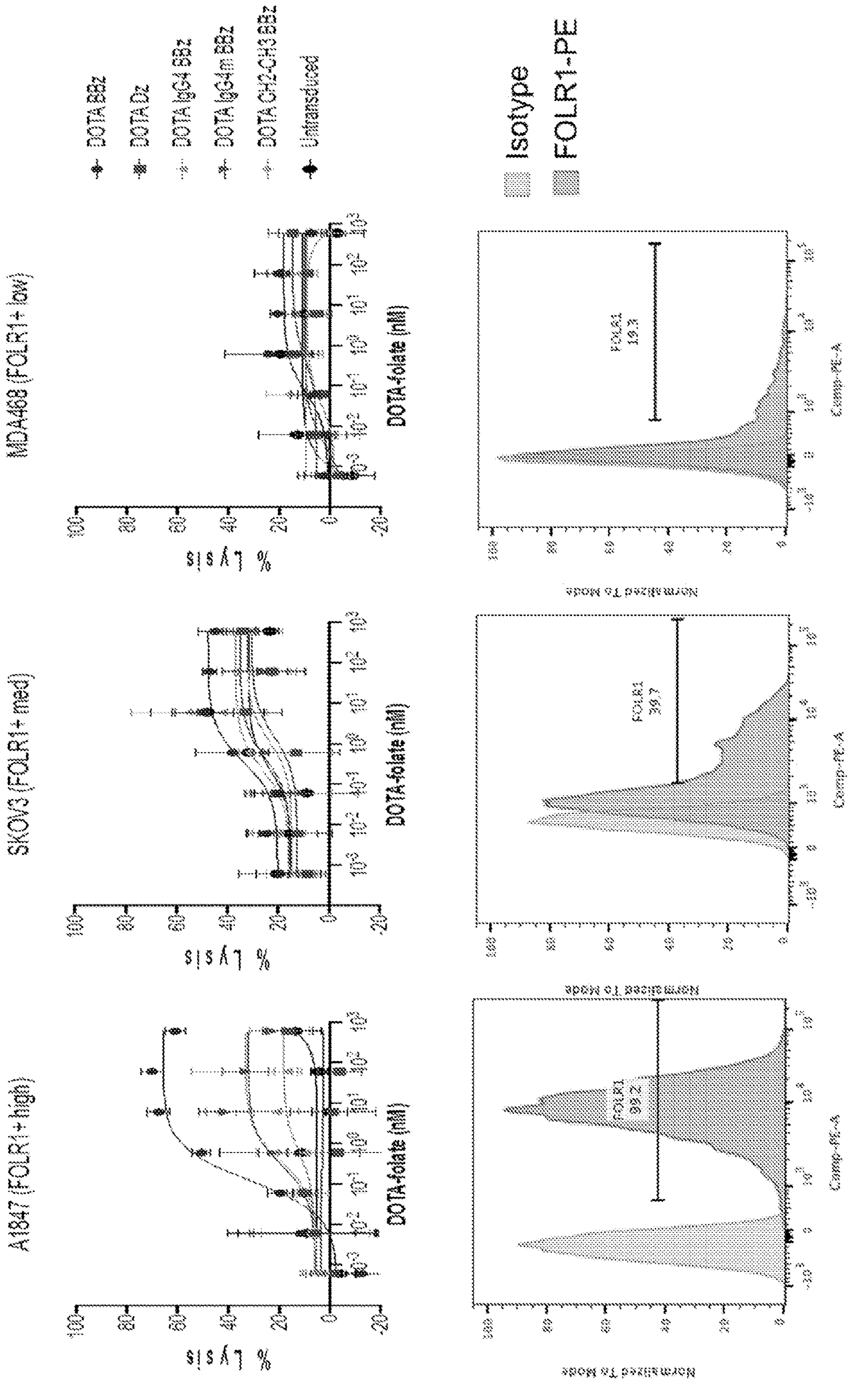
FIG. 24 illustrates the finding that anti-DOTA CAR can target FOLR1+ cells using folate-DOTA as a targeting ligand in folic acid free media. 2 technical replicates across 2 donors. 2.5:1 E:T ratio.
Figure 25:
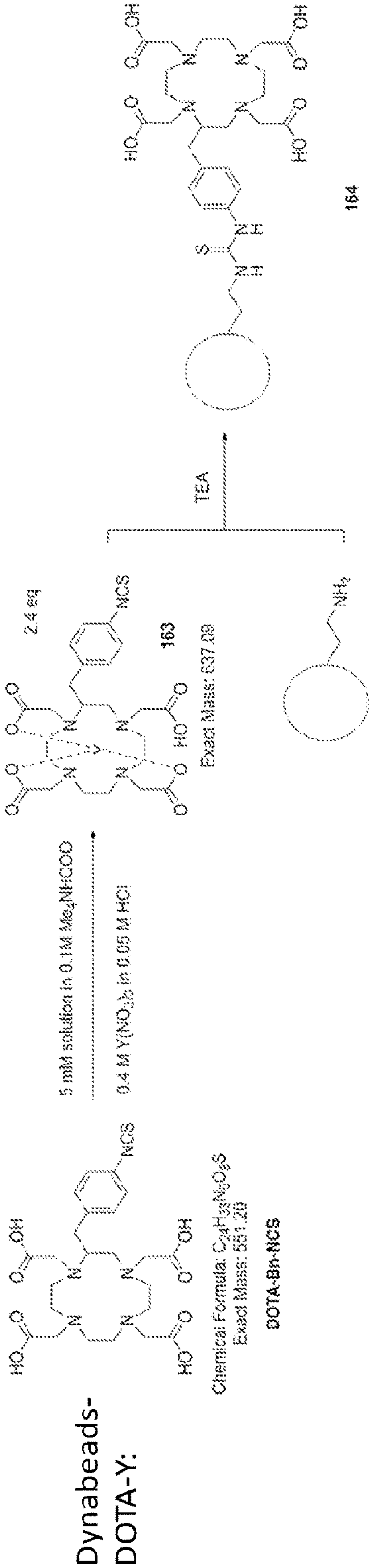
FIG. 25 illustrates the ability of Bis- or Tris-DOTA compounds of various lengths or Dynabeads conjugated with DOTA to activate anti-DOTA CAR T cells. DOTA BBz and DOTA Dz T cells were incubated for ~24 hours with: Dynabeads-DOTA-Y, Tris-DOTA (PEG-n), or Bis-DOTA (PEG-n).
Figure 25:
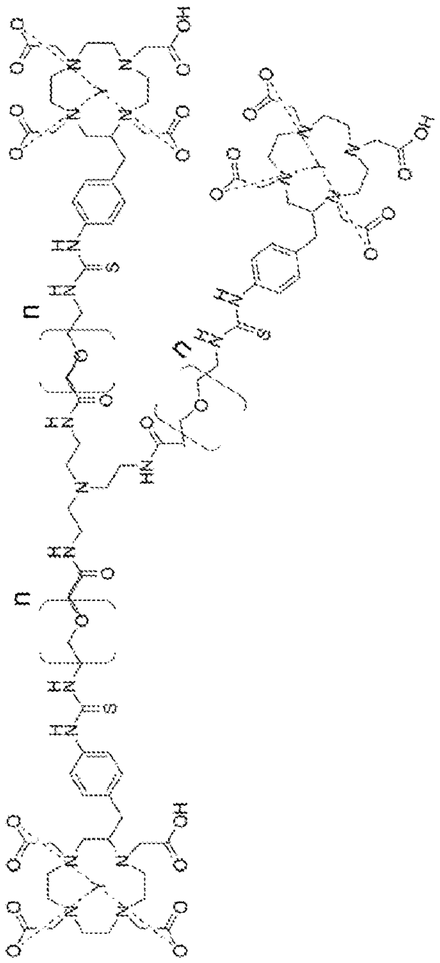
Figure 25:
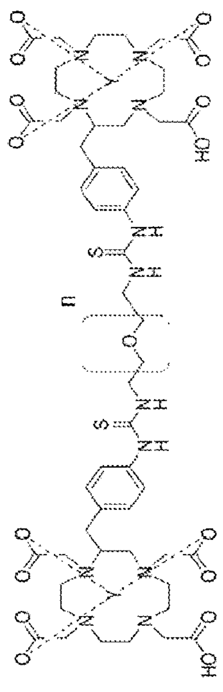

A1847 (FOLR1+ high), Skov3 (FOLR1+ medium), and MDA468 (FOLR1+ low) cells expressing fLuc were incubated in folic acid-free media for 16 hours with DOTA CAR T cells at a 2.5:1 E:T ratio and folate-DOTA at a range of concentrations. Luminescence was measured after co-culture and used to calculate specific lysis (FIG. 24, top panel). Each condition was run in triplicate. Results are from technical replicates using two T cell donors. FOLR1 expression on the three cell lines was confirmed by flow cytometry after staining with either a FOLR1 antibody or isotype control (FIG. 24, bottom panel). The standard DOTA BBz CAR was most effective at lysing the FOLR1+ high expressing target cells.

Example 12

Synthesis of DOTA-Folate

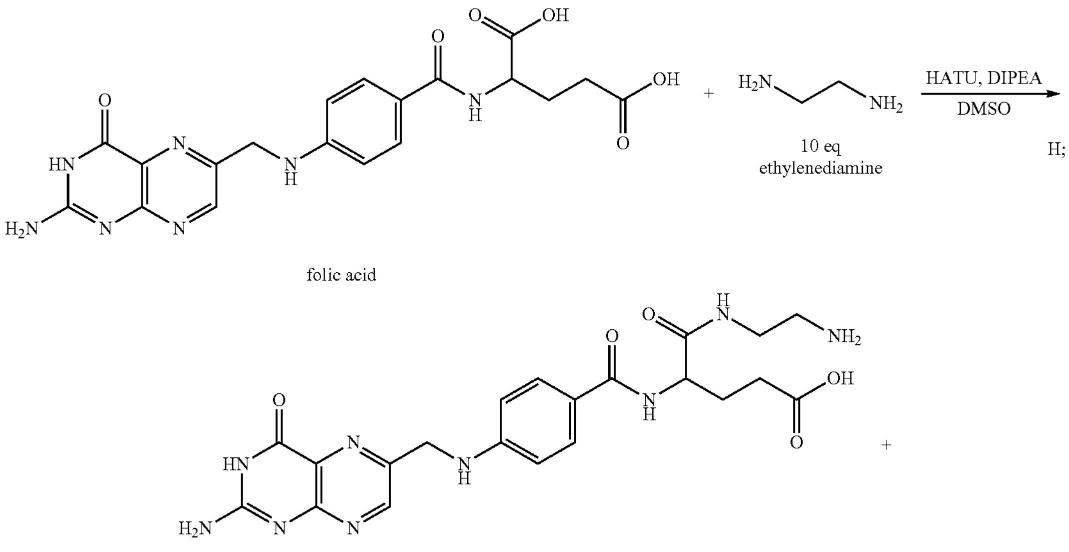

folic acid 10 eq ethylenediamine

EDA-folate(α)

-continued

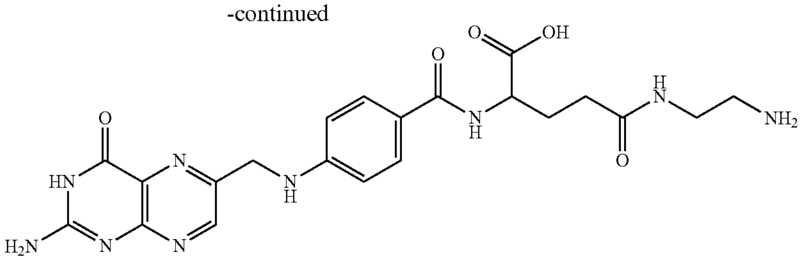

EDA-folate(γ)

$N^2$-(4-(((2-amino-4-oxo-3,4-dihydropteridin-6-yl)methyl)amino)benzoyl)-$N^5$-(2-aminoethyl)glutamine (EDA-folate (g)): Folic acid (441.4 mg, 1 mmol, 1 equiv) was dissolved in DMSO (20 mL) and ethylenediamine (669 μL, 10 mmol, 10 equiv), DIPEA (348 μL, 2 mmol, 2 equiv), and 1-[Bis(dimethylamino)methylene]-1H-1,2,3-triazolo[4,5-b]pyridinium 3-oxide hexafluorophosphate (HATU, 456 mg, 1.2 mmol, 1.2 equiv) were added. The reaction mixture was stirred at ambient temperature overnight. The crude product was precipitated by addition of 20 mL acetonitrile in a centrifuge tube (45 mL). The tube was centrifuged, the supernatant liquid discarded, and the remaining solid was washed with acetonitrile (2×20 mL). The residue was dissolved in water (10 mL) and purified by prep-HPLC (Phenomenex Luna C18 column, 150×21.2 mm, 5 μm; gradient: 10-15% acetonitrile in water with 0.1% TFA over 17 min; flow: 21.2 mL/min) to afford EDA-folate (g) (126 mg, 26% yield) and EDA-folate (a) (160 mg, 33% yield) as yellow solids. The chemical identities of the two EDA-folate monoisomers were confirmed by comparing $^1H$ NMR data with published literature (Bioconjugate Chem. 1997, 8, 673-679).

EDA-folate (g): $^1H$ NMR (400 MHz, DMSO-$d_6$) δ 8.73 (s, 1H), 8.37-8.21 (m, 2H), 8.01 (t, J=5.8 Hz, 1H), 7.77 (m, 3H), 7.67 (d, J=8.4 Hz, 2H), 6.66 (d, J=8.4 Hz, 2H), 4.39-4.32 (m, 3H), 3.38-3.27 (m, 1H), 3.25-3.13 (m, 1H), 2.84 (dt, J=11.5, 5.8 Hz, 2H), 2.29-2.17 (m, 2H), 2.11 (ddd, J=13.5, 10.6, 5.0 Hz, 1H), 1.90 (tt, J=13.5, 7.0 Hz, 1H).

EDA-folate (a): $^1H$ NMR (400 MHz, DMSO-$d_6$) δ 8.73 (s, 1H), 8.43 (m, 1H), 8.17-8.01 (m, 2H), 7.84-7.72 (m, 3H), 7.68 (d, J=8.3 Hz, 2H), 6.66 (d, J=8.4 Hz, 2H), 4.35-3.29 (m, 3H), 3.30 (q, J=7.1 Hz, 2H), 2.85 (q, J=6.3 Hz, 2H), 2.27 (t, J=7.8 Hz, 2H), 2.09-1.96 (m, 1H), 1.88 (dd, J=14.6, 7.5 Hz, 1H).

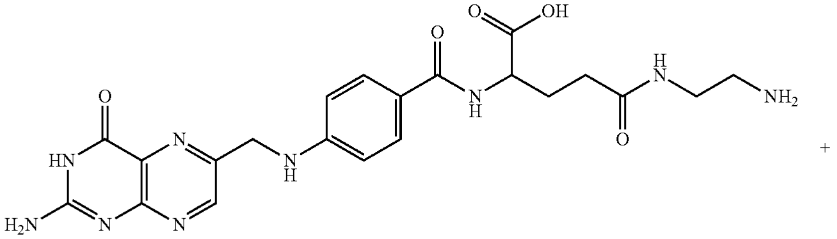

EDA-folate(γ)

+

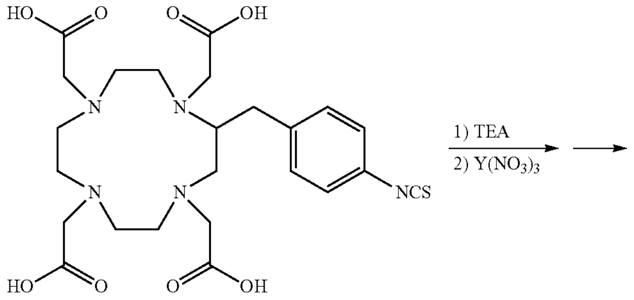

DOTA-NCS

-continued

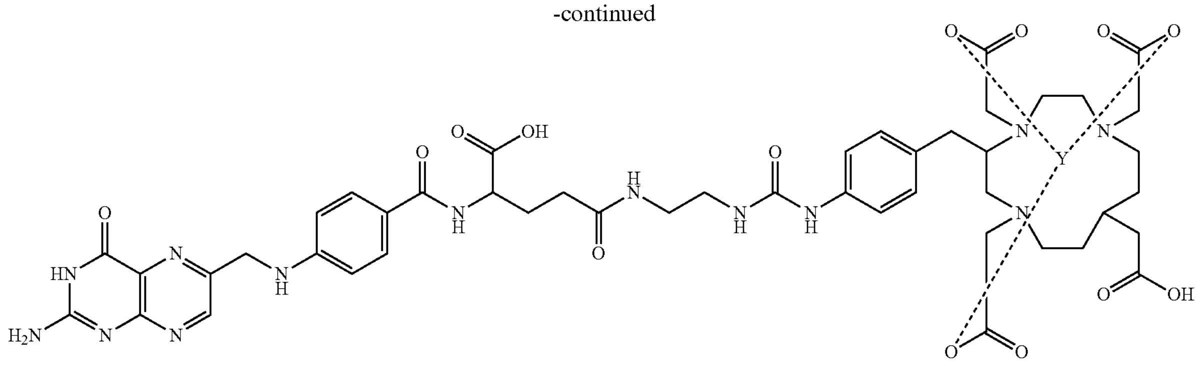

DOTA-folate

DOTA-folate: To the solution of EDA-folate (g) (9 mg, 0.0186 mmol, 1 equiv) in 0.1 M tetramethylammonium formate buffer (1.8 mL) was added a solution of DOTA-NCS (15.4 mg, 0.0223 mmol, 1.2 equiv) in 0.1 M tetramethylammonium formate buffer (0.9 mL) and TEA (26 µL, 0.186 mmol, 10 equiv). The reaction mixture was stirred at ambient temperature for 2 hours, and then a solution of $Y(NO_3)_3.6H_2O$ (21.4 mg, 0.0558 mmol, 3 equiv) in 0.05 M HCl buffer (140 µL) was added. The resulting mixture was stirred for another 1 hour and the crude sample was purified by prep-HPLC (Phenomenex Luna C18 column, 150×21.2 mm, 5 µm; gradient: 20-45% acetonitrile in water with 0.1% TFA over 15 min; flow: 21.2 mL/min) to afford the desired product (15 mg, 72%) as a yellow solid. The product was confirmed by $^1H$ NMR and high resolution mass spectrometry (HRMS).

$^1H$ NMR (400 MHz, DMSO-$d_6$) δ 8.65 (d, J=2.4 Hz, 1H), 8.28-8.19 (m, 1H), 8.04-7.94 (m, 1H), 7.65 (d, J=8.3 Hz, 2H), 7.63 (m, 1H), 7.43-7.27 (m, 2H), 7.22 (m, 1H), 7.08 (m, 1H), 6.64 (d, J=8.3 Hz, 2H), 4.49 (d, J=5.9 Hz, 2H), 4.30 (m, 1H), 3.25-2.85 (m, 12H), 2.67 (m, 1H), 2.54 (m, 10H), 2.33 (m, 2H), 2.25-2.15 (m, 4H), 2.13-1.85 (m, 4H). HRMS (ESI): m/z: calcd for $C_{45}H_{55}N_{14}O_{13}SY$ $[M/2-H]^-$: 559.1349; found:559.1339.

Synthesis of Bis/Tris-DOTA Compounds

Bis-DOTA-11, Bis-DOTA-13, Bis-DOTA-15, Tris-DOTA-3PEG, Tris-DOTA-4PEG, Tris-DOTA-5PEG were prepared by Method 1 or Method 2.

Method 1:

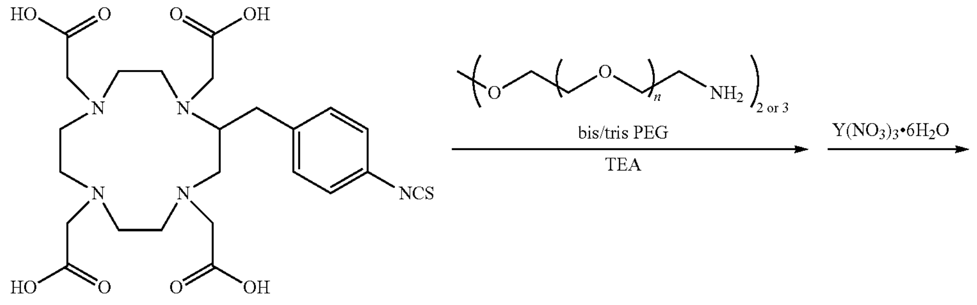

DOTA-NCS

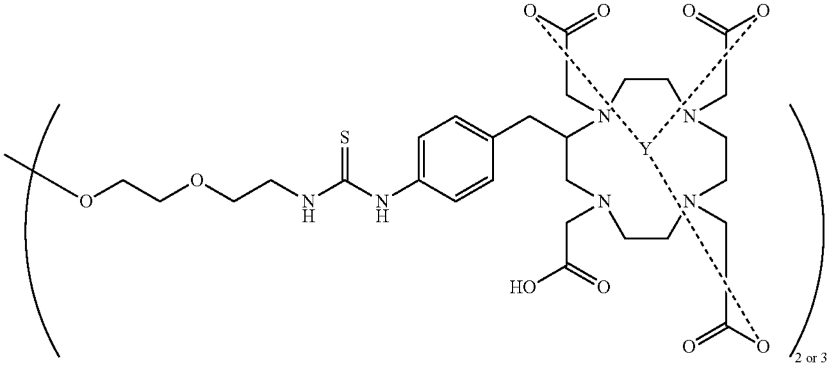

Bis/Tris-DOTA

Method 2

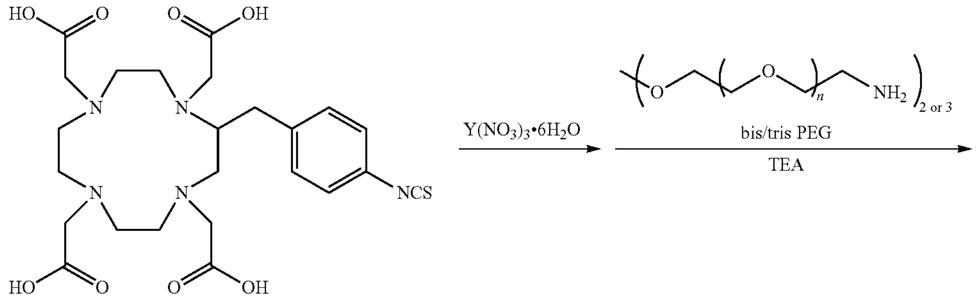

DOTA-NCS

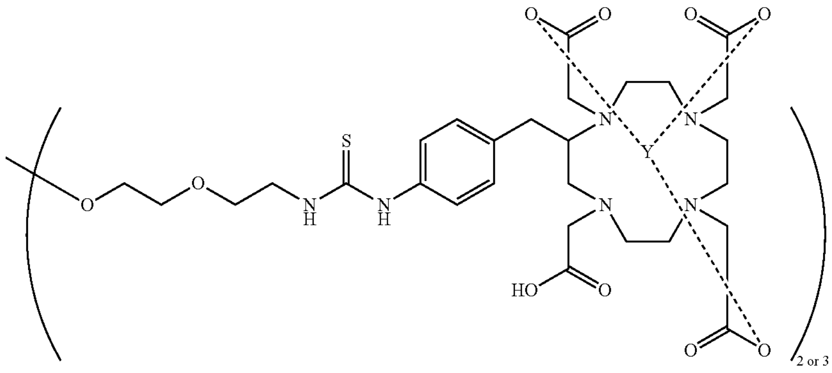

Bis/Tris-DOTA

Method 1: DOTA-NCS (14.5 mM, ~1.8 equiv per free amine) in 0.1 M tetramethylammonium formate buffer was added bis/tris PEG linker (1 equiv) and TEA (12 equiv per free amine). The reaction mixture was stirred at ambient temperature for 2 hours or longer until LC-MS showed the completion of the reactions. To the mixture was added the solution of $Y(NO_3)_3.6H_2O$ (0.5 M, 3 equiv per DOTA) in 0.05 M HCl buffer. The resulting mixture was stirred for another 1 hour and the crude sample was purified by Semi prep-HPLC (XBridge BEH C18 column, 150×10 mm, 5 μm; gradient: 0-45% acetonitrile in water over 20 min; flow: 4.7 mL/min) to afford the desired product as a white solid.

Method 2: The solution of DOTA-NCS (10 mM, ~1.8 equiv per free amine) in 0.1 M tetramethylammonium formate buffer was mixed with the solution of $Y(NO_3)_3.6H_2O$ (0.5 M, 3 equiv per DOTA) in 0.05 M HCl buffer. The reaction mixture was stirred at ambient temperature for 1 hour to afford Y-DOTA-NCS. To the mixture was added bis/tris PEG linker (1 equiv) and TEA (12 equiv per free amine). The reaction mixture was stirred at ambient temperature for 2 hours or longer until LC-MS showed the completion of the reactions. The crude sample was then purified by Semi prep-HPLC (XBridge BEH C18 column, 150×10 mm, 5 μm; gradient: 0-45% acetonitrile in water over 20 min; flow: 4.7 mL/min) to afford the desired product as a white solid.

Bis-DOTA-11

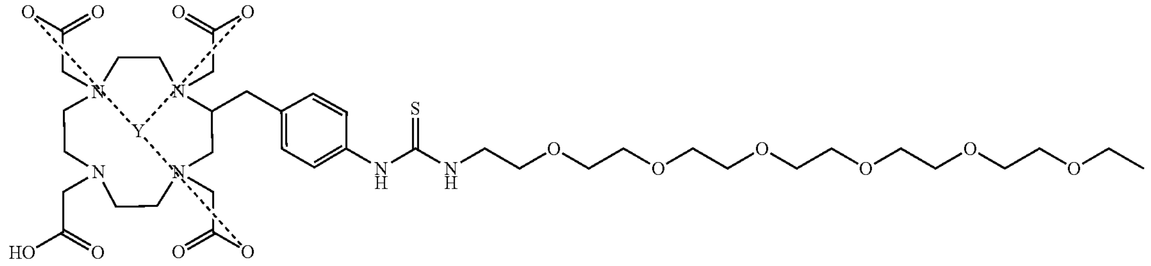

-continued
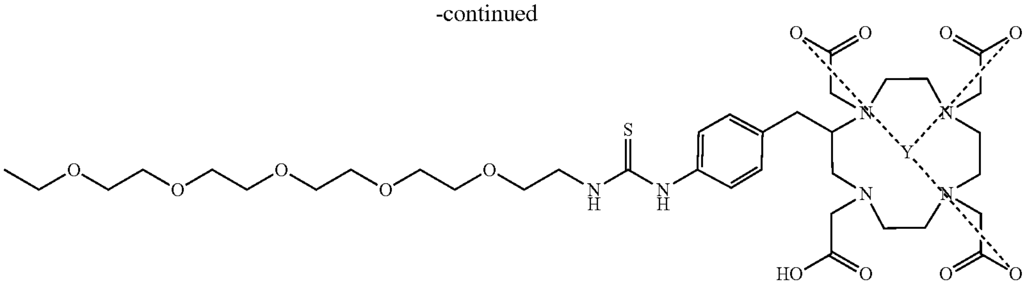
Exact Mass:1818.53
Bis-DOTA-11 was prepared by Method 1, starting with Amino-PEG11-amine (4.4 mg, 0.0081 mmol, 1 equiv) and DOTA-NCS (20 mg, 0.029 mmol, 3.6 equiv) to afford the product (11 mg, 75%) as a white solid.
Bis-DOTA-13
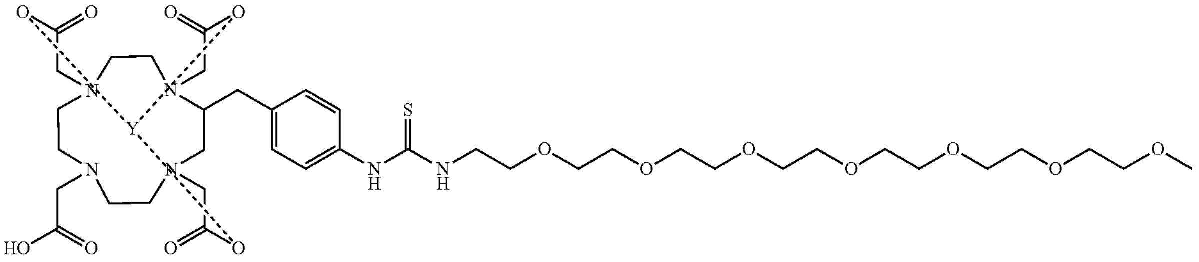
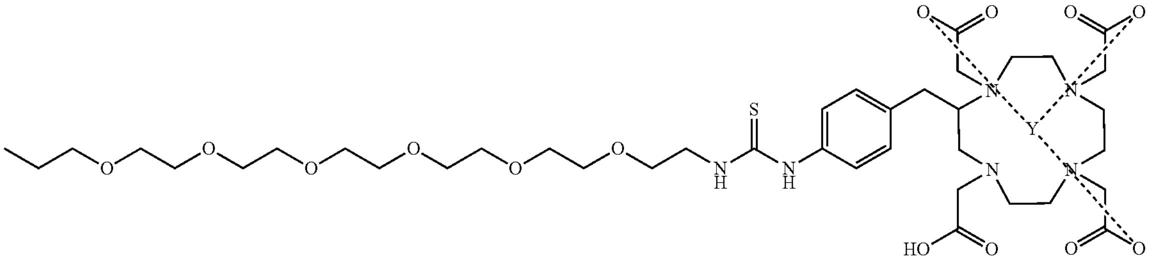
Exact Mass: 1906.58
Bis-DOTA-13 was prepared by Method 1, starting with Amino-PEG13-amine (5.1 mg, 0.0081 mmol, 1 equiv) and DOTA-NCS (20 mg, 0.029 mmol, 3.6 equiv) to afford the product (12 mg, 80%) as a white solid.
Bis-DOTA-15
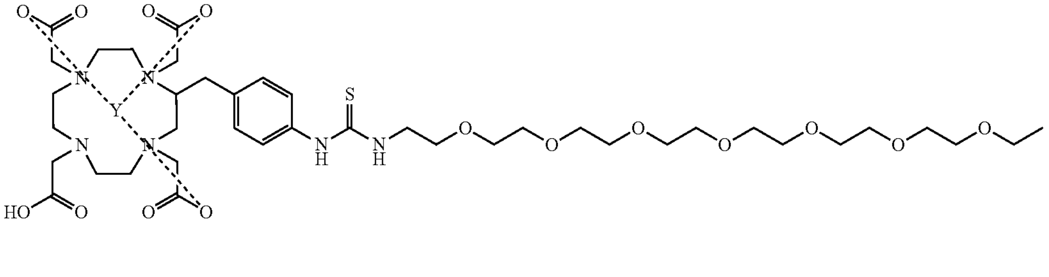

-continued

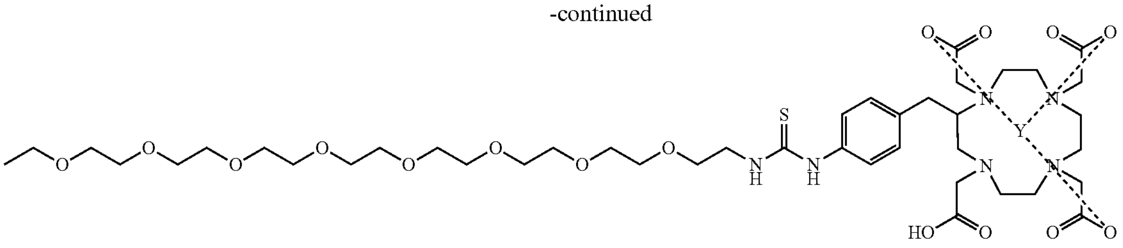

Chemical Formula: $C_{80}H_{128}N_{12}O_{31}S_2Y_2$
Exact Mass: 1994.64

Bis-DOTA-15 was prepared by Method 1, starting with Amino-PEG15-amine (4.4 mg, 0.0061 mmol, 1 equiv) and DOTA-NCS (15 mg, 0.0218 mmol, 3.6 equiv) to afford the product (9.2 mg, 76%) as a white solid. $^1H$ NMR (400 MHz, Deuterium Oxide) δ 7.35-7.26 (m, 8H), 3.82-3.63 (m, 60H), 3.55-3.26 (m, 20H), 3.22-3.06 (m, 10H), 2.93-2.38 (m, 22H), 2.25 (m, 2H). HRMS (ESI): m/z: calcd for $C_{80}H_{128}N_{12}O_{31}S_2Y_2$ $[M/2-H]^-$: 996.3105; found: 996.3117.

Tris-DOTA-3PEG

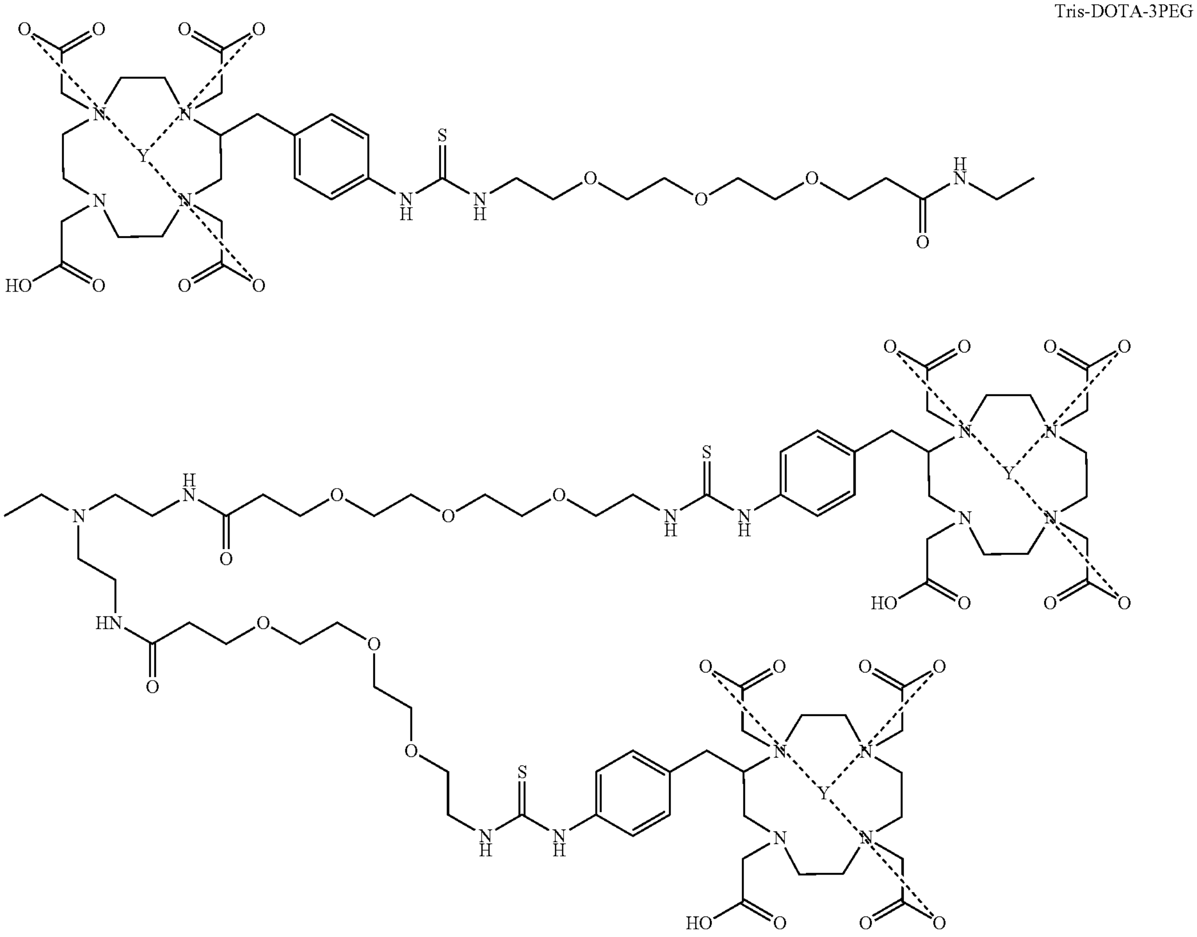

Exact Mass: 2666.76

Tris-DOTA-3PEG was prepared by Method 1, starting with tris-PEG3-$NH_2$ (3.9 mg, 0.00448 mmol, 1 equiv) and DOTA-NCS (18 mg, 0.026 mmol, 5.8 equiv) to afford the product (11 mg, 92%) as a white solid.

Tris-DOTA-4PEG
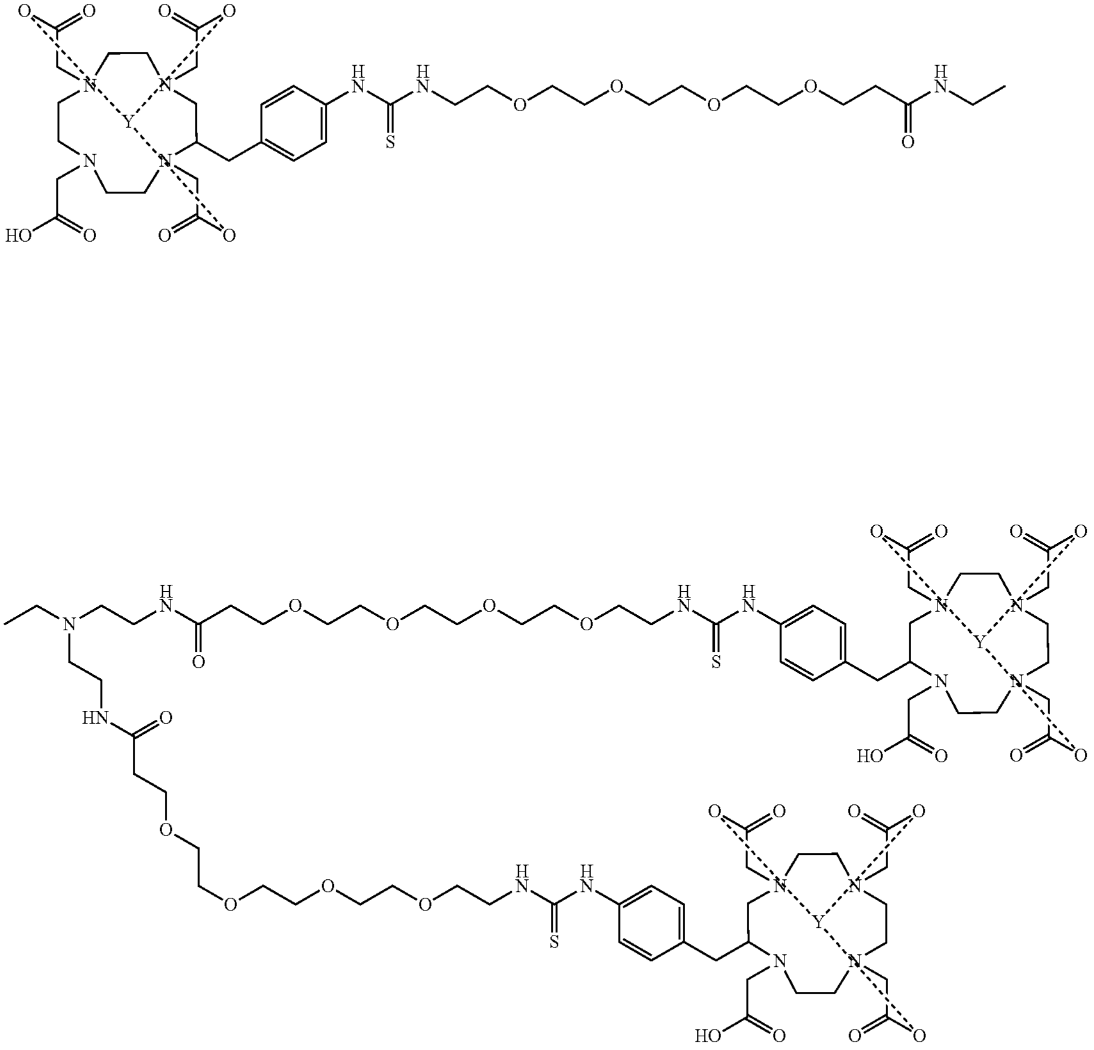
Exact Mass: 2798.84
Tris-DOTA-4PEG was prepared by Method 2, starting with tris-PEG4-$NH_2$ (4.8 mg, 0.00545 mmol, 1 equiv) and DOTA-NCS (23 mg, 0.0334 mmol, 6.1 equiv) to afford the product (12 mg, 79%) as white solid. $^{1}H$ NMR (400 MHz, Deuterium Oxide) δ 7.28 (m, 12H), 3.82-3.56 (m, 72H), 3.55-3.25 (m, 33H), 2.92-2.37 (m, 40H), 2.24-2.18 (m, 2H). HRMS (ESI): m/z: calcd for $C_{111}H_{171}N_{12}O_{39}S_3Y_3$ $[M/2-H]^-$: 1398.4128; found: 1398.4127.
Tris-DOTA-5PEG
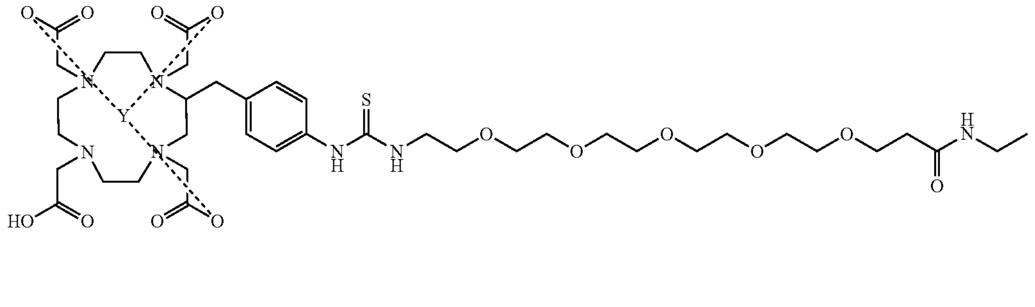

-continued

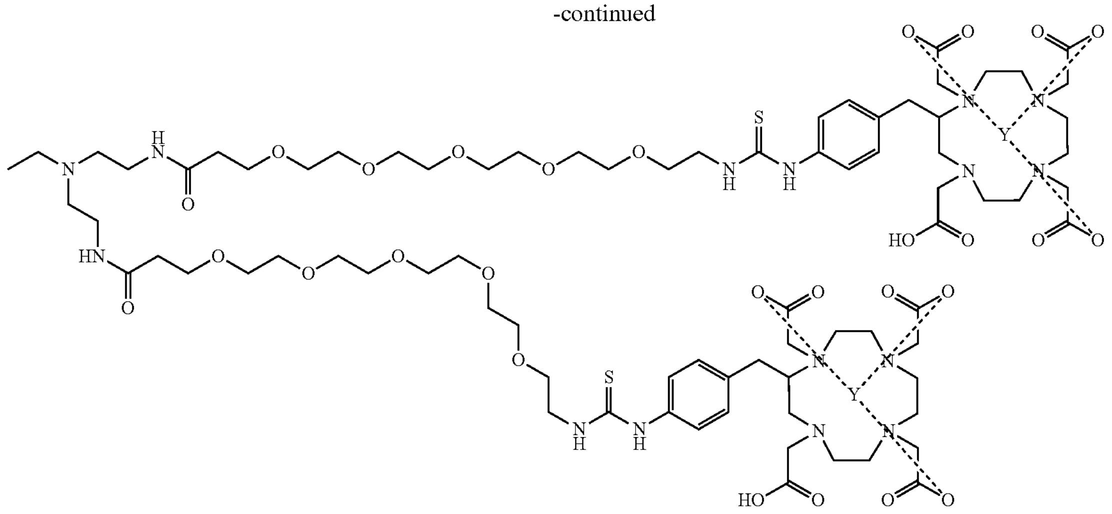

Exact Mass: 2930.92

Tris-DOTA-5PEG was prepared by Method 1, starting with tris-PEG5-$NH_2$ (5.5 mg, 0.00545 mmol, 1 equiv) and DOTA-NCS (15 mg, 0.0218 mmol, 4 equiv) to afford the product (7.5 mg, 47%) as a white solid. $^1H$ NMR (400 MHz, Deuterium Oxide) δ 7.42-7.16 (m, 12H), 3.92 (m, 2H), 3.85-3.57 (m, 84H), 3.55-3.26 (m, 27H), 3.19-2.99 (m, 10H), 2.93-2.37 (m, 32H), 2.31-2.14 (m, 4H). HRMS (ESI): m/z: calcd for $C_{117}H_{183}N_{12}O_{42}S_3Y_3$ $[M/2-H]^-$: 1464.4521; found: 1464.4520.

Figure 26:
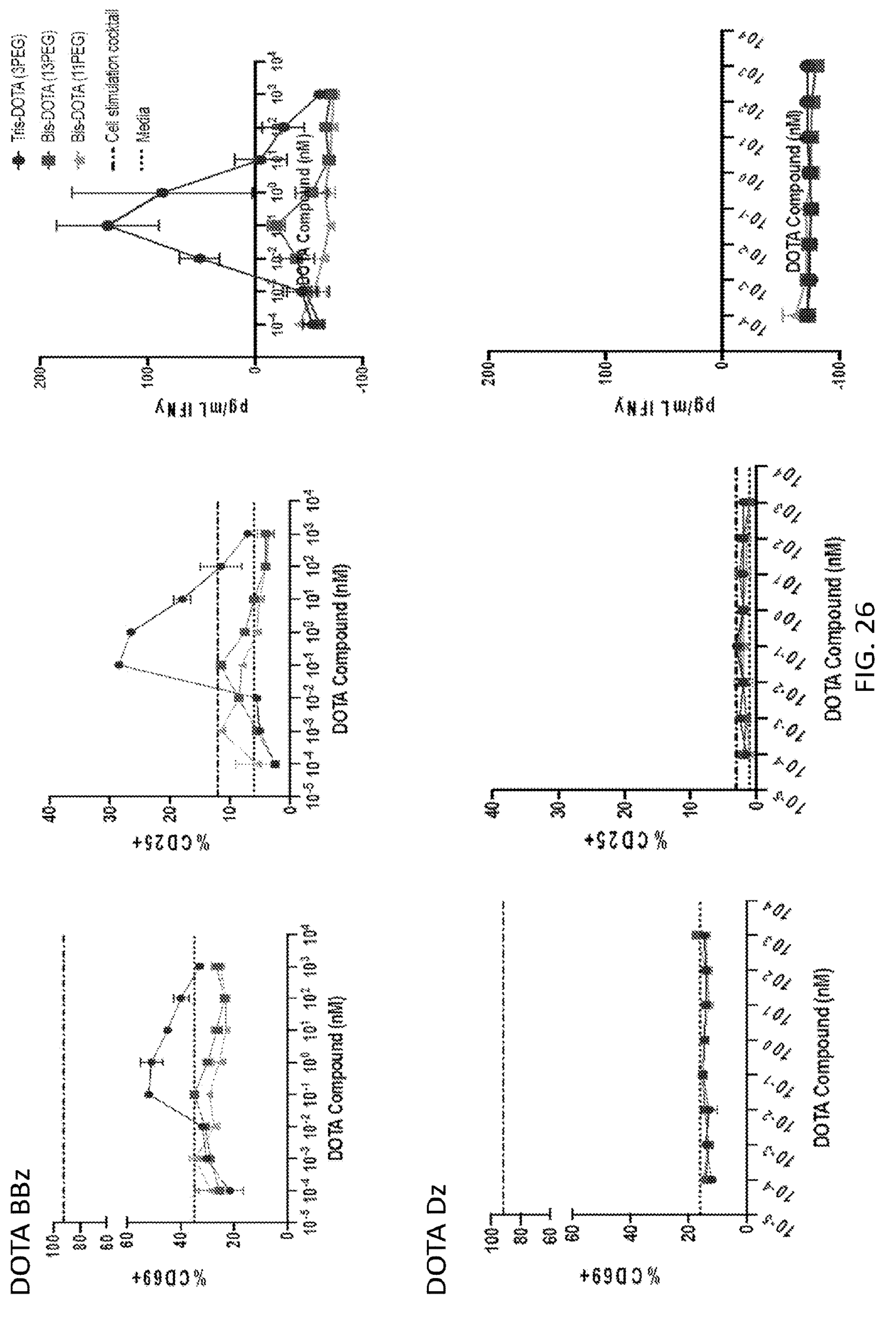
FIG. 26 illustrates the ability of Bis-DOTA compounds of various lengths and a Tris-DOTA compound to activate anti-DOTA CAR T cells.

Due to previous data showing that valency impacts off-target activity of DOTA CAR T cells in co-culture experiments, the ability of multiple DOTA molecules linked together to activate DOTA BBz T cells (FIG. 26, top panel) and DOTA Dz T cells (FIG. 26, bottom panel) was investigated. CAR-expressing T cells were cultured with Bis- and Tris-DOTA compounds for 24 hours and then analyzed for measures of activation. Each condition was run in duplicate. CD69 and CD25 expression was measured by flow cytometry and IFNγ secretion was measured by ELISA. A cell stimulation cocktail containing PMA and ionomycin was used as a positive control and media alone was used as a negative control. The Tris-DOTA compound was able to activate the DOTA BBz T cells with a peak in the 0.1-1 nanomolar range.

Figure 27:
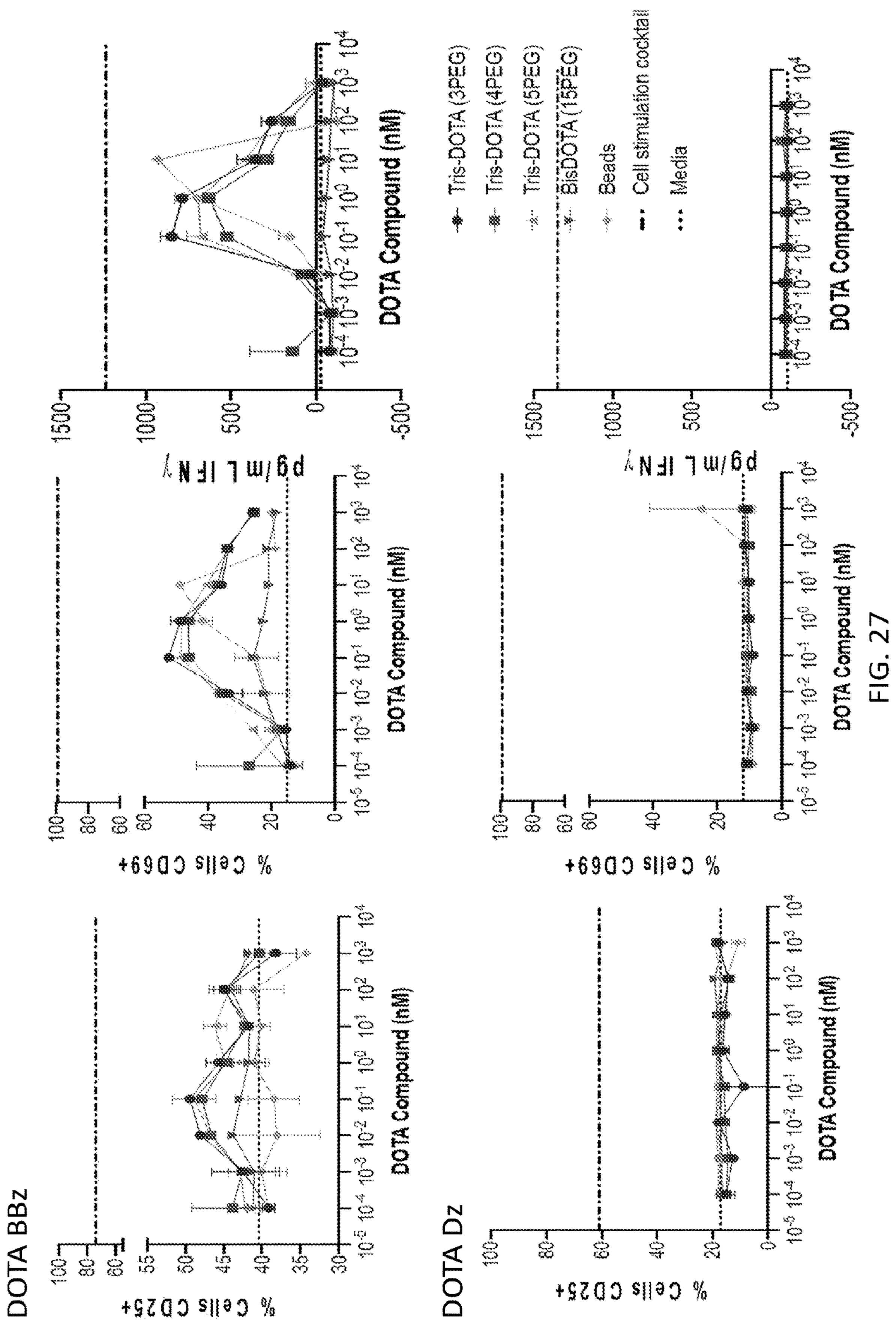
FIG. 27 illustrates the ability of Bis- or Tris-DOTA compounds of various lengths or Dynabeads conjugated with DOTA to activate anti-DOTA CAR T cells.

Bis- and Tris-DOTA compounds with longer linkers were synthesized and tested for the ability to activate CAR-expressing T cells. DOTA BBz T cells (FIG. 27, top panel) and DOTA Dz T cells (FIG. 27, bottom panel) were cultured with Bis- and Tris-DOTA compounds as well as DOTA conjugated to Dynabeads for 24 hours and analyzed for activation. Each condition was run in duplicate. CD69 and CD25 expression was measured by flow cytometry and IFNγ secretion was measured by ELISA. A cell stimulation cocktail containing PMA and ionomycin was used as a positive control and media alone was used as a negative control. The Tris-DOTA compounds were all able to activate the DOTA BBz T cells with a peak in the 0.1-1 nanomolar range. The Dynabeads activated the DOTA BBz T cells with a peak in the 1-10 nanomolar range.

Figure 28A:
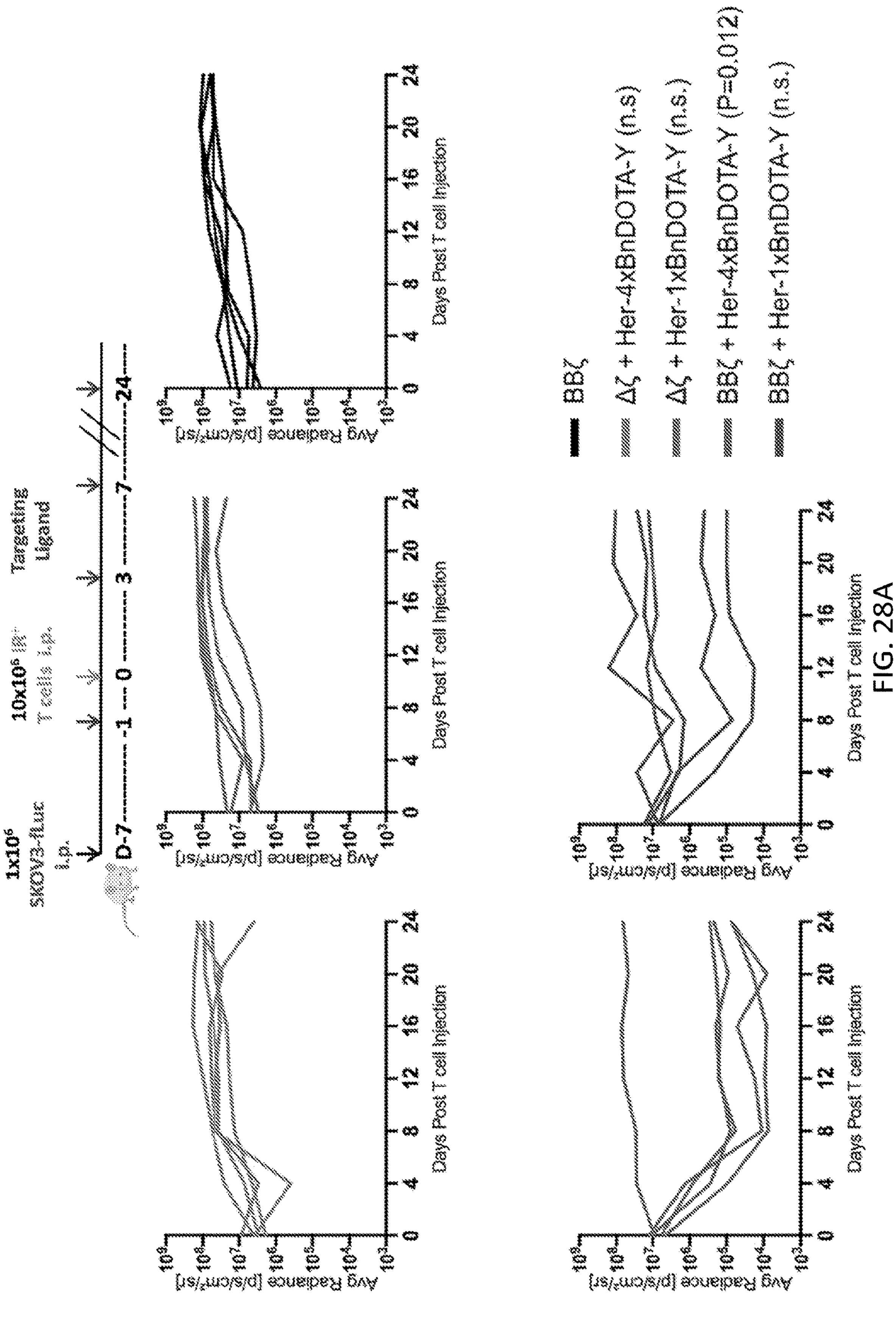
FIGS. 28A-28B illustrate the finding that DOTA-conjugation valency impacts anti-tumor activity in vivo.
Figure 28B:
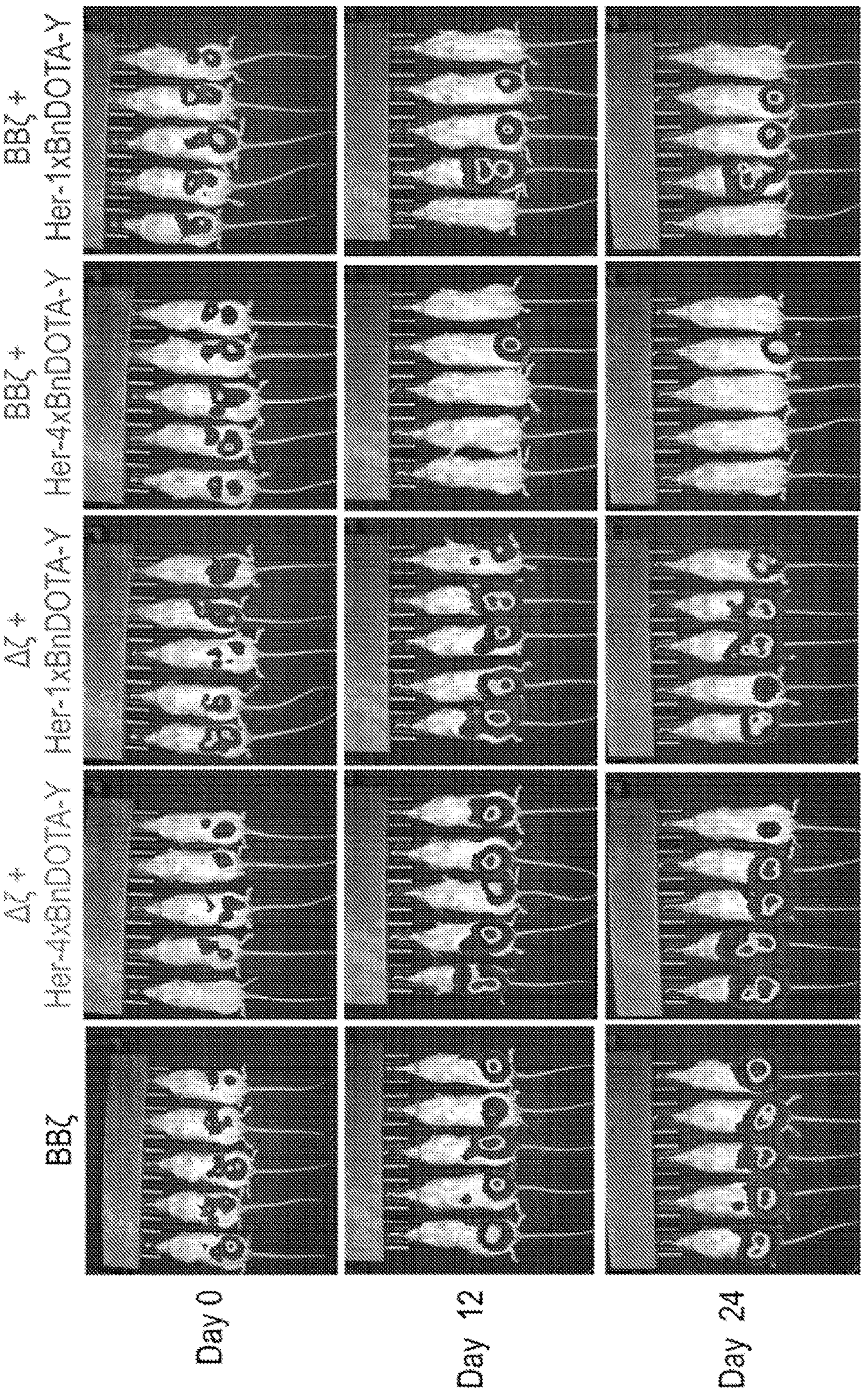

NOD.Cg-$Prkdc^{scid}$ $Il2rg^{tm1wjl}$/SzJ (NSG) mice were injected in the intraperitoneal (I.P.) cavity with $1\times10^6$ Skov3 cells expressing fLuc (FIGS. 28A-28B). After 6 days to allow tumor engraftment, 25 ug of targeting ligand was injected I.P. into each mouse. One day later, $10\times10^6$ CAR+ T cells were injected I.P. Treatment groups were given DOTA BBz T cells and either high valency or low valency Her-Bn-DOTA-Y. Control groups were given DOTA Dz T cells and targeting ligands or DOTA BBz T cells and saline. Targeting ligand was injected every 4 days and tumors were monitored via bioluminescence imaging. 24 days after CAR T cell injection, tumor burden was significantly reduced (p=0.012) in the high valency group. Tumor burden was reduced in two mice of the low valency group, but this was not significant. These data demonstrated that DOTA-conjugation valency impacts anti-tumor activity in vivo (FIGS. 28A-28B).

In summary, data herein demonstrated that a.) anti-DOTA UIR T cells secret cytokines in a dose-dependent fashion in response to immobilized DOTA-mAb, b.) specific lysis of antigen expressing tumor cells is seen upon addition of DOTA-mAb in vitro and in vivo, c.) DOTA IR affinity for DOTA-labeled targeting ligands can be tuned by changing the linker and/or the addition of a chelated metal (~3200× increase in EC50 between Herceptin-DOTA and Herceptin-Bn-DOTA), d.) activity of the DOTA system can be blocked via addition of excess monomeric DOTA, potentially serving as a safety switch.

The DOTA system disclosed herein provides many advantages over other systems including, but not limited to: 1.) It is non-immunogenic, 2.) There are multiple ways of regulating dose/activity (metal, DOTA, antibody dose) and 3.) Multiple DOTAylated tumor-specific antibodies are approved and in use in the clinic.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A modified cell comprising a chimeric antigen receptor (CAR), wherein the CAR comprises a DOTA (1,4,7,10-tetraazacyclododecane-1,4,7,10-tetraacetic acid)-binding domain, a transmembrane domain, and an intracellular domain, and wherein the CAR comprises an amino acid sequence selected from the group consisting of SEQ ID NOs: 6, 8, 10, 12, 14, and 16.

2. The modified cell of claim 1, wherein the DOTA-binding domain of the CAR is humanized.

3. The modified cell of claim 1, wherein the CAR is encoded by a nucleic acid sequence selected from the group consisting of SEQ ID NOs: 5, 7, 9, 11, 13, and 15.

4. The modified cell of claim 1, wherein the cell is selected from the group consisting of a T cell, a macrophage, and an NK cell.

* * * * *